US011266512B2

(12) United States Patent
Trabish et al.

(10) Patent No.: US 11,266,512 B2
(45) Date of Patent: Mar. 8, 2022

(54) SURGICAL APPARATUS TO SUPPORT INSTALLATION OF A PROSTHETIC COMPONENT AND METHOD THEREFORE

(71) Applicant: Orthosensor Inc., Dania, FL (US)

(72) Inventors: Masei Trabish, Folsom, CA (US); Martin Roche, Fort Lauderdale, FL (US); Ivan Delevic, Key Biscayne, FL (US); Daniel Lieffort, Fort Lauderdale, FL (US); Min Sic Roh, Yangcheon-Gu (KR); Seonguk Jeon, Guro-gu (KR)

(73) Assignee: Orthosensor Inc., Dania, FL (US)

( * ) Notice: Subject to any disclaimer, the term of this patent is extended or adjusted under 35 U.S.C. 154(b) by 168 days.

(21) Appl. No.: 16/414,036

(22) Filed: May 16, 2019

(65) Prior Publication Data

US 2019/0290451 A1    Sep. 26, 2019

Related U.S. Application Data

(63) Continuation-in-part of application No. 15/852,012, filed on Dec. 22, 2017, and a continuation-in-part of application No. 15/852,030, filed on Dec. 22, 2017, and a continuation-in-part of application No. 15/852,051, filed on Dec. 22, 2017.
(Continued)

(51) Int. Cl.
*A61F 2/46* (2006.01)
*A61B 17/02* (2006.01)
*A61B 5/107* (2006.01)
*A61F 2/30* (2006.01)

(52) U.S. Cl.
CPC ............ *A61F 2/4657* (2013.01); *A61B 5/107* (2013.01); *A61B 17/025* (2013.01); *A61F 2/461* (2013.01); *A61B 2017/0268* (2013.01); *A61F 2002/30535* (2013.01); *A61F 2002/4658* (2013.01); *A61F 2002/4662* (2013.01); *A61F 2002/4667* (2013.01); *A61F 2002/4668* (2013.01);
(Continued)

(58) Field of Classification Search
CPC ..... A61B 2017/0256; A61B 2017/0268; A61F 2/461; A61F 2/4657
See application file for complete search history.

(56) References Cited

U.S. PATENT DOCUMENTS 4,501,266 A   2/1985  McDaniel
4,566,448 A   1/1986  Rohr, Jr.
(Continued)

*Primary Examiner* — Nicholas W Woodall
(74) *Attorney, Agent, or Firm* — Lerner, David, Littenberg, Krumholz & Mentlik, LLP

(57) ABSTRACT

A surgical apparatus comprising a first distraction mechanism, a second distraction mechanism, and a third distraction mechanism. The surgical apparatus is configured to be placed in a joint of the musculoskeletal system to precisely separate the first bone from the second bone to support one or more bone cuts for installing a prosthetic joint. The first distraction mechanism simultaneously changes a height of a first side and a second side of the joint. The change in height is equal on the first and second sides. The second distraction mechanism changes the height on the first side of the joint but not the second side. The third distraction mechanism changes the height of the second side of the joint but not the first side. The surgical apparatus further includes at least one module to measure loading applied by the joint to the surgical apparatus.

17 Claims, 48 Drawing Sheets

Related U.S. Application Data

(60) Provisional application No. 62/438,406, filed on Dec. 22, 2016.

(52) U.S. Cl.
CPC .............. *A61F 2002/4672* (2013.01); *A61F 2002/4674* (2013.01)

(56) References Cited

U.S. PATENT DOCUMENTS

| | | | |
|---|---|---|---|
| 4,703,751 A | 11/1987 | Pohl | |
| 5,116,338 A | 5/1992 | Poggie et al. | |
| 5,213,112 A | 5/1993 | Niwa et al. | |
| 5,431,653 A | 7/1995 | Callaway | |
| 5,468,244 A | 11/1995 | Attfield et al. | |
| 5,470,354 A | 11/1995 | Hershberger et al. | |
| 5,540,696 A | 7/1996 | Booth, Jr. et al. | |
| 5,569,260 A | 10/1996 | Petersen | |
| 5,597,379 A | 1/1997 | Haines et al. | |
| 5,669,914 A | 9/1997 | Eckhoff | |
| 5,688,280 A | 11/1997 | Booth, Jr. et al. | |
| 5,733,292 A | 3/1998 | Gustilo et al. | |
| 5,800,438 A | 9/1998 | Tuke et al. | |
| 5,860,980 A | 1/1999 | Axelson, Jr. et al. | |
| 5,911,723 A | 6/1999 | Ashby et al. | |
| 6,022,377 A | 2/2000 | Nuelle et al. | |
| 6,478,799 B1 | 11/2002 | Williamson | |
| 6,648,896 B2 | 11/2003 | Overes et al. | |
| 6,758,850 B2 | 7/2004 | Smith et al. | |
| 6,770,078 B2 | 8/2004 | Bonutti | |
| 6,859,661 B2 | 2/2005 | Tuke | |
| 7,156,853 B2 | 1/2007 | Muratsu | |
| 7,179,295 B2 | 2/2007 | Kovacevic | |
| 7,309,339 B2 | 12/2007 | Cusick et al. | |
| 7,329,260 B2 | 2/2008 | Auger et al. | |
| 7,381,223 B2 | 6/2008 | Kovacevic | |
| 7,412,897 B2 | 8/2008 | Crottet et al. | |
| 7,442,196 B2 | 10/2008 | Fisher et al. | |
| 7,455,647 B2 | 11/2008 | Tarabichi | |
| 7,470,288 B2 | 12/2008 | Dietz et al. | |
| 7,575,602 B2 | 8/2009 | Amirouche et al. | |
| 7,578,821 B2 | 8/2009 | Fisher et al. | |
| 7,587,945 B2 | 9/2009 | Crottet et al. | |
| 7,591,854 B2 | 9/2009 | Wasielewski | |
| 7,615,055 B2 | 11/2009 | DiSilvestro | |
| 7,632,283 B2 | 12/2009 | Heldreth | |
| 7,635,369 B2 | 12/2009 | Cinquin et al. | |
| 7,651,500 B2 | 1/2010 | Supper et al. | |
| 7,837,691 B2 | 11/2010 | Cordes et al. | |
| 7,849,751 B2 | 12/2010 | Clark et al. | |
| 7,927,336 B2 | 4/2011 | Rasmussen | |
| 7,978,091 B2 | 7/2011 | Boillot | |
| 8,025,663 B2 | 9/2011 | Keeven et al. | |
| 8,065,927 B2 | 11/2011 | Crottet et al. | |
| 8,118,815 B2 | 2/2012 | van der Walt | |
| 8,137,361 B2 | 3/2012 | Duggineni et al. | |
| 8,141,437 B2 | 3/2012 | Amirouche et al. | |
| 8,162,951 B2 | 4/2012 | Kaufman | |
| 8,197,489 B2 | 6/2012 | Chessar et al. | |
| 8,197,549 B2 | 6/2012 | Amirouche et al. | |
| 8,211,041 B2 | 7/2012 | Fisher et al. | |
| 8,231,631 B2 | 7/2012 | Lavallee et al. | |
| 8,234,929 B2 | 8/2012 | Clark et al. | |
| 8,273,131 B2 | 9/2012 | Metzger et al. | |
| 8,303,597 B2 | 11/2012 | Rasmussen | |
| 8,323,290 B2 | 12/2012 | Metzger et al. | |
| 8,337,508 B2 | 12/2012 | Lavallee et al. | |
| 8,394,104 B2 | 3/2013 | DiSilvestro | |
| 8,414,653 B2 | 4/2013 | Burstein et al. | |
| 8,421,642 B1 | 4/2013 | McIntosh et al. | |
| 8,491,589 B2 | 7/2013 | Fisher et al. | |
| 8,506,571 B2 | 8/2013 | Chana et al. | |
| 8,551,023 B2 | 10/2013 | Sherman et al. | |
| 8,556,830 B2 | 10/2013 | Sherman et al. | |
| 8,562,617 B2 | 10/2013 | Chessar et al. | |
| 8,597,210 B2 | 12/2013 | Sherman et al. | |
| 8,603,101 B2 | 12/2013 | Claypool et al. | |
| 8,715,290 B2 | 5/2014 | Fisher et al. | |
| 8,721,568 B2 | 5/2014 | Rock et al. | |
| 8,734,454 B2 | 5/2014 | DiSilvestro | |
| 8,740,817 B2 | 6/2014 | Sherman et al. | |
| 8,758,355 B2 | 6/2014 | Fisher et al. | |
| 8,784,339 B2 | 7/2014 | Stein et al. | |
| 8,784,490 B2 | 7/2014 | Wasielewski | |
| 8,820,173 B2 | 9/2014 | Clark et al. | |
| 8,876,831 B2 | 11/2014 | Rasmussen | |
| 8,906,027 B2 | 12/2014 | Roche | |
| 8,945,026 B2 | 2/2015 | Moser et al. | |
| 8,945,132 B2 | 2/2015 | Plaβy et al. | |
| 8,945,133 B2 | 2/2015 | Stein et al. | |
| 8,974,459 B1 | 3/2015 | Axelson, Jr. et al. | |
| 8,998,910 B2 | 4/2015 | Borja et al. | |
| 8,998,917 B2 | 4/2015 | Colquhoun et al. | |
| 9,011,459 B2 | 4/2015 | Claypool et al. | |
| 9,044,218 B2 | 6/2015 | Young | |
| 9,050,107 B2 | 6/2015 | Sordelet et al. | |
| 9,050,197 B2 | 6/2015 | Lorio et al. | |
| 9,084,612 B2 | 7/2015 | Sordelet et al. | |
| 9,113,957 B2 | 8/2015 | Axelson, Jr. et al. | |
| 9,138,238 B2 | 9/2015 | Sordelet et al. | |
| 9,138,332 B2 | 9/2015 | Harris et al. | |
| 9,144,495 B2 | 9/2015 | Lin et al. | |
| 9,149,206 B2 | 10/2015 | Claypool et al. | |
| 9,168,032 B2 | 10/2015 | Hutchison et al. | |
| 9,192,391 B2 | 11/2015 | Haines | |
| 9,192,392 B2 | 11/2015 | van der Walt et al. | |
| 9,216,097 B2 | 12/2015 | Hauri et al. | |
| 9,241,801 B1 | 1/2016 | Parry et al. | |
| 9,248,030 B2 | 2/2016 | Amirouche | |
| 9,265,462 B2 | 2/2016 | McIntosh et al. | |
| 9,271,756 B2 | 3/2016 | van der Walt et al. | |
| 9,307,929 B2 | 4/2016 | Colwell, Jr. et al. | |
| 9,339,226 B2 | 5/2016 | van der Walt et al. | |
| 9,351,850 B2 | 5/2016 | Fischer et al. | |
| 9,370,375 B2 | 6/2016 | Kaneyama et al. | |
| 9,381,011 B2 | 7/2016 | Ruhling et al. | |
| 9,427,336 B2 | 8/2016 | Axelson, Jr. et al. | |
| 9,427,337 B2 | 8/2016 | Claypool et al. | |
| 9,439,656 B2 | 9/2016 | Chana et al. | |
| 9,456,769 B2 | 10/2016 | Stein et al. | |
| 9,480,482 B2 | 11/2016 | Sordelet et al. | |
| 9,492,179 B2 | 11/2016 | Rasmussen | |
| 9,492,180 B2 | 11/2016 | Rasmussen | |
| 9,492,186 B2 | 11/2016 | Ghijselings | |
| 9,492,290 B2 | 11/2016 | Claypool et al. | |
| 9,498,199 B2 | 11/2016 | Colquhoun et al. | |
| 9,498,235 B2 | 11/2016 | Ghijselings | |
| 9,538,953 B2 | 1/2017 | Sherman et al. | |
| 9,539,116 B2 | 1/2017 | Claypool et al. | |
| 9,545,459 B2 | 1/2017 | Scott et al. | |
| 9,554,745 B2 | 1/2017 | Nguyen et al. | |
| 9,572,586 B2 | 2/2017 | van der Walt et al. | |
| 9,572,588 B2 | 2/2017 | Fisher et al. | |
| 9,573,322 B2 | 2/2017 | Wasielewski | |
| 9,592,133 B2 | 3/2017 | Toler et al. | |
| 9,597,090 B2 | 3/2017 | Claypool et al. | |
| 9,597,096 B2 | 3/2017 | Aghazadeh | |
| 9,597,158 B2 | 3/2017 | Colwell, Jr. et al. | |
| 9,615,887 B2 | 4/2017 | Stein et al. | |
| 9,622,761 B2 | 4/2017 | Chana et al. | |
| 9,642,571 B2 | 5/2017 | McIntosh et al. | |
| 9,642,676 B2 | 5/2017 | Stein et al. | |
| 9,649,119 B2 | 5/2017 | Rock et al. | |
| 9,693,881 B2 | 7/2017 | Lorio et al. | |
| 9,724,110 B2 | 8/2017 | Cole | |
| 9,750,619 B2 | 9/2017 | Rock | |
| 9,763,807 B2 | 9/2017 | Claypool et al. | |
| 9,775,595 B2 | 10/2017 | Vogt | |
| 9,775,725 B2 | 10/2017 | van der Walt et al. | |
| 9,782,249 B2 | 10/2017 | Hauri et al. | |
| 9,808,356 B2 | 11/2017 | Haight et al. | |
| 9,820,678 B2 | 11/2017 | Stein et al. | |
| 9,839,533 B2 | 12/2017 | Nguyen et al. | |
| 9,855,057 B2 | 1/2018 | Axelson, Jr. et al. | |

(56) References Cited

U.S. PATENT DOCUMENTS

| | | |
|---|---|---|
| 9,901,331 B2 | 2/2018 | Toler et al. |
| 9,962,172 B2 | 5/2018 | Hutchison et al. |
| 9,980,735 B2 | 5/2018 | Chana et al. |
| 9,993,354 B2 | 6/2018 | Fisher et al. |
| 10,010,329 B2 | 7/2018 | Sordelet et al. |
| 10,010,330 B2 | 7/2018 | Claypool et al. |
| 10,064,671 B2 | 9/2018 | Sharkey et al. |
| 10,070,973 B2 | 9/2018 | Sherman et al. |
| 10,076,344 B2 | 9/2018 | Toler |
| 10,080,617 B2 | 9/2018 | Haider et al. |
| 10,092,362 B2 | 10/2018 | Wasielewski |
| 10,772,640 B2 | 9/2020 | Trabish et al. |
| 10,772,641 B2 | 9/2020 | Trabish et al. |
| 2003/0069644 A1 | 4/2003 | Kovacevic et al. |
| 2003/0187452 A1 | 10/2003 | Smith et al. |
| 2004/0097951 A1 | 5/2004 | Steffensmeier |
| 2004/0122441 A1 | 6/2004 | Muratsu |
| 2005/0038442 A1 | 2/2005 | Freeman |
| 2005/0149037 A1 | 7/2005 | Steffensmeier et al. |
| 2005/0256527 A1 | 11/2005 | Delfosse et al. |
| 2006/0111726 A1 | 5/2006 | Felt et al. |
| 2006/0241569 A1 | 10/2006 | DiSilvestro |
| 2006/0241640 A1 | 10/2006 | Briard et al. |
| 2006/0247646 A1 | 11/2006 | Bihary |
| 2007/0005073 A1 | 1/2007 | Claypool et al. |
| 2007/0066917 A1 | 3/2007 | Hodorek et al. |
| 2007/0162036 A1 | 7/2007 | Schifrine et al. |
| 2007/0233267 A1 | 10/2007 | Amirouche et al. |
| 2007/0239157 A1 | 10/2007 | Guillaume |
| 2007/0244488 A1* | 10/2007 | Metzger ............... A61B 90/36 606/90 |
| 2007/0293868 A1 | 12/2007 | Delfosse et al. |
| 2008/0051798 A1 | 2/2008 | Colquhoun et al. |
| 2008/0269596 A1 | 10/2008 | Revie et al. |
| 2009/0018544 A1 | 1/2009 | Heavener |
| 2009/0222089 A1 | 9/2009 | Hauri et al. |
| 2009/0264894 A1 | 10/2009 | Wasielewski |
| 2009/0270869 A1 | 10/2009 | Colquhoun et al. |
| 2010/0191068 A1 | 7/2010 | Bewernitz et al. |
| 2010/0198275 A1 | 8/2010 | Chana et al. |
| 2010/0249533 A1 | 9/2010 | Pierce et al. |
| 2010/0249534 A1 | 9/2010 | Pierce et al. |
| 2010/0249535 A1 | 9/2010 | Pierce et al. |
| 2010/0249665 A1 | 9/2010 | Roche |
| 2010/0249787 A1 | 9/2010 | Roche |
| 2010/0249788 A1 | 9/2010 | Roche |
| 2010/0249790 A1 | 9/2010 | Roche |
| 2010/0249791 A1 | 9/2010 | Roche |
| 2010/0250276 A1 | 9/2010 | Pierce et al. |
| 2010/0250284 A1 | 9/2010 | Roche et al. |
| 2010/0250571 A1 | 9/2010 | Pierce et al. |
| 2011/0046685 A1 | 2/2011 | Faure et al. |
| 2011/0196370 A1 | 8/2011 | Mikhail |
| 2011/0213221 A1 | 9/2011 | Roche |
| 2012/0172762 A1 | 7/2012 | Boyer et al. |
| 2012/0172881 A1 | 7/2012 | Hutchison |
| 2012/0179069 A1 | 7/2012 | Amirouche |
| 2012/0259342 A1 | 10/2012 | Chana et al. |
| 2012/0290088 A1 | 11/2012 | Amirouche et al. |
| 2013/0023794 A1 | 1/2013 | Stein et al. |
| 2013/0023795 A1 | 1/2013 | Stein et al. |
| 2013/0030538 A1 | 1/2013 | Metzger et al. |
| 2013/0079668 A1 | 3/2013 | Stein et al. |
| 2013/0079669 A1 | 3/2013 | Stein et al. |
| 2013/0079670 A1 | 3/2013 | Stein et al. |
| 2013/0102929 A1 | 4/2013 | Haight et al. |
| 2013/0138112 A1* | 5/2013 | Young ............... A61B 17/025 606/90 |
| 2013/0204157 A1 | 8/2013 | Clark et al. |
| 2013/0261503 A1 | 10/2013 | Sherman et al. |
| 2013/0261505 A1 | 10/2013 | Sherman et al. |
| 2013/0261631 A1 | 10/2013 | Ruhling |
| 2013/0261758 A1 | 10/2013 | Claypool et al. |
| 2013/0261759 A1 | 10/2013 | Claypool et al. |
| 2014/0025081 A1 | 1/2014 | Lorio |
| 2014/0066934 A1 | 3/2014 | Deirmengian et al. |
| 2014/0094715 A1 | 4/2014 | Stein et al. |
| 2014/0114319 A1 | 4/2014 | Wilkinson |
| 2014/0276861 A1 | 9/2014 | Stein et al. |
| 2014/0276886 A1 | 9/2014 | Stein et al. |
| 2014/0288563 A1 | 9/2014 | Claypool et al. |
| 2014/0309560 A1 | 10/2014 | Bonutti |
| 2015/0025537 A1 | 1/2015 | Ghijselings |
| 2015/0051455 A1 | 2/2015 | Wasielewski et al. |
| 2015/0088140 A1 | 3/2015 | Toler et al. |
| 2015/0105782 A1 | 4/2015 | D'Lima et al. |
| 2015/0201886 A1 | 7/2015 | Clark et al. |
| 2015/0209158 A1 | 7/2015 | Reeve |
| 2015/0230804 A1 | 8/2015 | Chana et al. |
| 2015/0238202 A1 | 8/2015 | Collins et al. |
| 2015/0265291 A1 | 9/2015 | Wilkinson |
| 2015/0359642 A1 | 12/2015 | Claypool et al. |
| 2016/0007909 A1 | 1/2016 | Singh et al. |
| 2016/0106409 A1 | 4/2016 | Moholkar |
| 2016/0135825 A1 | 5/2016 | Toler |
| 2016/0175117 A1 | 6/2016 | Colwell, Jr. et al. |
| 2016/0228193 A1 | 8/2016 | Moctezuma de la Barrera et al. |
| 2016/0278754 A1 | 9/2016 | Todorov et al. |
| 2016/0278787 A1 | 9/2016 | Axelson, Jr. et al. |
| 2016/0278944 A1 | 9/2016 | D'Lima et al. |
| 2016/0310122 A1 | 10/2016 | Ruhling et al. |
| 2016/0346044 A1 | 12/2016 | Brown et al. |
| 2017/0007225 A1 | 1/2017 | Ferro et al. |
| 2017/0007408 A1 | 1/2017 | Fitz et al. |
| 2017/0042554 A1 | 2/2017 | Chana et al. |
| 2017/0042558 A1 | 2/2017 | Ghijselings |
| 2017/0079670 A1 | 3/2017 | Haines |
| 2017/0079801 A1 | 3/2017 | Drury et al. |
| 2017/0128057 A1 | 5/2017 | Rasmussen |
| 2017/0128078 A1 | 5/2017 | Rasmussen |
| 2017/0143324 A1 | 5/2017 | Toler et al. |
| 2017/0156736 A1 | 6/2017 | Claypool et al. |
| 2017/0196515 A1 | 7/2017 | Clark et al. |
| 2017/0245872 A1 | 8/2017 | Rock et al. |
| 2017/0252186 A1 | 9/2017 | Lorio et al. |
| 2017/0312099 A1 | 11/2017 | Paszicsnyek |
| 2017/0325868 A1 | 11/2017 | Dungy |
| 2017/0333018 A1 | 11/2017 | Sehat |
| 2017/0333058 A1 | 11/2017 | Cabot |
| 2017/0333059 A1 | 11/2017 | Cole |
| 2017/0333220 A1 | 11/2017 | Reeve |
| 2017/0360512 A1 | 12/2017 | Couture et al. |
| 2017/0360576 A1 | 12/2017 | Rock |
| 2018/0000612 A1 | 1/2018 | Claypool et al. |
| 2018/0021151 A1 | 1/2018 | Mantovani et al. |
| 2018/0036015 A1 | 2/2018 | Bonutti |
| 2018/0049895 A1 | 2/2018 | Haight et al. |
| 2018/0085134 A1 | 3/2018 | Uthgenannt |
| 2018/0098774 A1 | 4/2018 | Bonutti |
| 2018/0132949 A1 | 5/2018 | Merette et al. |
| 2018/0168826 A1 | 6/2018 | van der Walt et al. |
| 2018/0177509 A1 | 6/2018 | Trabish et al. |
| 2018/0177607 A1 | 6/2018 | Trabish et al. |
| 2018/0177611 A1 | 6/2018 | Trabish et al. |
| 2018/0177612 A1 | 6/2018 | Trabish et al. |
| 2018/0199952 A1 | 7/2018 | Cole |
| 2018/0214283 A1 | 8/2018 | Johannaber et al. |
| 2018/0221008 A1 | 8/2018 | Todorov et al. |
| 2019/0008500 A1* | 1/2019 | Plaskos ............... A61F 2/389 |
| 2019/0110905 A1 | 4/2019 | Cabot |
| 2019/0167447 A1* | 6/2019 | Angibaud ............ A61F 2/3859 |
| 2020/0155135 A1* | 5/2020 | Cole ............... A61B 5/4528 |
| 2020/0305942 A1* | 10/2020 | Oden ............... A61B 17/025 |

\* cited by examiner

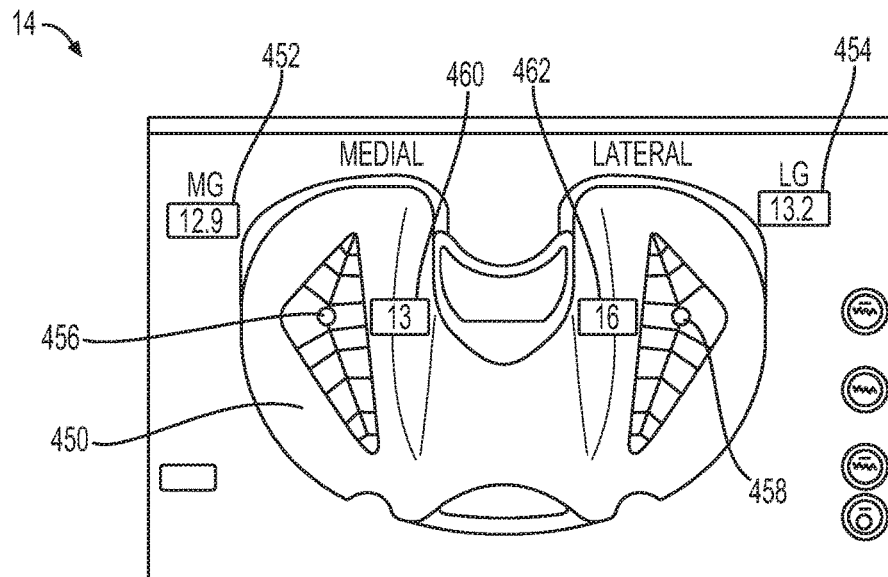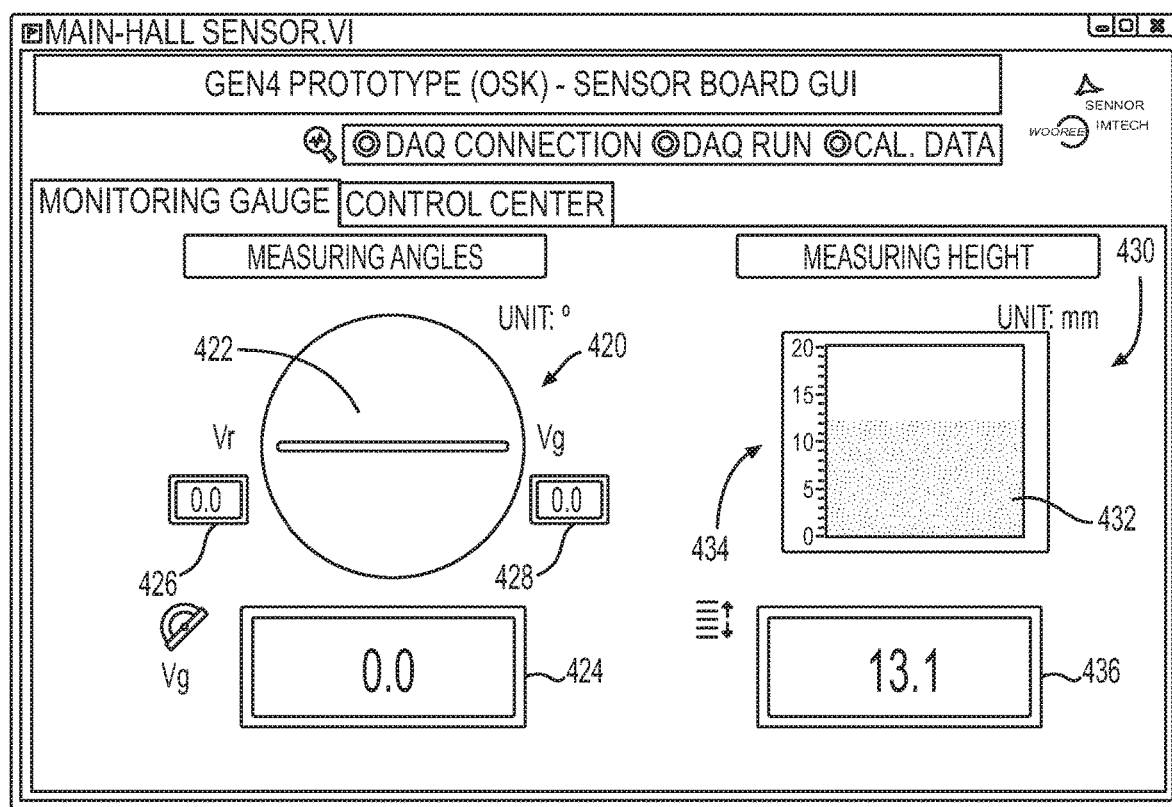
FIG. 33

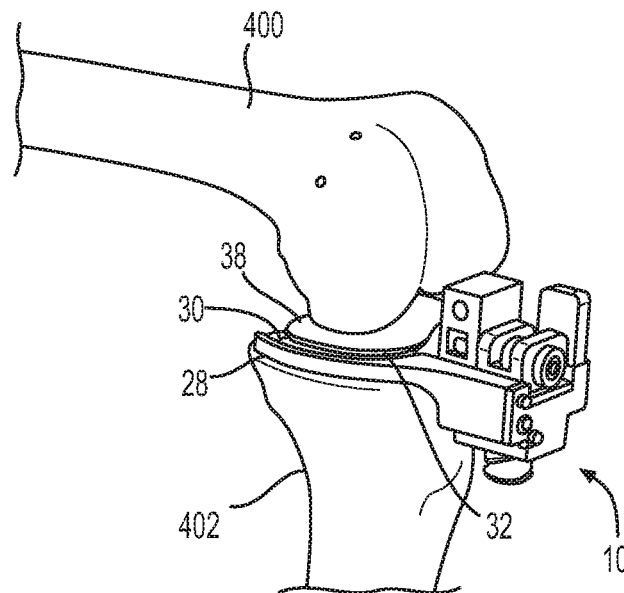
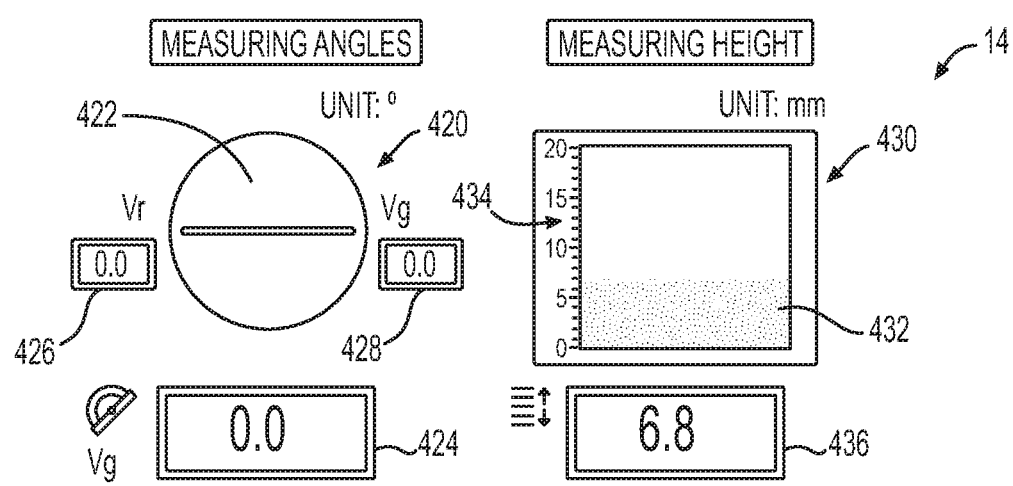
*FIG. 36*

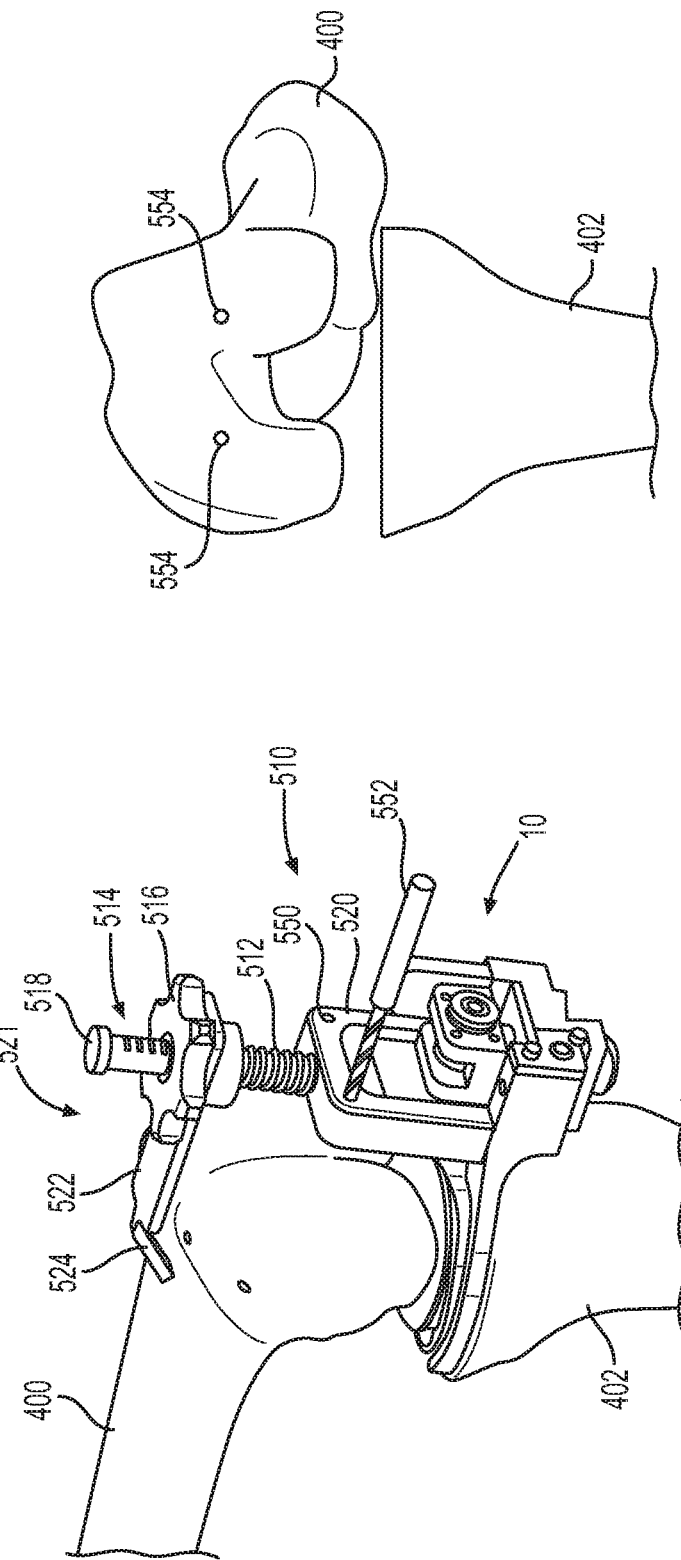

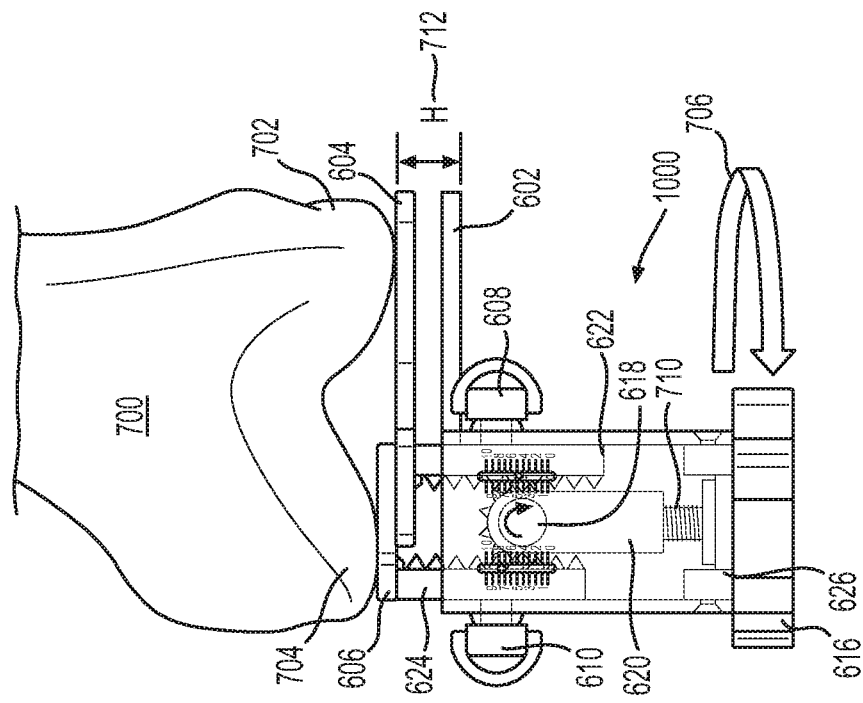
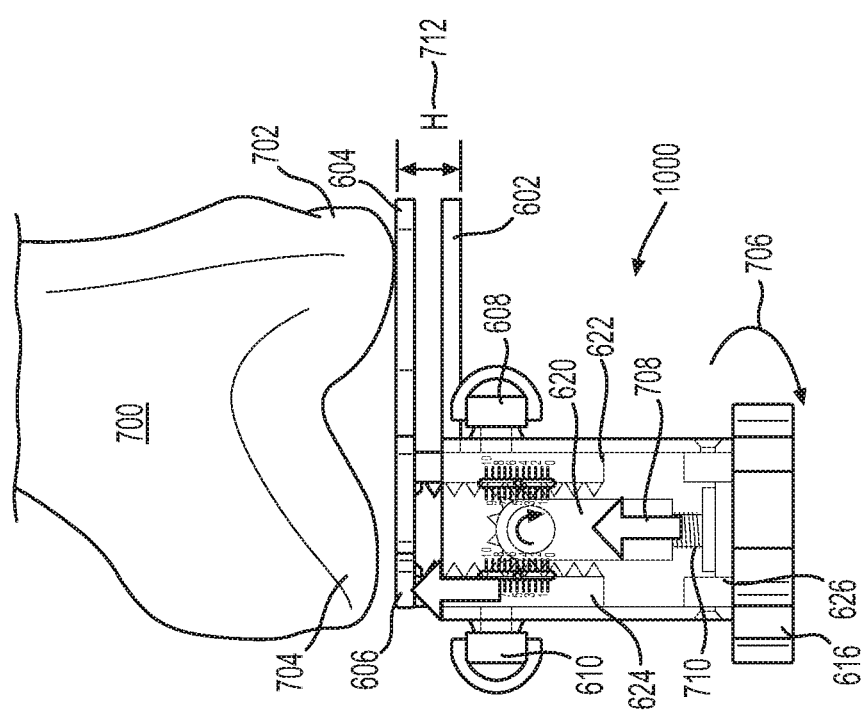

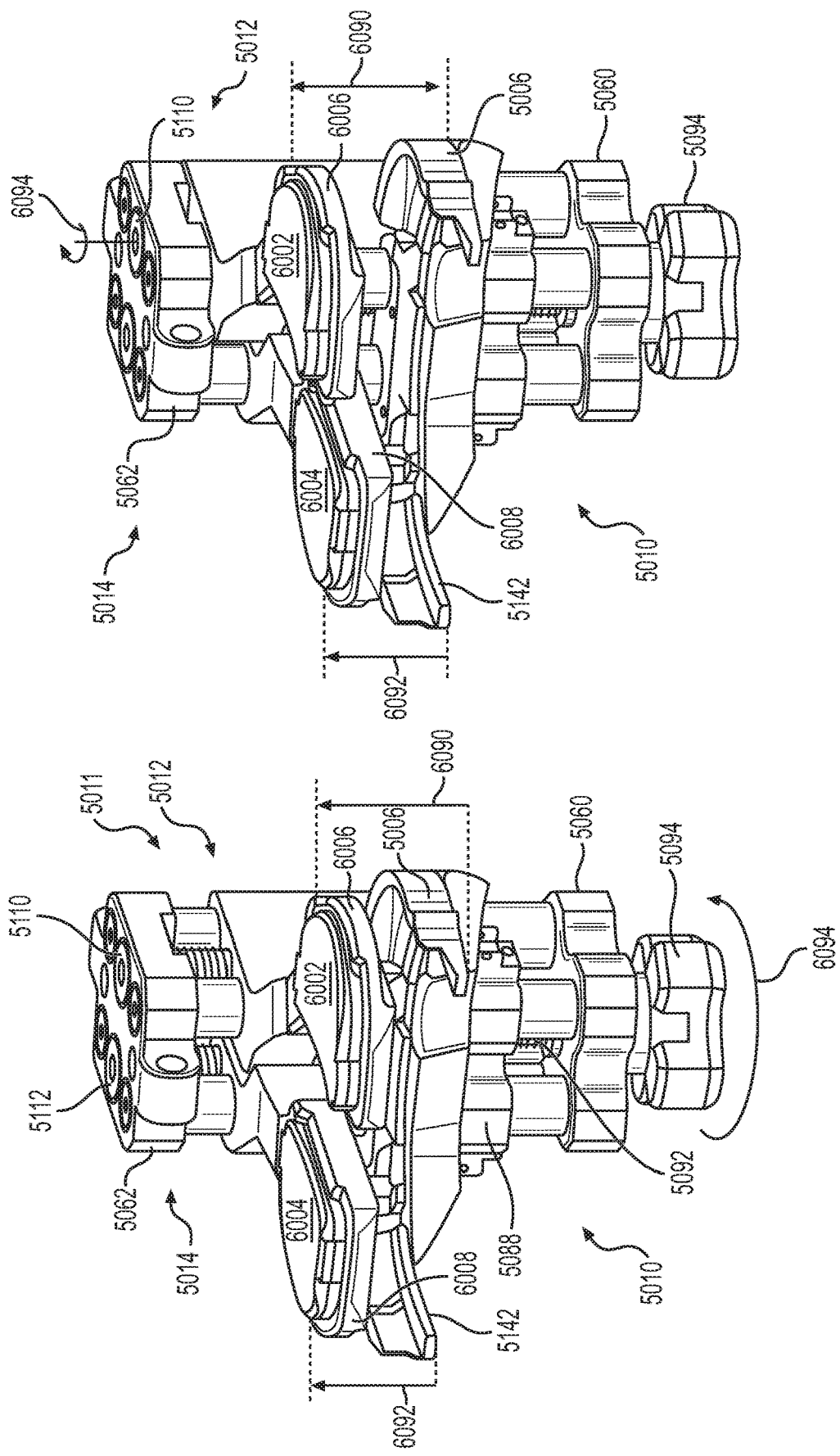

SURGICAL APPARATUS TO SUPPORT INSTALLATION OF A PROSTHETIC COMPONENT AND METHOD THEREFORE

FIELD

The present disclosure relates generally to orthopedic medical devices, and more specifically to devices that generate quantitative measurement data in real-time.

BACKGROUND

The skeletal system of a mammal is subject to variations among species. Further changes can occur due to environmental factors, degradation through use, and aging. An orthopedic joint of the skeletal system typically comprises two or more bones that move in relation to one another. Movement is enabled by muscle tissue and tendons attached to the skeletal system of the joint. Ligaments hold and stabilize the one or more joint bones positionally. Cartilage is a wear surface that prevents bone-to-bone contact, distributes load, and lowers friction.

There has been substantial growth in the repair of the human skeletal system. In general, prosthetic orthopedic joints have evolved using information from simulations, mechanical prototypes, and patient data that is collected and used to initiate improved designs. Similarly, the tools being used for orthopedic surgery have been refined over the years but have not changed substantially. Thus, the basic procedure for replacement of an orthopedic joint has been standardized to meet the general needs of a wide distribution of the population. Although the tools, procedure, and artificial joint meet a general need, each replacement procedure is subject to significant variation from patient to patient. The correction of these individual variations relies on the skill of the surgeon to adapt and fit the replacement joint using the available tools to the specific circumstance.

BRIEF DESCRIPTION OF THE DRAWINGS

FIG. 33 illustrates a step of monitoring equalization of the femur on the display in accordance of an example embodiment;

FIG. 36 illustrates a step of reducing the distraction distance of the distractor and placing the leg in flexion in accordance with an example embodiment;

FIG. 42 illustrates a step of drilling one or more holes in the distal end of the femur in flexion in accordance with an example embodiment; and FIG. 43 illustrates one or more holes drilled in the distal end of the femur in accordance with an example embodiment;

FIG. 48 illustrates a step in the knee joint installation procedure related to the alternate embodiment of the distractor coupling to the femur in accordance with an example embodiment;

FIG. 49 illustrates the step in a knee joint installation procedure related to the alternate embodiment of the distractor where the lateral plate and the medial plate contact the femur in accordance with an example embodiment;

FIG. 68 is an illustration of the surgical apparatus changing a height of the medial and lateral compartments simultaneously in accordance with an example embodiment;

FIG. 69 is an illustration of the surgical apparatus changing a height of the medial compartment in accordance with an example embodiment.

DETAILED DESCRIPTION

Figure 1:
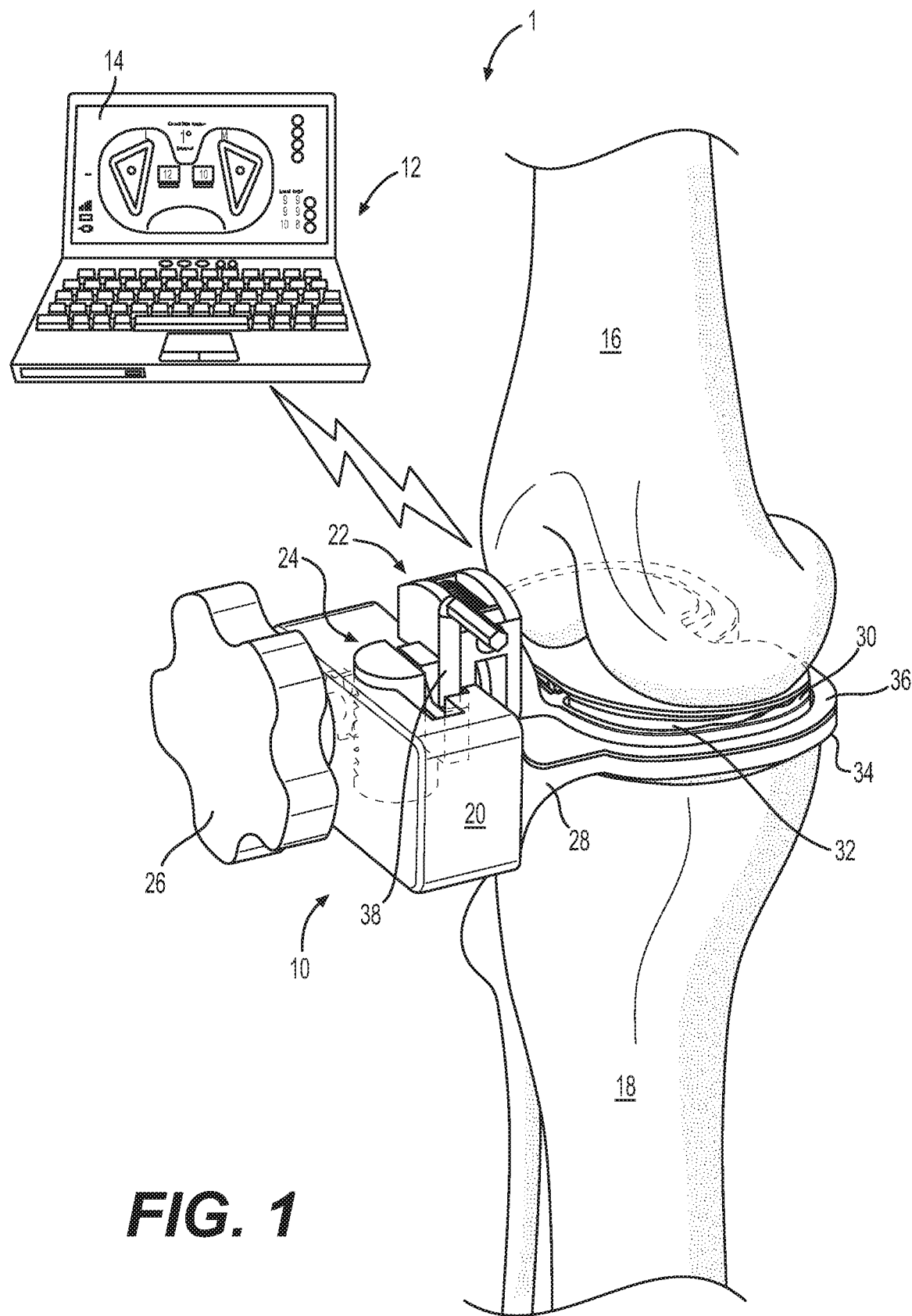
FIG. 1 is an illustration of an orthopedic measurement system generating quantitative measurement data to support installation of a prosthetic component in accordance with an example embodiment.

The following description of exemplary embodiment(s) is merely illustrative in nature and is in no way intended to limit the invention, its application, or uses.

Processes, techniques, apparatus, and materials as known by one of ordinary skill in the art may not be discussed in detail but are intended to be part of the enabling description where appropriate.

While the specification concludes with claims defining the features of the invention that are regarded as novel, it is believed that the invention will be better understood from a consideration of the following description in conjunction with the drawing figures, in which like reference numerals are carried forward.

The example embodiments shown herein below of the surgical apparatus are illustrative only and do not limit use for other parts of a body. The surgical apparatus can be used to measure, distract, align, cut, and support installation of prosthetic components to the musculoskeletal system. The surgical apparatus can be used on the knee, hip, ankle, spine, shoulder, hand, wrist, foot, fingers, toes, and other areas of the musculoskeletal system. In general, the principles disclosed herein are meant to be adapted for use in other locations of the musculoskeletal system. The following description of embodiment(s) is merely illustrative in nature and is in no way intended to limit the invention, its application, or uses.

For simplicity and clarity of the illustration(s), elements in the figures are not necessarily to scale, are only schematic and are non-limiting, and the same reference numbers in different figures denote the same elements, unless stated otherwise. Additionally, descriptions and details of well-known steps and elements are omitted for simplicity of the description. Notice that once an item is defined in one figure, it may not be discussed or further defined in the following figures.

The terms "first", "second", "third" and the like in the Claims or/and in the Detailed Description are used for distinguishing between similar elements and not necessarily for describing a sequence, either temporally, spatially, in ranking or in any other manner. It is to be understood that the terms so used are interchangeable under appropriate circumstances and that the embodiments described herein are capable of operation in other sequences than described or illustrated herein.

Processes, techniques, apparatus, and materials as known by one of ordinary skill in the art may not be discussed in detail but are intended to be part of the enabling description where appropriate.

The orientation of the x, y, and z-axes of rectangular Cartesian coordinates is assumed to be such that the x and y axes define a plane at a given location, and the z-axis is normal to the x-y plane. The axes of rotations about the Cartesian axes of the device are defined as yaw, pitch and roll. With the orientation of the Cartesian coordinates defined in this paragraph, the yaw axis of rotation is the z-axis through body of the device. Pitch changes the orientation of a longitudinal axis of the device. Roll is rotation about the longitudinal axis of the device. The orientation of the X, Y, Z axes of rectangular Cartesian coordinates is selected to facilitate graphical display on computer screens having the orientation that the user will be able to relate to most easily. Therefore the image of the device moves upward on the computer display whenever the device itself moves upward for example away from the surface of the earth. The same applies to movements to the left or right.

Although inertial sensors are provided as enabling examples in the description of embodiments, any tracking device (e.g., a GPS chip, acoustical ranging, accelerometer, magnetometer, gyroscope, inclinometers, or MEMs devices) can be used within the scope of the embodiments described.

At least one embodiment is directed to a kinetic orthopedic measurement system to aid a surgeon in determining real time alignment, range of motion, loading, impingement, and contact point of orthopedic implants. Although the system is generic to any orthopedic surgery (e.g., spinal, shoulder, knee, hip, ankle, wrist, finger, toe, bone, musculoskeletal, etc.) the following examples deal with orthopedic surgery as a non-limiting example of an embodiment of the invention.

The non-limiting embodiment described herein is related to quantitative measurement based orthopedic surgery and referred to herein as the kinetic system. The kinetic system includes a sensor system that provides quantitative measurement data and feedback that can be provided visually, audibly, or haptically to a surgeon or surgical team. The kinetic system provides the surgeon real-time dynamic data regarding force, pressure, or loading on the joint, contact and congruency through a full range of motion, and information regarding impingement.

In general, kinetics is the study of the effect of forces upon the motion of a body or system of bodies. Disclosed herein is a system for kinetic assessment of the musculoskeletal system. The kinetic system can be for the installation of prosthetic components or for monitoring and assessment of permanently installed components to the musculoskeletal system. For example, installation of a prosthetic component can require one or more bone surface to be prepared to receive a device or component. The kinetic system is designed to take quantitative measurements of at least the load, position of load, or alignment with the forces being applied to the joint similar to that of a final joint installation. The sensored measurement components are designed to allow ligaments, tissue, and bone to be in place while the quantitative measurement data is taken. This is significant because the bone cuts take into account the kinetic forces where a kinematic assessment and subsequent bone cuts could be substantial changed from an alignment, load, and position of load once the joint is reassembled.

A prosthetic joint installation can benefit from quantitative measurement data in conjunction with subjective feedback of the prosthetic joint to the surgeon. The quantitative measurements can be used to determine adjustments to bone, prosthetic components, or tissue prior to final installation. Permanent sensors can also be housed in final prosthetic components to provide periodic data related to the status of the implant. Data collected intra-operatively and long term can be used to determine parameter ranges for surgical installation and to improve future prosthetic components. The physical parameter or parameters of interest can include, but are not limited to, measurement of alignment, load, force, pressure, position, displacement, density, viscosity, pH, spurious accelerations, color, movement, particulate matter, structural integrity, and localized temperature. Often, several measured parameters are used to make a quantitative assessment. A graphical user interface can support assimilation of measurement data. Parameters can be evaluated relative to orientation, alignment, direction, displacement, or position as well as movement, rotation, or acceleration along an axis or combination of axes by wireless sensing modules or devices positioned on or within a body, instrument, appliance, vehicle, equipment, or other physical system.

At least one embodiment is directed to a system for adjusting or monitoring a contact position of a musculoskeletal joint for stability comprising: a prosthetic component configured to rotate after being coupled to a bone; a sensored prosthesis having an articular surface where the sensored prosthesis is configured to couple to the prosthetic component, where the sensored prosthesis has a plurality of load sensors coupled to the articular surface and a position measurement system configured to measure position, slope, rotation, or trajectory, and a remote system configured to wirelessly receive quantitative measurement data from the sensored prosthesis where the remote system is configured to display the articular surface, where the remote system is configured to display position of applied load to the articular surface, and where the remote system is configured to report impingement as the musculoskeletal joint is moved through a range of motion (ROM).

FIG. 1 is an illustration of an orthopedic measurement system 1 generating quantitative measurement data to support installation of a prosthetic component in accordance with an example embodiment. Orthopedic measurement system 1 comprises a distractor 10, a module 32, and a computer 12. Distractor 10 can also be called a surgical apparatus, tensor, device, or tool. Distractor 10 is not limited to distraction but can perform or support other functions such as alignment, bone cuts, and parameter measurement to name but a few. Distractor 10 includes at least one sensor configured to generate quantitative measurement data. Similarly, module 32 includes at least one sensor configured to generate quantitative measurement data. Distractor 10 and module 32 each includes electronic circuitry configured to control a measurement process and transmit measurement data to computer 12. Computer 12 includes a display 14 configured to display the quantitative measurement data received from distractor 10 and module 32, analyze the measurement data, provide visual, haptic, or audible feedback related to the measurement data. In general, a workflow of the surgery is provided on computer 12 based on preliminary information, medical data, and measurement data that can include X-Rays, MRI, and CT scan information to support an optimal installation. It is contemplated that measurement data from the distractor, surgical apparatus, or tool as described herein will update the plan and the software in the computer can suggest changes based on the quantitative measurement data. In one embodiment, any changes suggested by the computer and software have to be approved by the surgeon or surgical team performing the operation.

Distractor 10 is configured to be inserted into a joint of the musculoskeletal system. The joint can comprise natural bones or one or more prosthetic components. In one embodiment, distractor 10 can change a height on a first side or a second side of the device within the joint or musculoskeletal system. Distractor 10 is not limited to distracting the first and second sides but can be adapted to distract more than two sides in combination or alone. Distractor 10 is configured to be operated by a user such as a surgeon or can be operated by a robot. In one embodiment, distractor 10 is configured to provide quantitative measurement data that supports at least one bone cut on the joint. Distractor 10 includes a distraction mechanism that is configured to change the height on the first side and the second side by equal amount. Distractor 10 further includes a tilt mechanism that is configured to change height on the first and second sides by tilting. In one embodiment, distractor 10 is configured to support alignment, adjust load magnitude, and load balance between the first side and the second side prior to installation of a prosthetic component. The at least one bone cut supported by the distractor 10 incorporates alignment, load magnitudes and balance to the prosthetic component installation using quantitative measurement data thereby eliminating modification to the musculoskeletal system or prosthetic components after installation of the prosthetic components. In one embodiment, a distraction distance of distractor 10 and an M-L tilt angle of moving support structure 30 is measured and displayed on display 14 of computer 12.

Distractor 10 comprises a housing 20, distraction mechanism 24, medial-lateral (M-L) tilt mechanism 22, a fixed position support structure 28, and a moving support structure 30. In one embodiment, M-L tilt mechanism 22 couples between distraction mechanism 24 and fixed position support structure 28. Housing 20 partially houses distraction mechanism 24. A knob 26 or handle couples to distraction mechanism 24 to allow a user to increase or decrease a distraction distance of distractor 10. Housing 20 retains distraction mechanism 24 and supports movement of distraction mechanism 24 in a predetermined direction relative to fixed position support structure 28. In the example embodiment, fixed position support structure 28 couples to housing 20 and distraction mechanism 28 and moves perpendicular to a bottom surface 34 of fixed support structure 28. Moving support structure 30 couples to M-L tilt mechanism 22. Distraction mechanism 24 couples to M-L tilt mechanism 22 and is configured to raise or lower M-L tilt mechanism 22 and moving support structure 30 relative to fixed support structure 28. A distraction mechanism lock 38 is configured to lock distraction mechanism 24 from moving thereby holding a distance between moving support structure 30 and fixed support structure 28 constant.

M-L tilt mechanism 22 is configured to medially or laterally tilt moving support structure 30. A key or knob couples to M-L tilt mechanism 22 to change the M-L tilt. M-L tilt mechanism 22 can be disengaged from moving support structure 30 such that moving support structure 30 can freely tilt medially or laterally depending on how moving support structure 30 is loaded. Module 32 couples to and is supported by moving support structure 30. In one embodiment, module 32 couples to a major surface of moving support structure 30. A cover couples to module 32. The cover is removable and is an interface to the distal end of femur 16.

As shown in FIG. 1 the distraction distance of distractor 10 is at a minimum height. In the example, the proximal end of tibia 18 has a prepared surface. The prepared surface can be a planar surface and can also have a predetermined anterior-posterior (A-P) slope. In general, the word predetermined used herein above and below corresponds to a user selected value. The use of the word predetermined does not imply a specific value or range. A minimum distraction distance of distractor 10 occurs when surface 34 of fixed support structure 28 and a bottom surface of moving support structure 30 couples to the prepared surface of the proximal end of tibia 18. The distraction distance is the distance between the distal end of femur 16 and a proximal end of tibia 18 under distraction. Note that the cover couples to the condyles of femur 16 and fixed support structure 28 couples to the prepared surface of the proximal end of tibia 18. The distance between the cover and the fixed support structure corresponds to the distraction distance. In one embodiment, fixed support structure 28 comprises a frame 36. Frame 36 has an opening for receiving moving support structure 30 thereby allowing the bottom surface of moving support structure 30 to couple to the prepared bone surface of tibia 18.

Figure 2:
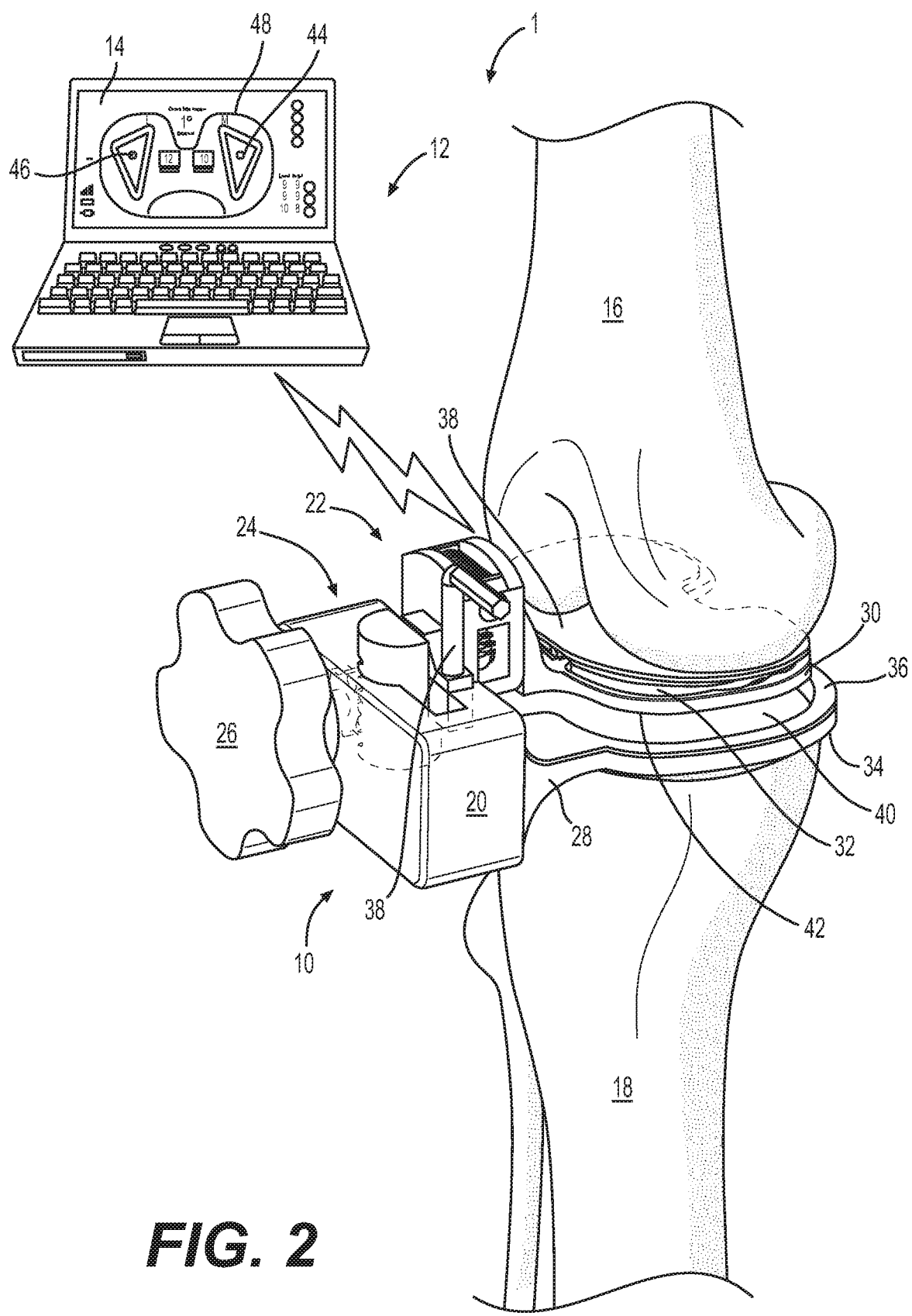
FIG. 2 is an illustration of the orthopedic measurement system distracting a knee joint of a leg in accordance with an example embodiment.

FIG. 2 is an illustration of orthopedic measurement system 1 distracting a knee joint of a leg in accordance with an example embodiment. As shown, the leg is in extension. Surface 34 of fixed support structure 28 couples to prepared surface 40 of the proximal end of tibia 18. Knob 26 couples to distraction mechanism 24. Rotating knob 26 increases or decreases separation between moving support structure 30 and fixed support structure 28. In the example, knob 26 is rotated to increase the distraction distance such that a bottom surface 42 of moving support structure 30 does not touch prepared bone surface 40. Module 32 and cover 38 are supported by moving support structure 30. Cover 38 couples to the condyles of the distal end of femur 16. Thus, the distraction distance includes the thickness of module 32 and cover 38 and is measured from the distal end of femur 16 to the prepared surface of tibia 18. In one embodiment, after distracting the joint the measurement data can indicate that the prepared surface needs to be recut when compared to the initial workflow. In the example, the workflow can be changed under surgeon approval and the distractor removed to recut the tibia. Subsequent reinsertion of the distractor and distraction of the joint would verify that the new workflow is now correct. The measurement data related to the recut of the tibia and visualization of the workflow could be displayed on the computer for viewing by the surgical team.

Distractor 10 includes a distance sensor on distractor 10 configured to measure the distraction distance. In one embodiment, the distance sensor couples to distraction mechanism 24. Similarly, distractor 10 includes an angle sensor configured to measure the M-L tilt angle of moving support structure 30. In one embodiment, the angle sensor couples to the M-L tilt mechanism 22. Distractor 10 includes electronic circuitry coupled to the distance sensor and the angle sensor. The electronic circuitry of distractor 10 controls a measurement process and transmits measurement data to computer 12. The measurement data can comprise distraction distance data and M-L tilt data from the distance sensor and the angle sensor. The distraction distance data and M-L tilt data can be displayed on display 14 in real-time. Alternatively, distractor 10 can have a mechanical distance gauge and an M-L tilt gauge on distractor 10.

Module 32 also includes electronic circuitry and one or more sensors. In one embodiment, module 32 includes a plurality of load sensors configured to measure loading applied to the cover 38. The load sensors are configured to measure load magnitudes at predetermined locations on cover 38. The electronic circuitry of module 32 is configured to control a load measurement process and transmit load data. Load data is transmitted from module 32 to computer 12. Computer 12 can process the load data from the plurality of load sensors (at predetermined locations) and calculate a load magnitude and a position of load where a condyle of femur 16 couples to cover 38. Computer 12 can provide visualization of the data to aid a surgeon in rapidly absorbing the quantitative measurement data. For example, a surface 48 of cover 38 or the surface of module 32 can be shown on display 14 of computer 12. Contact points 44 and 46 can indicate where each condyle couples to cover 38. The contact points 44 and 46 can move in real-time if a change occurs that results in a parameter change that affects the contact points. For example, performing soft tissue tensioning which changes loading applied by a medial condyle or a lateral condyle of femur 16 to distractor 10 can result in movement of contact points 44 and 46. The load magnitude at the point of contact can also be displayed. Thus, the surgeon can receive the information as the surgical procedure is being performed with little or no time penalty but greatly increased knowledge on the installation. It should be noted that module 32 is configured to be removed from moving support structure 30. This allows module 32 to be used in another piece of equipment later in the surgery to take further measurements, make adjustments, or verify that the final installation numbers are similar to that generated when preparing bone surfaces for prosthetic component installation. Similarly, cover 38 can be removed from module 32. Cover 38 can be substituted for other covers designed to interface with a different component. For example, cover 38 is configured to interface with the natural condyles of femur 16. A different cover can be used to interface with a prosthetic femoral component coupled to femur 16 later in the surgery to take further measurements or verify the previous quantitative measurement data.

Figure 3:
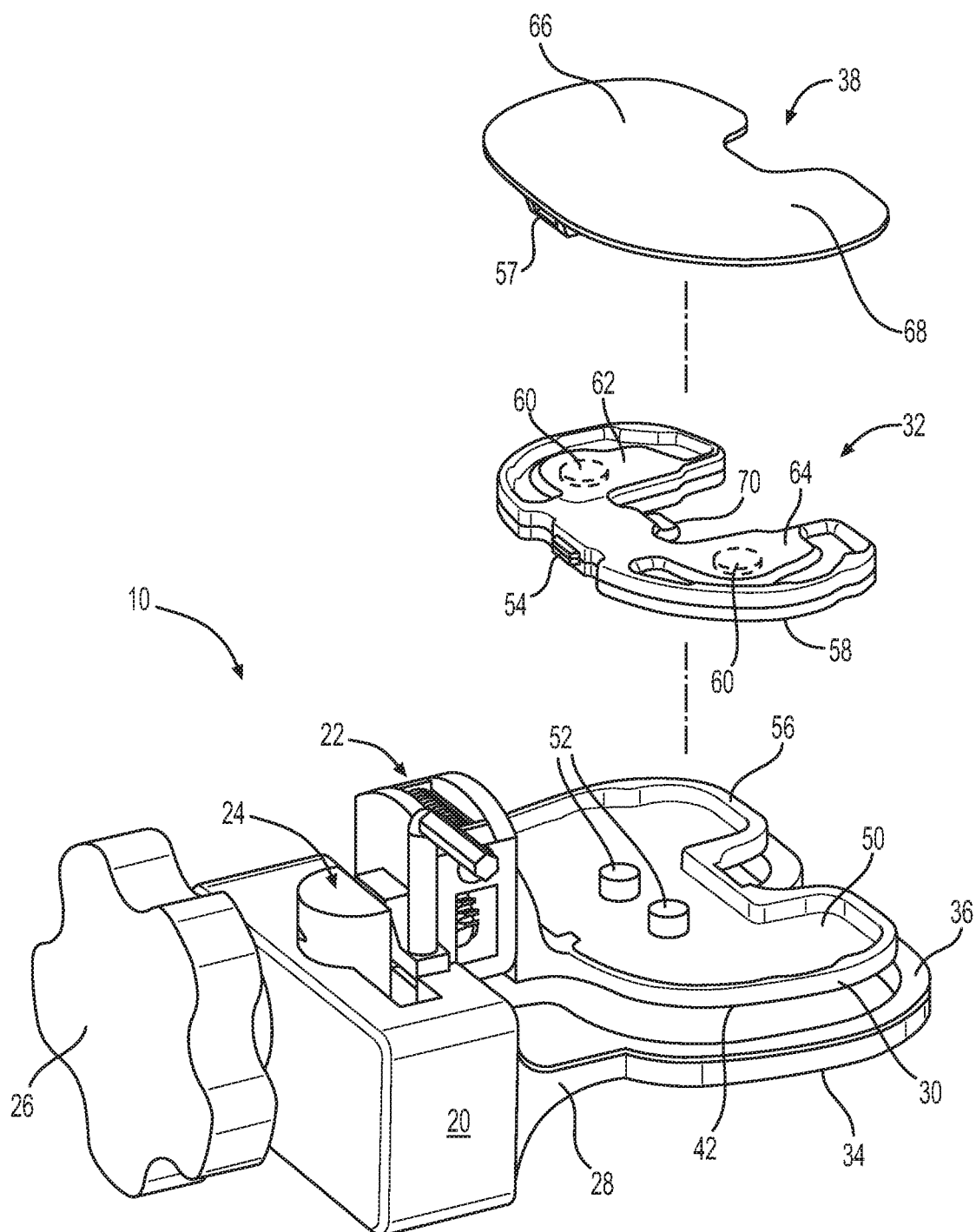
FIG. 3 illustrates the cover, the module, and the distractor in accordance with an example embodiment.

FIG. 3 illustrates cover 38, module 32, and distractor 10 in accordance with an example embodiment. Moving support structure 30 is shown separated from frame 36 of fixed support structure 28. Note that moving support structure 30 fits within an opening in frame 36 of fixed support structure 28 if the distraction distance is reduced by distraction mechanism 24. In one embodiment, moving support structure 30 has a major surface 50 configured to support module 32 when loaded by the knee joint. A surface 58 of module 32 couples to major surface 50 of moving support structure 30. In the example, module 32 comprises a medial side and a lateral side respectively configured to couple to a medial condyle and a lateral condyle of a knee joint. Major surface 50 of moving support structure 30 includes at least one alignment feature to retain and align module 32. For example, posts 52 extend from major surface 50 of moving support structure 30. Posts 52 are received within corresponding openings in module 32 when coupling a bottom surface 58 of module 32 to major surface 50 of moving support structure 30. Moving support structure 30 can further comprise a wall 56 or walls that align and retains module 32 to moving support structure 30. Posts 52 and wall 56 prevent lateral forces from detaching module 32 from moving support structure 30 under knee joint loading. Module 32 can be removed by lifting module 32 vertically from surface 50 of moving support structure 30. Module 32 is made to be removable so it can be placed in a prosthetic component such as an insert to make measurements later in the surgical installation of the knee joint. Although, at least one retaining feature is described for holding module 32 to major surface 50 it is contemplated that other locking or retaining features can be used. The locking features can be on the sides, front, or back and can comprise button locking that can be released to easily remove module 32 from support structure 30.

Module 32 has electronic circuitry configured to control the measurement process and transmit the measurement data. The electronic circuitry couples to one or more sensors for measuring parameters. In the example, a plurality of load sensors underlies the medial side and the lateral side of module 32. This supports measurement of the load magnitude and the position of load due to the medial condyle and the lateral condyle of a femur coupled to cover 38. Module 32 is hermetically sealed and includes a power source such as a battery, super capacitor, inductor, or other structure that can operate module 32 during a surgical procedure. In one embodiment, batteries 60 are used to power the electronic circuitry in module 32. Module 32 further includes retaining structures 54 and 70 extending from a periphery. Retaining structures 54 and 70 are configured to align and retain cover 38 to module 32. In the example, cover 38 slidably engages to module 32. In one embodiment, retaining feature 70 fits into an opening of retaining feature 57 on cover 38 as cover 38 slides across module 32. Retaining feature 57 can flexed and includes an opening. A force can be applied to cover 38 to flex retaining feature 57 of cover 38 over retaining feature 54 of module 32. Retaining feature 54 of module 32 couples through the opening in retaining feature 57 to retain cover 38 to module 32. Conversely, cover 38 can be removed by flexing retaining feature 57 such that retaining feature 54 of module 32 no longer extends through the opening in retaining feature 57. Cover 38 can then be lifted to separate cover 38 from module 32. Cover 38 can then be moved to disengage retaining feature 70 from the opening of the corresponding retaining feature of cover 38 (that is not shown) thereby completely separating cover 38 from module 32.

A surface 62 and a surface 64 of module 32 is configured to couple to corresponding interior surfaces of cover 38. The plurality of load sensors underlie and couple to surface 62 and surface 64 of module 32. The plurality of load sensors are configured to couple to predetermined locations of a surface 66 and a surface 68 of cover 38. The plurality of load sensors measures loading applied by condyles of the femur to surfaces 66 and 68 of cover 38. The load data from the plurality of load sensors is used to determine a load magnitude and position of load of each condyle to surfaces 62 and 64 in real-time thereby allowing adjustments in-situ.

Figure 4:
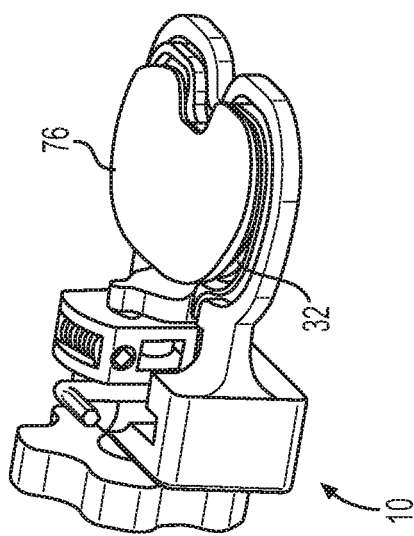
FIG. 4 illustrates a cover on the module configured having an anterior-posterior (A-P) slope of zero in accordance with an example embodiment.

FIG. 4 illustrates a cover 72 on module 32 configured having an anterior-posterior (A-P) slope of zero in accordance with an example embodiment. Cover 72 couples to module 32. Cover 72 is configured to couple to the natural condyles of a femur. In one embodiment, cover 72 is used prior to installation of the femoral prosthetic component and in conjunction with distractor 10 to support making one or more bone cuts to the distal end of a femur for receiving the femoral prosthetic component. Module 32 is configured to measure one or more parameters and transmit measurement data to a computer for further processing. In the example, disclosed above, module 32 measures loading applied by condyles of a femur on a medial and a lateral side of cover 72.

In one embodiment, a plurality of covers are provided with module 32. The covers can comprise a polymer or metal material. The covers can be molded to lower cost of manufacture. In one embodiment, the plurality of covers provided with module 32 have different anterior-posterior (A-P) slopes. The covers having different A-P slopes are used to change the biomechanics of the knee joint thereby affecting post-operative clinical outcome. Slope can be added to match the posterior tibial slope of the original anatomical condition. Matching the A-P slope supports greater knee flexion in the posterior cruciate ligament retaining total knee arthroplasty while a lesser slope can be used in a posterior-stabilized total knee arthroplasty. The A-P slope affects the flexion gap, knee joint stability, and posterior femoral rollback over the range of motion. Cover 72 has an anterior-posterior slope of zero degrees. Thus, cover 72 does not add A-P slope for assessment.

Alternatively, a mechanism could be added that can adjust the anterior-posterior slope of distractor 10 or surgical apparatus disclosed herein. In one embodiment, the mechanism would tilt support structure 30. The mechanism could precisely control the anterior-posterior slope which could be measured using a tilt measuring sensor as disclosed herein and the tilt measurement data could be sent to the computer for display for the surgical team to review. The tilt measurement data could also be shown on a display coupled to distractor 10.

Figure 5:
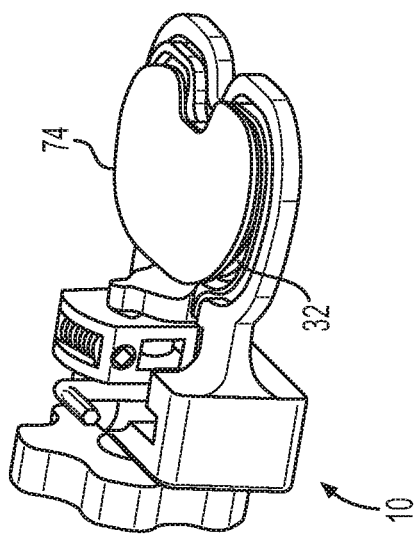
FIG. 5 illustrates a cover on the module configured having an anterior-posterior (A-P) slope of 2 degrees in accordance with an example embodiment.

FIG. 5 illustrates a cover 74 on the module configured having an anterior-posterior (A-P) slope of 2 degrees in accordance with an example embodiment. Cover 74 couples to module 32. Cover 74 is configured to couple to the natural condyles of a femur. Thus, cover 74 is used prior to installation of the femoral prosthetic component and in conjunction with distractor 10. Module 32 is configured to measure one or more parameters and transmit measurement data to a computer for further processing. In the example, module 32 measures loading applied by condyles of a femur on a medial and a lateral side of cover 74.

In general, a plurality of covers such as cover 74 and cover 72 of FIG. 4 are provided with module 32. The covers having different A-P slopes are used to change the biomechanics of the knee joint thereby affecting postoperative clinical outcome. Slope can be added to match the posterior tibial slope of the original anatomical condition. Matching the A-P slope supports greater knee flexion in the posterior cruciate ligament retaining total knee arthroplasty while a lesser slope can be used in a posterior-stabilized total knee arthroplasty. The A-P slope affects the flexion gap, knee joint stability, and posterior femoral rollback over the range of motion. Cover 74 has an anterior-posterior slope of +2 degrees for assessing the knee joint with added slope.

Figure 6:
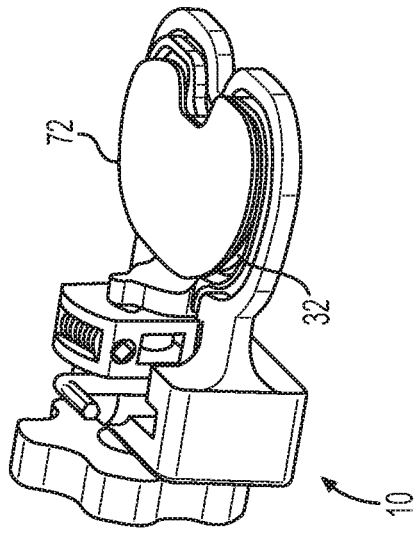
FIG. 6 illustrates a cover on the module configured having an anterior-posterior (A-P) slope of 4 degrees in accordance with an example embodiment.

FIG. 6 illustrates a cover 76 on the module configured having an anterior-posterior (A-P) slope of 4 degrees in accordance with an example embodiment. Cover 76 couples to module 32. Cover 76 is configured to couple to the natural condyles of a femur. Thus, cover 76 is used prior to installation of the femoral prosthetic component and in conjunction with distractor 10. Module 32 is configured to measure one or more parameters and transmit measurement data to a computer for further processing. In the example, module 32 measures loading applied by condyles of a femur on a medial and a lateral side of cover 76.

In general, a plurality of covers such as cover 76, cover 74 of FIG. 5, and cover 72 of FIG. 4 are provided with module 32. The covers having different A-P slopes are used to change the biomechanics of the knee joint thereby affecting postoperative clinical outcome. Slope can be added to match the posterior tibial slope of the original anatomical condition. Matching the A-P slope supports greater knee flexion in the posterior cruciate ligament retaining total knee arthroplasty while a lesser slope can be used in a posterior-stabilized total knee arthroplasty. The A-P slope affects the flexion gap, knee joint stability, and posterior femoral rollback over the range of motion. Cover 76 has an anterior-posterior slope of +4 degrees for assessing the knee joint with added slope. FIGS. 4, 5, and 6 are examples and the number of covers and A-P slopes can be more or less than shown.

Figure 7:
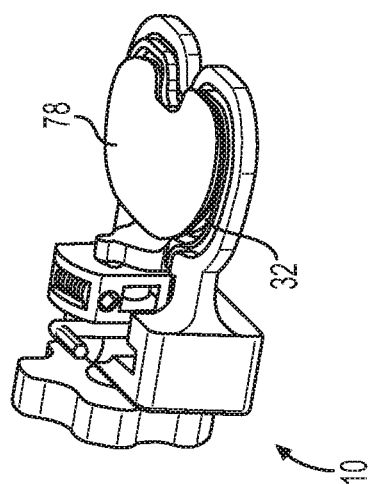
FIG. 7 illustrates a cover on the module configured to interface with natural condyles of the femur in accordance with an example embodiment.

FIG. 7 illustrates a cover 78 on module 32 configured to interface with natural condyles of a femur in accordance with an example embodiment. In one embodiment, distractor 10 is inserted in a knee joint with the proximal end of a tibia having a prepared bone surface and the distal end of a femur in a natural state. Natural condyles of the femur couple to cover 78. Cover 78 will support leg movement over a range of motion when the knee joint is distracted. In the example, module 32 measures loading applied by condyles of a femur on a medial and a lateral side of cover 78. A plurality of covers identical to cover 78 can be provided each having different A-P slopes to change the kinematics of the knee joint. Also, the plurality of covers can comprise different sizes for different knee sizes. For example, the covers can comprise small, medium, and large sizes that accommodate a large statistical sample of the population requiring knee joint replacement.

Figure 8:
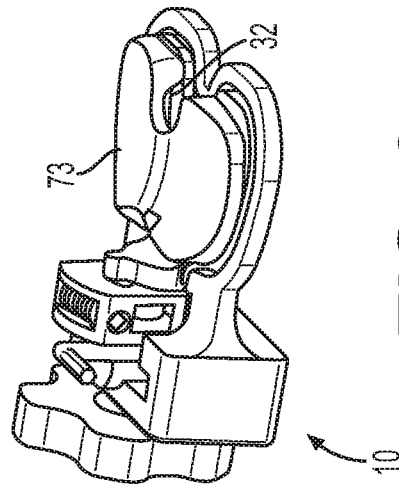
FIG. 8 illustrates a cover having a support structure on the module configured to interface with a femoral prosthetic component in accordance with an example embodiment.

FIG. 8 illustrates a cover 73 on module 32 configured to interface with a femoral prosthetic component coupled to a femur in accordance with an example embodiment. In one embodiment, distractor 10 is inserted in a knee joint with the proximal end of a tibia having a prepared bone surface and the distal end of fitted with a femoral prosthetic component. Cover 73 is configured to interface with the condyles of the femoral prosthetic component. In one embodiment, a surface of cover 73 has a contour to support leg movement under load with the condyles of the femoral prosthetic component coupled to the surface. Cover 73 supports all ligaments in place to stabilize the knee joint.

Cover 73 will support leg movement over a range of motion when the knee joint is distracted. In the example, module 32 measures loading applied on a medial side and a lateral side by the condyles of the femoral prosthetic component to cover 73. A plurality of covers identical to cover 73 can be provided each having different A-P slopes to change the kinematics of the knee joint. Also, the plurality of covers can comprise different sizes for different knee sizes having different femoral prosthetic component sizes. For example, the covers can comprise small, medium, and large sizes that accommodate a large statistical sample of the population requiring knee joint replacement.

Figure 9:
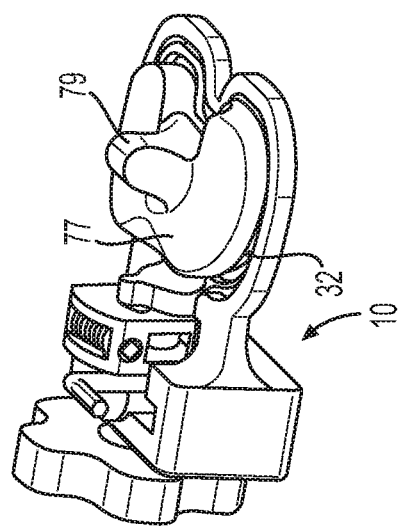
FIG. 9 illustrates a cover on the module configured to interface with a femoral prosthetic component having a support structure coupled to a femur in accordance with an example embodiment.

FIG. 9 illustrates a cover 77 on module 32 configured to interface with a femoral prosthetic component coupled to a femur in accordance with an example embodiment. In one embodiment, distractor 10 is inserted in a knee joint with the proximal end of a tibia having a prepared bone surface and the distal end fitted with a femoral prosthetic component. Cover 77 includes a support structure 79 that provides support when a ligament is removed from the knee joint. In one embodiment, support structure 79 is coupled to covers disclosed herein above to form cover 77. Alternatively, cover 77 can be provided having integral support structure 79. Cover 77 is configured to interface with the condyles of the femoral prosthetic component. A surface of cover 77 has a contour to support leg movement under load with the condyles of the femoral prosthetic component coupled to the surface.

Cover 77 will support leg movement over a range of motion when the knee joint is distracted and a ligament removed. In the example, module 32 measures loading applied on a medial side and a lateral side by the condyles of the femoral prosthetic component to cover 77. A plurality of covers identical to cover 77 can be provided each having different A-P slopes to change the kinematics of the knee joint. Support structure 79 can couple to each of the plurality of covers. Also, the plurality of covers can comprise different sizes for different knee sizes having different femoral prosthetic component sizes. For example, the covers can comprise small, medium, and large sizes that accommodate a large statistical sample of the population requiring knee joint replacement.

Figure 10A:
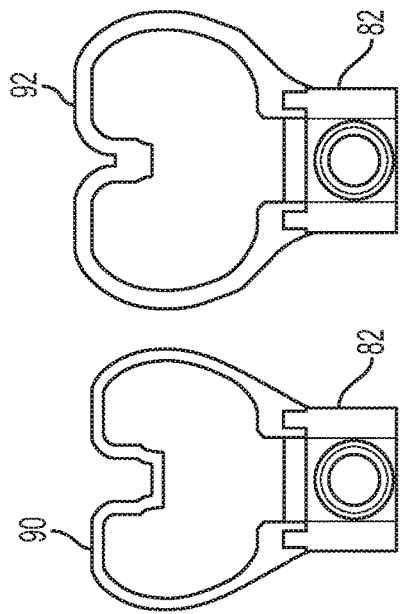
FIG. 10A illustrates the frame and a frame retaining support structure in accordance with an example embodiment.

FIG. 10A illustrates a frame 36 and a frame retaining support structure 82 in accordance with an example embodiment. In one embodiment, fixed support structure 28 of FIG. 1 comprises retaining support structure 82 and frame 36. Frame 36 is configured to be removable from frame retaining support structure 82. Frame retaining support structure 82 allows for different frame sizes and different frame shapes to couple to distractor 10. Alternatively, frame 36 and frame retaining support structure 82 could be formed as a single structure. In one embodiment, frame retaining support structure 82 is formed as part of housing 20 of FIG. 1. For example, a portion of housing 20 and frame retaining support structure 82 can be made as a single structure or formed in a mold thereby having a fixed geometric relationship between frame retaining support structure 82 and a distraction mechanism aligned and retained by housing 20. Housing 20 can be formed from a polymer material, metal, or metal alloy that supports loading applied by a knee joint when distracted. Frame retaining support structure 82 includes retaining structures 80 configured to retain and align frame 36 to frame retaining support structure 82. Frame 36 is coupled to frame retaining support structure 82 by pressing frame 36 into frame retaining support structure 82 as indicated by arrow 86. Frame 36 includes retaining structures 84 that interlock with retaining structures 80 of frame retaining support structure 82 such that frame 36 is rigid under loading of the knee joint and does not change a geometric relationship with frame retaining support structure 82 or housing 20 of FIG. 1. Conversely, frame 36 can be removed by applying a force in an opposite direction as arrow 86 to frame 36 to release frame 36 from frame retaining support structure 82. A larger or smaller frame 36 can replace frame 36 that better fits the bone structure of the patient.

Figure 10B:
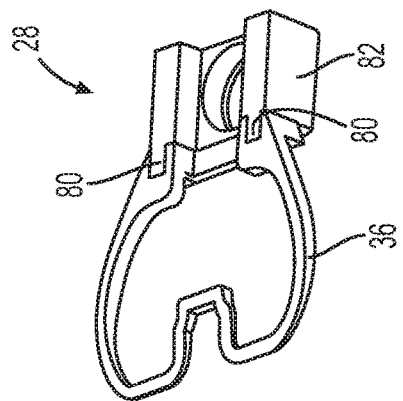
FIG. 10B illustrates the frame coupled to the frame retaining support structure in accordance with an example embodiment.

FIG. 10B illustrates the frame 36 coupled to frame retaining support structure 82 in accordance with an example embodiment. Retaining structures 84 of frame 36 of FIG. 10A are shown interlocking with retaining structures 80 of frame retaining support structure 82. Frame 36 is held in a predetermined position relative to frame retaining support structure 82 and the housing of the distractor. In one embodiment, frame 36 and frame retaining support structure 82 are rigid and do not flex or torque under loading applied by the knee joint. Alternatively, support structure 82 can be designed to flex. The amount of flex could be quantified though a load or displacement curve based on the forces applied to support structure 82. The displacement curve could be incorporated into the measurement data and processed by the computer to compensate for any flex incurred such that the measurement data is correct.

Figure 11:
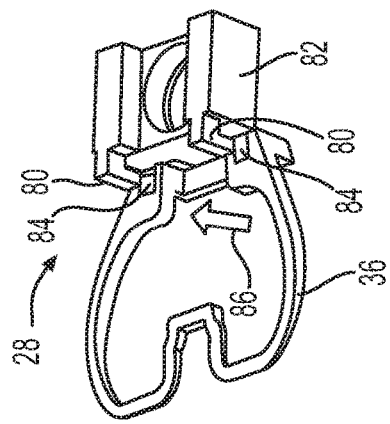
FIG. 11 illustrates different frame sizes in accordance with an example embodiment.

FIG. 11 illustrates different frame sizes in accordance with an example embodiment. Bone size varies across the population of patients requiring knee surgery. Different frame sizes are provided that support a majority of the total knee arthroplasty surgeries performed each year. A frame 90 is shown coupled to frame retaining support structure 82. A larger frame can be used if frame 90 is found to be too small for coupling to the prepared surface of a tibia. Frame 90 would then be removed from frame retaining support structure 82. A frame 92 can then be selected that is larger than frame 90 and installed onto frame retaining support structure 82. Thus, the distractor 10 of FIG. 1 supports removable frames and frames of different sizes to couple the distractor to the prepared surface of the tibia 18. The number of frame sizes provided can be more or less than shown in FIG. 11.

Figure 12A:
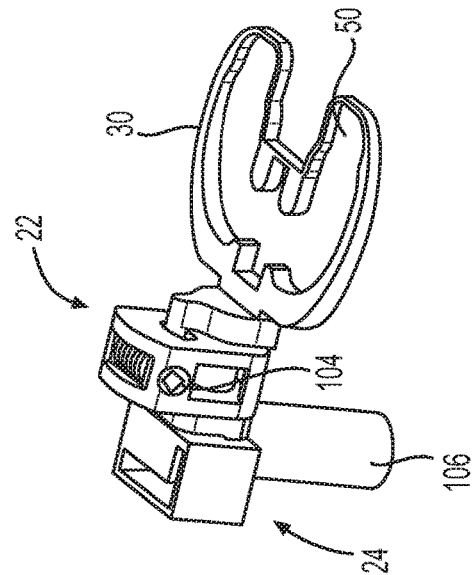
FIG. 12A illustrates the moving support structure disengaged from the M-L tilt mechanism in accordance with an example embodiment.

FIG. 12A illustrates moving support structure 30 disengaged from M-L tilt mechanism 22 in accordance with an example embodiment. M-L tilt mechanism 22 is shown coupling to a portion of distraction mechanism 24. Distraction mechanism 24 comprises a post 106 configured to raise or lower M-L tilt mechanism 22 and moving support structure 30 relative to the fixed support structure 28 of FIG. 1. A key or handle can be inserted into coupler 104 of M-L tilt mechanism 22. The key when rotated adjusts an M-L tilt angle of M-L tilt mechanism 22 when enabled. M-L tilt mechanism 20 further includes a coupler 102 that is configured to rotate as the key is rotated.

Moving support structure 30 includes a coupler 100 configured to couple to coupler 102 of M-L tilt mechanism 22. Coupler 100 is inserted into coupler 102 thereby retaining and aligning moving support structure 30 to M-L distraction mechanism 22. M-L tilt mechanism 22 can be disengaged from coupler 102 thereby allowing coupler 102 and moving support structure 30 to freely rotate. In one embodiment, coupler 100 has a square or rectangular shape that fits into a corresponding square or rectangular opening of coupler 102. Couplers 100 or 102 can be configured to have a temporary locking mechanism that retains moving support structure 30 to M-L tilt mechanism 22 while supporting removability. Similar to fixed support structure 28, 90, and 92 disclosed in FIGS. 10A, 10B, and 11 that are also removable, a plurality of moving support structures can be provided of different sizes or styles. In general, two or more moving support structures are provided with distractor 10 of FIG. 1.

Figure 12B:
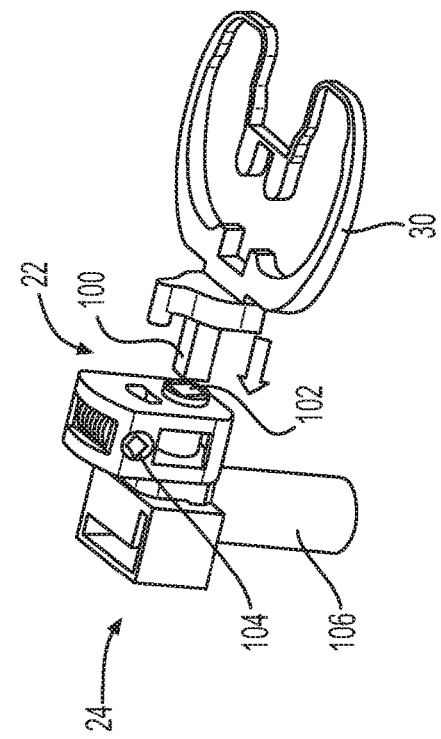
FIG. 12B illustrates the moving support structure coupled to M-L tilt mechanism in accordance with an example embodiment.

FIG. 12B illustrates moving support structure 30 coupled to M-L tilt mechanism 22 in accordance with an example embodiment. Moving support structure 30 as mentioned previously is removable from M-L tilt mechanism 22. This allows other moving support structures of different sizes or styles to be used with distractor 10 shown FIG. 1. A module having electronic circuitry and at least one sensor is placed on major surface 50 of moving support structure 30 to measure at least one parameter. A cover configured to interface with natural condyles of a femur or a cover configured to interface with a femoral prosthetic component couples to the module. Distraction mechanism 24 is configured to increase or decrease a distraction distance between moving support structure 30 and the fixed support structure 28 of FIG. 1. Distraction mechanism 24 raises or lowers both M-L tilt mechanism 22 and moving support structure 30. Moving support structure 30 is also configured to tilt medially or laterally when M-L tilt mechanism 22 is adjusted. In general, moving support structure 30 can be removed from distractor 10. A plurality of moving support structures is provided to be used to fit different anatomies with distractor 10. The moving support structures can comprise different sizes and different styles. The different moving support structures can correspond to the different frames disclosed in FIG. 11. The moving support structures can accommodate the wide diversity and variation of patient bone structure that is seen in an operating room.

Figure 13:
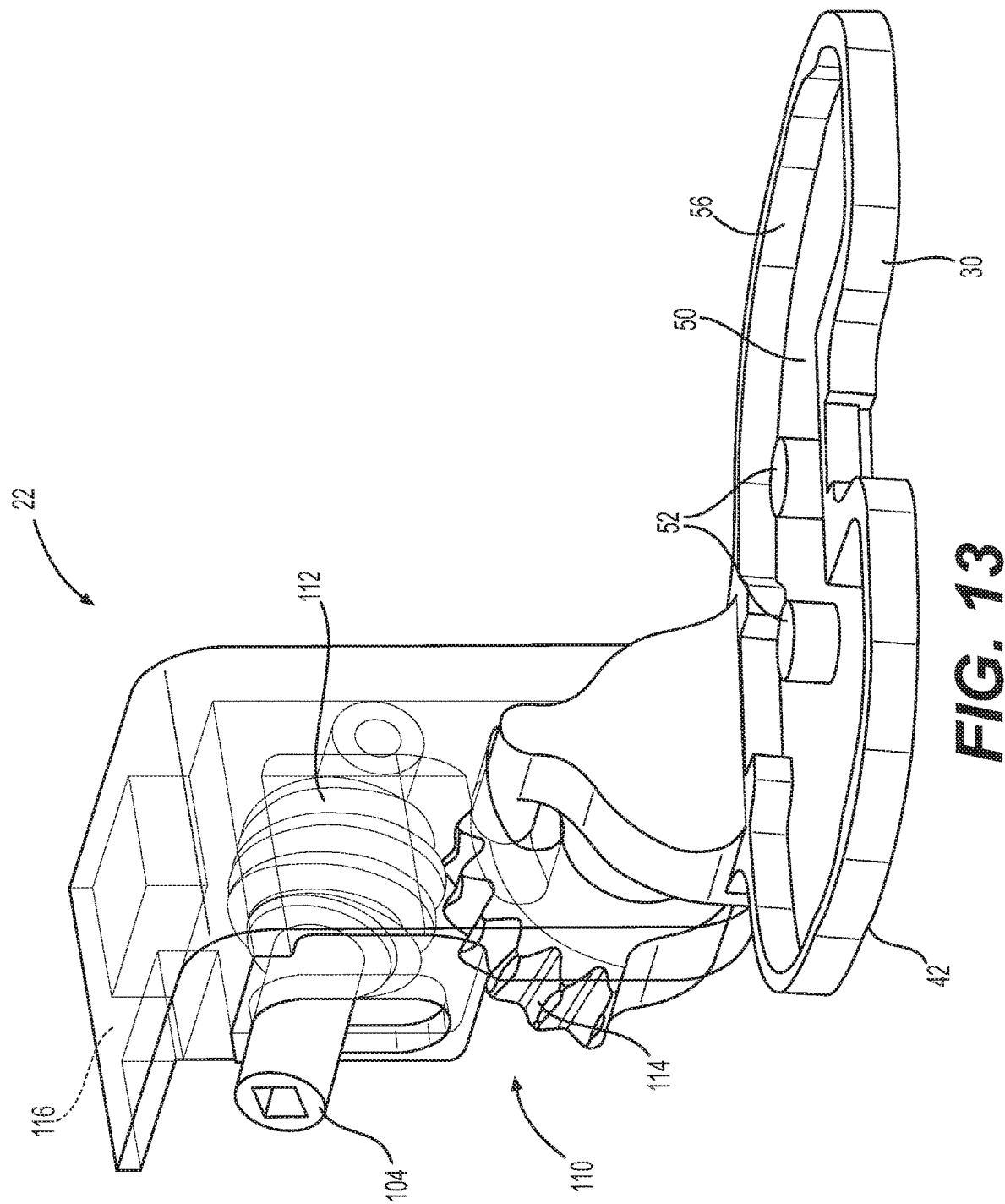
FIG. 13 is an illustration of the M-L tilt mechanism in accordance with an example embodiment.

FIG. 13 is an illustration of M-L tilt mechanism 22 in accordance with an example embodiment. In the example, M-L tilt mechanism 22 is a worm gear drive 110. Worm gear drive 110 comprises two or more gears of which at least one is a worm gear. As shown, worm gear drive 110 comprises a worm gear 112 and a gear 114. A housing 116 at least partially houses worm gear 112 and gear 114. Housing 116 retains, aligns, and supports rotation of worm gear 112 to gear 114. Coupler 104 couples to worm gear 112. In one embodiment, coupler 104 is a shaft of worm gear 112. Typically a key or handle couples to the opening in coupler 104 to allow a user to rotate worm gear 112.

Gear 114 couples to moving support structure 30. Housing 116 retains, aligns, and supports rotation of gear 114 when coupled to worm gear 112. As shown, M-L tilt mechanism 22 is decoupled from adjusting an M-L tilt angle of moving support structure 30. M-L tilt mechanism 22 is decoupled when the gear teeth of worm gear 112 are positioned such that the gear teeth of gear 114 do not couple to worm gear 112. Moving support structure 30 is free to tilt medially or laterally when M-L tilt mechanism 22 is decoupled and loaded by a knee joint. Gear 114 rotates as moving support structure 30 rotates and vice versa. The module 32 and cover 38 disclosed in FIG. 2 couple between the condyles of the femur and moving support structure 30. The module 32 is supported by major surface 50 of moving support structure 30. Module 32 is aligned and retained to moving support structure 30 by posts 52 and sidewall 56. The medial or lateral tilt of the knee joint corresponds to the balance of the knee joint and alignment of the leg.

In one embodiment, the teeth of worm gear 112 are coupled to the teeth of gear 114 to engage M-L tilt mechanism 22 after moving support structure 30 has been allowed to freely move to an unequalized M-L tilt angle. The teeth of worm gear 112 are configured to couple to gear 114 in a manner where they are self-locking. In other words, worm gear 112 and gear 114 hold the position of the moving support structure 30 at the unequalized M-L tilt angle when engaged. The key or handle is inserted into coupler 104 to rotate worm gear 112. In one embodiment, M-L tilt mechanism 22 is rotated an amount that equalizes the M-L tilt angle. This corresponds to a medial compartment being at an equal in height to a lateral compartment height. Worm gear drive 110 when rotated will change the medial or lateral tilt depending on the direction of rotation and maintains self-locking at an adjusted medial or lateral tilt. Quantitative measurement data from a sensor is used to determine when the M-L tilt angle is equalized. Typically, the loading on the medial and lateral compartments will be unequal. Soft tissue tensioning can be used to adjust the loading applied by the condyles of the femur to the cover of the module. Equalizing the M-L tilt angle reduces an offset of the femur to the mechanical axis of the leg.

Figure 14:
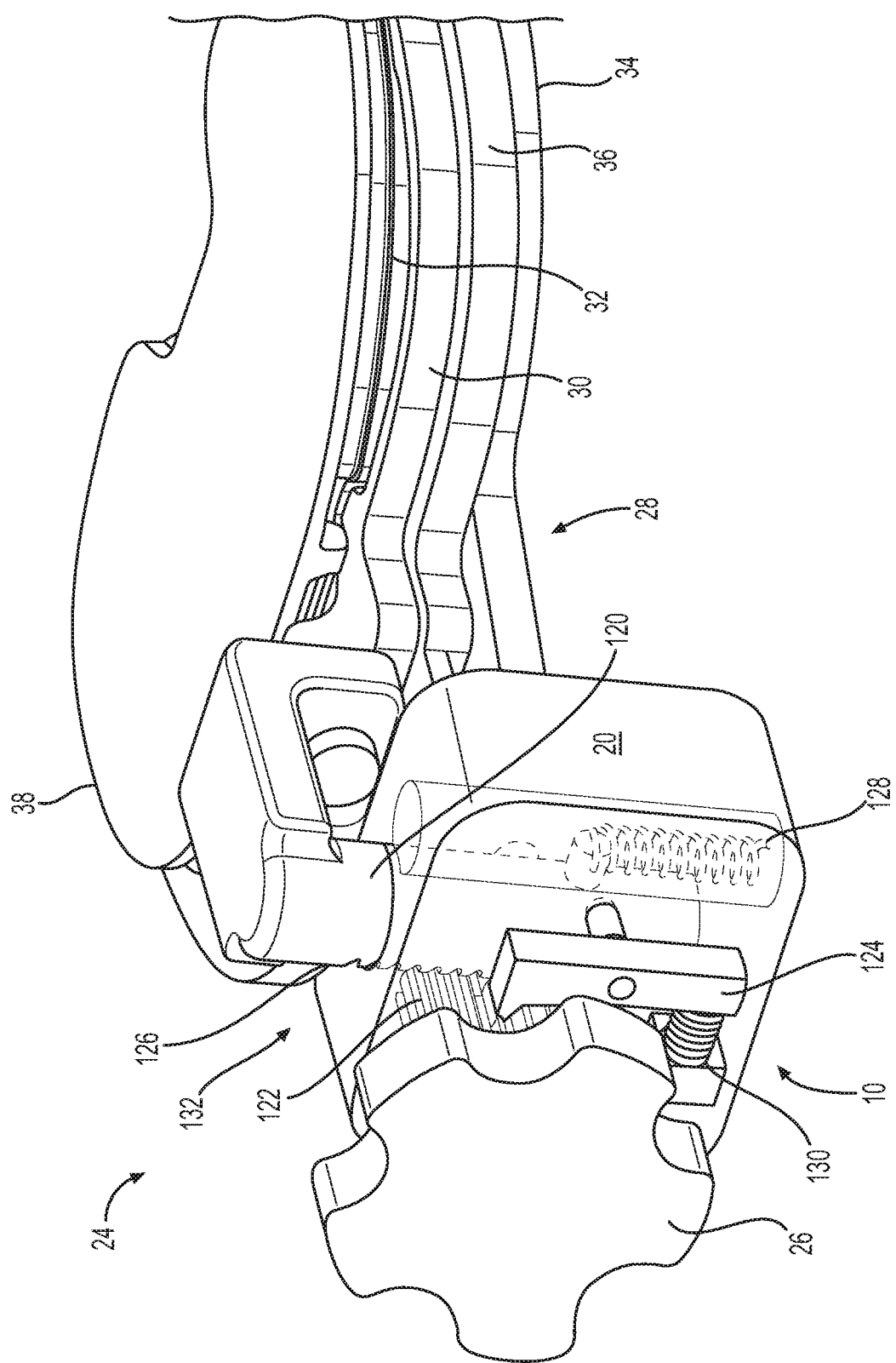
FIG. 14 is an illustration of the distraction mechanism in accordance with an example embodiment.

FIG. 14 is an illustration of distraction mechanism 24 in accordance with an example embodiment. In one embodiment, distraction mechanism 24 comprises a gear drive 132. Gear drive 132 can comprise two or more gears and is configured to increase or decrease separation between fixed support structure 28 and moving support structure 30 of distractor 10. Gear drive 132 comprises a post 120 and a gear 122. Post 120 extends outside housing 20 and is coupled to moving support structure 30. Housing 20 is configured to align, retain, and support movement of post 120 and gear 122. Housing 20 positions gear 122 adjacent to post 120 such that teeth of gear 122 engage with gear teeth 126 of post 120. Knob 26 couples to gear 122 to facilitate rotation. In one embodiment, housing 20 supports movement of post 120 perpendicular to a plane of fixed support structure 28.

Rotating knob 26 rotates gear 122 which in turn raises or lowers post 120 depending on the direction of rotation. A spring 128 can be coupled to post 120 and housing 20. Spring 128 can provide a spring resistance as post 120 is being raised from a minimum distraction distance. As mentioned previously, the minimum distraction distance corresponds to distractor 10 having support structure 30 within the opening of fixed support structure 28. In one embodiment, the minimum distraction distance occurs when both moving support structure 30 and fixed support structure 28 couples to a prepared surface of a tibia. In one embodiment, a minimum height for a medial compartment and a lateral compartment of a knee joint occurs when a bottom surface 34 of fixed support structure is co-planar with a bottom surface of moving support structure 30.

A distraction mechanism lock 124 is configured to prevent movement of gear drive 132. Distraction lock mechanism 124 is coupled to housing 20 and is configured to pivot. Distraction lock mechanism 124 is configured to be enabled and disabled. A spring 130 supports pivoting of distraction lock mechanism 124 in a locked position whereby a tooth of distraction lock mechanism 124 is configured to engage with gear 122 to prevent movement. Spring 128 supports retention of the tooth of distraction lock mechanism 124 in gear 122 by applying a force on post 120 that holds gear 122 against distraction lock mechanism 124 that prevents a user from rotating knob 26. Moving support structure 30 will maintain a distraction distance to fixed support structure 28 until distraction lock mechanism 124 is released or disabled.

Figure 15:
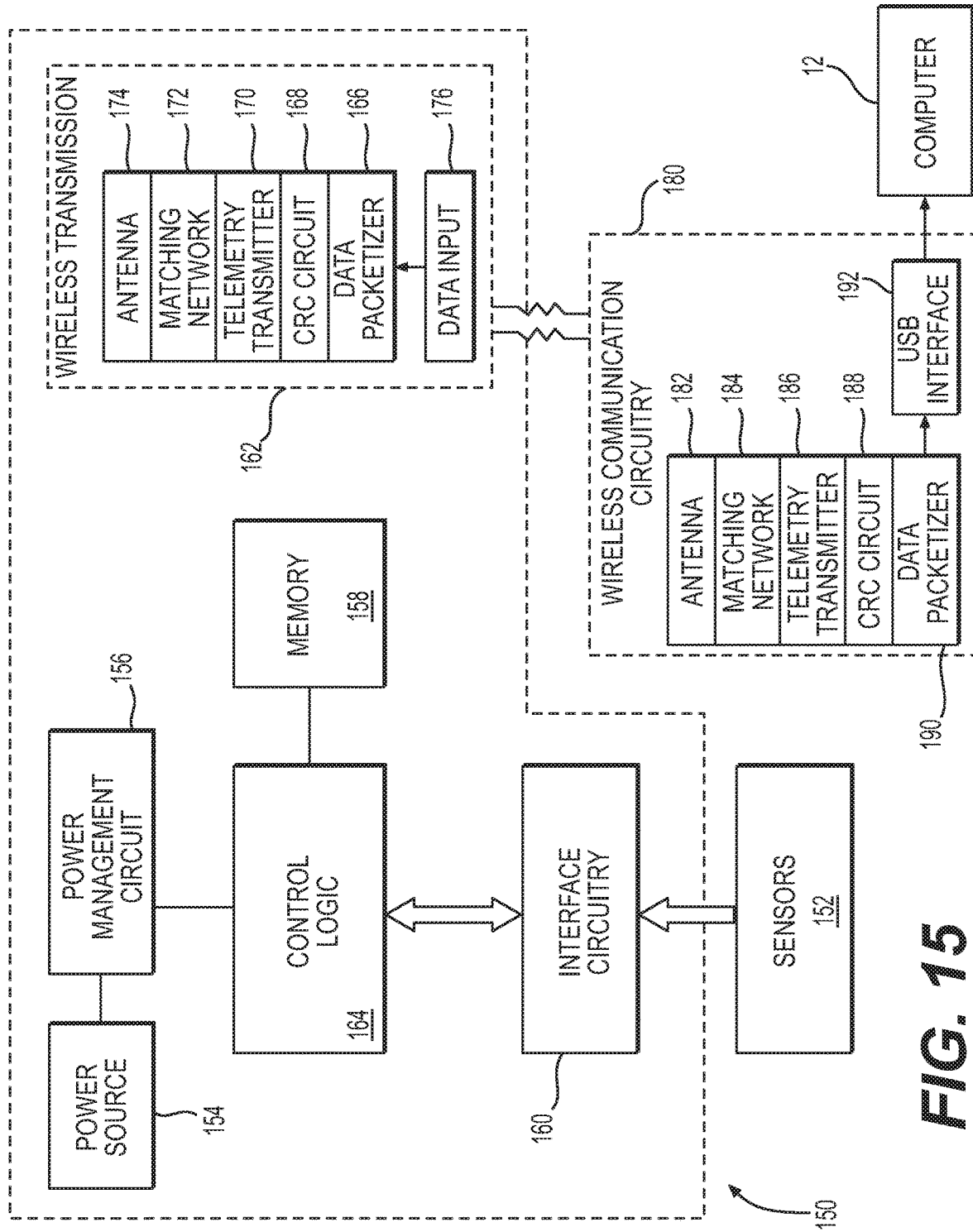
FIG. 15 is a block diagram of electronic circuitry in the distractor of FIG. 1 or the module of FIG. 1 in accordance with an example embodiment.

FIG. 15 is a block diagram of electronic circuitry 150 in distractor 10 of FIG. 1 or module 32 of FIG. 1 in accordance with an example embodiment. Components of FIG. 1 may be referred to herein in the discussion of electronic circuitry 150. Electronic circuitry 150 couples to sensors 152 in distractor 10 or module 32. Electronic circuitry 150 is configured to control a measurement process, receive measurement data from sensors 152 and transmit the measurement data to computer 12 of FIG. 1 for further analysis and feedback. Parameters are measured by sensors 152 coupled to electronic circuitry 150 in module 32 or distractor 10. Electronic circuitry 150 comprises a power management circuit 156, control logic 164, memory 158, and interface circuitry 160. A power source 154 couples to electronic circuitry 150 to power a measurement process. Electronic circuitry 150 further includes a transceiver 162 and an antenna 174 that can be positioned on or within, or engaged with, or attached or affixed to or within, a wide range of physical systems including, but not limited to instruments, equipment, devices, prosthetic components, or other physical systems for use on or in human bodies and configured for sensing and communicating parameters of interest in real time.

In general, electronic circuitry 150 is configured to provide two-way communication between distractor 10 or module 32 and computer 12. In one embodiment, distractor 10 provides quantitative measurement data related to a distraction distance, medial-lateral tilt, or anterior-posterior tilt of distractor 10. In one embodiment, module 32 provides quantitative measurement data related to load magnitude, position of load, position, tilt, balance, and alignment. Alternatively, distractor 10 can have mechanical gauges to provide measurement data local to the device. The measurement data from distractor 10 or module 32 can be used by computer 12 in a kinematic assessment to support installation of prosthetic components to ensure optimal loading, balance, and alignment that improves performance and reliability based on clinical evidence.

Power source 154 provides power to electronic circuitry 150 and sensors 152. The power source 154 can be temporary or permanent. In one embodiment, the power source can be rechargeable. Charging of the power source 154 can comprise wired energy transfer or short-distance wireless energy transfer. A charging power source to recharge power source 154 can include, but is not limited to, a battery or batteries, an alternating current power supply, a radio frequency receiver, an electromagnetic induction coil, a photoelectric cell or cells, a thermocouple or thermocouples, or a transducer energy transfer. Power source 154 has sufficient energy to operate electronic circuitry 150 in distractor 10 or module 32 for one or more surgeries with a single charge. Distractor 10 or module 32 can utilize power management technologies to minimize the power drain of power source 154 while in use and when it is idling. In one embodiment, distractor 10, module 32, or both can be a disposable device after a surgery is completed.

In one embodiment, power source 154 in distractor 10 or module 32 is a rechargeable battery. The rechargeable battery can be recharged by the methods disclosed herein above. Alternatively, power source 154 can be a super capacitor, an inductor, or other energy storage device. An external charging source can be coupled wirelessly to the rechargeable battery, capacitor, or inductive energy storage device through an electromagnetic induction coil by way of inductive charging. The charging operation can be controlled by power management circuit 156 within electronic circuitry 150. In one embodiment, power management circuit 156 supports operation of distractor 10 or module 32 during charging thereby allowing the surgery to continue if a low charge on power source 154 is detected. For example, power can be transferred to the battery, capacitive energy storage device, or inductive energy storage device by way of efficient step-up and step-down voltage conversion circuitry. This conserves operating power of circuit blocks at a minimum voltage level to support the required level of performance.

Power management circuit 156 is configured to operate under severe power constraints. In one embodiment, power management circuit 156 controls power up, power down, and minimizes power usage. The power management circuit 156 can also reduce power during operation of the system. The power management circuit 156 can turn off or reduce the power delivered to circuits that are not being used in a specific operation. Similarly, if the system is idle and not being used, the power management circuit 156 can put other unused circuitry in a sleep mode that awakens prior to the next measurement being made. Power management circuit 156 can include one or more voltage regulation circuits that provide a plurality of different stable voltages to electronic circuitry 150 and sensors 152 to minimize power dissipation.

In one configuration, a charging operation of power source 154 can further serve to communicate downlink data to electronic circuitry. For instance, downlink control data can be modulated onto the energy source signal and thereafter demodulated from an inductor in electronic circuitry 150. This can serve as a more efficient way for receiving downlink data instead of configuring an internal transceiver within electronic circuitry 150 for both uplink and downlink operation. As one example, downlink data can include updated control parameters that distractor 10 or module 32 uses when making a measurement, such as external positional information or for recalibration purposes. It can also be used to download a serial number or other identification data.

Control logic 164 controls a measurement process or sequence that engages the sensors, converts the measurement data into a useable format, and transmits the information. Control logic 164 can comprise digital circuitry, a microcontroller, a microprocessor, an ASIC (Application Specific Integrated Circuit), a DSP (Digital Signal Processing), a gate array implementation, a standard cell implementation, and other circuitry. Control logic 164 couples to memory 158. Memory 158 is configured to store measurement data, software routines, diagnostics/test routines, calibration data, calibration algorithms, workflows, and other information or programs. In one embodiment, one or more sensors may be continuously enabled and control logic 164 can be configured to receive the measurement data, store the measurement data in memory, or transmit the measurement data in real-time. Prior to sealing the device and sterilizing the device for packaging, sensors coupled to electronic circuitry 150 can be calibrated. Typically, the sensors are exercised against a reference that can include varying conditions such as environmental changes. Differences between a sensor and the reference can be stored in memory 158. The calibration data can then be used in conjunction with the measurements taken by the sensor to correct the sensor output. Alternatively, the calibration data can be provided from the device to a computer used to display the measurement data in the surgical environment. The computer then uses the calibration data to correct the measurement data from the sensor before displaying it to the surgical team. Control logic 164 can include dedicated ports that couple to a sensor to continuously receive measurement data or receive at high sample rates measurement data. Alternatively, control logic 164 can select a sensor to be measured. For example, multiple sensors can be coupled to control logic 164 via a multiplexer. Control logic 164 controls which sensor is coupled through the multiplexer to receive measurement data. Multiplexed measurement data works well when the measurement data is not critical or can be sampled occasionally as needed. Control logic 164 can also select and receive measurement data from different sensors in a sequence. Control logic 164 can be configured to monitor the measurement data from a sensor but transmit measurement data only when a change occurs in the measurement data. Furthermore, control logic 164 can modify the measurement data prior to transmitting the measurement data to computer 12. For example, the measurement data can be corrected for non-linearity using calibration data.

Interface circuitry 160 couples between sensors 152 and control logic 164. Interface circuitry 160 supports conversion of a sensor output to a form that can be received by computer 12. Interface circuitry 160 comprises digital circuitry and analog circuitry. The analog circuitry can include multiplexers, amplifiers, buffers, comparators, filters, passive components, analog to digital converters, and digital to analog converters to name but a few. In one embodiment interface circuitry 160 uses one or more multiplexers to select a sensor for providing measurement data to control logic 164. Control logic 164 is configured to provide control signals that enable the multiplexer to select the sensor for measurement. The multiplexer can be enabled to deliver the measurement data to control logic 164, memory 158, or to be transmitted in real-time. Typically, at least one analog to digital conversion or digital to analog conversion of the measurement data occurs via the interface circuitry 160.

Sensors 152 couple through interface circuitry 160 to control logic 164. Alternatively, interface circuitry 160 can couple directly to circuitry for transmitting measurement data as it is measured. The physical parameter or parameters of interest measured by sensors 152 can include, but are not limited to, height, length, width, tilt/slope, position, orientation, load magnitude, force, pressure, contact point location, displacement, density, viscosity, pH, light, color, sound, optical, vascular flow, visual recognition, humidity, alignment, rotation, inertial sensing, turbidity, bone density, fluid viscosity, strain, angular deformity, vibration, torque, elasticity, motion, and temperature. Often, a measured parameter is used in conjunction with another measured parameter to make a kinetic and qualitative assessment. In joint reconstruction, portions of the muscular-skeletal system can be prepared to receive prosthetic components. Preparation includes bone cuts or bone shaping to mate with one or more prosthesis. Parameters can be evaluated relative to orientation, alignment, direction, displacement, or position as well as movement, rotation, or acceleration along an axis or combination of axes by wireless sensing modules or devices positioned on or within a body, in an instrument, an appliance, a tool, equipment, prosthesis, or other physical system.

The sensors can directly or indirectly measure a parameter of interest. For example, a load sensor in module 32 of FIG. 1 can comprise a capacitor that has an elastic dielectric that can compress when a load is applied to the capacitor. This is an indirect form of sensing a parameter (load) where the capacitance of the capacitor varies with loading. The capacitive measurement data is sent to computer 12 of FIG. 1 for further processing. Computer 12 can include software and calibration data related to the elastic capacitors. The load measurement data can be converted from capacitance values to load measurements. The calibration data can be used to curve fit and compensate for non-linear output of a sensor over a range of operation. Furthermore, the individual sensor measurement can be combined to produce other measurement data by computer 12. In keeping with the example of load measurement data, the individual load measurement data can be combined or assessed to determine a location where the load is applied to a surface to which the load sensors couple. The measurement data can be displayed on a display that supports a surgeon rapidly assimilating the measurement data. For example, the calculated measurement data on the location of applied load to a surface may have little or no meaning to a surgeon. Conversely, an image of the surface being loaded with a contact point displayed on the surface can be rapidly assimilated by the surgeon to determine if there is an issue with the contact point.

In one embodiment, the orthopedic measurement system transmits and receives information wirelessly. Wireless operation reduces clutter within the surgical area, wired distortion, wired disconnect, or limitations on, measurements caused by the potential for physical interference by, or limitations imposed by, cables connecting a device with an internal power with data collection, storage, or display equipment in an operating room environment. Electronic circuitry 150 includes wireless communication circuitry 162. In one embodiment, wireless communication circuitry 162 is low power and configured for short range telemetry. Typically, distractor 10, module 32, and computer 12 are located in an operating room such that the transmission of measurement data from distractor 10 or module 32 to computer 12 is less than 10 meters. As illustrated, the exemplary communications system comprises wireless communication circuitry 162 of distractor 10 or module 32 and receiving system wireless communication circuitry 180 of computer 12. The distractor 10 or module 32 wireless communications circuitry are inter-operatively coupled to include, but not limited to, the antenna 174, a matching network 172, the telemetry transceiver 170, a CRC circuit 168, a data packetizer 166, and a data input 176. Wireless communication circuitry 162 can include more or less than the number of components shown and are not limited to those shown or the order of the components.

Similarly, computer 12 includes wireless communication circuitry 180 that comprises an antenna 182, a matching network 184, a telemetry receiver 186, a CRC circuit 188, and a data packetizer 190. Notably, other interface systems can be directly coupled to the data packetizer 190 for processing and rendering sensor data. In general, electronic circuitry 150 couples to sensors 152 and is configured to transmit quantitative measurement data to computer 12 in real-time to process, display, analyze, and provide feedback. In one embodiment, distractor 10 includes a magnetic linear sensor configured to measure a distance of distraction and a magnetic angle sensor to measure tilt, slope, or angle. Electronic circuitry 150 is coupled to the magnetic linear sensor and the magnetic angle sensor in distractor 10. The distraction distance data and the M-L tilt measurement data is transmitted by electronic circuitry 150 in distractor 10 to computer 12 and is displayed on display 14. In one embodiment, module 32 includes a plurality of load sensor configured to measure load magnitude at predetermined locations of cover 38 of FIG. 14. Electronic circuitry 150 in module 32 couples to the plurality of load sensors. Module 32 can further include inertial sensors and other parameter measurement sensors. The measurement data from the plurality of load sensors and the inertial sensors is transmitted to computer 12. Computer 12 can further calculate a point of contact to the surface of the cover 38 on a medial side and a lateral side. Computer 12 can calculate the load magnitude at the point of contact on the medial side or the lateral side. The module can further use the inertial sensors as a position measurement system or a tracking system. The tracking data is also sent to computer 12. The results can also be displayed on display 14 of computer 12. Redundant measurement data can be generated from distractor 10 and module 32 such as M-L tilt or A-P tilt. The redundant measurement data can be compared to ensure accuracy of the measurement.

In general, electronic circuitry 150 is operatively coupled to one or more sensors 152 to control a measurement process and to transmit measurement data. Electronic circuitry 150 can be placed near sensors 152 or housed with the sensors to simplify coupling to the sensors. As mentioned previously, electronic circuitry 150 can be placed in distractor 10 and electronic circuitry 150 can be placed in module 32 to control a measurement process and transmit measurement data in each device. Electronic circuitry 150 couples to the magnetic angle sensor and the magnetic distance sensor in distractor 10. Electronic circuitry 150 controls a measurement process of the magnetic angle sensor and the magnetic distances sensor of distractor 10 and transmits measurement data to computer 12. Similarly, electronic circuitry 150 couples to sensors of module 32. Electronic circuitry 150 controls a measurement process of the sensors of module 32 and transmits measurement data to computer 12. In one embodiment, the process of transmitting data from distractor 10 is independent from module 32. Alternatively, the electronic circuitry 150 of distractor 10 can be in communication with the electronic circuitry 150 of module 32 to control the measurement processes and transmission of measurement data. In one embodiment, the transmission of the measurement data from different components can be sent on different channels or the measurement data can be sent at different times on the same channel.

As mentioned previously, wireless communication circuitry comprises data input 176, data packetizer 166, CRC circuit 168 telemetry transmitter 170, matching network 172, and antenna 174. In general, measurement data from sensors 152 is provided to data input 176 of wireless communication circuitry 162. The measurement data can be provided from interface circuitry 160, from the control logic 164, from memory 158, or from control logic 164 thru interface circuitry 160 to data input 176. The measurement data can be stored in memory 158 prior to being provided to data input 176. The data packetizer 166 assembles the sensor data into packets; this includes sensor information received or processed by control logic 164. Control logic 164 can comprise specific modules for efficiently performing core signal processing functions of the distractor 10 or module 32. Control logic 164 provides the further benefit of reducing the form factor to meet dimensional requirements for integration into distractor 10 or module 32.

The output of data packetizer 166 couples to the input of CRC circuit 168. CRC circuit 168 applies error code detection on the packet data. The cyclic redundancy check is based on an algorithm that computes a checksum for a data stream or packet of any length. These checksums can be used to detect interference or accidental alteration of data during transmission. Cyclic redundancy checks are especially good at detecting errors caused by electrical noise and therefore enable robust protection against improper processing of corrupted data in environments having high levels of electromagnetic activity. The output of CRC circuit 168 couples to the input of telemetry transceiver 170. The telemetry transceiver 170 then transmits the CRC encoded data packet through the matching network 172 by way of the antenna 174. Telemetry transceiver 170 can increase a carrier frequency in one or more steps and add the information or measurement data from distractor 10 or module 32 to the carrier frequency. The matching network 172 provides an impedance match for achieving optimal communication power efficiency between telemetry transmitter 170 and antenna 174.

The antenna 174 can be integrated with components of the distractor 10 or module 32 to provide the radio frequency transmission. The substrate for the antenna 174 and electrical connections with the electronic circuitry 150 can further include the matching network. In one embodiment, the antenna and a portion of the matching network 172 can be formed in the printed circuit board that interconnects the component that comprise electronic circuitry 150. This level of integration of the antenna and electronics enables reductions in the size and cost of wireless equipment. Potential applications may include, but are not limited to any type musculoskeletal equipment or prosthetic components where a compact antenna can be used. This includes disposable modules or devices as well as reusable modules or devices and modules or devices for long-term use.

The process for receiving wireless communication circuitry 180 is the opposite of the sending process. Antenna 182 receives transmitted measurement data from wireless communication circuitry 162. Wireless communication circuitry 162 can transmit at low power such that receiving wireless communication circuitry 180 must be in proximity, for example within an operating room to receive measurement data. Antenna 182 couples to matching network 184 that efficiently couples the measurement data to telemetry transmitter circuit 186. The measurement data can be sent on a carrier signal that supports wireless transmission. The measurement data is stripped off from the carrier signal by telemetry transmitter 186. The measurement data is received by CRC circuit 188 from telemetry transmitter 186. CRC circuit 188 performs a cyclic redundancy check algorithm to verify that the measurement data has not been corrupted during transmission. The CRC circuit 188 provides the checked measurement data to data packetizer 190. Data packetizer 190 reassembles the measurement data where it is provided to usb interface 192. USB interface 192 provides the measurement data to computer 12 for further processing. It should be noted that the measuring, transmitting, receiving, and processing of the measurement data can be performed in real-time for use by a surgeon installing the knee joint.

Figure 16:
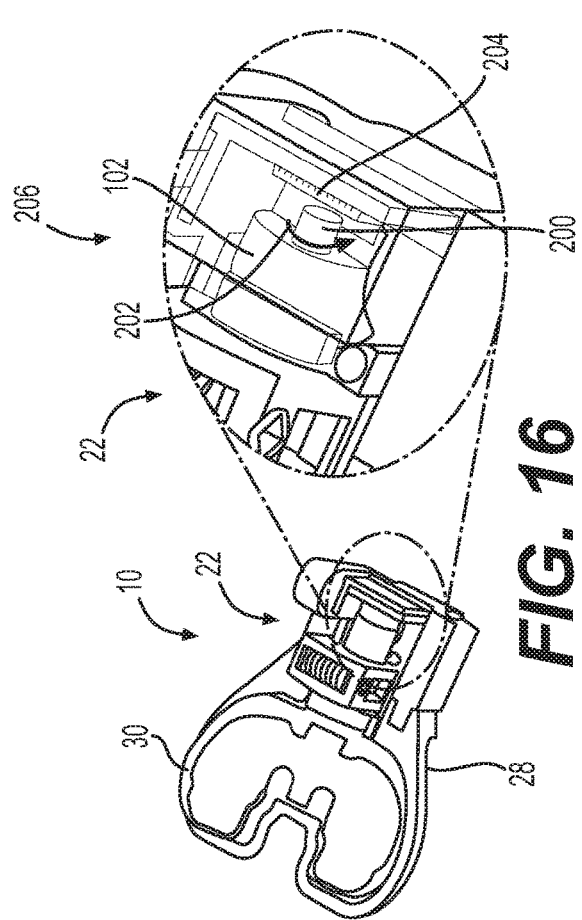
FIG. 16 is an illustration of a magnetic angle sensor coupled to the M-L tilt mechanism in accordance with an example embodiment.

FIG. 16 is an illustration of a magnetic angle sensor 206 coupled to M-L tilt mechanism 22 in accordance with an example embodiment. The illustration includes a magnified view of distractor 10 corresponding to M-L tilt mechanism 22. M-L tilt mechanism 22 couples to moving support structure 30 and can adjust the M-L tilt angle of moving support structure 30. M-L tilt mechanism 22 can be disengaged from moving support structure 30 thereby allowing moving support structure 30 to freely move medially or laterally. A neutral or 0 degrees medial-lateral tilt occurs when a plane of moving support structure 30 is parallel to a plane of fixed support structure 28. Referring briefly to FIG. 12A a coupler 100 of moving support structure 30 is inserted into a coupler 102 of M-L tilt mechanism 22 to retain and align moving support structure 30 to M-L tilt mechanism 22. Coupler 102 freely rotates with M-L tilt mechanism 22 when worm gear 112 of FIG. 13 is disengaged. Conversely, the movement of coupler 102 and moving support structure 30 are locked into the movement of M-L tilt mechanism 22 when worm gear 112 is engaged with gear 114. In other words, M-L tilt mechanism 22 when engaged can forcibly adjust the M-L tilt angle thereby rotating moving support structure 30 and coupler 102 of FIG. 12A medially or laterally.

In one embodiment, magnetic angle sensor 206 comprises a Hall Effect Sensor 204 and a magnet 200. The Hall Effect Sensor 204 can be an integrated circuit that is placed in proximity to magnet 200. In general, the Hall Effect Sensor 204 comprises an array of sensors that detects the perpendicular component of a magnetic field generated by magnet 200. Each sensor generates a signal and the signals are summed and amplified. In one embodiment, the array of sensors are aligned in a circle. Thus, any rotation of the magnet 200 is detected and the amount of rotation can be calculated. In the example, magnet 200 is coupled to coupler 102 thereby rotating as coupler 102 rotates. Hall Effect Sensor 204 is placed adjacent to magnet 200 and within the magnetic field generated by magnet 200. Magnetic angle sensor 206 is a sensor that couples to electronic circuitry 150 as disclosed in FIG. 15 to store angle sensor data or transmit angle sensor data in real-time. Arrow 202 indicates rotation of magnetic 200 in a clockwise direction when facing distractor 10. For example, the clockwise direction can correspond to a medial tilt. Magnetic angle sensor 206 can be calibrated to measure zero degrees when the plane of fixed support structure 28 is parallel with the plane of moving support structure 30. Hall Effect Sensor 204 measures the rotation of magnetic 200 and is calibrated to measure the degrees of rotation as moving support structure 30 tilts medially. The angle sensor data is sent to the computer 12 of FIG. 1 and the amount of medial tilt is displayed on display 14 of FIG. 1 in real-time. Other sensor types are also contemplated for measuring tilt or angle. For example, an inclinometer, an accelerometer, a gyroscope, a mechanical sensor, GPS, an altimeter, a level gauge, an optical sensor, an acoustic sensor, video sensing, a pitch and roll indicator are but a few of the sensors that can be adapted to measuring tilt and generating quantitative measurement data that can be sent to a computer for use by a surgical team.

Figure 17:
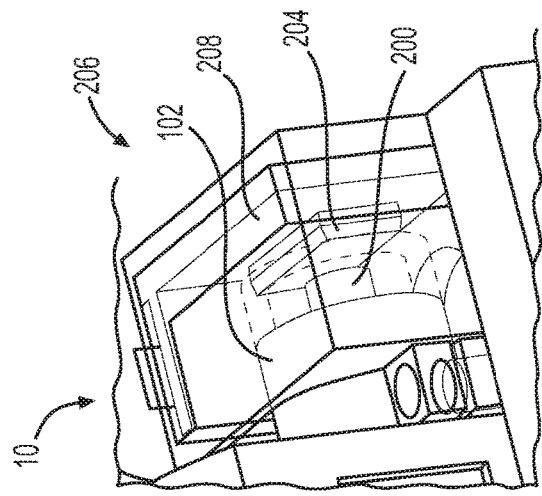
FIG. 17 is an illustration of the magnetic angle sensor in the distractor in accordance with an example embodiment.

FIG. 17 is an illustration magnetic angle sensor 206 in distractor 10 in accordance with an example embodiment. Magnetic angle sensor 206 comprises Hall Effect Sensor 204 and magnet 200. In one embodiment, magnet 200 is coupled to and centered on coupler 102 such that magnet 200 rotates with coupler 102. Hall Effect Sensor 204 can be mounted on a printed circuit board 208 that couples to electronic circuitry 150 of FIG. 15 that can be located in a different area of distractor 10. A planar surface of magnet 200 is positioned centrally to a planar surface of Hall Effect Sensor 204. As mentioned previously, the Hall Effect Sensor 204 is placed within the magnetic field generated by magnet 200.

Figure 18:
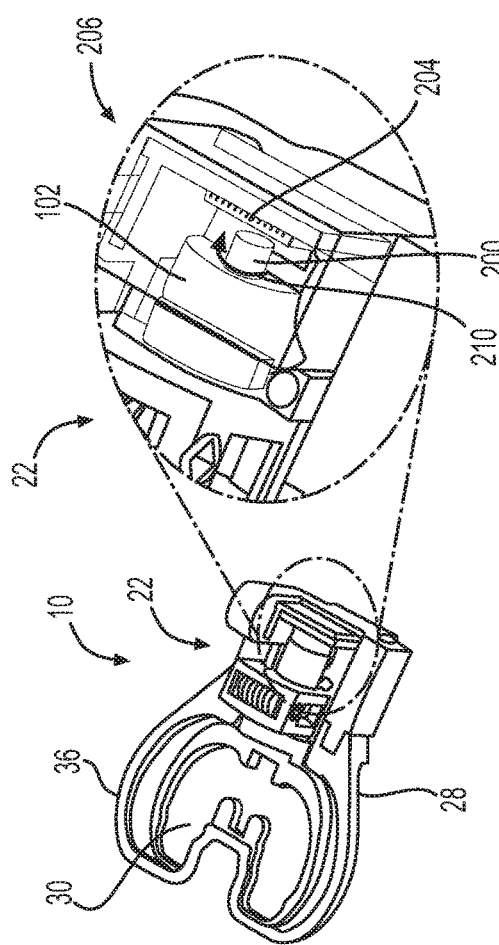
FIG. 18 is an illustration of the moving support structure tilting laterally in accordance with an example embodiment.

FIG. 18 is an illustration of moving support structure 30 tilting laterally in accordance with an example embodiment. In the example, magnet 200 is coupled to coupler 102 thereby rotating as coupler 102 rotates. Hall Effect Sensor 204 is placed adjacent to magnet 200 and within the magnetic field generated by magnet 200. The magnetic angle sensor 206 couples to electronic circuitry 150 as disclosed in FIG. 15 to receive and transmit magnetic angle sensor data. Arrow 210 indicates rotation of magnetic 200 in a counter-clockwise direction when facing distractor 10. For example, the counter-clockwise direction can correspond to a lateral tilt. Magnetic angle sensor 206 can be calibrated to measure zero degrees when the plane of fixed support structure 28 is parallel with the plane of moving support structure 30. Hall Effect Sensor 204 measures the rotation of magnetic 200 and is calibrated to measure the degrees of rotation as moving support structure 30 tilts laterally as shown. The magnetic angle sensor data is sent to the computer 12 of FIG. 1 and the amount of medial tilt is displayed on display 14 of FIG. 1 in real-time.

Figure 19:
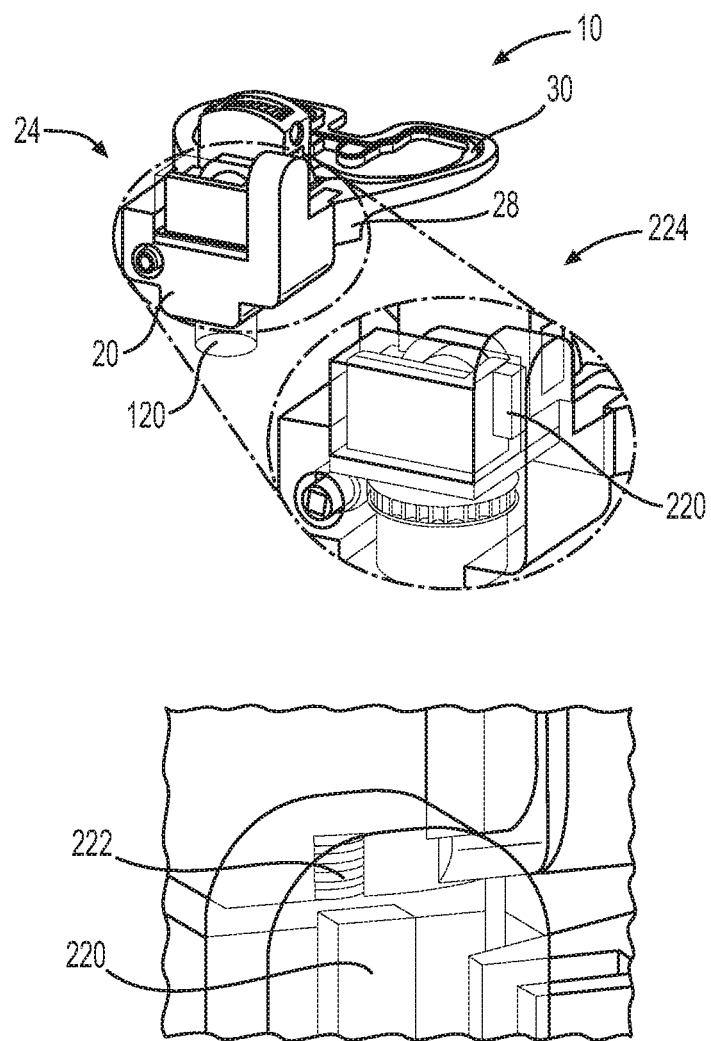
FIG. 19 is an illustration of a magnetic distance sensor in the distractor in accordance with an example embodiment.

FIG. 19 is an illustration of a magnetic distance sensor 224 in distractor 10 in accordance with an example embodiment. In one embodiment magnetic distance sensor 224 comprises a magnet 220 and a Linear Hall Sensor 222. The magnetic distance sensor 224 provides contactless position measurement. Magnet 220 is a two pole magnet. Linear Hall Sensor 222 can measure absolute position of lateral movement when placed in the magnetic field of magnet 220. The strength of the magnetic field measured by Linear Hall Sensor 222 corresponds to distance but is not linear to distance. Linear Hall Sensor 222 relates the non-linear change in magnetic field strength per unit distance and linearizes the output. Linear Hall Sensor 222 couples to electronic circuitry 150 of FIG. 15 in distractor 10 where electronic circuit 150 is configured to control a measurement process and transmit distraction distance data. Other sensor types are also contemplated for measuring distance. For example, an optical sensors, an ultrasonic sensors, GPS, mechanical gauges, lasers, displacement sensors, video sensing, contact sensors, eddy current sensors are but a few of the sensors that can be adapted to measuring distance and generating quantitative measurement data that can be sent to a computer for use by a surgical team.

In one embodiment, Linear Hall Sensor 222 is coupled to a portion of distraction mechanism 24 that moves relative to housing 20 and fixed support structure 28 of FIG. 14. For example, Linear Hall Sensor 222 can couple to post 120 of distraction mechanism 24 that increases or decreases a distraction distance of moving support structure 30 relative to fixed support structure 28. Operation of distraction mechanism 24 and post 120 is disclosed in more detail in FIG. 14. Magnet 220 is coupled to housing 20 such that Linear Hall Sensor 222 is in proximity to magnet 220. In one embodiment, Linear Hall Sensor 222 and magnet 220 align to an axis to which a distance is measured. In the example, the axis can align with pole 120. A reference distance can be established corresponding to distractor 10 being at a minimum distraction distance for the medial and lateral compartment heights with a medial-lateral tilt angle of zero. The reference distance can be displayed on display 14 of computer 12 of FIG. 1. As post 120 changes position to increase a distraction distance of distractor 10, Linear Hall Sensor 222 measures the magnetic field from magnet 220 whereby the measured magnetic field strength corresponds to distance of Linear Hall Sensor 222 from magnet 220. The measured change in height can be added to the reference distance to arrive at the medial and lateral compartment heights. Electronic circuitry 150 in distractor 10 receives and transmits distraction distance data from Linear Hall Sensor 222 to computer 12 of FIG. 1. Alternatively, Linear Hall Sensor 222 can be placed on housing 20 and magnet 220 can be coupled to post 120 such that magnet 220 moves relative to Linear Hall Sensor 222. In one embodiment, Magnetic distance sensor 224 can be used in conjunction with magnetic angle sensor 206 to calculate medial or lateral compartment heights. Computer 12 can receive the height measurement data and the angle measurement data geometrically calculate the medial height and the lateral compartments heights. In one embodiment, the medial height and the lateral compartment heights will be measured at a known position on the medial surface of the module 32 and a known position on the lateral surface of module 32.

Figure 20:
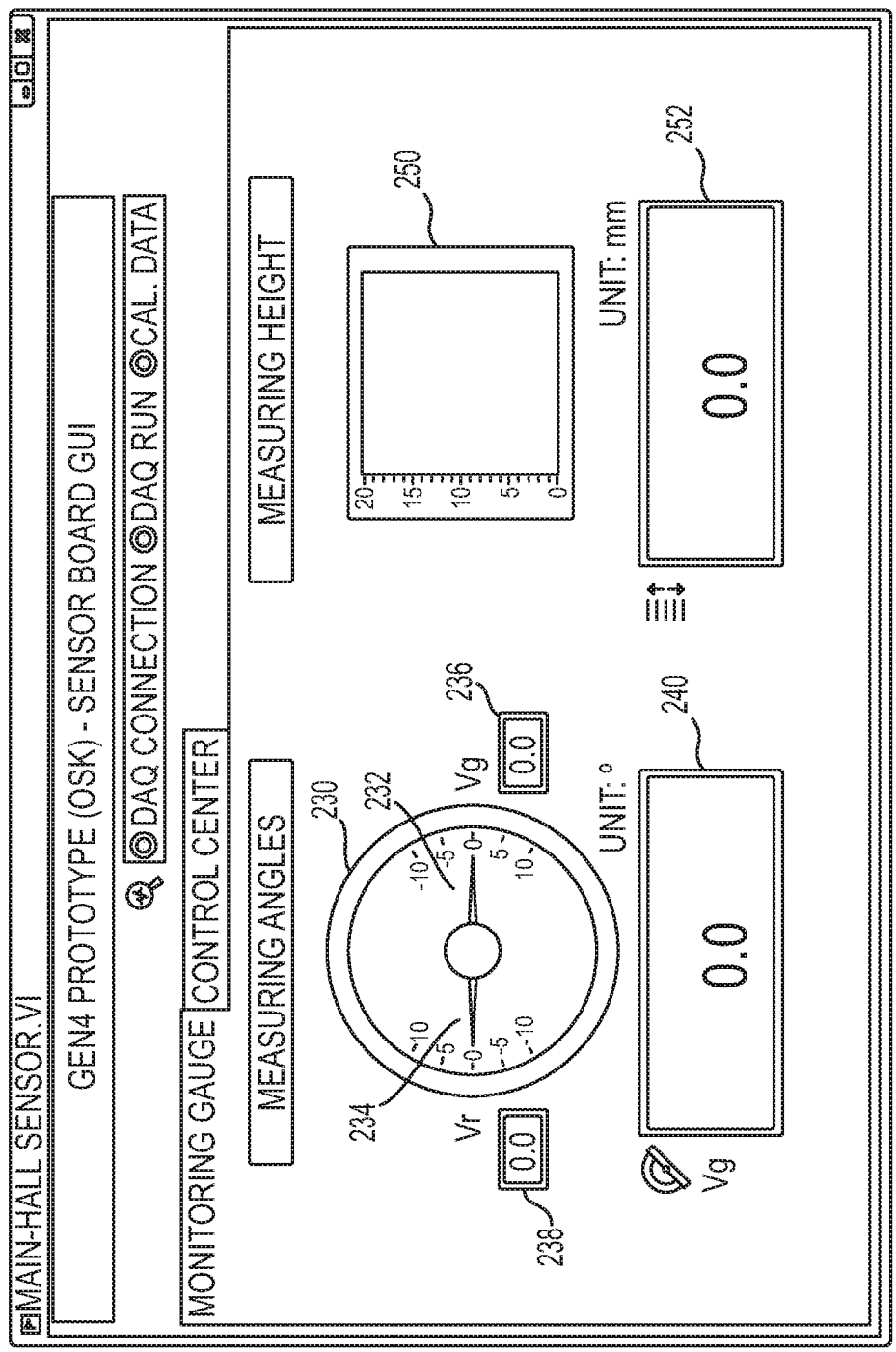
FIG. 20 is an illustration of the display of the computer as shown in FIG. 1 in accordance with an example embodiment.

FIG. 20 is an illustration of display 14 of computer 12 as shown in FIG. 1 in accordance with an example embodiment. Electronic circuitry 150 of FIG. 15 in distractor 10 transmits distraction distance data and M-L tilt data to computer 12. In a surgical environment reducing patient time under anesthesia lowers patient risk of complication or death. A surgeon using quantitative measurement data during orthopedic surgery must absorb the measurement data rapidly to support installation of prosthetic components in the shortest possible time. Display 14 of FIG. 1 can visualize data in a manner that allows the surgeon to rapidly determine if the measurement data verifies the subjective feel of an installation or if the installation needs correction and how much. Moreover, display 14 of FIG. 1 supports real-time measurement as a correction or adjustment is made.

In one embodiment, M-L tilt data is displayed on a meter 230. Meter 230 can comprise a first indicator 232 and a second indicator 234. Indicators 232 and 234 comprises opposing pointers that point to a graduated scale on either side of meter 230 corresponding to degrees of medial or lateral tilt. This supports at a glance an imbalance or offset of alignment. Meter 230 can also be used during an equalization step. The equalization step engages M-L tilt mechanism 22 of FIG. 1 to forcibly adjust the M-L tilt to zero. The M-L tilt at zero degrees corresponds to a plane of fixed support structure 28 of FIG. 1 being parallel to a plane of moving support structure 30 of FIG. 1. The actual quantitative measurement data related to M-L tilt can be displayed with boxes 236, 238, and 240 on display 14.

In one embodiment, distraction distance data is displayed on display 14. Distraction distance corresponds to a distance between a distal end of a femur and a proximal end of a tibia and is displayed visually on display 14. A bar chart 250 provides a visual representation of the distraction distance. Distraction distance values are displayed on one side of the bar graph. A bar in bar chart 250 indicates the distance and is adjacent to the distance values. The distraction distance value can also be display in a box 252 on display 14. A medial or lateral height respectively of the medial compartment and the lateral compartment of a knee joint can be calculated by computer 12 and displayed by display 14.

Figure 21:
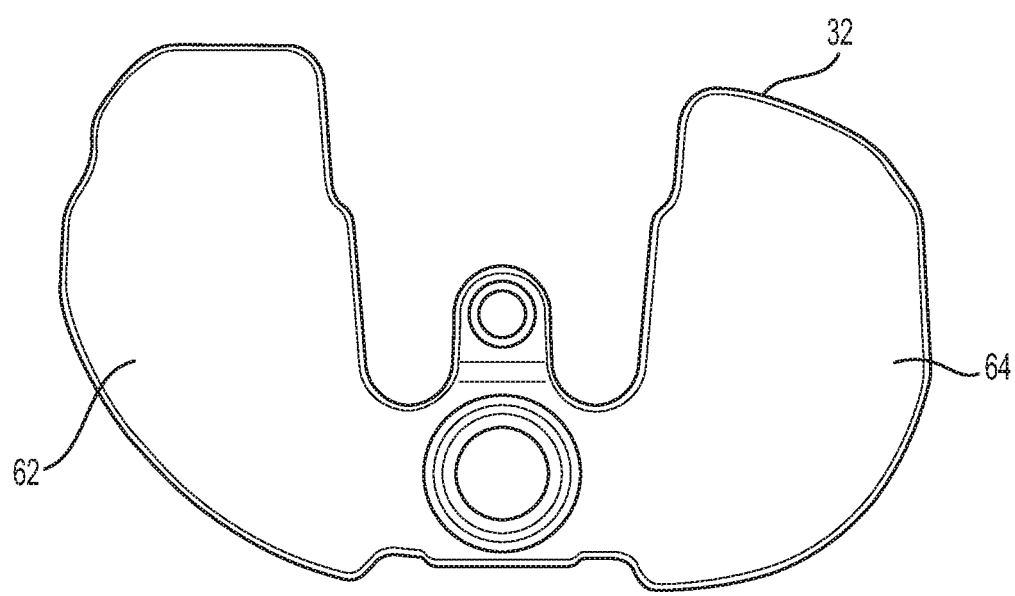
FIG. 21 is an illustration of a top view of the module in accordance with an example embodiment.

FIG. 21 is an illustration of a top view of module 32 in accordance with an example embodiment. Module 32 includes at least one sensor for measuring a parameter of the musculoskeletal system. In the example, module 32 includes a plurality of load sensors configured to measure a load applied to a surface 62 and a surface 64 also shown in FIG. 3. The plurality of load sensors are coupled to predetermined locations of surface 62 and 64 that define an area of contact. In one embodiment, each load sensor couples to a vertex of a polygon. As previously mentioned, cover 38 as shown in FIG. 2 couples to module 32 when placed in distractor 10. Cover 38 couples to surface 62 and 64. The predetermined locations of the plurality of load sensors translates to locations on cover 38 that determine a location of medial or lateral condyle contact on cover 38.

Module 32 can also be used in trialing the knee joint prior to a final installation of final prosthetic components. For example, a tibial prosthetic component and femoral prosthetic component are installed using the quantitative measurement data from distractor 10 and module 32 as shown in FIG. 1 to determine bone cuts, alignment, and balance. A trialing insert can then be inserted in the tibial prosthetic to take further measurements. The trialing insert can comprise module 32 and a cover. The cover is configured to couple to the femoral prosthetic component. The combined thickness of module 32 and the cover is determined by the bone cuts and measurements made by distractor 10. In one embodiment, the insert comprising module 32 and the cover is inserted in the tibial prosthetic component. Measurements from module 32 as a trialing insert should be similar to the measurements taken with distractor 10 and module 32. Further adjustments can be made to fine tune the prosthetic component installation using quantitative measurement data. The trialing insert can then be removed and the final insert installed in the knee joint. The final insert should have loading, position of load, balance, and alignment approximately equal to that measured using the trialing insert.

Figure 22:
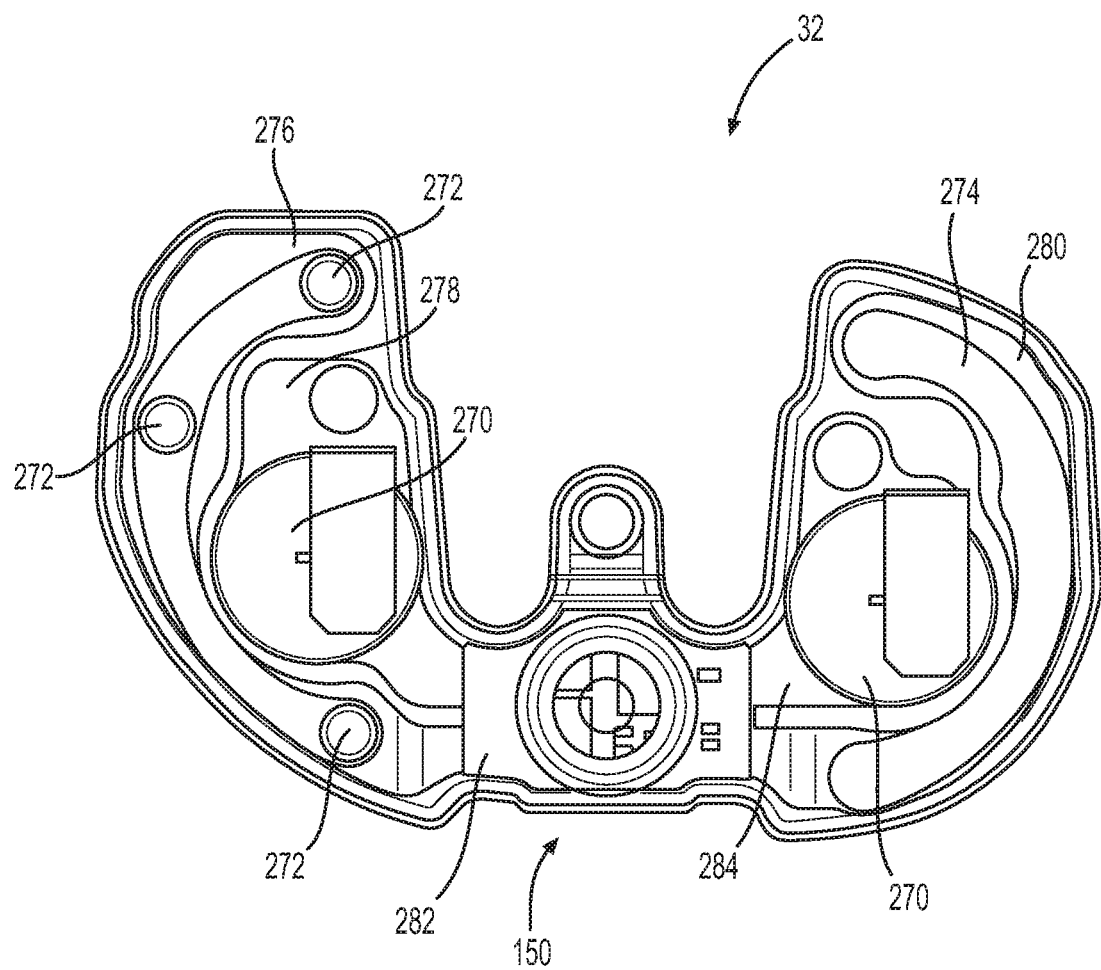
FIG. 22 is an illustration of the module with a portion of an enclosure removed in accordance with an example embodiment.

FIG. 22 is an illustration of module 32 with a portion of an enclosure removed in accordance with an example embodiment. Module 32 comprises electronic circuitry 150 and at least one sensor configured to measure a parameter. Module 32 comprises a first support structure and a second support structure configured to form a housing that is hermetically sealed. In the example embodiment, a plurality of load sensors 272 are shown on a medial side of module 32 to measure loading applied to the medial side of module 32. Plurality of load sensors 272 are placed at predetermined locations in module 32 to support measuring a position of load applied to the medial side. A load plate that is not shown would overlie plurality of load sensors 272. A plurality of load sensors are also placed at predetermined locations on a lateral side of module 32 although they cannot be seen in FIG. 22. A load plate 274 overlies the plurality of load sensors on the lateral side. Load plate 274 distributes loading to a load sensor. In one embodiment, the plurality of load sensors 272 are formed in flexible interconnect 276. Similarly, the plurality of load sensors underlying load plate 274 can be formed in interconnect 280. The leads of the plurality of load sensors 272 couple to electronic circuitry 150 as previously disclosed in FIG. 15.

Electronic circuitry 150 can be coupled to a printed circuit board 282. Electronic components can be coupled to, formed in, or interconnected to form a circuit on printed circuit board 282. In one embodiment, leads from plurality of load sensors 272 on flexible interconnect 276 and 280 can be coupled to printed circuit board 282 by solder bumping. Electronic circuitry 150 is placed in a region of module 32 that is not subject to loading by the musculoskeletal system. Electronic circuitry 150 controls a measurement process and transmits measurement data from plurality of load sensors 272. Electronic circuitry 150 receives power from a power source. In one embodiment, the power source comprises batteries 270. At least a portion of each battery underlies a portion of a surface that is loaded by the musculoskeletal system. The battery form factor is such that compression of module 32 under load by the musculoskeletal system does not touch batteries 270. Batteries 270 are coupled to electronic circuitry 150 by flexible interconnect 278 and 284. Flexible interconnect 278 and 284 can couple to electronic circuitry 150 by solder bump to printed circuit board 282.

Figure 23:
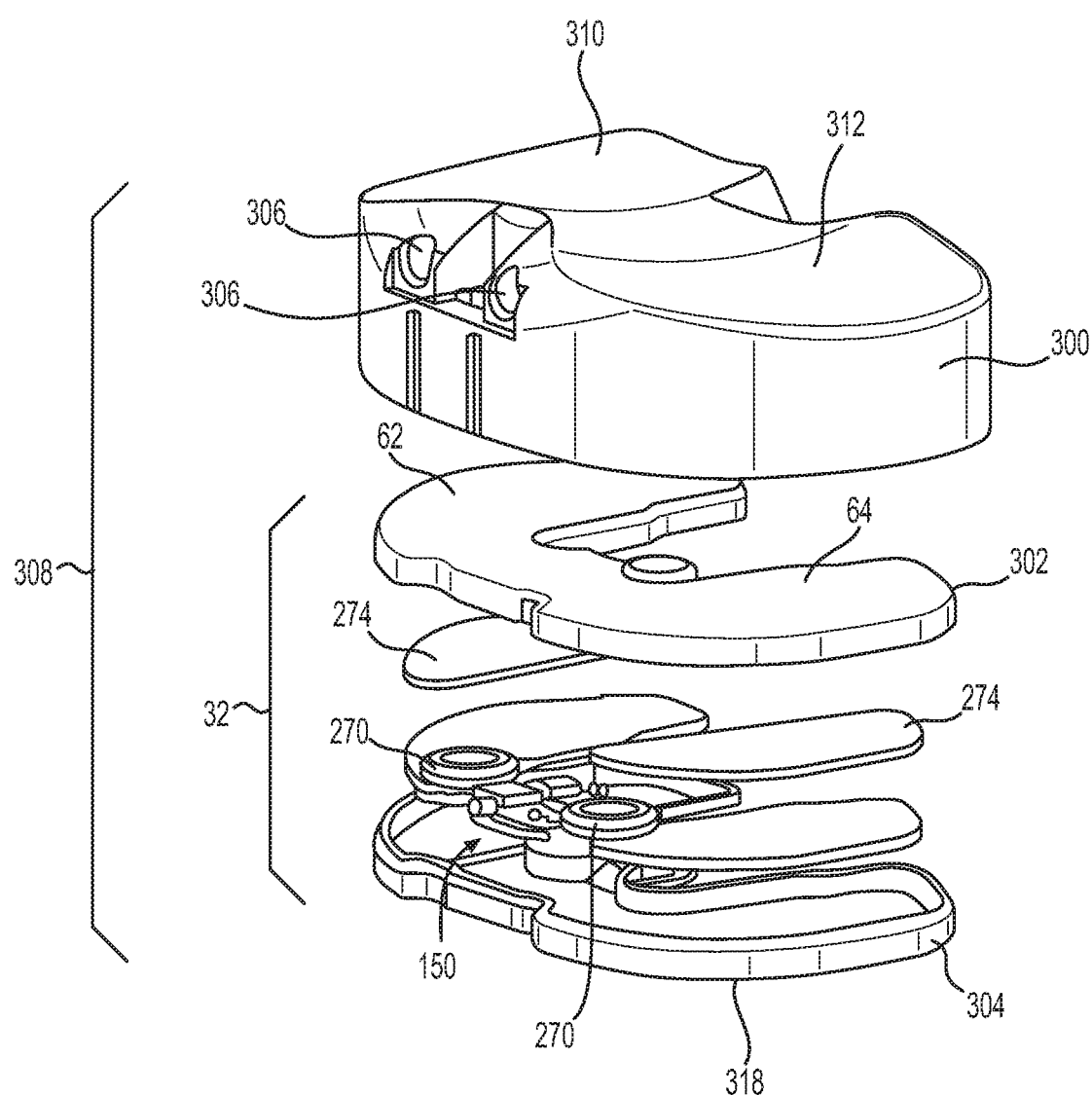
FIG. 23 is an exploded view of an insert prosthetic component in accordance with an example embodiment.

FIG. 23 is an exploded view of an insert 308 prosthetic component in accordance with an example embodiment. Insert 308 comprises a cover 300 and module 32. Distractor 10 of FIG. 1 uses module 32 to support one or more bone cuts for installation of one or more prosthetic components of the knee joint. In general, the load magnitude, position of load, balance, and alignment of the knee joint is measured. The size and height of the prosthetic components are taken into account in the bone cuts supported by distractor 10. After a tibial bone cut has been completed a tibial prosthetic component can be installed in a proximal end of a tibia. The tibial prosthetic component can be a trial tibial prosthetic component or a final tibial prosthetic component. Similarly, a femoral prosthetic component can be installed on a distal end of a femur after the femoral bone cuts on a distal end of the femur are made.

Module 32 comprises a support structure 302 and a support structure 304. Support structures 302 and 304 when coupled together form a housing for at least one sensor, a power source, and electronic circuitry 150. The housing is hermetically sealed by welding, adhesive, glue, mechanical coupling, blocking channels or other techniques. Support structure 302 has a surface 62 and a surface 64 configured to respectively couple to an articular surface 310 and an articular surface 312 of cover 300. Articular surfaces 310 and 312 support movement of the knee joint over a range of motion of the leg. Support structure 304 has a surface 318 that couples to a surface of the tibial prosthetic component.

Electronic circuitry 150 is placed in a lightly loaded or unloaded area of module 32. Electronic circuitry 150 controls a measurement process and transmits measurement data to a computer 12 shown in FIG. 1. The computer 12 is in the operating room and the transmission of the measurement data is short range. In one embodiment, a first plurality of load sensors underlie and couple to surface 64 at predetermined locations. Similarly, a second plurality of load sensors underlie and couple to surface 62 at predetermined locations. The predetermined locations correspond to vertexes of a polygon that define a measurement region. Load plates 274 couple between surface 64 and surface 62 of support structure 302 and the first or second plurality of load sensors. Load plates 274 distribute loading applied to surface 260 or surface 262 to the first or second plurality of load sensors. A power source couples to electronic circuitry 150 and the first and second plurality of load sensors. In one embodiment, the power source comprises batteries 270. Batteries 270 can be single use or rechargeable batteries.

Cover 300 couples to module 32. Module 32 and cover 300 have one or more retaining features that couple module 32 to cover 300. The retaining features allow cover 300 to be removed from module 32. Cover 300 further includes openings 306 that are configured to receive a handle to direct and install insert 308 in the knee joint. In one embodiment, a plurality of covers can be provided. The plurality of covers each have a different height or thickness. The combined thickness of module 32 and a cover corresponds to a height or thickness of a final insert that is installed into the prosthetic knee joint. The plurality of covers can also include covers of a different size that support optimal fitting for different bone sizes. In general, a cover is selected that corresponds to a patient femur and tibia bone size and a thickness corresponding to a spacing between the femoral prosthetic component and the tibial prosthetic component.

Insert 308 is installed in the knee joint. Insert 308 couples to and is retained by the trial or permanent tibial prosthetic component. Cover 300 and module 32 have a height or thickness that corresponds to the distraction distance of the knee joint when using distractor 10 as disclosed herein above to support prosthetic component installation. Condyles of the femoral component couple to articular surfaces 310 and 312 of cover 30. Articular surfaces 310 and 312 of cover 300 respectively couple to surfaces 62 and 64 of module 32. The first plurality of load sensors and the second plurality of load sensor generate load measurement data that is sent to from module 32 to the computer 12 shown in FIG. 1. Typically, computer 12 is in the operating room where the surgeon can review the quantitative measurement data while performing the knee joint installation. The predetermined locations of the first or second plurality of sensors correspond to locations on articular surfaces 310 and 312. The computer uses load data from the load sensors to calculate a load magnitude and a position of load where a condyle contacts an articular surface and displays it on the computer in real-time. The load magnitudes, position of load, balance, and alignment of the knee joint should be similar to the measurement data using distractor 10 of FIG. 1. Further adjustments or refinements can be made to change a load magnitude, a position of load, balance, or knee joint alignment. Typically, the adjustment can comprise rotating a prosthetic component or applying soft tissue release but bone resection is also an option if the measurement data justifies the change. The changes in quantitative measurement data can be viewed on the display as the adjustments are made to ensure optimal joint installation. The final insert is then placed in the knee joint. The final knee joint should see load magnitudes, position of load, balance, and alignment equal to insert 308. Thus, module 32 is used in distractor 10 of FIG. 1 to generate quantitative measurement data to support one or more bone cuts prior to installation of at least one prosthetic component and module 32 is used in an insert 308 to provide quantitative measurement data on the prosthetic knee joint.

Figure 24:
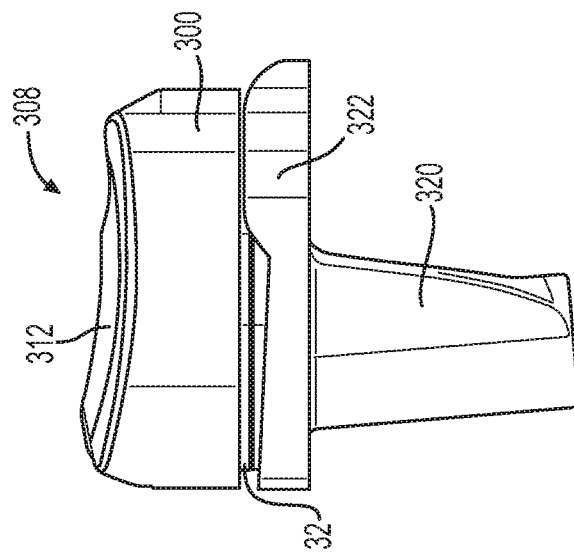
FIG. 24 is an anterior view of the insert installed on a tibial prosthetic component in accordance with an example embodiment.

FIG. 24 is an anterior view of insert 308 installed on a tibial prosthetic component 320 in accordance with an example embodiment. Insert 308 comprises cover 300 coupled to module 32. In one embodiment, tibial prosthetic component 320 includes a tibial tray 322. The tibial tray 322 is configured to align and retain module 32 to tibial prosthetic component 320. In one embodiment, load data is transmitted from insert 308 to the computer 12 shown in FIG. 1.

Figure 25:
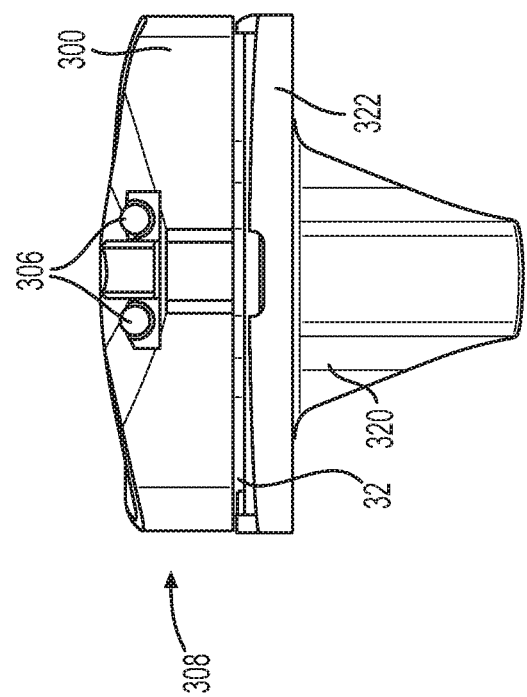
FIG. 25 is a side view of the insert installed on the tibial prosthetic component in accordance with an example embodiment.

FIG. 25 is a side view of insert 308 installed on the tibial prosthetic component 320 in accordance with an example embodiment. Articular surface 312 of cover 300 has a curved surface that supports coupling to a condyle of a femoral prosthetic component.

Figure 26:
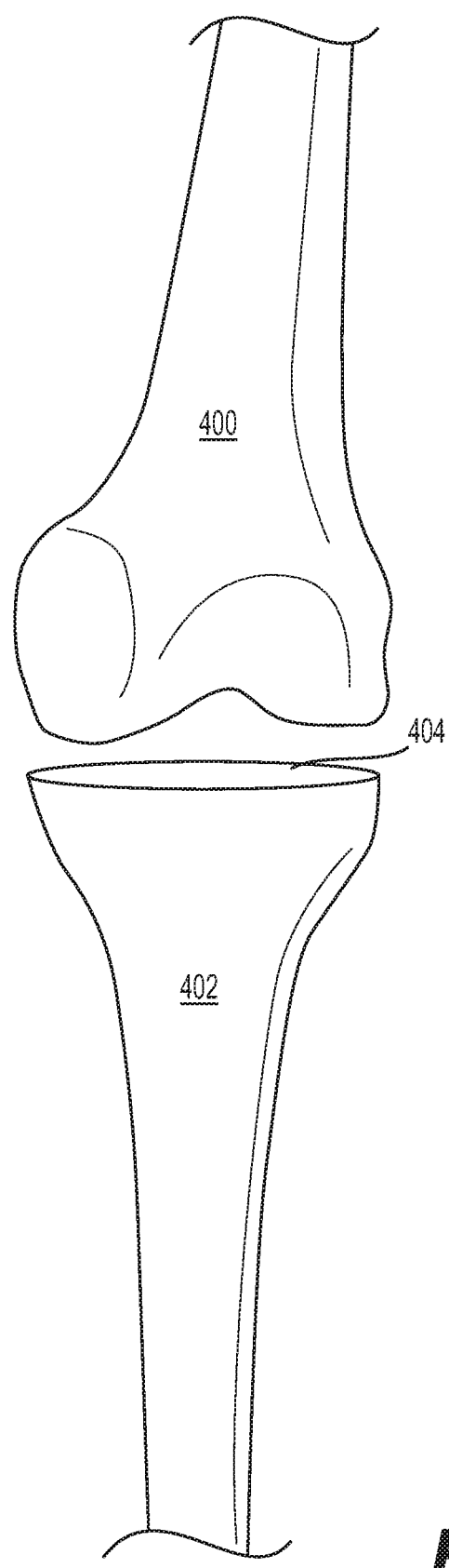
FIG. 26 illustrates a step in a knee joint installation procedure in accordance with an example embodiment.

FIG. 26 illustrates a step in a knee joint installation procedure in accordance with an example embodiment. In general, a bone in a knee joint is prepared to interface with distractor 10 shown in FIG. 1. In the example, a tibia 402 is selected for resection. A proximal end of a tibia is resected and is prepared to receive a tibial prosthetic component. In one embodiment, the proximal end of tibia 402 is cut perpendicular to the tibia anatomical axis using an alignment jig. For example, an extramedullary alignment tool can be used align and cut the proximal end of the tibia 402. The resection can also include an anterior-posterior (A-P) slope to the prepared bone surface 404. In one embodiment an (A-P) slope of 6 degrees slanted posteriorly is made. The distal end of femur 400 is left in a natural state.

Figure 27:
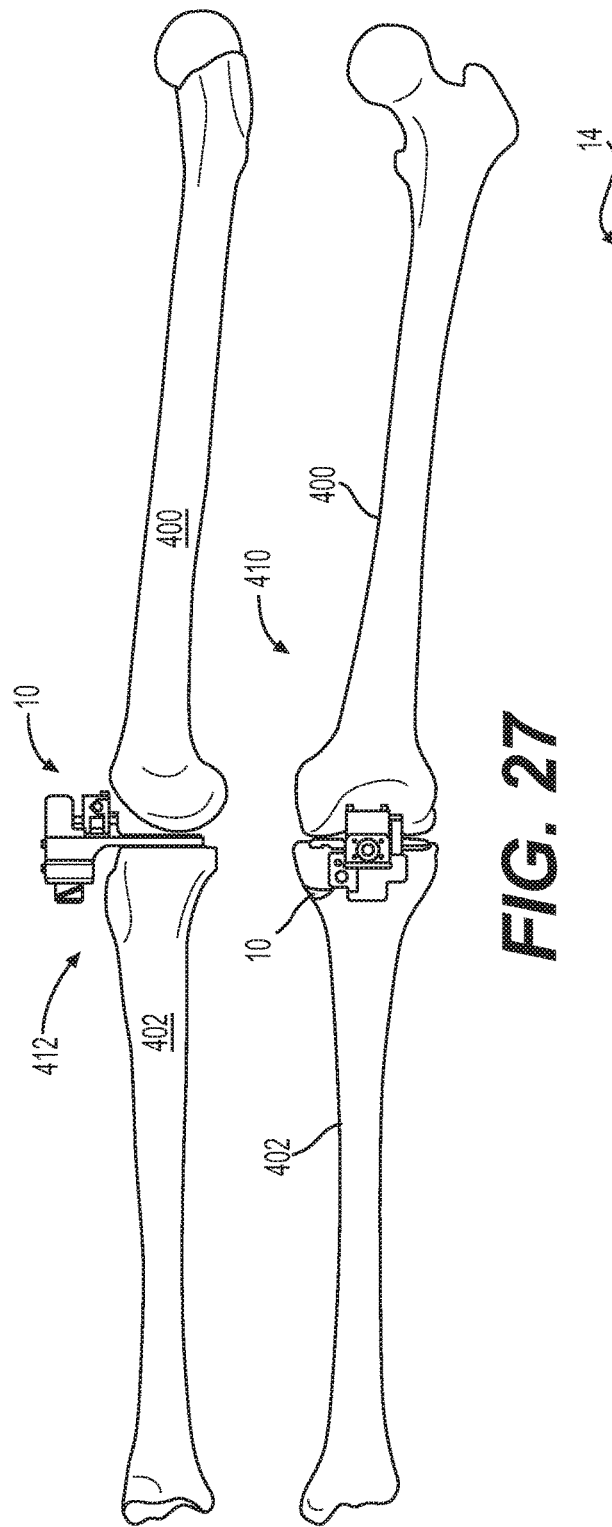
FIG. 27 illustrates a step of placing the distractor in the knee joint of the leg in accordance with an example embodiment.

FIG. 27 illustrates a step of placing distractor 10 in the knee joint of the leg in accordance with an example embodiment. A lateral view 412 of the leg and a top view of the 410 leg is shown in FIG. 27. In the example, the leg is placed in extension. The distractor 10 is reduced to a minimum distraction distance and placed on the prepared surface of the proximal end of tibia 402. In general, a distractor, surgical apparatus, or tool as disclosed herein can be coupled to a prepared bone surface, a natural surface, or a prosthetic component. For example, distractor 10 can be pinned to a natural tibia for initial support. At the minimum distraction distance distractor 10 should not require substantial force to fit within the knee joint. Placing distractor 10 at a minimum distraction distance is also called zeroing distractor 10. A module 32 and a cover 38 are placed on moving support structure 30 as shown in FIG. 1. In one embodiment, a bottom surface of both the moving support structure and the fixed support structure contact the prepared bone surface of tibia 402.

An M-L tilt lock on distractor 10 is then released. The M-L tilt lock releases moving support structure 30 as shown in FIG. 13 to freely swivel medially or laterally. In one embodiment, the moving support structure 30 cannot tilt when distractor 10 is at the minimum height. In one embodiment, the knee joint is not stable with distractor 10 zeroed. The knee joint can be supported to prevent the leg from hyperextending due to laxity. The distraction distance of distractor 10 is increased until the knee joint does not require support because the knee joint pressure is sufficient to prevent hyperextension when the leg is raised by supporting the ankle while observing the knee joint pressure medially and laterally. Condyles of the femur couple to cover 38 as shown in FIG. 3. Module 32 underlying cover 38 measures loading applied to cover 38 and transmits the load data to a computer 12 shown in FIG. 1 for further processing. Distractor 10 also measures and transmits distraction distance data and M-L tilt angle data to computer 12 shown in FIG. 1.

Figure 28:
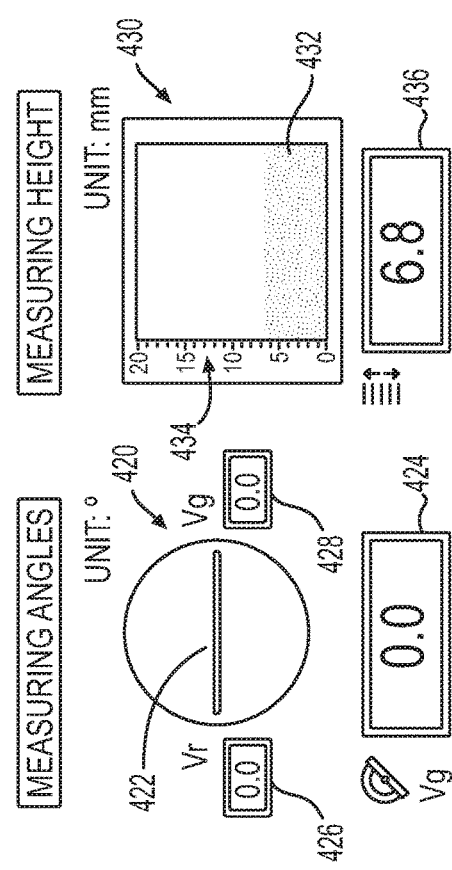
FIG. 28 illustrates a step of displaying the distraction distance data and the M-L tilt angle on a display in real-time in accordance with an example embodiment.

FIG. 28 illustrates a step of displaying the distraction distance data and the M-L tilt angle on a display in real-time in accordance with an example embodiment. A display 14 couples to the computer 12 receiving distraction distance data and M-L tilt angle data from distractor 10 similar to that shown in FIG. 20. The computer 12 provides the M-L tilt angle data and the distraction distance data on display 14 in real-time. Display 14 shows an M-L tilt meter 420 configured to display the M-L tilt angle of moving support structure 30 as shown in FIG. 1. M-L tilt meter 420 comprises an indicator bar 422 that indicates medial and lateral tilt. A surgeon at a glance can determine the amount of M-L tilt and whether the M-L tilt is medial or lateral. The value of the medial tilt angle and the lateral tilt angle can also be seen in boxes 426 and 428 on display 14. A tilt angle can also be placed in box 424 for increased visibility to the surgeon. Alternatively, M-L tilt meter 420 can have a graduated scale on either side of M-L tilt meter 420 that allows indicator bar 422 to point to the medial or lateral tilt angle value.

Display 14 also shows a bar graph 430 configured to indicate the distraction distance of distractor 10. A scale 434 indicates the distraction distance and is adjacent to bar graph 430. A bar 432 in bar graph 430 indicates the distraction distance but the exact distraction distance can be read by reading the height of bar 432 from scale 434. The distraction distance can also be read from a box 436. Similar to M-L tilt meter 420, bar graph 430 allows the surgeon to determine the distraction distance at a glance. In one embodiment, there will two bar graphs, a first bar graph is a measure of a height of the medial compartment and a second bar graph is a measure of a height of the lateral compartment of the knee joint. Each bar graph can indicate distance by graph or numeric value.

Figure 29:
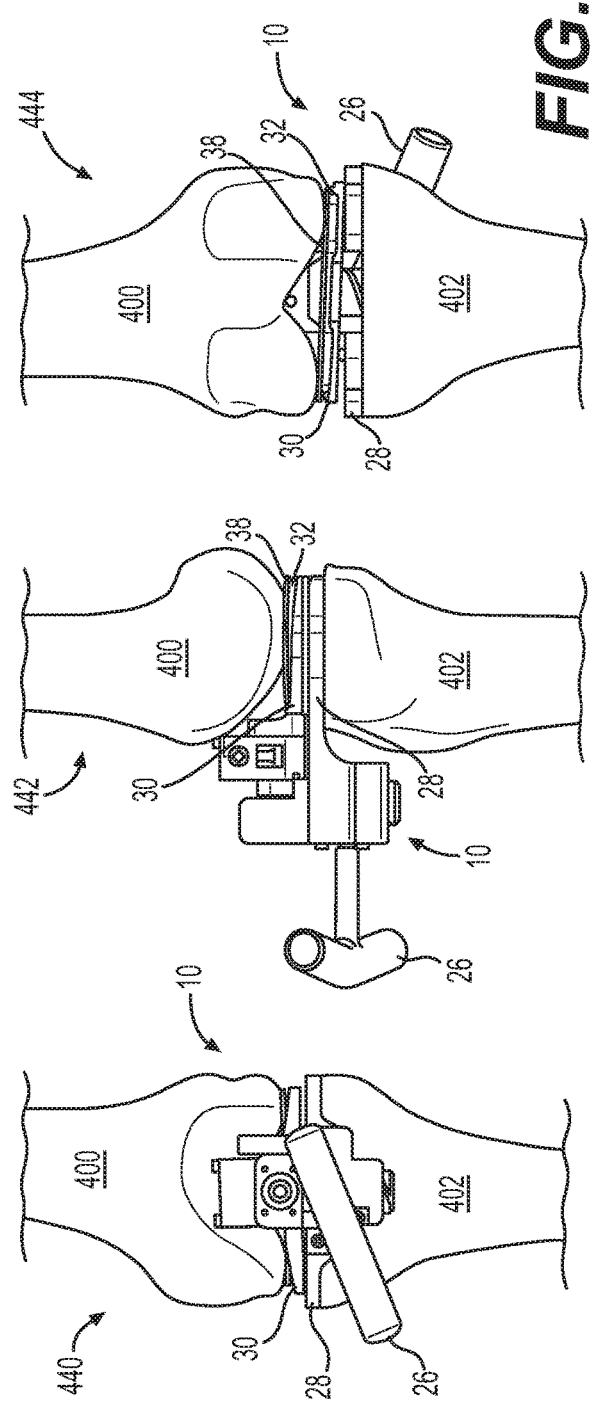
FIG. 29 illustrates a step of increasing the distraction distance until a predetermined loading is achieved in accordance with an example embodiment.

FIG. 29 illustrates a step of increasing the distraction distance until a predetermined loading is achieved in accordance with an example embodiment. In general, a predetermined loading as disclosed herein above and below does not imply a specific load value but a value chosen by a user. The predetermined loading can also be within a range or predetermined range. For example, the predetermined loading can be within a range of 20-40 lbs. or 20-60 lbs. for a knee joint. It can vary greatly depending on the musculoskeletal system or the joint system surgical apparatus 10 is used on. The user of surgical apparatus 10 will select the predetermined load value a medial or lateral compartment is set at. Similarly, a predetermined height is a height selected by the user or within a predetermined range set by the user or a component manufacturer. An anterior view 440, a side view 442, and a posterior view 444 of the knee joint is shown in FIG. 29 to illustrate placement of distractor 10. Fixed support structure 28 couples to the prepared bone surface of the proximal end of tibia 402. Module 32 is placed on moving support structure 30. Cover 38 couples to module 32. The condyles of femur 400 couple to cover 38. The load applied by the condyles of femur 400 to cover 38 is measured by load sensors in module 32 and transmitted to computer 12 as shown in FIG. 1.

Knob 26 couples to the distraction mechanism in distractor 10. Rotating knob 26 increases or decreases the distraction distance of distractor 10. In one embodiment, knob 26 is rotated to increase the distraction distance. Increasing the distraction distance will increase the tension on the ligaments of the knee thereby increasing the loading applied by the condyles to cover 38 and thereby module 32. In general, module 32 measures the loading applied to cover 38 and is displayed on display 14 as shown in FIG. 1. The surgeon increases the distraction distance until a predetermined loading is achieved. The predetermined loading corresponds to a known value that supports increased performance and reliability of the knee joint. In the example, moving support structure 30 has been released to swing freely medially or laterally. Typically, only one side (medial or lateral) will be distracted to the predetermined loading. The side not at the predetermined loading will be at a lesser value. The distractor 10 is then locked such that moving support structure 30 cannot increase or decrease the distraction distance.

Figure 30:
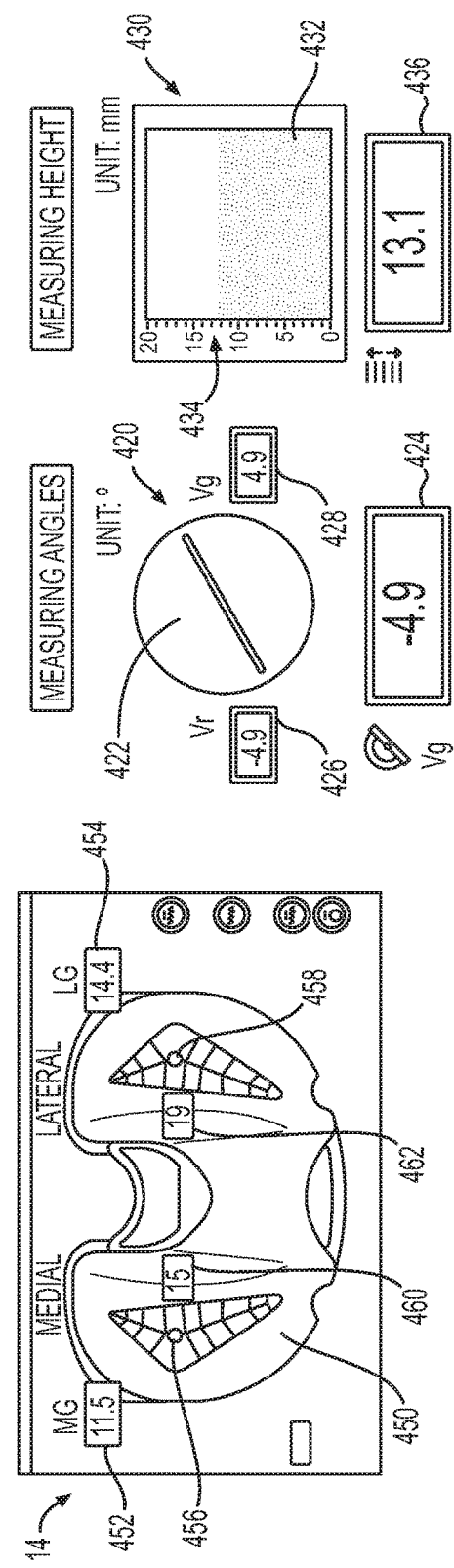
FIG. 30 illustrates a step of reviewing the position of load, the load magnitude, M-L tilt angle, and the distraction distance on the display as the distraction distance of the distractor is increased in accordance with an example embodiment.

FIG. 30 illustrates a step of reviewing the position of load, the load magnitude, M-L tilt angle, and the distraction distance on display 14 as the distraction distance of distractor 10 is increased in accordance with an example embodiment. The description will include components of FIG. 1 and FIG. 29. The quantitative measurement data is sent to computer 12 from distractor 10 and module 32. Display 14 includes a top view of cover 38. Circle 456 and circle 458 represent a location where the medial and lateral condyles of femur 400 respectively couple to a medial and lateral side of cover 38. Medial load magnitude data is indicated in box 460 and lateral load magnitude data is indicated in box 462. As mentioned previously, moving support structure 30 is allowed to freely rotate in a medial or lateral direction. Knob 26 is rotated until the distraction distance of distractor 10 is increased to the predetermined loading. In the example, the distraction distance is no longer increased when the lateral side of cover 38 measures 19 pounds at circle 458. Note that the loading is not balanced and the medial side of cover 38 measures 15 pounds at circle 460. Distractor 10 is then locked to prevent movement of moving support structure 30 shown in FIG. 29. In one embodiment, the predetermined load on the medial and lateral surface of cover 38 is in a range from 20 to 40 pounds.

Tilt meter 420 also shows an imbalance related to the M-L tilt angle of moving support structure 30 as shown in FIG. 29. Tilt meter 420 indicates the lateral side of moving support structure 30 is higher than the medial side. The measured M-L tilt angle is indicated in box 424 and corresponds to an angle between the plane of moving support structure 30 and the plane of fixed support structure 28. In the example, box 424 indicates an M-L tilt angle of −4.9 degrees. The distraction distance is also indicated on display 14. Bar graph 434 illustrates the distraction distance while box 436 provides a value of the distraction distance. In the example, box 436 indicates the distraction distance is 13.1 millimeters. In one embodiment, the distraction distance is an average because moving support structure 30 has an M-L tilt angle.

The height of the lateral compartment and the height of the medial compartment can also calculated from the distraction distance data and the M-L angle data. In one embodiment, the height of the medial compartment corresponds to a distance from the prepared bone surface of the tibia to the point where the medial condyle couples to the medial side of cover 38. Similarly, the height of the lateral compartment corresponds to a distance from the prepared bone surface of the tibia to the point where the lateral condyle couples to the lateral side of cover 38. The height of the medial compartment and the height of the latera compartment take into account the slope of moving support structure 30. The height of the medial compartment is indicated in box 452 and the height of the lateral compartment is indicated in box 454. In the example, the medial gap is 11.5 millimeters and the lateral gap is 14.4 millimeters. The difference in the height of the medial compartment and the height of the lateral compartment corresponds to an offset of the femur relative to the mechanical axis of the leg.

Figure 31:
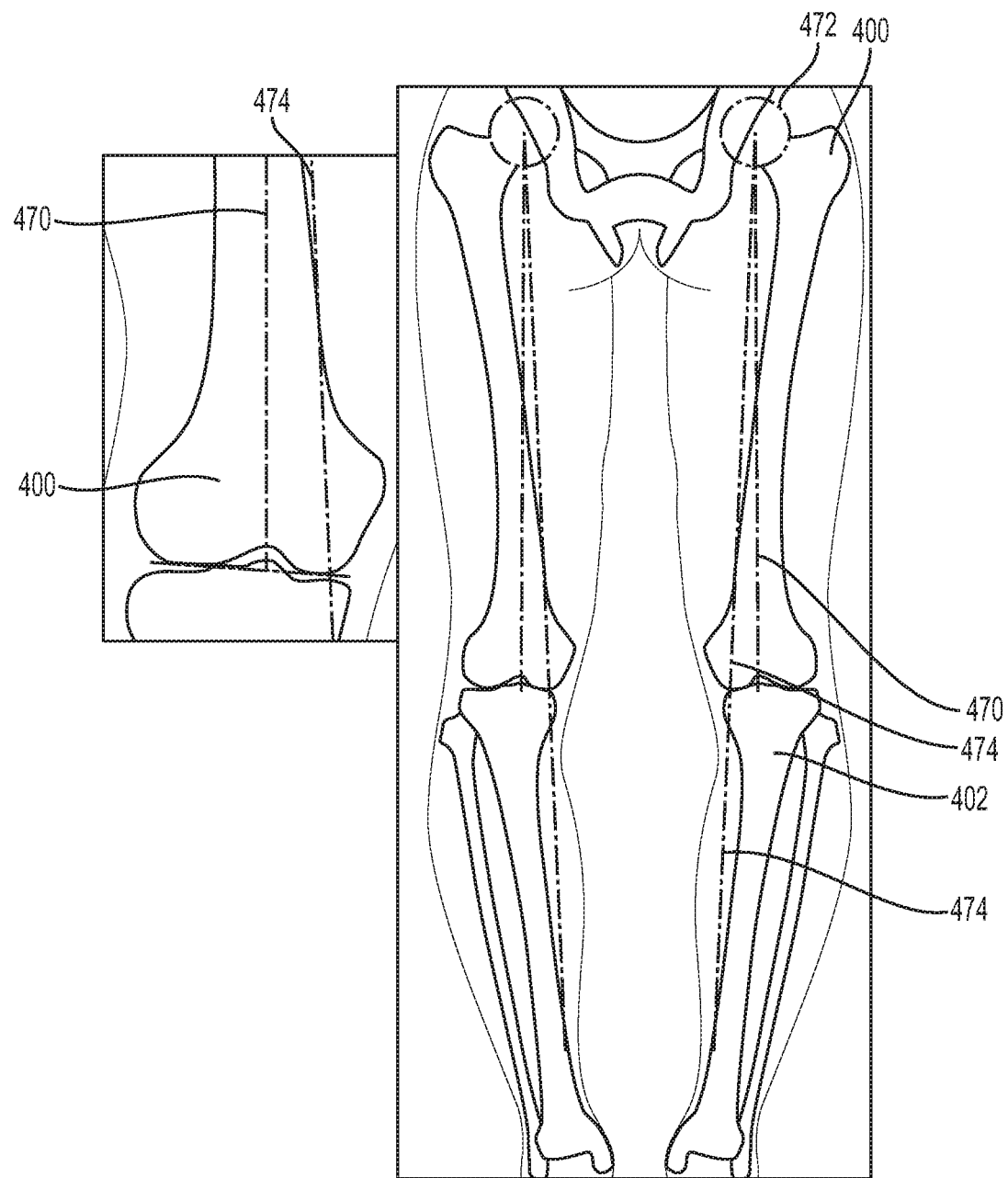
FIG. 31 illustrates a step of reviewing an x-ray in accordance with an example embodiment.

FIG. 31 illustrates a step of reviewing an x-ray of the leg in accordance with an example embodiment. The x-ray illustrates a femoral offset relative to the mechanical axis of the leg. Femur 400 is shown in the x-ray. A line 470 corresponds to a mechanical axis through femur 400. The mechanical axis couples through a center of a femoral head 472 to a center of the intercondylar notch of a distal end of femur 400. An offset or misalignment of femur 400 from the mechanical axis corresponds to line 474. Line 474 is a line drawn from the center of femoral head 472 to a center of the ankle.

Typically, the offset of femur 400 is measured prior to or during a knee replacement surgery. As shown, lines 470 and 474 can be drawn on the x-ray and the offset can be measured with a protractor or other angle measurement device. In one embodiment, the angle formed by lines 470 and 474 corresponds to the M-L tilt angle measured in FIG. 30. The offset measured in the x-ray is compared against the M-L tilt angle measured by distractor 10 as seen in FIG. 1. In general, the M-L tilt angle and the offset angle measured in the x-ray should be approximately equal.

Figure 32:
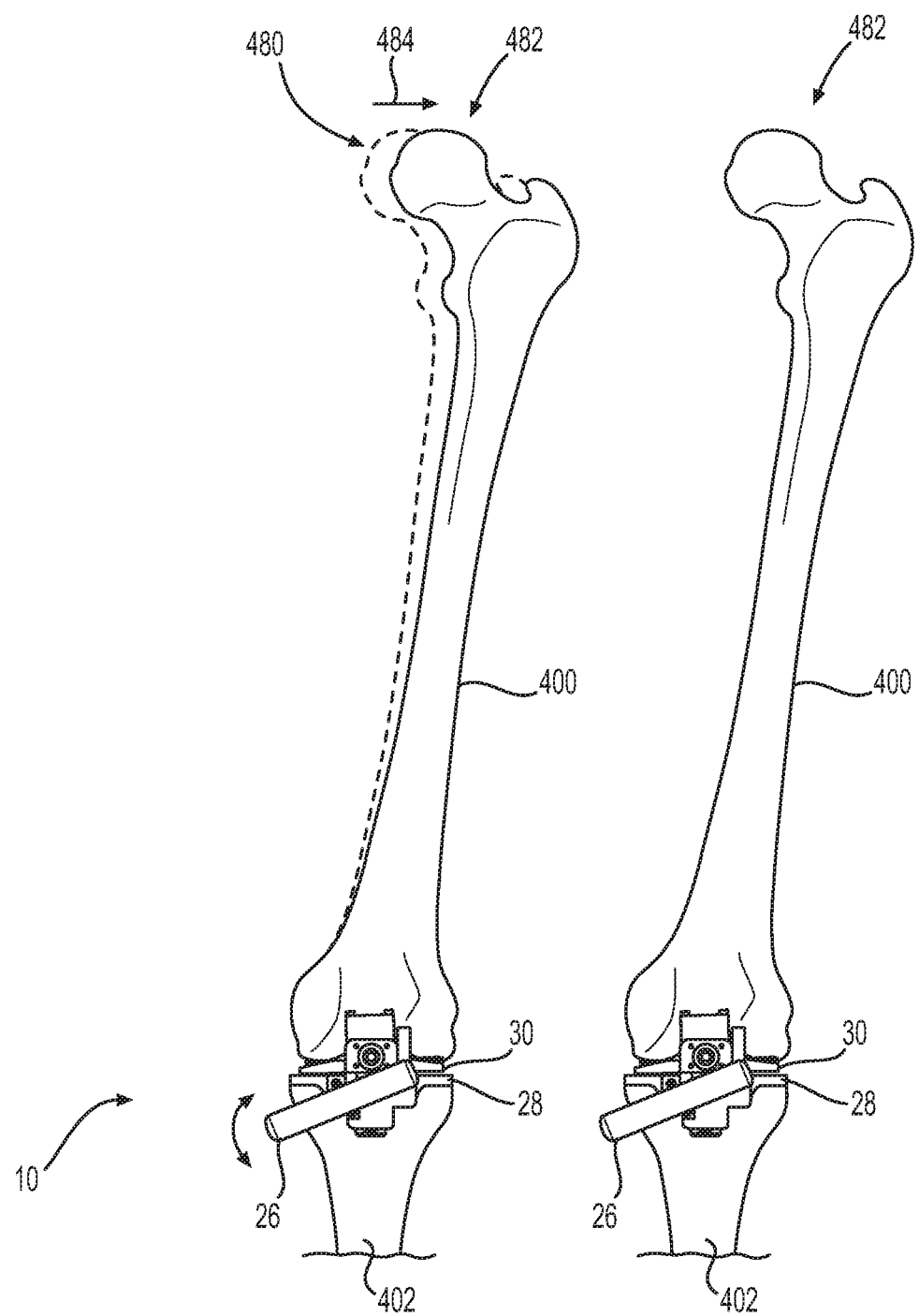
FIG. 32 illustrates an equalizing step where the M-L angle of the moving support structure is adjusted in accordance with an example embodiment.

FIG. 32 illustrates an equalizing step where the M-L angle of moving support structure 30 is adjusted in accordance with an example embodiment. As mentioned previously, distractor 10 is locked such that moving support structure 30 cannot increase or decrease the distraction distance. Also, moving support structure 30 had been allowed to freely rotate medially or laterally. In one embodiment, the M-L tilt mechanism of distractor 10 can be engaged to moving support structure 30 and is self-locking when changing an M-L tilt angle. A key, handle, or knob is coupled to the M-L tilt mechanism to change the M-L tilt angle of moving support structure 30. In one embodiment, the key is rotated to adjust the M-L tilt mechanism. Initially, as indicated in FIG. 30, the M-L tilt angle of moving support structure 30 is −4.9 degrees. Femur 400 with the M-L tilt angle of −4.9 degrees corresponds to a position 480. The key is rotated to adjust the M-L tilt mechanism thereby changing the M-L tilt angle from −4.9 degrees to zero degrees. Changing the M-L tilt angle rotates the femur 400 as indicated by arrow 484 until a position 482 is reached. The position 482 is shown without any further movement in FIG. 32 where the M-L tilt angle measured by distractor 10 is zero degrees. It should be noted that the loading on the medial and lateral side of cover 38 of FIG. 29 can change as well as the position of loading on the medial and lateral side.

FIG. 33 illustrates a step of monitoring equalization of femur 400 of FIG. 32 on display 14 in accordance of an example embodiment. In one embodiment, the surgeon can monitor display 14 as the key is rotated on the M-L tilt mechanism. The surgeon rotates the key until M-L tilt angle is zero. This also corresponds to the condition where the plane of fixed support structure 28 of FIG. 32 and the plane of moving support structure 30 are parallel to one another. Note that the average distraction distance as indicated in box 436 does not change. The medial gap as indicated in box 452 and the lateral gap as indicated by box 454 does change because the M-L tilt has changed to zero. The medial gap indicated in box 452 reads 12.9 millimeters and the lateral gap indicated in box 454 reads 13.2. Referring briefly to FIG. 31, the step of equalizing moves the center of the femoral head 472 medially as shown in FIG. 32. Note on FIG. 31 that moving the center of the femoral head 427 medially reduces the offset angle formed by lines 470 and 474 thereby placing the leg in better alignment. In general, the step of equalizing eliminates or reduces the offset of the femur 400 to an acceptable alignment based on clinical evidence.

Alternatively, referring to FIGS. 27-35, distractor 10 respectively couples a support structure 30 to femur 400 and a support structure 28 to a tibia 402. Femur 400 and tibia 402 can have natural surfaces or prepared bone surfaces. In the example, distractor 10 is configured to support at least one bone cut to femur 400 for an installation of a femoral prosthetic component that is in alignment, loaded correctly, and balanced. In one embodiment, fluoroscope images, CT scans, MRI, or other assessment techniques can be used prior to surgery and in surgery to provide information related to alignment, loading, balance, contact point, contact point rotation to support the one or more bone cut to achieve an optimal outcome. The leg is placed in a first predetermined pose. In one embodiment, the leg is placed in extension. Distractor 10 is inserted into a knee joint and knob 26 in a minimum height configuration. Distraction mechanism 24 is configured to increase or decrease a distance between support structures 28 and 30 by rotating knob 26. Distraction mechanism 24 is rotated until a predetermined load value is measured by distractor 10 and indicated on the computer receiving the quantitative measurement data. Typically, a single side (medial or lateral) of measurement module 32 will measure the predetermined load value while the remaining side will not be at the predetermined load value. Also, support structure 30 will be at a first tilt relative to support structure 28. In one embodiment, the tilt of support structure 30 corresponds to a difference in heights of the medial and lateral compartments being distracted. The computer will display the tilt value of support structure 30 and load values on the medial and laterals sides of measurement module 32 in real time. As mentioned herein above, the medial and lateral compartment heights are also measured and displayed on the display. Tilt mechanism 22 is then adjusted under user control such that the medial and lateral sides are loaded equally. Adjusting tilt mechanism 22 changes a position of support structure 30 from the first tilt to a second tilt. The medial and lateral compartment heights change on the display of the computer as support structure 30 changes to the second tilt. In one embodiment, a bone cut is subsequently made to the femur that corresponds to the second tilt that yields the predetermined load value. It should be noted that the example sets the load values on the medial and lateral compartments equal. The medial and lateral compartments can be set to different load values if desired. In one embodiment, the final insert coupling to the femoral prosthetic component in a prosthetic knee joint comprises a surface of equal heights on the medial and lateral sides. Cutting a portion of the distal end of the femur related to the second tilt compensates for differences in height for balanced loading measured by distractor 10 when using the final insert having equal medial and lateral heights for the leg in extension. As mentioned previously, other bone cut compensation can also be added with or to the second tilt value to adjust for defects, alignment issues, or other anomalies found in the assessments prior to surgery. Although described for distractor 10, the use applies to all surgical apparatus disclosed herein as they all operate similarly.

Figure 34:
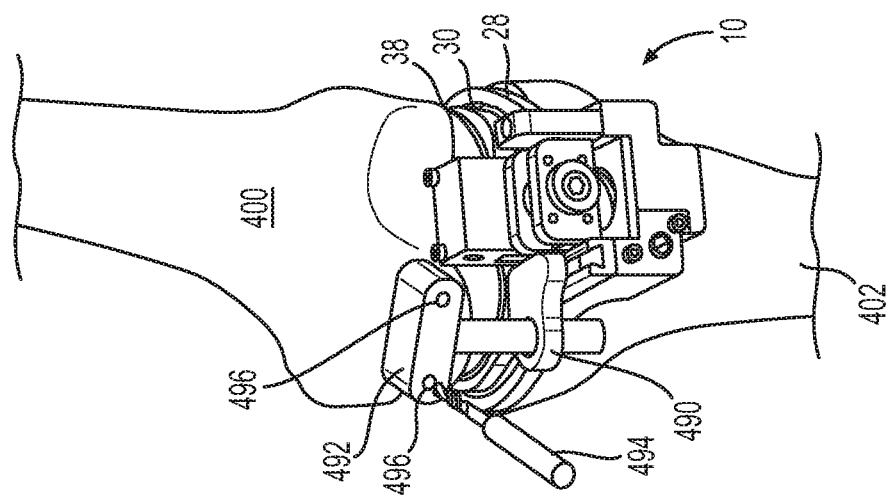
FIG. 34 illustrates a step of drilling guide holes in the femur in accordance with an example embodiment.

FIG. 34 illustrates a step of drilling guide holes in femur 400 in accordance with an example embodiment. As disclosed in FIG. 32 and FIG. 33, distractor 10 the height of the medial compartment and the height of the lateral compartment have been made equal. Equalizing the medial and lateral compartment heights eliminates or reduces the femoral offset relative to the mechanical axis of the leg such that the leg is in alignment. Moving support structure 30 has been locked to prevent movement or change of the distraction distance. The medial compartment height and the lateral compartment height having an M-L tilt angle of zero are also locked in place. In one embodiment, the M-L tilt mechanism is self-locking. The knob coupled to the M-L tilt mechanism has been removed so the M-L tilt angle cannot be changed. Adjustments to change the applied loading to the medial or lateral surface of cover 38 are performed prior to drilling guide holes. For example, soft tissue release can be performed to adjust the load values.

Femur 400 is in alignment with the mechanical axis having the height of the medial compartment equal to the height of the lateral compartment. The load and position of load on the medial side and the lateral side of cover 38 have been quantitatively measured and verified within acceptable predetermined ranges for the prosthetic knee joint system. The measured distraction height relates to a thickness of an installed final tibial prosthetic component, a final insert, and a final femoral prosthetic component. Thus, femur 400 guide pin holes can be drilled to align and support a resection guide for the distal end of femur 400. A drill guide holder 490 is coupled to distractor 10. A drill guide 492 couples to drill guide holder 490. Drill guide holder 490 aligns and retains drill guide 492 adjacent to the distal end of femur 400. Drill guide 492 includes one or more openings 496 that receive a drill bit 494 to drill openings in the distal end of femur 400.

Figure 35:
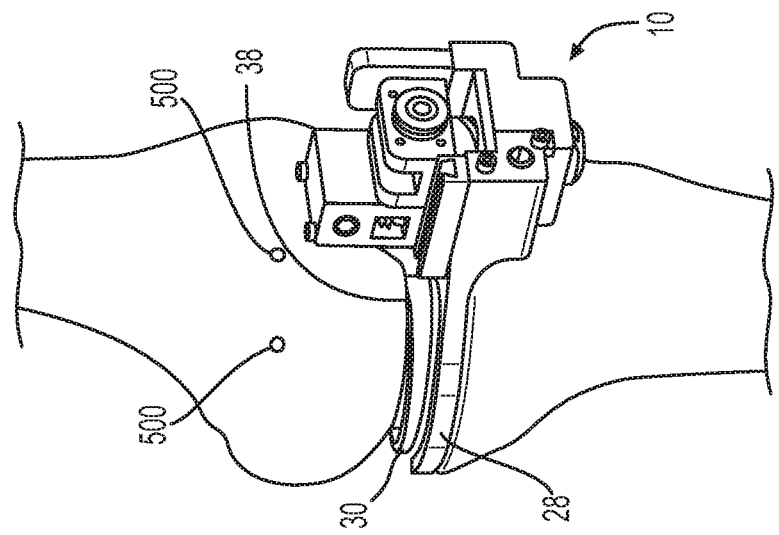
FIG. 35 illustrates a step of removing a drill guide and drill guide holder from the distractor in accordance with an example embodiment.

FIG. 35 illustrates a step of removing drill guide 492 and drill guide holder 490 of FIG. 34 from distractor 10 in accordance with an example embodiment. Holes 500 are drilled using drill guide holder 490 and drill guide 492 coupled to distractor 10 as shown in FIG. 34. Holes 500 will subsequently be used to couple a resection guide to femur 500 and make one or more cuts for fitting a femoral prosthetic component to the distal end of femur 400.

FIG. 36 illustrates a step of reducing the distraction distance of distractor 10 and placing the leg in flexion in accordance with an example embodiment. The M-L tilt mechanism is released allowing moving support structure 30 to freely swing medially or laterally. Distractor 10 is adjusted to a minimum distraction distance. In one embodiment, the minimum distraction distance occurs when both fixed support structure 28 and moving support structure 30 couple to the prepared surface at the proximal end of tibia 402. As mentioned previously, the plane of fixed support structure 28 corresponds to zero degrees M-L tilt. In one embodiment, the minimum distraction distance is 6.8 millimeters. The leg can be placed in flexion where tibia 402 and femur 400 form a 90 degree angle. In one embodiment, module 32 includes an inertial sensor configured to measure the angle between femur 400 and tibia 402. The inertial sensor data is transmitted to the computer and can be displayed on display 14.

Display 14 is shown with tilt meter 420 and bar graph 430. Tilt meter 420 indicates an M-L tilt angle of zero degrees. Since moving support structure 30 can swing freely medially or laterally it couples to the prepared surface of tibia 402 with fixed support structure 28. Thus, both are coupled to the same plane and the M-L tilt angle is zero degrees. The M-L tilt mechanism was enabled in FIG. 32 and adjusted to equalize the medial and lateral gap such that the M-L tilt angle is zero. The M-L tilt angle of 0.0 degrees is indicated in box 424. The bar graph 430 indicates a minimum distraction distance on bar 432. The minimum distraction distance of 6.8 millimeters is shown in box 436.

Figure 37:
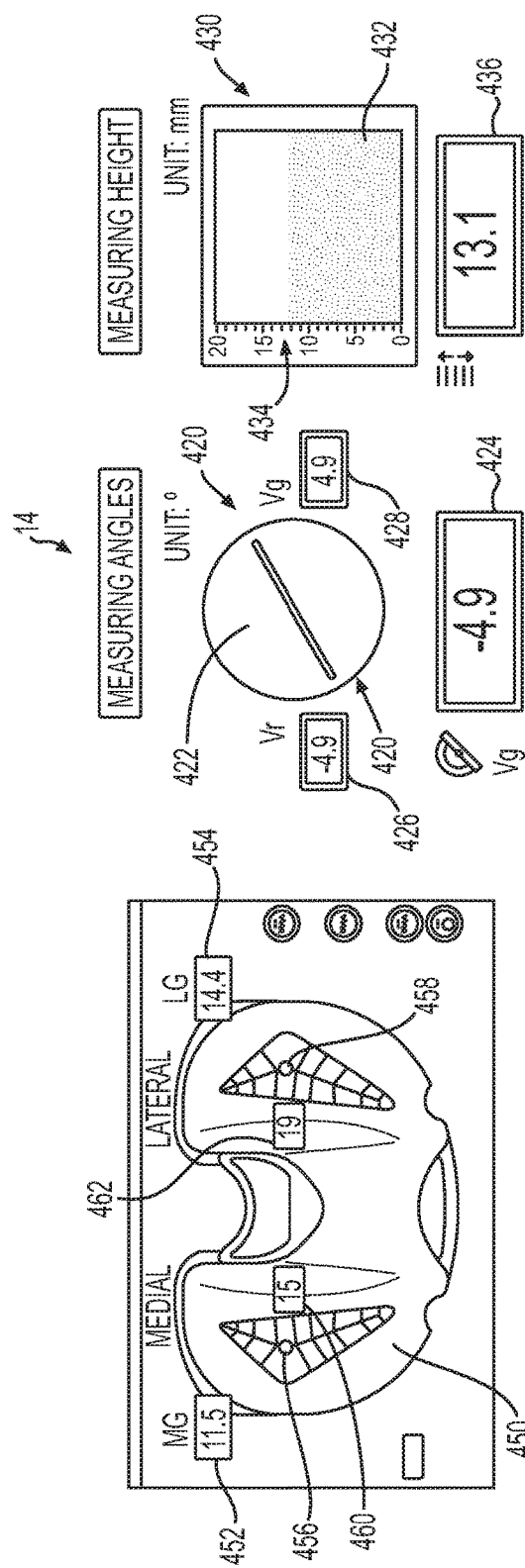
FIG. 37 illustrates a step of adjusting the distraction distance while the leg is in flexion in accordance with an example embodiment.

FIG. 37 illustrates a step of adjusting the distraction distance while the leg is in flexion in accordance with an example embodiment. The step of adjusting the distraction distance is similar to when the leg was in extension. Distractor 10 of FIG. 36 is adjusted to increase the distraction distance from the minimum distraction distance. The loading on the medial and lateral sides of cover 38 of FIG. 36 will increase as the distraction distance increases. In one embodiment, the surgeon is viewing the load magnitude on display 14 as the distraction distance is increased. This is indicated in box 460 and box 462 on display 14 showing the position of load on the medial and lateral surface of cover 38. The distraction distance is increased until the loading on cover 38 reaches a predetermined value. Note that the values on the medial and lateral sides of cover 38 are not equal under flexion but the maximum load value corresponds to the desired predetermined value.

The moving support structure of FIG. 36 was released from the M-L tilt mechanism to allow it to freely swing medially or laterally when in flexion. M-L tilt meter 420 indicates the M-L tilt angle and the value is displayed in box 424 as −4.9 degrees. The distraction distance is also displayed in bar graph 430 and the value of 13.1 millimeters is displayed in box 436. The distraction distance is an average distance. The height of the medial compartment and the height of the lateral compartment is calculated by computer 12 of FIG. 1 using the measurement data such as the M-L tilt angle, the position of load, and distraction distance. The height of the medial compartment is measured as 11.5 millimeters as shown in box 452 of display 14. The height of the lateral compartment is measured as 14.4 millimeters as shown in box 454 of display 14. The measurement data listed herein above can be stored in memory of computer 12 shown in FIG. 1.

Figure 38:
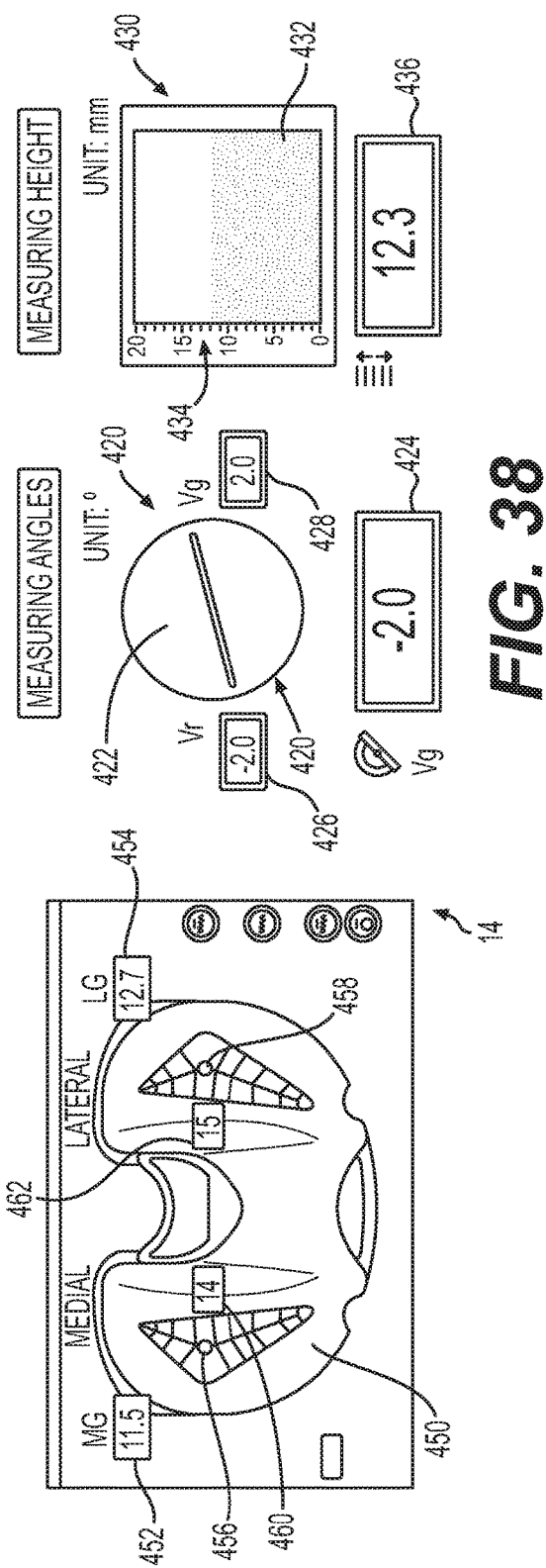
FIG. 38 illustrates a step of equalizing the medial gap and the lateral gap with the leg in flexion in accordance with an example embodiment.

FIG. 38 illustrates a step of equalizing the height of the medial compartment and the height of the lateral compartment with the leg in flexion in accordance with an example embodiment. The distraction mechanism is locked to prevent movement of moving support structure 30 of FIG. 36. The M-L tilt mechanism is engaged to adjust the M-L tilt angle of moving support structure 30. As mentioned previously, M-L tilt mechanism is self-locking. The M-L tilt angle is adjusted to equalize the M-L tilt angle to zero degrees with the leg in flexion. Adjusting the M-L tilt angle to zero degrees equalizes the height of the medial and lateral compartments with the leg in flexion. Similar to FIG. 31 an offset of the leg alignment in flexion is reduced when the medial gap and the lateral gap equalized. The loading on the medial and lateral sides of cover 38 is viewed on display 14 and adjusted if the loading is too high or the balance is significantly off. Typically, soft tissue release is used to adjust the loading and balance.

After adjustments have been made under equalized conditions the distraction mechanism lock is released and the M-L tilt mechanism is disengaged to allow moving support structure 30 to freely rotate medially and laterally. Measurement data should indicate that the medial and lateral gap are closer than was previously measured in flexion. The measurement data should also indicate the medial and lateral sides are in better balance and the load magnitude is within a predetermined range that supports performance and reliability of the knee joint. In the example, the medial gap is listed in box 452 as 11.5 millimeters. The lateral gap is listed in box 454 as 12.7 millimeters. The difference between the applied load between the medial and lateral sides is 1 lb and the highest load magnitude is 15 lbs on the lateral side of cover 38. The difference in the gap height between the knee joint in extension and the knee joint in flexion can be due to knee geometry or position of applied load on cover 38. The gap data, load data, balance data, and M-L tilt angle is stored in memory on computer 12 as shown in FIG. 1. It should be noted that the values disclosed herein above for the knee in extension and flexion can vary significantly from the data disclosed and is only used as an example.

Figure 39:
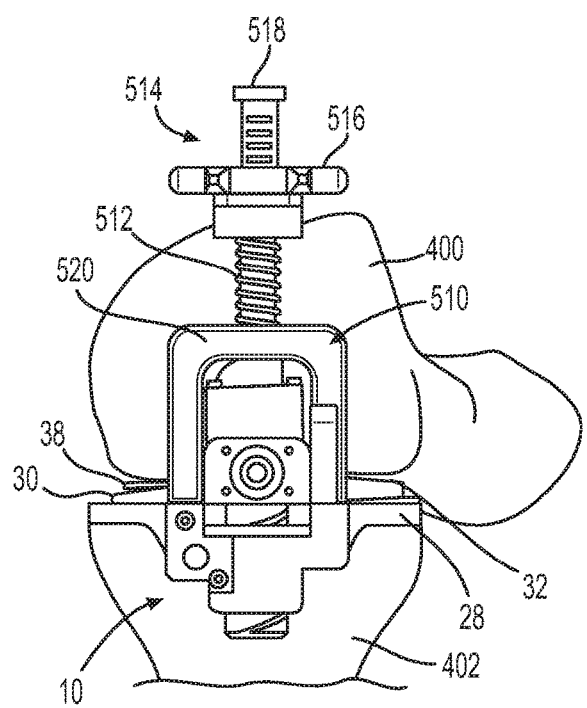
FIG. 39 illustrates a step of placing a sizer on the distractor to support selection of a femoral prosthetic component in accordance with an example embodiment.

FIG. 39 illustrates a step of placing a sizer 510 on distractor 10 to support selection of a femoral prosthetic component in accordance with an example embodiment. Selecting a correct size for the femoral prosthetic component minimizes overhang of the femoral prosthetic component, minimizes bone resection, and maximize coverage using algorithms to determine an optimal installation for different models of the femoral prosthetic component. Previously, the leg was equalized and adjusted in flexion using quantitative measurement information from module 32 and distractor 10 as shown in FIG. 36. A sizer 510 is configured to couple to distractor 10 with the leg in flexion. In the example embodiment, tibia 402 is at approximately a 90 degree angle to femur 400. The exact angle can be quantitatively measured with an inertial sensor in module 32. Sizer 510 comprises a fork 520, a femur coupler, a threaded cylinder 518, a spring 512, a knob 516, and a scale 514. Fork 520 includes one or more retaining features that align and retain fork 520 to distractor 10. Threaded cylinder 518 extends from fork 520 above femur 400 in flexion. Spring 512 overlies threaded cylinder 518 and is supported by fork 520. The femur coupler couples to the threaded cylinder 518 and femur 400. In one embodiment, threaded cylinder 518 couples through an opening of the femur coupler such that a portion of the femur coupler is supported by spring 512. The femur coupler also couples to a location on femur 400. Knob 516 threads onto threaded cylinder 518 and couples to the femur coupler. Spring 512 provides resistance against the femur coupler and knob 516. Scale 514 is formed on threaded cylinder 518 and is visible above a top surface of knob 516. Scale 514 is used to select a femoral prosthetic component size.

Figure 40:
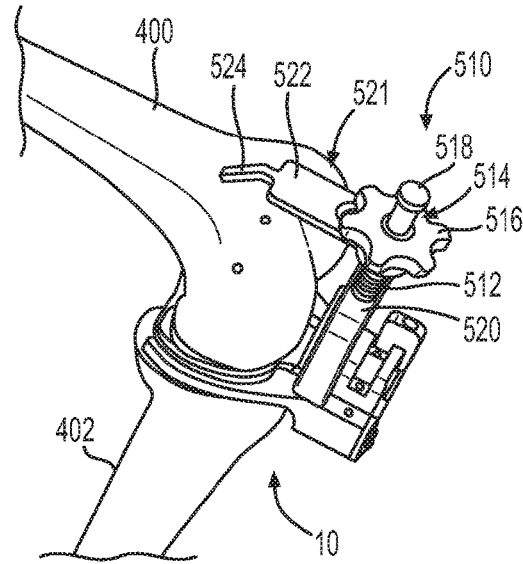
FIG. 40 illustrates a step of coupling a femur coupler to the femur with the leg in flexion in accordance with an example embodiment.

FIG. 40 illustrates a step of coupling a femur coupler 521 to femur 400 with the leg in flexion in accordance with an example embodiment. Femur coupler 521 comprises a body 522 and an extension 524. Body 522 extends femur coupler 521 from threaded cylinder 518 over femur 400. Extension 524 extends from body 522 and couples to femur 400. In one embodiment, extension 524 includes at least one bend that supports coupling to femur 400 without body 522 coupling to femur 400. Extension 524 can couple to a predetermined location on femur 400 or a bone landmark of femur 400. As mentioned previously scale 514 can be read above a surface of knob 514 to support selection of the femoral prosthetic component.

Figure 41:
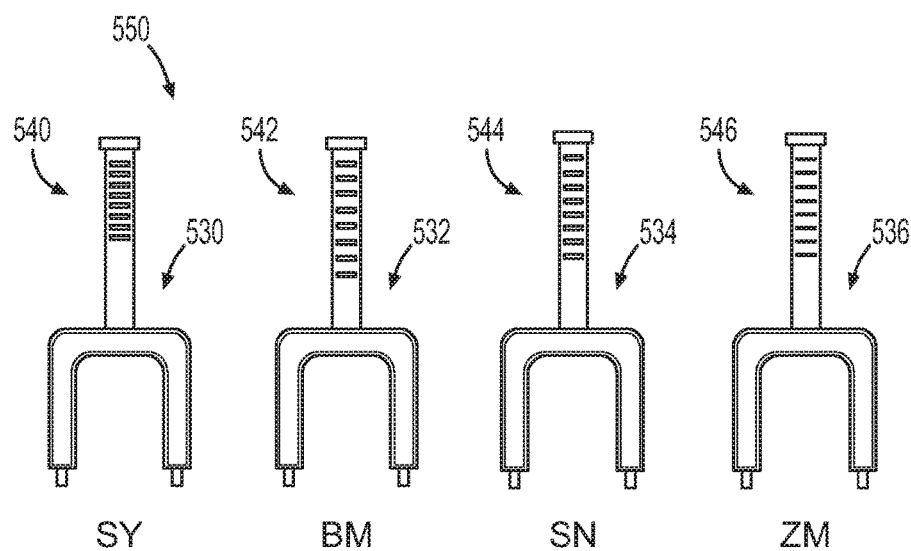
FIG. 41 illustrates a step of providing a plurality of sizers to support selection of the femoral prosthetic component.

FIG. 41 illustrates a step of providing a plurality of sizers 550 to support selection of the femoral prosthetic component. In one embodiment, four different sizers are provided to select the femoral prosthetic component that best fits the knee joint. A sizer 530 is labeled SY and includes a scale 540. A sizer 532 is labeled BM and includes a scale 542. A sizer 534 is labeled SN and includes a scale 544. A sizer 536 is labeled ZM and includes a scale 546. The scales 540, 542, 544, and 546 are all different and support selection of the femoral prosthetic component. Sizers 530, 532, 534, and 536 can have one or more drill guide holes configured to support drilling holes in the distal end of the femur 400.

FIG. 42 illustrates a step of drilling one or more holes in the distal end of femur 400 in flexion in accordance with an example embodiment. The one or more holes will be used to align or support a cutting guide configured to prepare a surface of the femur 400. The leg is in flexion having femur 400 and tibia 402 at approximately a 90 degree angle. Distractor 10 has been used to equalize the knee joint, align the leg, and the load magnitudes have been adjusted if needed. A sizer 510 has been selected as providing the best fit for femur 400. Sizer 510 has one or more drill guides 550 for receiving a drill bit 552 to drill femur 400. A drill using drill bit 552 is used to drill a hole in femur 400 using drill guide 550.

FIG. 43 illustrates one or more holes drilled in the distal end of the femur in accordance with an example embodiment. Holes 554 are drilled in the distal end of the femur to support the cutting guide for preparing a bone surface of the femur 400 for receiving the femoral prosthetic component. Distractor 10 and sizer 510 of FIG. 42 were used to drill holes 554 at predetermined locations. The distractor 10 is removed from the knee joint.

Bone surfaces of the distal end of femur 400 are prepared and the femoral prosthetic component is installed. Similarly, the tibial prosthetic component can be installed. Module 32 can be installed in an insert 308 as disclosed in FIG. 24 and FIG. 25. Insert 308 can be installed in the knee joint such that insert 308 is coupled to and retained by the tibial prosthetic component. The knee joint can be moved through a range of motion for the surgeon to gain subjective feedback on the knee joint installation. Module 32 will send quantitative measurement data to the computer 12 as shown in FIG. 1 for further evaluation. In general, module 32 should provide similar measurement data as generated in flexion and extension using distractor 10. In one embodiment, computer 12 checks the measurement data from insert 308 and compare it to the previously measured data using distractor 10. Thus, module 32 and insert 308 can be used to verify proper installation of the knee joint. Moreover, fine adjustments can be made to further improve the joint installation prior to finalizing the installation. The insert 308 is then removed and a final insert equal in size is inserted to complete the knee joint installation.

Alternatively, referring to FIGS. 36-43, distractor 10 respectively couples a support structure 30 to femur 400 and a support structure 28 to a tibia 402 in a second predetermined pose. As shown, the leg is placed in flexion at a 90 degree angle. Femur 400 and tibia 402 can have natural surfaces or prepared bone surfaces. In the example, distractor 10 is configured to support at least one bone cut to femur 400 for an installation of a femoral prosthetic component that is in alignment, loaded correctly, and balanced in flexion. In one embodiment, fluoroscope images, CT scans, MRI, or other assessment techniques can be used prior to surgery and in surgery to provide information related to alignment, loading, balance, contact point, contact point rotation to support the one or more bone cut to achieve an optimal outcome in flexion. The leg is placed in the second predetermined pose and distractor inserted after being placed in the minimum height configuration. Distraction mechanism 24 is configured to increase or decrease a distance between support structures 28 and 30 by rotating knob 26. Distraction mechanism 24 is rotated until a predetermined load value is measured by distractor 10 and indicated on the computer receiving the quantitative measurement data in flexion. Typically, a single side (medial or lateral) of measurement module 32 will measure the predetermined load value while the remaining side will not be at the predetermined load value in flexion. Also, support structure 30 will be at a first tilt relative to support structure 28 in flexion. In one embodiment, the tilt of support structure 30 corresponds to a difference in heights of the medial and lateral compartments being distracted in flexion. The computer will display the tilt value of support structure 30 and load values on the medial and laterals sides of measurement module 32 in real time. As mentioned herein above, the medial and lateral compartment heights are also measured and displayed on the display in flexion. Tilt mechanism 22 is then adjusted under user control such that the medial and lateral sides are loaded equally in flexion. Adjusting tilt mechanism 22 changes a position of support structure 30 from the first tilt to a second tilt in flexion. The medial and lateral compartment heights change on the display of the computer as support structure 30 changes to the second tilt in flexion. In one embodiment, a bone cut is subsequently made to the femur that corresponds to the second tilt that yields the predetermined load value in flexion. It should be noted that the example sets the load values on the medial and lateral compartments equal in flexion. The medial and lateral compartments can be set to different load values if desired in flexion. In one embodiment, the final insert coupling to the femoral prosthetic component in a prosthetic knee joint comprises a surface of equal heights on the medial and lateral sides. Cutting a second portion of the distal end of the femur related to the second tilt in flexion compensates for differences in height for balanced loading measured by distractor 10 when using the final insert having equal medial and lateral heights for the leg in extension. In one embodiment, the cut of the second portion of the distal end of the femur is designed to work with the cut of the first portion of the distal end of the femur to allow optimal loading, balance, and alignment over the full range of motion of the leg with the femoral prosthetic component, final insert, and tibial prosthetic component. All the quantitative measurements taken using distractor 10 translates to the final knee prosthetic component installation. As mentioned previously, other bone cut compensation can also be added with or to the second tilt value to adjust for defects, alignment issues, or other anomalies found in the assessments prior to surgery. Although described for distractor 10, the use applies to all surgical apparatus disclosed herein as they all operate similarly.

Figures 44, 45:
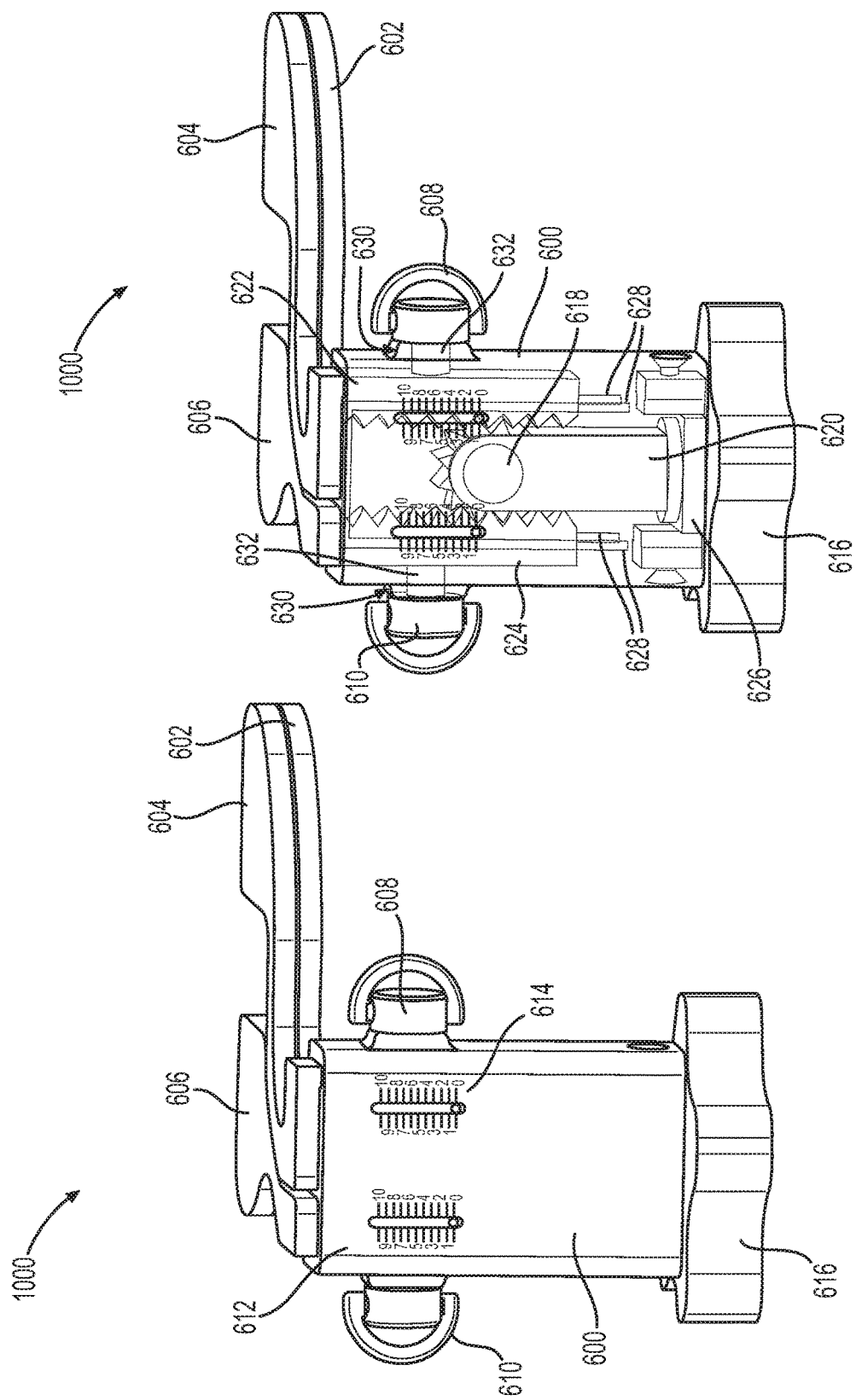
FIG. 44 is an illustration of an alternate embodiment of a distractor in accordance with an example embodiment.
FIG. 45 is an illustration of the alternate embodiment of the distractor with a transparent housing to illustrate components therein in accordance with an example embodiment.

FIG. 44 is an illustration of a distractor 1000 in accordance with an example embodiment. Referring briefly to FIG. 1 distractor 10 is configured to distract a knee joint, transmit measurement data to a remote system such as a computer 12, and display the measurement data in real-time on display 14 in an operating room. Distractor 1000 is an alternate embodiment of distractor 10. Distractor 1000 can be used similarly to distractor 10 as disclosed herein above. Distractor 1000 can include one or more sensors to measure distraction height, medial-lateral angle, load magnitude applied by the musculoskeletal system to the distractor, leg position, support one or more bone cuts, support alignment, and measure position of load applied to the medial and lateral surfaces of the distractor.

Referring back to FIG. 44, the distractor 1000 comprises a housing 600, a fixed plate 602, lateral plate 604 (for a knee joint of a left leg), a medial plate 606 (for the knee joint of the left leg), a lateral brake 608, a medial brake 610, a knob 616, a lateral height scale 614, and a medial height scale 612. Knob 616 is used to raise and lower lateral plate 604 and medial plate 606 in relation to fixed plate 602. Fixed plate 602 couples to a prepared surface of a tibia. In one embodiment, knob 616 is rotated counter clockwise or clockwise to raise or lower plates 604 and 606. The amount of lateral distraction and medial distraction can be respectively read off of lateral scale 614 and medial scale 612 on housing 600. One or more magnetic height sensors can be used to measure the lateral and medial distraction heights as disclosed herein above. The electronic circuitry as disclosed in FIG. 15 is coupled to the one or more magnetic height sensors and placed within housing 600 to control a measurement process and transmit the height data to be displayed on a display within the operating room. Distractor 1000 can be used in a knee joint of the right leg with the knowledge that the medial and lateral sides of distractor 1000 are transposed. Alternatively, a second distractor could be provided for a right leg. Note that distractor 1000 has plates 604 and 606 offset. The offset supports placement of the patella on a lateral side of the knee joint and allows the patella to be placed back on the knee joint after distractor 1000 is inserted. The patella loads the knee joint which is taken into account in all the measurement data and subsequent steps taken prior to the knee joint installation. The second or right leg distractor provided with distractor 1000 would have an opposite offset to support placement of the patella laterally on the right knee joint prior to installation of the second distractor.

Distractor 1000 is configured to distract, equalize, and support alignment of a leg to the mechanical axis of the leg by one or more bone cuts to the femur. The bone cuts to a distal end of the femur support installation of a femoral prosthetic component that aligns the femur and tibia to the mechanical axis. Distractor 1000 is used to drill guide holes for a cutting jig with the leg in extension and flexion. The cutting jig is then coupled to the distal end using the guide holes and the bone cuts are made. In general, distractor 1000 is configured to generate an offset on the prepared surfaces of the distal end of the femur that reduces or eliminates a varus or vargus leg deformity that supports an installation of a prosthetic knee joint in alignment to the mechanical axis of the leg.

FIG. 45 is an illustration of the distractor 1000 with a transparent housing to illustrate components therein in accordance with an example embodiment. Knob 616 is configured to rotate to raise and lower slide block 620. In one embodiment, a threaded shaft extends from knob 616. The threaded shaft is aligned and retained by a structure 626 formed in housing 600. In one embodiment, structure 626 can have an opening with a bearing surface. The threaded shaft can have a region that is not threaded that couples to the bearing surface of structure 626 to support alignment of the threaded shaft within housing 600 and rotation of the threaded shaft. Alternatively, structure 626 can have a threaded opening for receiving the threaded shaft. Slide block 620 includes a threaded opening configured for receiving the threaded shaft coupled to knob 616. In one embodiment, slide block 620 is not fastened to housing 600 whereas structure 626 is attached or integrated as part of housing 600. Thus, rotating knob 616 can raise or lower slide block 620 in relation to structure 626 but only slide block 620 can move in relation to housing 600.

Slide block 620 is housed within housing 600 and includes a free wheel gear 618. In one embodiment, free wheel gear 618 is located at a proximal end of slide block 620 and configured to rotate. A post 622 extends from lateral plate 604 and is configured to move parallel to slide block 620 and the threaded shaft. Post 624 has gear teeth engaging with free wheel gear 618. Similarly, a post 624 extends from medial plate 606 and is configured to move parallel to slide block 620 and the threaded shaft. Post 622 has gear teeth engaging with free wheel gear 618. Posts 622 and 624 extend through openings in a proximal end of housing 600 into an interior of the housing. Housing 600 aligns, retains, and supports movement of lateral plate 606 and medial plate 604. In one embodiment, grooves are formed in posts 622 and 624. Housing 600 has corresponding tongues 628 that fit within the grooves that align and retain post 622 and post 624 to the housing. Tongues 628 extending from an interior surface of housing 600 are received within the grooves of posts 622 and 624 and are configured to support movement parallel to the threaded shaft and slide block 620.

In the illustration, knob 616 cannot be rotated clockwise as slide block 620 contacts structure 626 whereby no gap exists to allow further rotation or the threaded shaft. In this position, lateral plate 606 and medial plate 604 are in a minimum height position corresponding to lateral plate 606 and medial plate 604 contacting fixed plate 602. Fixed plate 602 is coupled to housing 600. In one embodiment, fixed plate 602 extends from housing 600 and is molded or machined as part of housing 602. Fixed plate 602 can be at a 90 degree angle relative to the movement of post 622, post 624, slide block 620, and the threaded shaft.

Brakes 608 and 610 respectively prevent movement of post 622 and post 624. In one embodiment, brakes 608 and 610 are friction brakes. Brakes 608 or 610 can include a threaded shaft 632. The threaded shaft 632 of brakes 608 or 610 couples through a threaded opening 630 formed in housing 600. Rotating threaded shaft 632 in opening 630 clockwise or counter clockwise can respectively increase or decrease the depth of threaded shaft 632 within housing 600. In one embodiment, threaded shaft 632 of brake 608 contacts and applies pressure to post 622 as brake 608 is rotated clockwise. The pressure applied to post 622 presses tongues 628 against the corresponding grooves on post 622. The friction created between tongues 628 and post 622 by brake 608 prevents movement of post 622 and thereby lateral plate 604. Similarly, threaded shaft 632 of brake 610 can be rotated to contacts and apply pressure to post 624 as brake 610 is rotated clockwise. The pressure applied to post 624 presses tongues 628 against the corresponding grooves on post 624. The friction created between tongues 628 and post 624 by brake 610 prevents movement of post 624 and thereby medial plate 606. Conversely, rotating brakes 608 and 610 counter-clockwise where brakes 608 and 610 do not respectively contact posts 622 and 624 allows posts 622 and 624 to move without friction.

Figure 46:
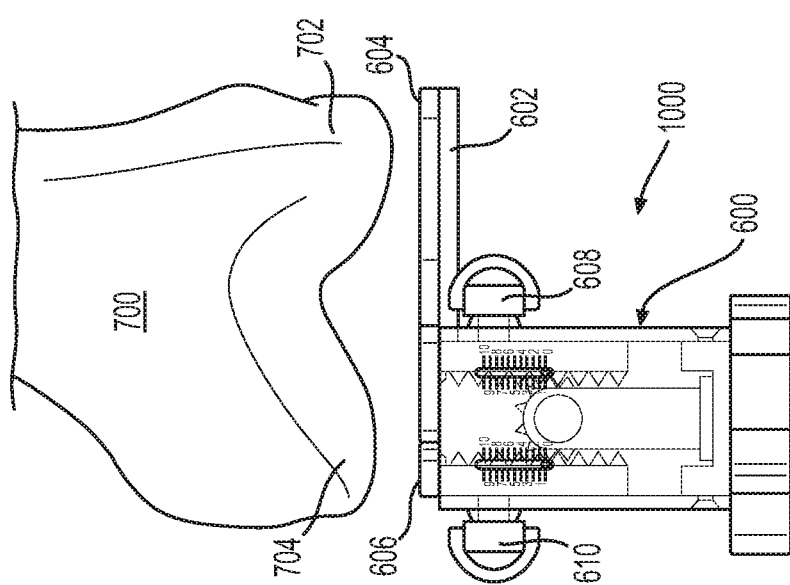
FIG. 46 illustrates a step in a knee joint installation procedure related to the alternate embodiment of the distractor shown in FIG. 44 in accordance with an example embodiment.

FIG. 46 illustrates a step in a knee joint installation procedure related to distractor 1000 shown in FIG. 44 in accordance with an example embodiment. The listing of the steps herein below does not imply any order or sequence. Distractor 1000 is placed in the knee joint similar to that shown in FIG. 1. A proximal end of the tibia has a prepared surface and the leg is positioned in extension. The fixed position plate 602 couples to the prepared surface of tibia. The proximal end of tibia can be cut perpendicular to the tibia anatomical axis using an alignment jig. The resection of tibia can also include an anterior-posterior (A-P) slope.

A computer receives transmitted measurement data from distractor 1000. Referring back to FIG. 46 load sensors (not shown) can be embedded in medial plate 606 and lateral plate 604 to support measurement of a load magnitude and position of load applied to plates 604 and 606. Alternatively, the load sensors can comprise a module that rests on a surface of medial plate 604 or lateral plate 606. Distractor 1000 can also include one or more magnetic sensors configured to measure a distraction distance between lateral plate 604 and fixed plate 602 as disclosed herein above. The one or more magnetic sensors can also be configured to measure a distraction distance between medial plate 606 and fixed position plate 602. The distraction distance data and the load measurement data is transmitted to the computer for further processing. In one embodiment, the load sensors and the one or more magnetic height sensors couple to electronic circuitry such as shown in FIG. 15. The electronic circuitry of FIG. 15 is configured to control a measurement process and transmit measurement. The electronic circuitry and the one or more magnetic height sensors can be housed in housing 600 of distractor 1000. The load measurement data received by the computer can be used to calculate the load magnitude and the position of load applied to lateral plate 604 and medial plate 606. The load magnitude and the position of load can be displayed on a display coupled to the computer in real-time to the surgeon in the operating room. Similarly, the distraction height measurement data related to the lateral plate 604 and the medial plate 606 received by the computer can be displayed on the display. The distraction height measurement data can also be used to calculate a medial-lateral slope between lateral plate 604 and medial plate 606. The slope would correspond to a line through contact point (e.g. position of load) on the lateral plate 604 and the medial plate 606.

In the illustration, distractor 1000 is placed in the knee joint. The natural femur 700 is shown having a medial condyle 704 and a lateral condyle 702 respectively overlying the lateral plate 604 and the medial plate 606. Distractor 1000 is inserted in a minimum distraction height. As mentioned previously, the minimum distraction height corresponds to the lateral plate 604 and the medial plate 606 coupling to the fixed position plate 602. Brakes 608 and 610 are not enabled for respectively preventing movement of lateral plate 604 and medial plate 606.

Figure 47:
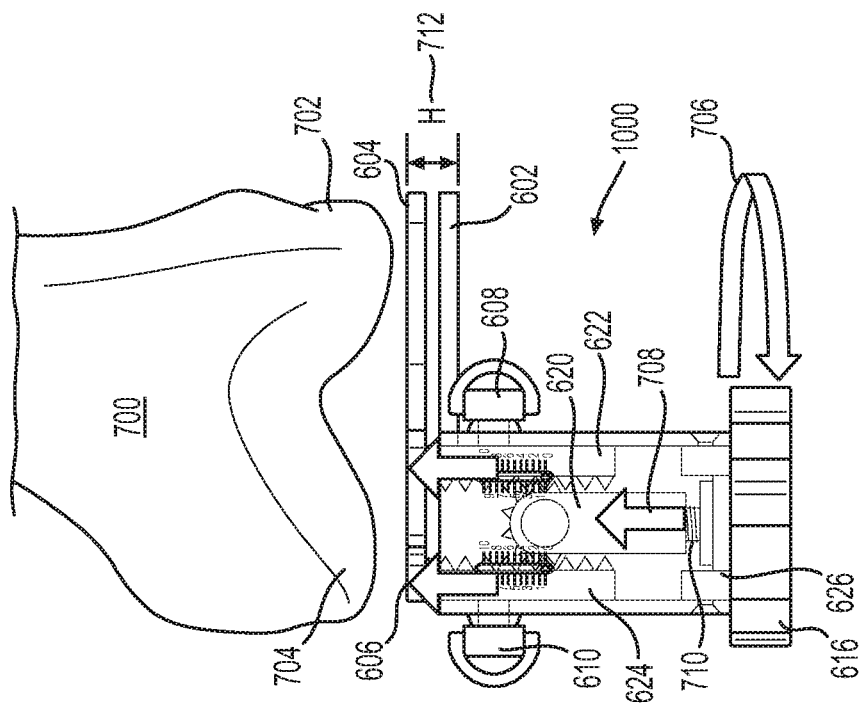
FIG. 47 illustrates a step in the knee joint installation procedure related to the alternate embodiment of the distractor wherein the knob is rotated counter clockwise in accordance with an example embodiment.

FIG. 47 illustrates a step in the knee joint installation procedure related to distractor 1000 wherein knob 616 is rotated counter clockwise in accordance with an example embodiment. The direction of rotation of knob 616 is indicated by arrow 706. Rotating knob 616 counter clockwise rotates threaded shaft 710 such that slide block 620 moves away from structure 626. In the example, lateral plate 604 and medial plate 606 are unloaded and posts 622 and 624 are free to move. Slide block 620 moves in a direction indicated by arrow 708. In the unloaded state, slide block 620 moves both lateral plate 606 and medial plate 604 equally in the direction indicated by arrow 708. A distraction height corresponds to the separation between lateral plate 604 or medial plate 606 and fixed position plate 602. The distraction height is indicated by double sided arrow 712 and is labeled H. As mentioned, medial plate 606 is raised simultaneously with lateral plate 604 and by an equal amount from fixed position plate 602. The distraction data from magnetic distance sensor can be transmitted to the computer and the distraction distance H can be displayed on the display of the computer within the operating room to review the distraction distance in real-time. Note that the lateral condyle 702 and the medial condyle 704 are not in contact with lateral plate 604 or medial plate 606.

FIG. 48 illustrates a step in the knee joint installation procedure related to distractor 1000 coupling to femur 700 in accordance with an example embodiment. As mentioned previously, fixed position plate 602 rests against a prepared surface of a tibia (not shown). Brakes 608 and 610 are not enabled thereby allowing posts 622 and 624 to move freely. Knob 616 rotates threaded shaft 710 counter clockwise to increase a gap between slide block 620 and structure 624 as indicated by arrow 708. Slide block 620, post 622, and post 624 are motivated by threaded shaft 710 to raise lateral plate 604 and medial plate 606 thereby increasing a distraction height as indicated by double sided arrow 712. Lateral plate 604 and medial plate 606 move simultaneously and by the same amount. In the example, lateral condyle 702 contacts lateral plate 604. In one embodiment, load sensors coupled to lateral plate 604 would register a measurable load as lateral condyle 702 couples to lateral plate 604. The load measurement data can be displayed on the display coupled to the computer receiving the load measurement data. Note that medial plate 606 is not in contact with medial condyle 704. In one embodiment, the counter clockwise rotation of knob 616 continues until a predetermined load magnitude is reached applied by lateral condyle 702 to lateral plate 604. As mentioned, the change in load magnitude can be viewed on the display in real-time. Typically, the predetermined load magnitude can be within a predetermined load magnitude range that has been clinically proven to provide performance, reliability, and longevity of the prosthetic knee joint.

FIG. 49 illustrates the step in a knee joint installation procedure related to distractor 1000 where lateral plate 604 and medial plate 606 contact femur 700 in accordance with an example embodiment. As previously stated, the lateral plate 604 is in contact with lateral condyle 702 and distracted to a predetermined load magnitude. The lateral plate 604 measuring the predetermined load magnitude also corresponds to a predetermined distraction distance. Brake 608 is rotated clockwise to contact post 622 to prevent any further movement of lateral plate 604. Brake 610 is not enabled and post 624 is free to move as slide block 620 moves.

Knob 616 is rotated counter clockwise to increase the gap between slide block 620 and structure 626. Brake 608 prevents post 622 from moving but free wheel gear 618 rotates clockwise as threaded shaft 710 is rotated counter clockwise. Free wheel gear 618 engages with the gear teeth of post 624 as it rotates clockwise. The clockwise rotation of free wheel gear 618 increases the distraction distance between medial plate 606 and fixed position plate 602. Thus, lateral plate 604 does not move while the distraction distance between medial plate 606 and fixed position plate 602 increases until medial plate 606 contacts medial condyle 704 of femur 700. Similar to lateral plate 604, load sensors coupled to medial plate 606 would register a measurable load as medial condyle 704 contacts medial plate 606. Loading and position of load on medial plate 606 is displayed on the display coupled to the computer receiving the load measurement data. In one embodiment, knob 616 is rotated counter clockwise to increase the load magnitude applied to medial plate 606 until it is equal to the load magnitude applied to lateral plate 604 (e.g. the predetermined load magnitude). Thus, the tension of medial collateral ligament is the same as the lateral collateral ligament.

Figure 50:
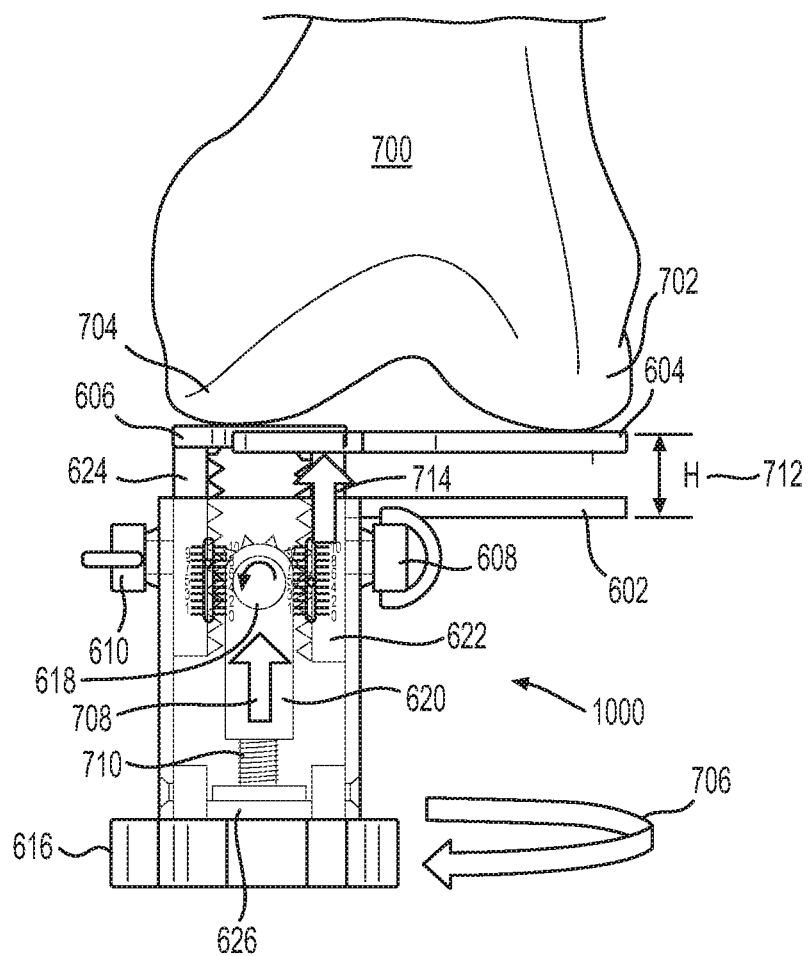
FIG. 50 illustrates a step in the knee joint installation procedure related to the alternate embodiment of the distractor where equalization of the medial gap and the lateral gap occurs in accordance with an example embodiment.

FIG. 50 illustrates a step in the knee joint installation procedure related to distractor 1000 where equalization of the medial gap and the lateral gap occurs in accordance with an example embodiment. In general, the medial gap is the distraction distance in the medial compartment of the knee joint. Similarly, the lateral gap is the distraction distance in lateral compartment of the knee joint. Referring briefly to FIG. 49, the medial gap is larger than the lateral gap but both are set such that the tension of the medial collateral ligament is the same as the lateral collateral ligament.

Referring back to FIG. 50, brake 610 is enabled to prevent movement of post 624. Conversely, brake 608 is released whereby post 622 can move freely to increase or decrease the distraction distance between lateral plate 604 and fixed position plate 602. In the example, the lateral gap is smaller than the medial gap. Thus, a process of equalizing the medial and lateral gaps corresponds to increasing the lateral gap. Knob 616 is rotated counter clockwise as indicated by arrow 706. Knob 616 rotates threaded shaft 710 counter clockwise to increase the distance between slide block 620 and structure 626. Free wheel gear 618 rotates counter clockwise by engagement with the gear teeth of post 624 in a fixed position (e.g. locked by brake 610) as slide block 620 moves as indicated by arrow 708. The counter clockwise rotation of free wheel gear 618 moves post 622 in a direction indicated by arrow 714 as the gear teeth of post 622 engages with free wheel gear 618. As mentioned, brake 608 is disabled allowing post 622 to move as free wheel gear 618 rotates.

The distraction distance between lateral plate 604 and fixed position plate 602 is increased until the lateral gap is the same as the medial gap. Increasing the medial gap increases the tension on the medial collateral ligament. Conversely, the tension on the medial collateral ligament is not raised significantly because medial plate 606 does not move. In one embodiment, soft tissue release can be practiced on the lateral collateral ligament to reduce the tension and equalize the tensions between the medial collateral ligament and the lateral collateral ligament. Load sensors coupled to medial plate 606 and lateral plate 604 provide load measurement data to the computer whereby the load magnitude data applied to medial plate 606 and lateral plate 604 can be viewed in real-time. Thus, the soft tissue release can be performed until the load magnitude on medial plate 606 and the lateral plate 604 are the same which corresponds to approximately equal lateral and medial collateral ligament tension. Alternatively, the soft tissue release can be performed to set different loadings in each compartment relative to one another. Equalizing the medial and lateral gap is disclosed in FIG. 31 whereby the process of equalization reduces the total error of the femur and tibia in relation to the mechanical axis of the leg as discussed herein above for distractor 10.

In general, the prepared surface of the tibia is resected to align the tibia to the mechanical axis. Note that the distal end of the femur is forcibly aligned to have equal medial and lateral gaps at substantially equal loading in each compartment of the knee which is the process of equalizing or equalization of the knee joint for receiving knee joint prosthetic components. In one embodiment, a guide hole jig can be coupled to distractor 1000 or to the distal end of the femur for drilling guide holes for a bone cutting jig. The guide holes are drilled to align the cutting jig to cut one or more surfaces of the distal end of the femur to produce the equalized knee compartments. The guide holes are drilled at an angle that counters offset of the femur relative to the mechanical axis whereby a prepared surface of the distal end of the femur cut by the femoral cutting jig coupled to the guide holes produces an installed femoral prosthetic component that is aligned to the mechanical axis.

Brake 610 can be released after drilling the guide holes for the equalization process using distractor 1000. Knob 616 can then be rotated clockwise to bring the lateral plate 604 and medial plate 606 to a minimum height. The leg can then be placed in flexion. For example, the leg can be placed where the tibia is at a 90 degree angle relative to the femur. A similar process to that disclosed herein above using distractor 1000 can be used to equalize the compartments in flexion. In one embodiment, with the leg in flexion, knob 616 is rotated counter clockwise to raise lateral plate 604 and medial plate 606 into contact with a posterior portion of the lateral condyle and a posterior portion of the medial condyle. Knob 616 is rotated counter clockwise until a predetermined load magnitude is measured. The load magnitude on the medial and lateral condyles can be viewed on the display coupled to the computer in real-time that receives load measurement data. Typically, a single condyle will be at the predetermined load magnitude.

The brake is applied to the side that measures the predetermined load magnitude. For example, lateral plate 604 measures at the predetermined load magnitude and brake 608 is applied. Medial plate 606 is free to move by rotation of knob 616. Knob 616 is rotated counter clockwise to increase the distraction distance between medial plate 606 and fixed position plate 602 thereby increasing the load magnitude applied to medial plate 606. The increase in load magnitude and the distraction distance is displayed on the display coupled to the computer receiving load measurement data and distraction distance data. In one embodiment, the distraction distance between medial plate 606 and fixed position plate 602 is increased until the predetermined load magnitude is measured. Thus, the load magnitude on medial plate 606 and lateral plate 604 are equal to the predetermined load magnitude. The height of the medial compartment and the height of the lateral compartment can be different at the predetermined load magnitude. For example the lateral compartment height can be greater than the lateral compartment height.

Brake 608 is released with the load magnitude applied to the medial plate 606 equal to the load magnitude applied to the lateral plate 604. Brake 610 is enabled such that medial plate 606 cannot move. Knob 606 is rotated counter clockwise to increase the distraction distance between medial plate 604 and fixed position plate 602. The distraction distance is increased until the lateral compartment height is equal to the medial compartment height. Increasing the distraction distance between lateral plate 604 and fixed position plate 602 will increase the tension on the lateral collateral ligament. After the medial compartment height and the lateral compartment height are equalized in flexion the tension on the lateral collateral ligament will be greater than the tension on the medial collateral ligament. In one embodiment, a drill guide can be coupled to distractor 1000 or the distal end of the femur 700. Drill guide holes are drilled into the distal end of the femur with the medial gap and the lateral gap equalized to support at least one bone cut for installation of a femoral prosthetic component. The load magnitude applied to the lateral plate 604 and the medial plate 606 can also be equalized. For example, soft tissue release can be used to reduce the tension of the lateral collateral ligament until the measured load magnitude on the lateral plate 604 equals the load magnitude on the medial plate 606. Thus, the installation of the femoral prosthetic component on the distal end of femur 700 results in the medial compartment of the knee joint spaced equal to the lateral compartment (or a spacing chosen by the surgeon), equal load magnitudes applied in each compartment (or a load distribution chosen by the surgeon), with the leg in alignment to the mechanical axis. Note also that the equalization is performed in the leg in extension and flexion thereby maintaining the alignment and balance throughout the range of motion. In general, the measurement data generated during the use of distractor 1000 should correspond to measurement data generated after installation of the final prosthetic components of the knee joint.

Figure 51:
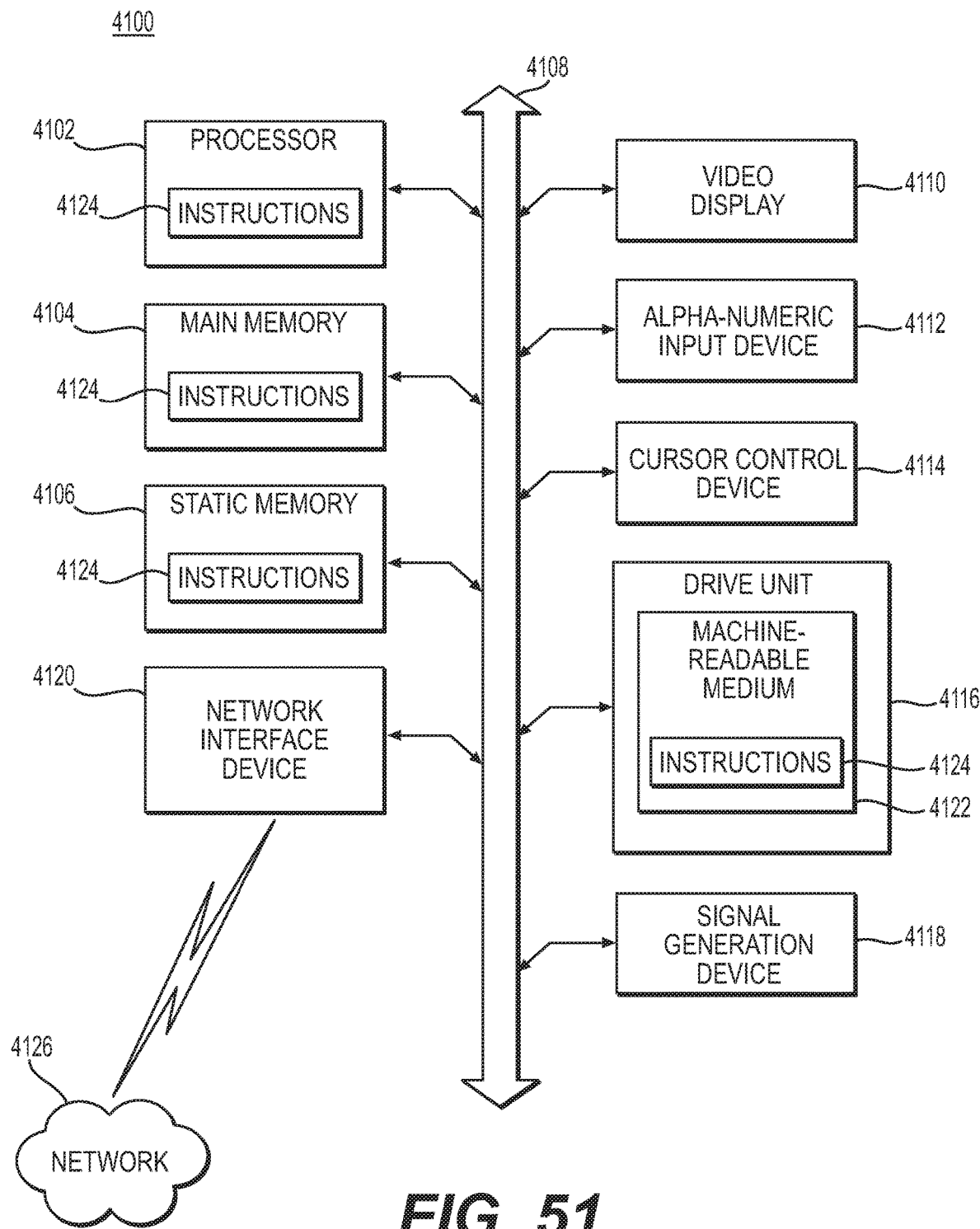
FIG. 51 depicts an exemplary diagrammatic representation of a machine in the form of a system in accordance of an example embodiment.

FIG. 51 depicts an exemplary diagrammatic representation of a machine in the form of a system 4100 within which a set of instructions, when executed, may cause the machine to perform any one or more of the methodologies discussed above. In some embodiments, the machine operates as a standalone device. In some embodiments, the machine may be connected (e.g., using a network) to other machines. In a networked deployment, the machine may operate in the capacity of a server or a client user machine in server-client user network environment, or as a peer machine in a peer-to-peer (or distributed) network environment.

The machine may comprise a server computer, a client user computer, a personal computer (PC), a tablet PC, a laptop computer, a desktop computer, a control system, logic circuitry, a sensor system, an ASIC, an integrated circuit, a network router, switch or bridge, or any machine capable of executing a set of instructions (sequential or otherwise) that specify actions to be taken by that machine. It will be understood that a device of the present disclosure includes broadly any electronic device that provides voice, video or data communication. Further, while a single machine is illustrated, the term "machine" shall also be taken to include any collection of machines that individually or jointly execute a set (or multiple sets) of instructions to perform any one or more of the methodologies discussed herein.

System 4100 may include a processor 4102 (e.g., a central processing unit (CPU), a graphics processing unit (GPU, or both), a main memory 4104 and a static memory 4106, which communicate with each other via a bus 4108. System 4100 may further include a video display unit 4110 (e.g., a liquid crystal display (LCD), a flat panel, a solid state display, or a cathode ray tube (CRT)). System 4100 may include an input device 4112 (e.g., a keyboard), a cursor control device 4114 (e.g., a mouse), a disk drive unit 4116, a signal generation device 4118 (e.g., a speaker or remote control) and a network interface device 4120.

The disk drive unit 4116 can be other types of memory such as flash memory and may include a machine-readable medium 4122 on which is stored one or more sets of instructions (e.g., software 4124) embodying any one or more of the methodologies or functions described herein, including those methods illustrated above. Instructions 4124 may also reside, completely or at least partially, within the main memory 4104, the static memory 4106, and/or within the processor 4102 during execution thereof by the system 4100. Main memory 4104 and the processor 4102 also may constitute machine-readable media.

Dedicated hardware implementations including, but not limited to, application specific integrated circuits, programmable logic arrays and other hardware devices can likewise be constructed to implement the methods described herein. Applications that may include the apparatus and systems of various embodiments broadly include a variety of electronic and computer systems. Some embodiments implement functions in two or more specific interconnected hardware modules or devices with related control and data signals communicated between and through the modules, or as portions of an application-specific integrated circuit. Thus, the example system is applicable to software, firmware, and hardware implementations.

In accordance with various embodiments of the present disclosure, the methods described herein are intended for operation as software programs running on a computer processor. Furthermore, software implementations can include, but not limited to, distributed processing or component/object distributed processing, parallel processing, or virtual machine processing can also be constructed to implement the methods described herein.

The present disclosure contemplates a machine readable medium containing instructions 4124, or that which receives and executes instructions 4124 from a propagated signal so that a device connected to a network environment 4126 can send or receive voice, video or data, and to communicate over the network 4126 using the instructions 4124. The instructions 4124 may further be transmitted or received over a network 4126 via the network interface device 4120.

While the machine-readable medium 4122 is shown in an example embodiment to be a single medium, the term "machine-readable medium" should be taken to include a single medium or multiple media (e.g., a centralized or distributed database, and/or associated caches and servers) that store the one or more sets of instructions. The term "machine-readable medium" shall also be taken to include any medium that is capable of storing, encoding or carrying a set of instructions for execution by the machine and that cause the machine to perform any one or more of the methodologies of the present disclosure.

The term "machine-readable medium" shall accordingly be taken to include, but not be limited to: solid-state memories such as a memory card or other package that houses one or more read-only (non-volatile) memories, random access memories, or other re-writable (volatile) memories; magneto-optical or optical medium such as a disk or tape; and carrier wave signals such as a signal embodying computer instructions in a transmission medium; and/or a digital file attachment to e-mail or other self-contained information archive or set of archives is considered a distribution medium equivalent to a tangible storage medium. Accordingly, the disclosure is considered to include any one or more of a machine-readable medium or a distribution medium, as listed herein and including art-recognized equivalents and successor media, in which the software implementations herein are stored.

Although the present specification describes components and functions implemented in the embodiments with reference to particular standards and protocols, the disclosure is not limited to such standards and protocols. Each of the standards for Internet and other packet switched network transmission (e.g., TCP/IP, UDP/IP, HTML, HTTP) represent examples of the state of the art. Such standards are periodically superseded by faster or more efficient equivalents having essentially the same functions. Accordingly, replacement standards and protocols having the same functions are considered equivalents.

Figure 52:
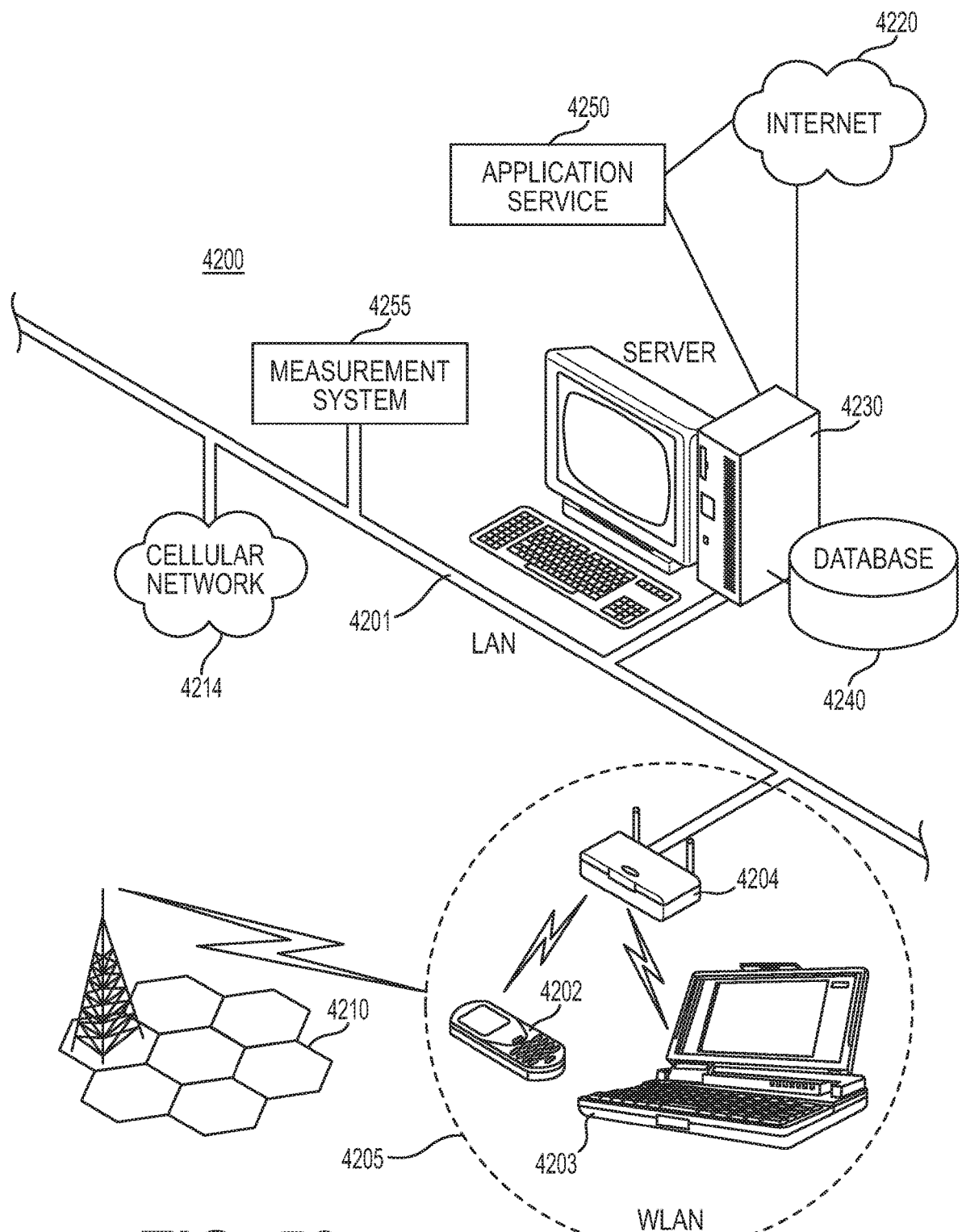
FIG. 52 is an illustration of a communication network for measurement and reporting in accordance with an exemplary embodiment.

FIG. 52 is an illustration of a communication network 4200 for measurement and reporting in accordance with an exemplary embodiment. Briefly, the communication network 4200 expands broad data connectivity to other devices or services. As illustrated, the measurement and reporting system 4255 can be communicatively coupled to the communications network 4200 and any associated systems or services.

As one example, measurement system 4255 can share its parameters of interest (e.g., angles, load, balance, distance, alignment, displacement, movement, rotation, and acceleration) with remote services or providers, for instance, to analyze or report on surgical status or outcome. This data can be shared for example with a service provider to monitor progress or with plan administrators for surgical monitoring purposes or efficacy studies. The communication network 4200 can further be tied to an Electronic Medical Records (EMR) system to implement health information technology practices. In other embodiments, the communication network 4200 can be communicatively coupled to HIS Hospital Information System, HIT Hospital Information Technology and HIM Hospital Information Management, EHR Electronic Health Record, CPOE Computerized Physician Order Entry, and CDSS Computerized Decision Support Systems. This provides the ability of different information technology systems and software applications to communicate, to exchange data accurately, effectively, and consistently, and to use the exchanged data.

The communications network 4200 can provide wired or wireless connectivity over a Local Area Network (LAN) 4201, a Wireless Local Area Network (WLAN) 4205, a Cellular Network 4214, and/or other radio frequency (RF) system (see FIG. 4). The LAN 4201 and WLAN 4205 can be communicatively coupled to the Internet 4220, for example, through a central office. The central office can house common network switching equipment for distributing telecommunication services. Telecommunication services can include traditional POTS (Plain Old Telephone Service) and broadband services such as cable, HDTV, DSL, VoIP (Voice over Internet Protocol), IPTV (Internet Protocol Television), Internet services, and so on.

The communication network 4200 can utilize common computing and communications technologies to support circuit-switched and/or packet-switched communications. Each of the standards for Internet 4220 and other packet switched network transmission (e.g., TCP/IP, UDP/IP, HTML, HTTP, RTP, MMS, SMS) represent examples of the state of the art. Such standards are periodically superseded by faster or more efficient equivalents having essentially the same functions. Accordingly, replacement standards and protocols having the same functions are considered equivalent.

The cellular network 4214 can support voice and data services over a number of access technologies such as GSM-GPRS, EDGE, CDMA, UMTS, WiMAX, 2G, 3G, WAP, software defined radio (SDR), and other known technologies. The cellular network 4214 can be coupled to base receiver 4210 under a frequency-reuse plan for communicating with mobile devices 4202.

The base receiver 4210, in turn, can connect the mobile device 4202 to the Internet 4220 over a packet switched link. The internet 4220 can support application services and service layers for distributing data from the measurement system 4255 to the mobile device 4202. Mobile device 4202 can also connect to other communication devices through the Internet 4220 using a wireless communication channel.

The mobile device 4202 can also connect to the Internet 4220 over the WLAN 4205. Wireless Local Access Networks (WLANs) provide wireless access within a local geographical area. WLANs are typically composed of a cluster of Access Points (APs) 4204 also known as base stations. The measurement system 4255 can communicate with other WLAN stations such as laptop 4203 within the base station area. In typical WLAN implementations, the physical layer uses a variety of technologies such as 802.11b or 802.11g WLAN technologies. The physical layer may use infrared, frequency hopping spread spectrum in the 2.4 GHz Band, direct sequence spread spectrum in the 2.4 GHz Band, or other access technologies, for example, in the 5.8 GHz ISM band or higher ISM bands (e.g., 24 GHz, etcetera).

By way of the communication network 4200, the measurement system 4255 can establish connections with a remote server 4230 on the network and with other mobile devices for exchanging data. The remote server 4230 can have access to a database 4240 that is stored locally or remotely and which can contain application specific data. The remote server 4230 can also host application services 4250 directly, or over the internet 4220.

In general, a robot can support or assist the distraction of a knee joint in under control of a surgeon. The distractor 10 or distractor 1000 disclosed herein above can be coupled to the robot. One example of the robot is the Robodoc surgical robot with a robotic assisted TKA application. A robot can also include surgical CNC robots, surgical haptic robots, surgical teleoperative robots, surgical hand-held robots, or any other surgical robot. Distractor 10 can be automated to couple to and work with the robot thereby replacing direct hand control by the surgeon. The actions taken by the robot in control of distractor 10 can be smoother and more accurate by having the robot use the measurement data in real-time and providing feedback to distractor 10 for subsequent steps. An added benefit can be shortening the time of surgery that reduces the time a patient is under anesthesia.

The robot can be configured to perform computer-assisted surgery and more specifically knee surgery with distractor 10. Typically, the robot and distractor 10 is used for computer-assisted surgery to improve performance, reduce time, and minimize variation in the distraction, alignment, bone cuts, and installation of one or more prosthetic components for a prosthetic knee joint. The robot can control distraction, medial-lateral tilt, loading, tissue release, braking, and drilling guide holes using the real-time measurement data sent from distractor 10.

In general, measurement data from distractor 10 can be wirelessly transmitted to a computer of the robot. Alternatively, the measurement data can be hard wired to the robot. Examples of measurement data from distractor 10 can be position data, distraction distance, load, medial-lateral tilt, or other data relevant to a prosthetic knee installation. The measurement data received by the robot can be further processed to calculate and display measurement data needed by the surgeon for the distraction and preparation of the bone surfaces of the knee joint. The prepared bone surfaces will receive a prosthetic component that supports alignment to the mechanical axis of the leg. In one embodiment, the computer includes one or more algorithms that are used at various stages of the surgery. The measurement data is input to the algorithms of the robot and the algorithms can convert the data into information displayed on the display for robotic actions that are used to make bone cuts, pin placements, prosthetic component sizing, etc. . . . or provide feedback on actions that the surgeon may take. The feedback may take the form of audible, visual, or haptic feedback that guides the surgeon on the distraction or subsequent steps taken by the robot to support or resist an action based on the measurement data. The feedback can also smooth or prevent motions by a user that could be detrimental to the surgery. Furthermore, the status of the measurement data can be used to generate a workflow that is subsequently implemented by a surgeon or automatically by the robot to enhance performance and reliability of the knee joint installation.

Figure 53:
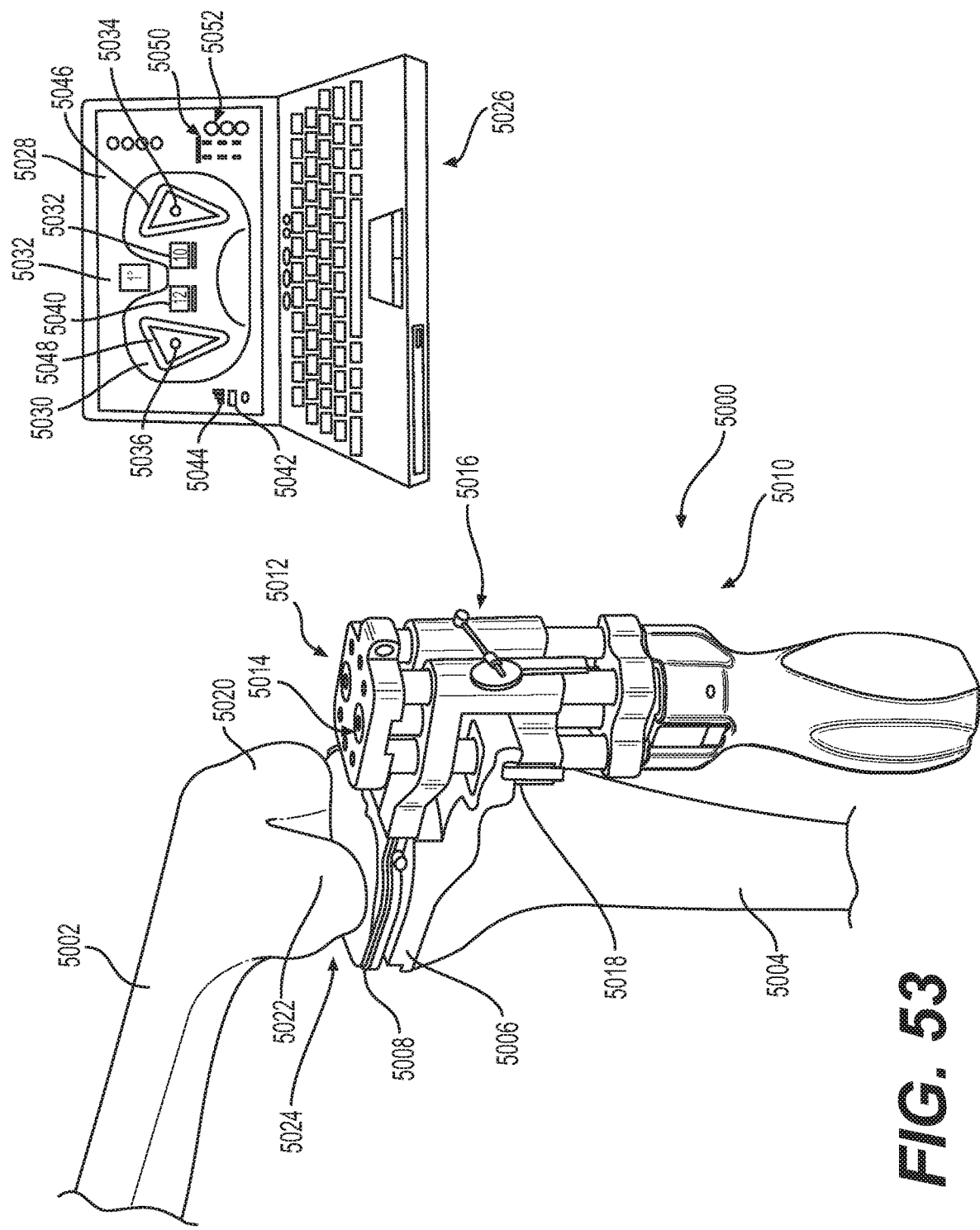
FIG. 53 illustrates a surgical apparatus having three distracting mechanisms configured to distract a knee joint in accordance with an example embodiment.
Figure 64:
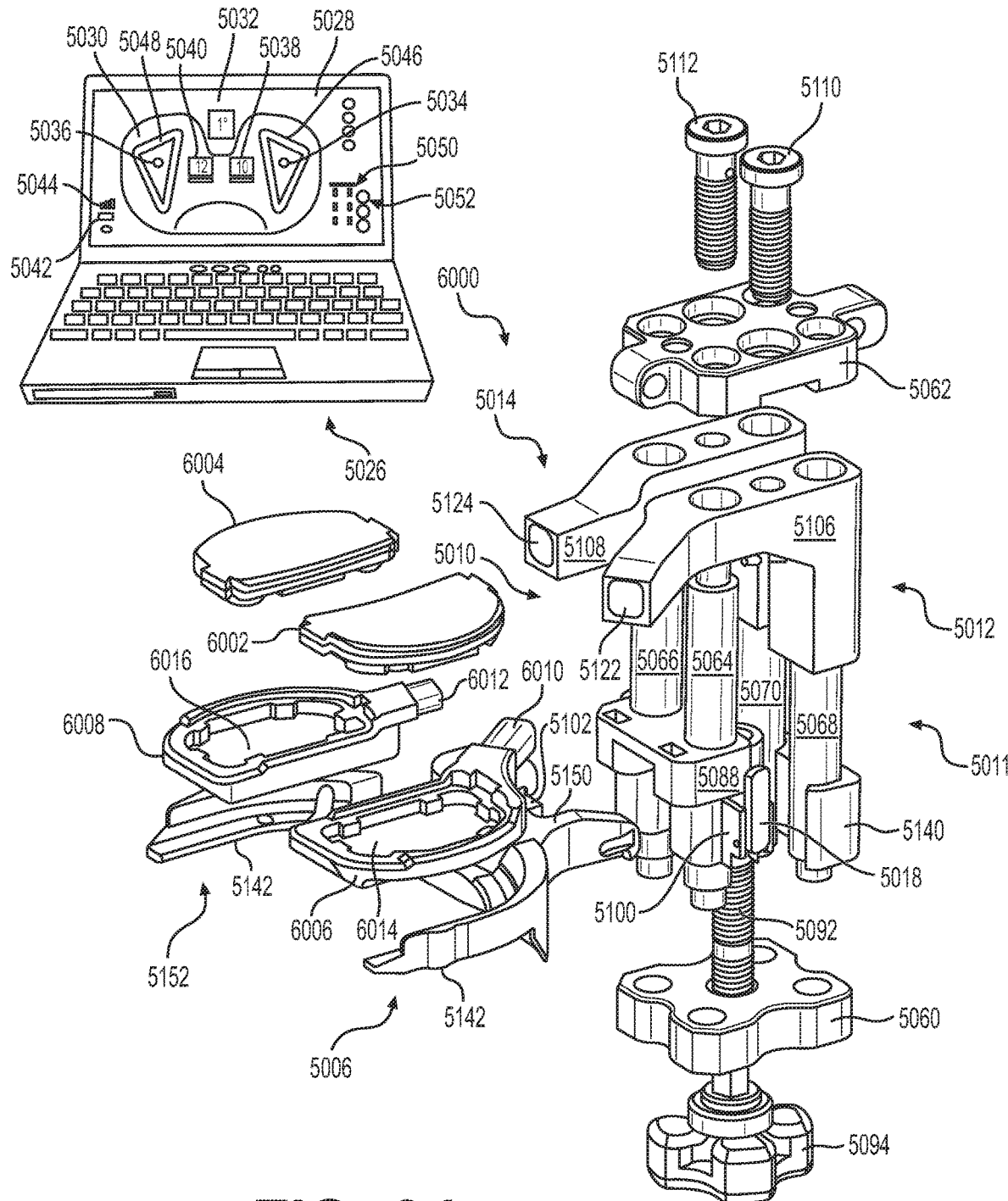
FIG. 64 is an illustration of a surgical apparatus in accordance with an example embodiment.

FIG. 53 illustrates a surgical apparatus 5000 having three distracting mechanisms configured to distract a knee joint in accordance with an example embodiment. In general, surgical apparatus 5000 and surgical apparatus 6000 disclosed herein below in FIG. 64 is configured for use in the musculoskeletal system to generate quantitative measurement data using one or more sensors. In one embodiment, surgical apparatus 5000 and surgical apparatus 6000 is adapted for use for providing a kinetic assessment having quantitative measurement data for the musculoskeletal system, knee, hip, shoulder, spine, ankle, wrist, hand, foot, or bone. In one embodiment, surgical apparatus 5000 and 6000 is configured to support installation of a prosthetic joint of the musculoskeletal system. Surgical apparatus 5000 and 6000 can include, but are not limited to measurement of parameters such as height, length, width, tilt/slope, position, orientation, alignment, offset, rotation, tension, load magnitude, force, pressure, contact point location, displacement, density, viscosity, pH, light, color, sound, optical, vascular flow, visual recognition, humidity, alignment, rotation, inertial sensing, turbidity, bone density, fluid viscosity, strain, angular deformity, vibration, torque, elasticity, motion, and temperature. Electronic circuitry 150 as disclosed herein in FIG. 15 can be coupled to surgical apparatus 5000 to control a measurement process and transmit measurement data. For example, electronic circuitry 150 of FIG. 15 can be coupled or housed on or in surgical apparatus 5000 to couple to one or more sensors for measuring a parameter and transmitting quantitative measurement data. A computer 5026 with a display is configured to receive and provide the quantitative measurement data. For example, Hall Effect sensor 204 or linear Hall sensor 222 of FIGS. 16-20 can be configured to measure femoral support tilt or compartment height on surgical apparatus 5000 as disclosed herein above. Surgical apparatus 5000 can further comprise a measurement module having at least one sensor. The measurement module includes at least one sensor configured to measure a parameter. In one embodiment, the measurement module is removable from surgical apparatus 5000 and can be used as a trialing device later during the surgical procedure. The measurement module generates quantitative measurement data and transmits the measurement data to the computer for display. The computer can include a GUI and convert the quantitative measurement data into visual, audible, or haptic forms that supports the rapid assimilation of the data to reduce surgical time. For example, quantitative measurement data from surgical apparatus 5000 or the measurement module received by computer 5026 and displayed on display 5028 can be presented as shown in FIG. 28, FIG. 30, FIG. 33, FIG. 37, and FIG. 38 as disclosed herein above. The computer can further provide workflows based on the quantitative measurement data that results in at least one adjustment or change that optimizes the installation.

In general, surgical apparatus 5000 comprises a first distraction mechanism, a second distraction mechanism, and a third distraction mechanism. Surgical apparatus 5000 is configured to separate portions of the musculoskeletal system in a predetermined manner and generate quantitative measurement data. In one embodiment, surgical apparatus 5000 is configured to be inserted between a first bone and a second bone of the musculoskeletal system. The first or second bones can be natural, prepared, or have a prosthetic component coupled to it. The inserted portion of surgical apparatus 5000 distracts a first side and a second side of the musculoskeletal system. The first distraction mechanism of surgical apparatus 5000 is configured to increase or decrease a height on the first side and the second side simultaneously by an equal amount. The second distraction mechanism is configured to increase or decrease a height on the first side. The third distraction mechanism is configured to increase or decrease a height on the second side. The first, second, and third distraction mechanisms can be operated by the hand of the user or controlled by a robot. Although surgical apparatus 5000 is shown adjusting the height on a first side and a second side of the musculoskeletal system, surgical apparatus 5000 can have more than two areas that are distracted in combination or independently distracted. In one embodiment, surgical apparatus 5000 is configured to provide quantitative measurement data that supports at least one bone cut on a joint. A tilt is generated by independently changing a height on a first side or the second side. The tilt or heights of the first and second sides is measured and provided to a computer in viewing distance from the surgery. In one embodiment, surgical apparatus 5000 is configured to support alignment, adjust load magnitude, and load balance between the first side and the second side prior to installation of a prosthetic component. The at least one bone cut supported by the surgical apparatus 5000 incorporates alignment, load magnitudes and balance to the prosthetic component installation using quantitative measurement data thereby eliminating modification to the musculoskeletal system or prosthetic components after installation of the prosthetic components. The description of surgical apparatus 5000 also applies to surgical apparatus 6000 shown in FIG. 64.

In one embodiment, surgical apparatus 5000 is used to support installation of a prosthetic component or a prosthetic joint. In one embodiment, surgical apparatus 5000 is configured to support one or more bone cuts that support improved alignment, optimal loading, position of load, or load balance. Components of surgical apparatus 5000 can comprise plastic, metal, structural fibers, metal alloys, or other structural materials. In one embodiment, stainless steel is used for structural components. Surgical apparatus 5000 can be a disposable surgical tool. Alternatively, surgical apparatus 5000 can be a reusable tool that is sterilized between each use. In the example, surgical apparatus 5000 is illustrated for use in a knee joint. Surgical apparatus 5000 is shown placed in a knee joint with a leg in flexion. A tibial support 5006 and a femoral support 5008 couples to surgical apparatus 5000. Tibial support 5006 couples to tibia 5004. Femoral support 5008 couples to femur 5002. A medial compartment and a lateral compartment of the knee joint can be distracted independently or by equal amounts by surgical apparatus 5000. A module 5024 couples to femoral support 5008. Module 5024 includes one or more sensors to measure at least one parameter. In one embodiment, module 5024 includes force, pressure, or load sensors configured to measure loading applied to the medial compartment or the lateral compartment of the knee joint. The one or more sensors are operatively coupled to electronic circuitry in module 5024. The electronic circuitry is configured to control a measurement process and to transmit measurement data. The measurement data from the one or more sensors can be transmitted to a computer 5026 for further processing and to be displayed on a display 5028. In one embodiment, surgical apparatus 5000 is configured to measure parameters such compartment height, medial-lateral tilt, load, alignment, or balance where the sensor output can be viewed on display 5028 coupled to computer 5026. In one embodiment, display 5028 can have a graphical user interface that supports graphical data implemented to support rapid assimilation of measurement data from surgical apparatus 5000 to reduce surgical time while installing one or more prosthetic components using quantitative measurement data. Alternatively, gauges 5016 can be coupled to surgical apparatus 5000. In one embodiment, gauges 5016 can be mechanical gauges that couple to the three distracting mechanisms to mechanically measure and display the compartment heights (medial, lateral, or both), balance, alignment, load, or the medial-lateral height.

Surgical apparatus 5000 is configured to measure, distract, align, balance, tilt, and support bone cuts in a joint of the musculoskeletal system prior to installation of a prosthetic component. In the example, surgical apparatus 5000 is adapted for use to support a total knee arthroplasty. As mentioned previously, surgical apparatus 5000 can be used for the musculoskeletal system, bone, spine, knee, shoulder, hip, ankle, elbow, wrist, hand, foot, and other areas where quantitative measurement is useful. Surgical apparatus 5000 can be used to set or adjust the height of the medial compartment, the height of the lateral compartment, or both knee compartments by adjustment of tibial support 5006 and femoral support 5008 under user control. In one embodiment, a predetermined flow is established using surgical apparatus 5000 that reduces alignment error of the knee joint by one or more corrective bone cuts that support installation of a tibial prosthetic component or a femoral prosthetic component to correct for the misalignment.

Tibial support 5006 of surgical apparatus 5000 couples to a proximal end of tibia 5004. In the example, tibial support 5006 couples to a prepared bone surface of tibia 5004. In one embodiment, the prepared bone surface at the proximal end of tibia 5004 is cut relative to the mechanical axis of the leg as a reference surface. Surgical apparatus 5000 comprises a distraction mechanism 5010, a distraction mechanism 5012, and a distraction mechanism 5014 where each can change a distraction height of at least one compartment on the knee joint. Distraction mechanism 5010 is configured to move tibial support 5006 relative to femoral support 5008. In one embodiment, distraction mechanism 5010 simultaneously distracts the medial compartment and the lateral compartment of a knee joint by an equal distance or an equal amount. In one embodiment, distraction mechanism 5010 includes a screw that is rotated to change a position of tibial support 5006 relative to the position of femoral support 5008. In one embodiment, distraction mechanism 5012 and distraction mechanism 5014 work together or separately as a tilt mechanism. The tilt mechanism changes the medial compartment height relative to the lateral compartment height. In general, the tilt mechanism changes the position of a first support structure such as femoral support 5008 relative to a second support structure such as tibial support 5006 of a tensor such as surgical apparatus 5000.

Femoral support 5008 of surgical apparatus 5000 couples to a distal end of femur 5002. Module 5024 has a medial surface and a lateral surface configured to respectively couple to a medial condyle 5020 and a lateral condyle 5022 of femur 5002. In one embodiment, surgical apparatus 5000 couples to a natural femur (before bone cuts for a femoral prosthetic component) and surgical apparatus 5000 supports movement of femur 5002 relative to tibia 5004. Medial condyle 5020 and lateral condyle 5022 respectively couple to and rotate on the medial surface and the lateral surface of module 5024. Alternatively, the medial condyle and the lateral condyle can be femoral prosthetic component coupled to femur 5002. The position and the movement of the leg can be monitored by a position sensor in module 5024. For example, a gyroscope, accelerometer, or other position tracking device can be used to report leg or knee joint position. Femoral support 5008 couples to distraction mechanism 5012 and distraction mechanism 5014. Distraction mechanism 5012 changes a height of the medial compartment of the knee joint. Distraction mechanism 5012 is configured to move femoral support 5008 to raise or lower a height of the medial compartment of the knee joint. Distraction mechanism 5014 changes a height of the medial compartment of the knee joint. Similarly, distraction mechanism 5014 is configured to move femoral support 5008 to raise or lower a height of the lateral compartment of the knee joint. In one embodiment, distraction mechanisms 5012 and 5014 each comprise a screw that can rotated to respectively change the height of the medial compartment and the height of the lateral compartment such that the position of femoral support 5008 moves relative to tibial support 5006 and changes the medial-lateral tilt of the femoral support 5008.

In general, surgical apparatus 5000 is configured to distract a joint region to support one or more bone cuts that support installation of one or more prosthetic components. In the example, the bone cuts support placement of a tibial prosthetic component on the proximal end of tibia 5004, a femoral prosthetic component on the distal end of femur 5002, and an insert there between. The insert is retained by the tibial prosthetic component and provides a medial articular surface and a lateral articular surface that respectively couples to the medial condyle and the lateral condyle of the femoral prosthetic component to support leg movement. In one embodiment, surgical apparatus 5000 supports measuring or checking alignment of femur 5002 relative to tibia 5004 in a kinetic assessment where the joint is loaded similar to a final prosthetic installation. In one embodiment, surgical apparatus 5000 is offset, more specifically, tibial support 5006 and femoral support 5006 are offset to allow loading of the knee joint with a patella or extensor mechanism anatomically positioned under distraction with full rotation of the knee joint. Surgical apparatus 5000 further supports at least one bone cut for installing a prosthetic component. In one embodiment, the at least one bone cut supports balanced loading or setting the medial compartment or the lateral compartment respectively to a predetermined medial loading and a predetermined lateral loading. Furthermore, the loading in each compartment can be measured over a range of motion of the leg to determine if the loading in each compartment stays within a predetermined load range over a range of motion of the knee joint. Further correction can be made in real-time to adjust the loading in each compartment. A bone cutting jig can couple to surgical apparatus 5000 or a bone cutting jig can be positioned by surgical apparatus 500 to support at least one bone cut that installs a prosthetic component to reduce alignment error or improve balance. Surgical apparatus 5000 further can monitor or support change of the position of contact points to the medial and lateral compartment and the absolute loading at the contact points on the medial and lateral compartment over the range of motion.

Module 5024 transmits measurement data to computer 5026. Information is displayed on display 5028. Display 5028 displays the measurement data that allows a user to obtain information at a glance during an operation in a surgical environment. Computer 5026 is typically placed outside the surgical field of an operating room but in a location where it can easily be seen by a surgical team. In one embodiment, a module portion 5030 corresponding to module 5024 is displayed on display 5028. In one embodiment, module portion 5030 includes the medial (M) and lateral (L) articular surfaces. Medial loading 5038 and lateral loading 5040 are measured loadings on the medial articular surface and the lateral articular surface of module 5024 and displayed on module portion 5030 on display 5028. In one embodiment, medial loading 5038 and lateral loading 5040 correspond to a height of the medial compartment and a height of the lateral compartment as distracted by surgical apparatus 5000. The medial compartment height and the lateral compartment height can be measured by surgical apparatus 5000 and displayed on display 5028. An area 5046 and an area 5048 can also be displayed respectively on the medial articular surface and the lateral articular surface of module portion 5030 on display 5028. In the example, area 5046 and area 5048 are triangular in shape. Area 5046 and 5048 can differ in shape and size. In general, area 5046 and area 5048 respectively define a region of contact of medial condyle 5020 and lateral condyle 5022 to ensure reliability and performance of the knee joint over a range of motion. In general, the contact points should not go outside area 5046 or area 5048 over the range of motion of the knee joint. In one embodiment, an adjustment or modification may have to be performed to correct movement of the contact points outside area 5046 or area 5048. In one embodiment, computer 5026 can provide a workflow of one or more adjustments that can be performed with real-time feedback on display 5028 that brings the contact points within area 5046 and 5048. Contact points 5034 and 5036 on display 5028 respectively correspond to a contact point of medial condyle 5020 and a contact point of lateral condyle 5022 coupling to the medial articular surface and the lateral articular surface of module 5024. As mentioned contact points 5034 and 5036 will move in real-time from transmitted measurement data as the position of the leg is changed or moved over the range of motion.

One adjustment to keep contact points 5034 and 5036 within areas 5046 and 5048 over the range of motion is to change the position of the tibial support 5006 on the prepared surface of tibia 5004. Rotating tibial support 5006 on the prepared surface of tibia 5004 can reposition the contact points 5034 and 5036. The leg can be rotated over a range of motion and contact points 5034 and 5036 can be monitored in real-time. Alternatively, areas 5046 or 5048 can be highlighted or indicate when contact points 5034 and 5036 are near or outside the boundary of areas 5046 and 5048. The amount of contact point rotation 5032 of tibial support 5006 can be measured by a sensor in module 5024 and displayed on display 5028 in a display box 5032 on display 5028. In one embodiment, the tibial prosthetic component would also be installed having this rotation after removal of surgical apparatus 5000.

In one embodiment, measurement data is transmitted wirelessly. A signal strength meter 5044 of the transmission from the module to computer 5026 is shown on display 5028. In one embodiment, module 5024 has an internal power source. For example, module 5024 can include one or more batteries to power the electronic circuitry. In one embodiment, module 5024 is a disposable surgical apparatus as the batteries in module 5024 are configured to last a single operation. In one embodiment, opening module 5024 cannot be opened to replace the batteries without damage. Battery symbol indicates the remaining power within module 5024 and is shown on display 5028. The leg or knee joint position in flexion or extension is indicated by in area 5050 of display 5028. Similarly, measured alignment of the leg is indicated in area 5052 of display 5028.

Tibial support 5006 and femoral support 5008 are provided with surgical apparatus 5000 in more than one size. In one embodiment, tibial support 5006 and femoral support 5008 are provided in small, medium, and large sizes that can be used for a majority of the population. In one embodiment, femoral support 5008 couples through a first pivot point and a second pivot point respectively to distraction mechanism 5012 and distraction mechanism 5014. Loading on femoral support 5008 is distributed between the first and second pivot points to surgical apparatus 5000. The first and second pivot points are configured to tilt femoral support 5008 when the height of the medial compartment differs from the height of the lateral compartment. The tibial support 5006 is retained to distraction mechanism using clips 5018. Clips 5018 can further include one or more magnets that align and retain tibial support 5006 or clips 5018 to surgical apparatus 5000.

Figure 54:
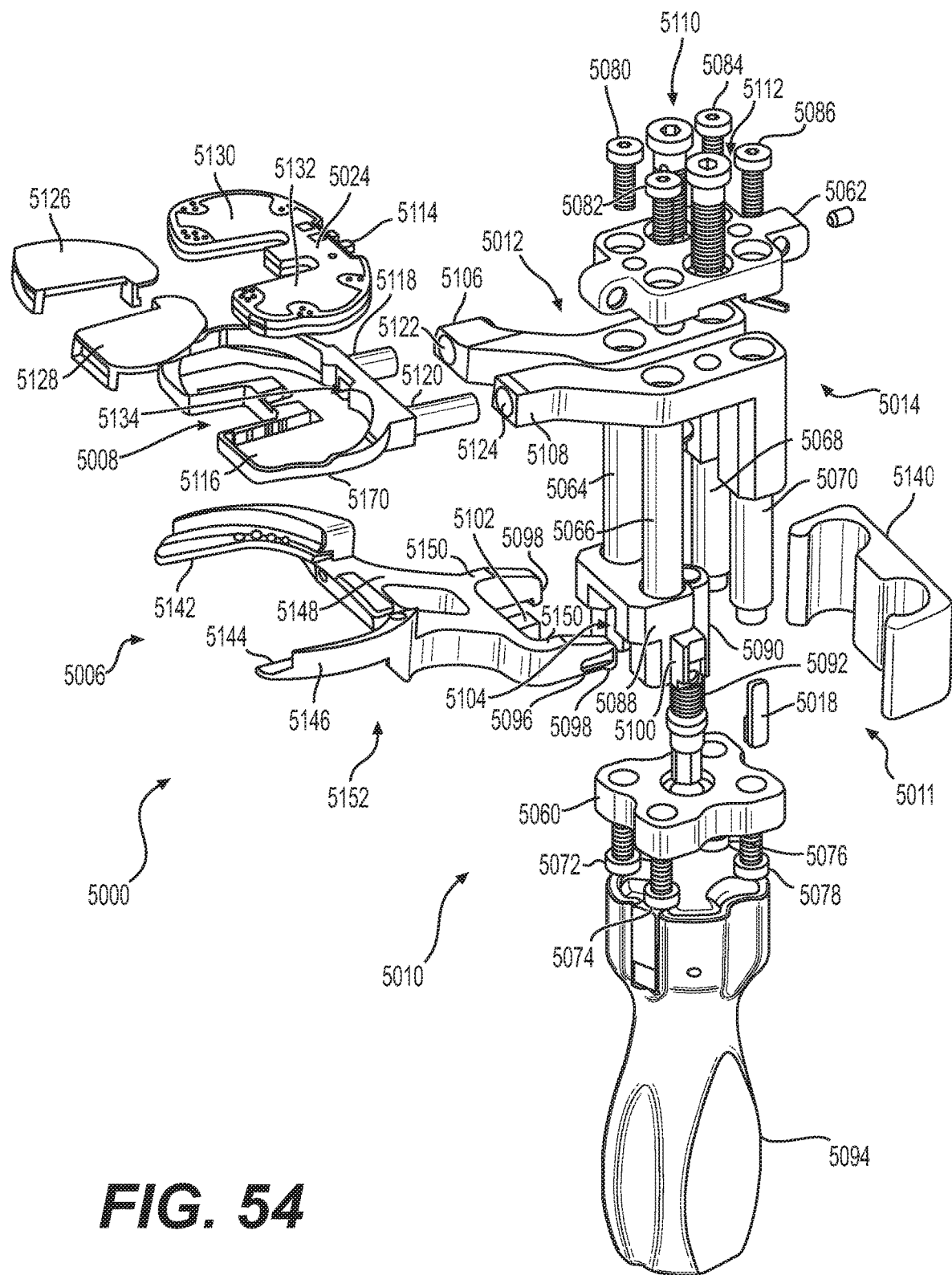
FIG. 54 is an exploded view of the surgical apparatus in accordance with an example embodiment.

FIG. 54 is an exploded view of surgical apparatus 5000 in accordance with an example embodiment. In general, a left knee distractor is provided for a left knee joint and a right knee distractor is provided for a right knee joint. The right and left knee distractors each have an offset toward the medial side. The patella is reflected laterally during distraction or tensor insertion, once inserted the patella is able to rest over the center of the knee joint because of the medial offset placed in the right or left knee distractor. This allows the patella to load the knee joint through a range of motion with the right or left knee distractor in place. In the example, surgical apparatus 5000 is configured for distracting the left knee joint. In other words, the medial offset of surgical apparatus 5000 is on the medial side for a left leg. Surgical apparatus 5000 for the left knee cannot be used on the right knee. Similarly, if surgical apparatus 5000 has an offset for a right knee, it cannot be used for a left knee. The right knee distractor is not shown, as the components and operation are the same except for the offset.

Distraction mechanism 5010, distraction mechanism 5012, and distraction mechanism 5014 of surgical apparatus 5000 is supported and aligned by a cage system 5011. Cage system 5011 comprises a cap 5062, an anterior medial guide shaft 5064, an anterior lateral guide shaft 5066, a posterior medial guide shaft 5068, a posterior lateral guide shaft 5070, and a base 5060. In one embodiment, anterior medial guide shaft 5064, anterior lateral guide shaft 5066, posterior medial guide shaft 5068, and posterior lateral guide shaft 5070 couple between base 5060 and cap 5062. In one embodiment, anterior medial guide shaft 5064, anterior lateral guide shaft 5064, posterior medial guide shaft 5068, and posterior lateral guide shaft 5070 couple between base 5060 and cap 5062 in a square or rectangular pattern to support movement of distraction mechanism 5010, distraction mechanism 5012, and distraction mechanism 5014.

A distal end of anterior medial guide shaft 5064 couples to a medial anterior opening in base 5060. Screw 5072 couples through the medial anterior opening in base 5060 coupling the distal end of anterior medial guide shaft 5064 to base 5060. Similarly, a proximal end of anterior medial guide shaft 5064 couples to a medial anterior opening in cap 5062. Screw 5080 couples through the medial anterior opening in cap 5062 coupling the proximal end of anterior medial guide shaft 5064 to cap 5062. In one embodiment, the proximal and distal ends of anterior medial guide shaft 5064 have threaded openings configured to respectively receive screws 5080 and 5072. In one embodiment, a portion of the proximal and distal ends of anterior medial guide shaft 5064 can have a reduced diameter to fit within the first openings in base 5060 and cap 5062 to support alignment.

A distal end of anterior lateral guide shaft 5066 couples to a lateral anterior opening in base 5060. Screw 5074 couples through the lateral anterior opening in base 5060 coupling the distal end of anterior lateral guide shaft 5066 to base 5060. Similarly, a proximal end of anterior lateral guide shaft 5066 couples to a lateral anterior opening in cap 5062. Screw 5082 couples through the lateral anterior opening in cap 5062 coupling the proximal end of anterior lateral guide shaft 5066 to cap 5062. In one embodiment, the proximal and distal ends of anterior lateral guide shaft 5066 have threaded openings configured to respectively receive screws 5082 and 5074. In one embodiment, a portion of the proximal and distal ends of anterior lateral guide shaft 5066 can have a reduced diameter to fit within the second openings in base 5060 and cap 5062 to support alignment.

A distal end of posterior medial guide shaft 5068 couples to a medial posterior opening in base 5060. Screw 5076 couples through the medial posterior opening in base 5060 coupling the distal end of posterior medial guide shaft 5068 to base 5060. Similarly, a proximal end of posterior medial guide shaft 5068 couples to a medial posterior opening in cap 5062. Screw 5084 couples through the medial posterior opening in cap 5062 coupling the proximal end of posterior medial guide shaft 5068 to cap 5062. In one embodiment, the proximal and distal ends of posterior medial guide shaft 5068 have threaded openings configured to respectively receive screws 5084 and 5076. In one embodiment, a portion of the proximal and distal ends of posterior medial guide shaft 5068 can have a reduced diameter to fit within the third openings in base 5060 and cap 5062 to support alignment.

A distal end of posterior lateral guide shaft 5070 couples to a lateral posterior opening in base 5060. Screw 5078 couples through the lateral posterior opening in base 5060 coupling the distal end of posterior lateral guide shaft 5070 to base 5060. Similarly, a proximal end of posterior lateral guide shaft 5070 couples to a lateral posterior opening in cap 5062. Screw 5086 couples through the lateral posterior opening in cap 5062 coupling the proximal end of posterior lateral guide shaft 5070 to cap 5062. In one embodiment, the proximal and distal ends of posterior lateral guide shaft 5070 can have threaded openings configured to respectively receive screws 5086 and 5078. In one embodiment, a portion of the proximal and distal ends of anterior lateral guide shaft 5066 can have a reduced diameter to fit within the fourth openings in base 5060 and cap 5062 to support alignment. In one embodiment, anterior medial guide shaft 5064, anterior lateral guide shaft 5066, posterior medial guide shaft 5068, and posterior lateral guide shaft 5070 are parallel to one another. In general, cap 5062, base 5060, anterior medial guide shaft 5064, anterior lateral guide shaft 5066, posterior medial guide shaft 5068, and posterior lateral guide shaft 5068 are configured to support movement and trajectory of the three distraction mechanisms that comprise surgical apparatus 5000.

Distraction mechanism 5010 comprises tibial support holder 5088, cage system 5011, distraction lead screw 5092, and handle 5094. Distraction mechanism 5010 is configured to move tibial support 5006 relative to femoral support 5008. In one embodiment, tibial support 5006 couples to a prepared bone surface of a proximal end of a tibia. In one embodiment, distraction mechanism 5010 simultaneously distracts a medial compartment and a lateral compartment of a knee joint by equal amounts. Tibial support holder 5088 comprises a structure having a medial opening and a lateral opening. Anterior medial guide shaft 5064 and anterior lateral guide shaft 5066 respectively couple through the medial opening and the lateral opening of tibial support holder 5088. Distraction lead screw 5092 is configured to move tibial support holder 5088 under user control. Distraction lead screw 5092 couples through an opening in base 5060 to couple to threaded structure 5090 of tibial support structure 5088. Threaded structure 5090 has a threaded opening configured to receive distraction lead screw 5092. Distraction lead screw 5092 couples thru the threaded opening of threaded structure 5090 to motivate tibial support holder 5088 when rotated. In one embodiment, the opening in base 5060 for receiving distraction lead screw 5092 can be centrally located in base 5060. The surface in the opening in base 5060 can act as a bearing surface to support alignment and rotation of distraction lead screw 5092. In one embodiment, distraction lead screw 5092 can be non-threaded in a portion of distraction lead screw 5092 that couples to the bearing surface in the opening of base 5060. Handle 5094 couples to the distal end of distraction lead screw 5092. Rotating handle 5094 engages distraction lead screw 5092 to threads within threaded structure 5090 of tibial support holder 5088 to move tibial support holder 5088 along a trajectory defined by anterior medial guide shaft 5064 and anterior lateral guide shaft 5066. Tibial support holder 5088 can move towards or away from base 5060 depending on the direction of rotation of distraction lead screw 5092.

Tibial support 5006 couples to tibial support holder 5088. In one embodiment, tibial support 5006 comprises a U-shaped structure 5152, beam structure 5148, and arms 5150. U-shaped structure 5152 is configured to couple to a bone or bone surface. In the example, U-shaped structure 5152 has a bottom surface 5142 configured to couple to a prepared bone surface at the proximal end of a tibia and sidewalls 5146. The bottom surface 5142 couples to the bone or bone surface. Femoral support 5008 is configured to fit within U-shaped structure 5152 thereby minimizing a height during initial insertion in the knee joint. A beam structure 5148 couples U-shaped structure 5152 to arms 5150. Beam structure 5148 locates U-shaped structure 5152 at a predetermined position. In one embodiment, beam structure 5148 has a medial offset to support placement of the patella onto the knee joint after surgical apparatus 5000 is inserted such that all measurements include patellar loading. In one embodiment, U-shaped structure 5152, beam structure 5148, and arms 5150 are rigid and do not flex when distracting a joint of the musculoskeletal system. U-shaped structure 5142, beam structure 5148, and arms 5150 can be formed as a single structure from one or more materials such as metal, metal alloys, plastics, or composite materials.

Arms 5150 are configured to couple tibial support 5006 to tibial support holder 5088. In one embodiment, tibial support holder 5088 has support structures 5100 having surfaces configured to couple to arms 5150 on a medial side and a lateral side of tibial support holder 5088. Tips 5098, cavities 5096, and retaining clip 5018 are configured to retain tibial support 5006 to tibial support holder 5088. A first arm of arms 5150 couples to support structure 5100 on the medial side of tibial support holder 5088. A second arm of arms 5150 couples to support structure 5100 on the lateral side of tibial support holder 5088. A medial side and a lateral side retaining clip 5100 of support structure 5100 respectively couples to a medial side and a lateral side cavity 5096 on arms 5150. Tibial support 5006 further includes a structure 5102 that is received by an opening 5104 in tibial support holder 5088. Structure 5102 couples to tibial support holder 5088 in a manner that loading applied to tibial support 5006 is distributed to major structural surfaces of tibial support holder 5088. Structure 5102 and the surface in opening 5104 of tibial support holder 5088 are designed to distribute loads seen by surgical apparatus 5000. In one embodiment, retaining clips 5018 are spring loaded and couple to the medial or lateral sides of tibial support holder 5088. In one embodiment, pressing retaining clip 5018 allows room for arms 5150 to clear retaining clips 5018 during a coupling process. Releasing retaining clip 5018 places a portion of retaining clip 5018 into cavity 5096 to prevent movement. In one embodiment, retaining clips 5018 are shaped to fit within cavities 5096 to lock and hold arms 5150 to tibial support holder 5088. Thus, retaining clip 5018 locks tibial support 5006 to tibial support holder 5088. In one embodiment, tibial support 5006 has a retaining structure 5098 that extends past support structures 5100. Retaining structure 5098 couples to a posterior surface of support structures 5100 on the medial and lateral sides. Retaining structure 5098 prevents movement of arms 5150 and retains tibial support 5006 to tibial support holder 5088 when retaining clips 5018 are engaged with cavities 5096. In one embodiment, tibial support 5006 cannot be removed from tibial support holder 5088 unless retaining clips 5018 are freed from cavities 5096 and retaining structure 5098 is lifted above support structure 5100 such that tibial support 5006 can be freely pulled away from tibial support holder 5088. In one embodiment, portions of tibial support holder 5088 or tibial support 5006 can include magnets. For example, cavities 5096 or retaining clip 5018 can include one or magnets that support retention of the portion of retaining clip 5018 to cavities 5096 that hold tibial support 5006 to tibial support holder 5006.

Distraction mechanism 5012 comprises a medial support structure 5106, cage system 5011, and a medial tilting screw 5110. Medial support structure 5106 includes a first opening, a second opening, and a threaded opening. Distraction mechanism 5012 is configured to move medial support structure 5106 relative to tibial support 5006. Femoral support 5008 is configured to couple to medial support structure 5106. Raising or lowering medial support structure 5106 changes a height of the medial compartment of the knee joint. In one embodiment, a direction of movement of medial support structure 5106 is determined by cage system 5011. Anterior medial guide shaft 5064 couples through the first opening in medial support structure 5106. Similarly, posterior medial guide shaft 5068 couples through the second opening in medial support structure 5106. Movement and trajectory of medial support structure 5106 are aligned to anterior medial guide shaft 5064 and posterior medial guide shaft 5068. The surfaces within the first and second openings of medial support structure 5106 can be bearing surfaces to reduce friction as medial support structure 5106 moves up or down within cage system 5011. Medial tilting screw 5110 couples through an opening in cap 5062 and the head of medial tilting screw 5110 is supported by cap 5062. In one embodiment, the opening in cap 5062 is between openings for anterior medial guide shaft 5064 and posterior medial guide shaft 5068 in cap 5062. Medial tilting screw 5110 couples through the opening into the threaded opening of medial support structure 5106. In one embodiment, medial tilting screw 5110 couples to the threaded opening of medial support structure 5106 parallel to anterior medial guide shaft 5064 or posterior medial guide shaft 5068. In one embodiment, the threads of medial tilting screw 5110 engage with the threads in the threaded opening of medial support structure 5106 to hold medial support structure 5106 in a fixed position. The engaged threads between medial tilting screw 5110 and the threaded opening in medial support structure 5106 can support loading applied to femoral support 5008 and will not change the medial compartment height unless medial tilting screw 5110 is rotated. The opening in cap 5062 for receiving medial tilting screw 5110 can be threaded or non-threaded. In one embodiment, medial tilting screw 5110 is an Allen head screw. An Allen wrench can be used to rotate medial tilting screw 5110. Rotating medial tilting screw 5110 can pull medial support structure 5106 towards cap 5062 or away from cap 5062 depending on the direction of rotation.

Distraction mechanism 5014 comprises a lateral support structure 5108, cage system 5011 and a lateral tilting screw 5112. Medial support structure 5108 includes a first opening, a second opening, and a threaded opening. Distraction mechanism 5014 is configured to move lateral support structure 5108 relative to tibial support 5006. Femoral support 5008 is configured to couple to lateral support structure 5108. Raising or lowering lateral support structure 5108 changes a height of the lateral compartment of the knee joint. In one embodiment, a direction of movement of medial support structure 5108 is determined by cage system 5011. Anterior lateral guide shaft 5066 couples through the first opening in lateral support structure 5108. Similarly, posterior lateral guide shaft 5070 couples through the second opening in lateral support structure 5108. Movement and trajectory of lateral support structure 5108 are aligned to anterior lateral guide shaft 5066 and posterior lateral guide shaft 5070. The surfaces within the first and second openings of medial support structure 5108 can be bearing surfaces to reduce friction as lateral support structure 5108 moves up or down within cage system 5011. Lateral tilting screw 5112 couples through an opening in cap 5062 and the head of lateral tilting screw 5112 is supported by cap 5062. In one embodiment, the opening in cap 5062 is between openings for anterior lateral guide shaft 5066 and posterior lateral guide shaft 5070 in cap 5062. Lateral tilting screw 5112 couples through the opening in cap 5062 into the threaded opening of lateral support structure 5108. In one embodiment, lateral tilting screw 5112 couples to the threaded opening of lateral support structure 5106 parallel to anterior lateral guide shaft 5066 or posterior lateral guide shaft 5070. In one embodiment, the threads of lateral tilting screw 5112 engage with the threads in the threaded opening of lateral support structure 5108 to hold lateral support structure 5108 in a fixed position. The engaged threads between lateral tilting screw 5112 and the threaded opening in lateral support structure 5108 can support loading applied to femoral support 5008 and will not change the lateral compartment height unless lateral tilting screw 5112 is rotated. The opening in cap 5062 for receiving lateral tilting screw 5112 can be threaded or non-threaded. In one embodiment, lateral tilting screw 5112 is an Allen head screw. An Allen wrench can be used to rotate lateral tilting screw 5112. Rotating lateral tilting screw 5112 can pull lateral support structure 5108 towards cap 5062 or away from cap 5062 depending on the direction of rotation.

Distraction mechanisms 5010, 5012, and 5014 can be motivated by means other than screws or non-manually as disclosed herein above. For example, movement of distraction mechanism 5010, 5012, or 5014 can be controlled pneumatically or by actuators. The process can also be automated to precisely turn distraction mechanisms 5010, 5012, or 5014 via a control system using feedback from sensors on surgical apparatus 5000 or module 5024. Thus, distraction mechanism 5010, 5012, and 5014 are adaptable for use in robotic surgery or can be used manually under surgeon control. The implementation of distraction mechanism 5010, 5012, and 5014 with cage system 5011 supports higher loading at lower weight than other designs.

In one embodiment, a spacer 5140 is used to place medial support structure 5106 and lateral support structure 5108 in a reference position. Spacer 5140 has a predetermined height that determines the reference position. Spacer 5140 has a first opening and a second opening that respectively couples through posterior medial guide shaft 5068 and posterior lateral guide shaft 5070 of cage system 5011. Spacer 5140 couples between base 5060 and medial support structure 5106. Similarly, spacer 5140 couples between base 5060 and lateral support structure 5108. In one embodiment, the reference position is established when surgical apparatus 5000 is in a minimum height position. In one embodiment, the minimum height position corresponds to a minimum height of surgical apparatus 5000 measured from a bottom surface 5142 of tibial support 5006 to exposed surfaces of covers 5126 and 5128 that couple to module 5024. Module 5024 is placed on and retained by femoral support 5008. A first side of spacer 5140 will couple to base 5060 and second side of spacer 5140 will couple to medial support structure 5106 and lateral support structure 5108. In one embodiment, the minimum height of surgical apparatus 5000 corresponds to a bottom surface 5170 of femoral support 5008 being co-planar with bottom surface 5142 of tibial support 5006. In one embodiment, the position of spacer 5140 can be fixed such that spacer 5140 remains coupled to base 5060 when medial or lateral compartment heights are changed.

Femoral support 5008 is configured to couple to a femur of a knee joint. In one embodiment, femoral support 5008 couples to a medial condyle and a lateral condyle at a distal end of the femur. A module 5024 couples between the condyles of the femur and femoral support 5008. In one embodiment, cover 5126 and cover 5128 respectively overlie a medial side 5130 and a lateral side 5132 of module 5024. In one embodiment, covers 5126 and 5128 are rigid and do not flex. Module 5024 includes at least one sensor to measure a parameter, a power source, and electronic circuitry to control a measurement process and transmit measurement data to a computer. In one embodiment, surgical apparatus 5000 is in a surgical field of an operating room and the computer is placed in the operating room where the surgeon or surgical team can view the information generated by module 5024 and surgical apparatus 5000. In one embodiment, measurement data from module 5024 and surgical apparatus 5000 can be used to calculate alignment, leg position, measure medial compartment loading, measure lateral compartment loading, identify a medial condyle contact point on medial side 5130 of module 5024, identify a lateral condyle contact point on lateral side 5132 of module 5024, and measure contact point rotation of surgical apparatus 5000 to name but a few parameters that can be provided. In one embodiment, cover 5126 or cover 5128 distributes loading to underlying load sensors in module 5024. In one embodiment, module 5024 can be used after removing surgical apparatus 5000 from the knee joint in a trialing process with installed prosthetic components of the knee joint to take further measurements.

Module 5024 couples to and is retained by femoral support 5008. Module 5024 has at least one retaining feature. In one embodiment, module 5024 has a retaining feature 5114 that couples to an opening 5134 formed in femoral support 5008. In one embodiment, module 5024 is tilted to allow retaining feature 5114 to be placed into opening 5134 and then released. Sidewalls of femoral support 5008 prevent module 5024 from moving during a distraction or measurement process. In one embodiment, module 5024 cannot be removed unless module 5024 is tilted upward from surface 5116 of femoral support 5008 such that module 5024 clears the sidewalls of femoral support 5008 and then is moved such that retaining feature 5114 is no longer within opening 5134.

Femoral support 5008 couples to medial support structure 5106 and lateral support structure 5108 respectively at a first pivot point and a second pivot point. Rotating medial tilting screw 5110 raises or lowers medial support structure 5106 to change a medial-lateral tilt of femoral support 5008. Similarly, rotating lateral tilting screw 5112 raises or lowers lateral support structure 5108 to change the medial-lateral tilt of femoral support 5008. The first and second pivot points pivot when the height of the medial compartment differs from the height of the lateral compartment. Loading applied to femoral support 5008 during distraction is distributed through the first and second pivot points of surgical apparatus 5000. In one embodiment, the first pivot point comprises a pin 5118 extending from femoral support 5008 on a medial side that fits into an opening 5122 at a proximal end of medial support structure 5106. In one embodiment, the second pivot point comprises a pin 5120 extending from femoral support 5008 on a lateral side that fits into an opening 5124 at a proximal end of lateral support structure 5108. Openings 5122 and 5124 have bearing surfaces that respectively allow pins 5118 and 5120 to rotate thereby pivoting femoral support 5008.

Figure 55:
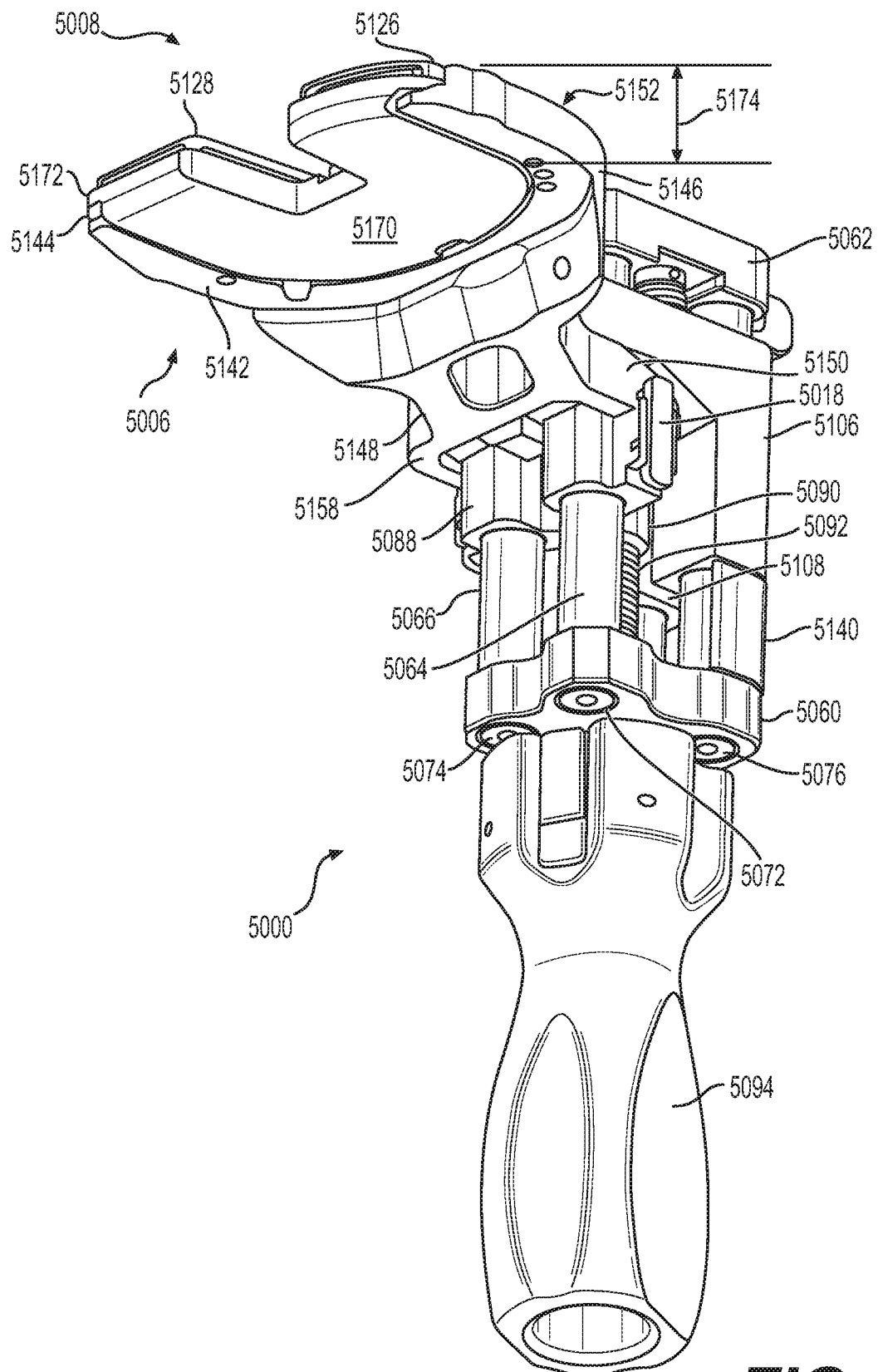
FIG. 55 is an illustration of the surgical apparatus showing bottom surfaces of the femoral support and the tibial support in accordance with an example embodiment.

FIG. 55 is an illustration of surgical apparatus 5000 showing bottom surfaces of femoral support 5008 and tibial support 5006 in accordance with an example embodiment. Typically, surgical apparatus 5000 is inserted into the musculoskeletal system at the minimum height. In the example, surgical apparatus 5000 is shown in the minimum height and is configured to be inserted into a knee joint before increasing the distraction height. In one embodiment, a distraction height corresponds to a measurement of a distance between bottom surface 5142 of tibial support 5006 and a surface of covers 5126 or 5128 as indicated by double sided arrow 5174. In one embodiment, the minimum height of surgical apparatus 5000 occurs when handle 5094 is rotated such that bottom surface 5170 of femoral support 5008 is co-planar to bottom surface 5142 of tibial support 5006.

In general, surgical apparatus 5000 as shown in FIG. 55 is set to the minimum height. Femoral support 5008 fits within the opening of U-shaped structure 5152 at the minimum height. In one embodiment, medial support structure 5106 and lateral support structure 5108 couple to spacer 5140 at the minimum height. Medial support structure 5106 and lateral support structure 5108 are positioned at the same height when coupled to spacer 5140. In one embodiment, there is a gap between medial support structure 5106 and cap 5062. Similarly, there is a gap between lateral support structure 5108 and cap 5062. Medial support structure 5106 and lateral support structure 5108 can move towards cap 5062 but cannot move towards base 5060 because spacer 5140 prevents movement at the minimum height. In one embodiment, a portion 5172 of femoral support 5008 overlies surface 5144 of U-shaped structure 5152. A peripheral surface of the portion 5172 of femoral support 5008 couples to surface 5144 of U-shaped structure 5152 when at the minimum height. As mentioned previously, bottom surface 5170 of femoral support 5008 will be co-planar to bottom surface 5142 of when at the minimum height. Note that there is a gap between tibial support holder 5088 and base 5060 at the minimum height. Tibial support holder 5088 cannot be raised at the minimum height. Lowering tibial support holder 5088 by rotating handle 5094 (clockwise) increases the distraction height from the minimum.

Figure 56A:
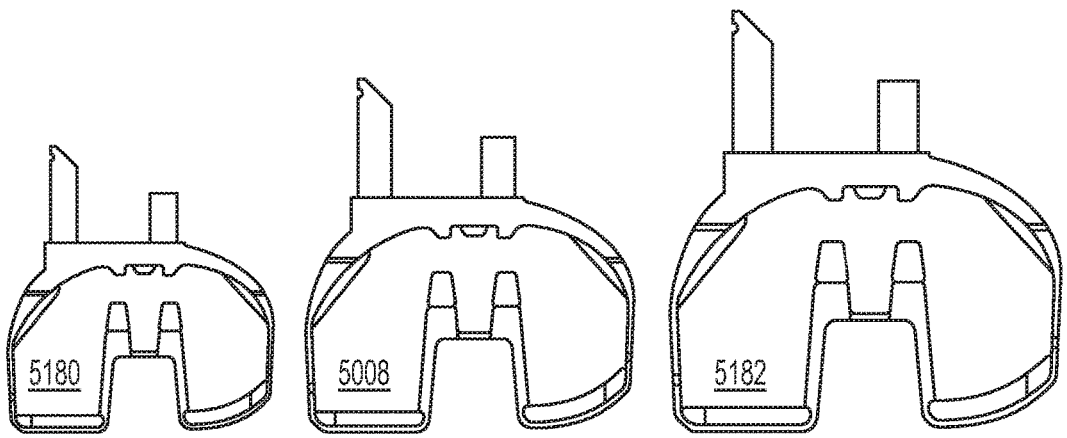
FIG. 56A is an illustration of a plurality of femoral supports in accordance with an example embodiment.

FIG. 56A is an illustration of a plurality of femoral supports in accordance with an example embodiment. In one embodiment, surgical apparatus 5000 of FIG. 53 is provided in a right leg surgical apparatus and a left leg surgical apparatus having a leg offset that supports patellar loading over the range of motion for a kinetic assessment that provides quantitative measurement data for the installation of a prosthetic right knee joint or a prosthetic left knee joint. In general, bone sizes vary significantly over a large population. Different size femoral supports and tibial supports are also provided to accommodate different bone sizes. In FIG. 56A a femoral support 5180, femoral support 5008, and a femoral support 5182 respectively correspond to small, medium, and large size femoral supports that are suitable for use over a large variation of the population. The surgeon selects and uses an appropriate size femoral support for a bone size of a patient. Femoral support 5180, femoral support 5008, and femoral support 5182 can be provided in right leg versions and left leg versions. In one embodiment, right leg versions of femoral support 5180, femoral support 5008, and femoral support 5182 cannot be used on surgical apparatus 5000 for a left leg. Similarly, left leg versions of femoral support 5180, femoral support 5008, and femoral support 5182 cannot be used on surgical apparatus 5000 for a right leg. In one embodiment, femoral support 5180, femoral support 5008, and femoral support 5182 does not have an offset can be used in both a right leg and left leg surgical apparatus 5000 whereby the offset is in surgical apparatus 5000. In one embodiment, module 5024 fits in each of femoral support 5180, femoral support 5008, and femoral support 5182 such that a single module is required for a surgical operation independent of the bone size of the patient.

Figure 56B:
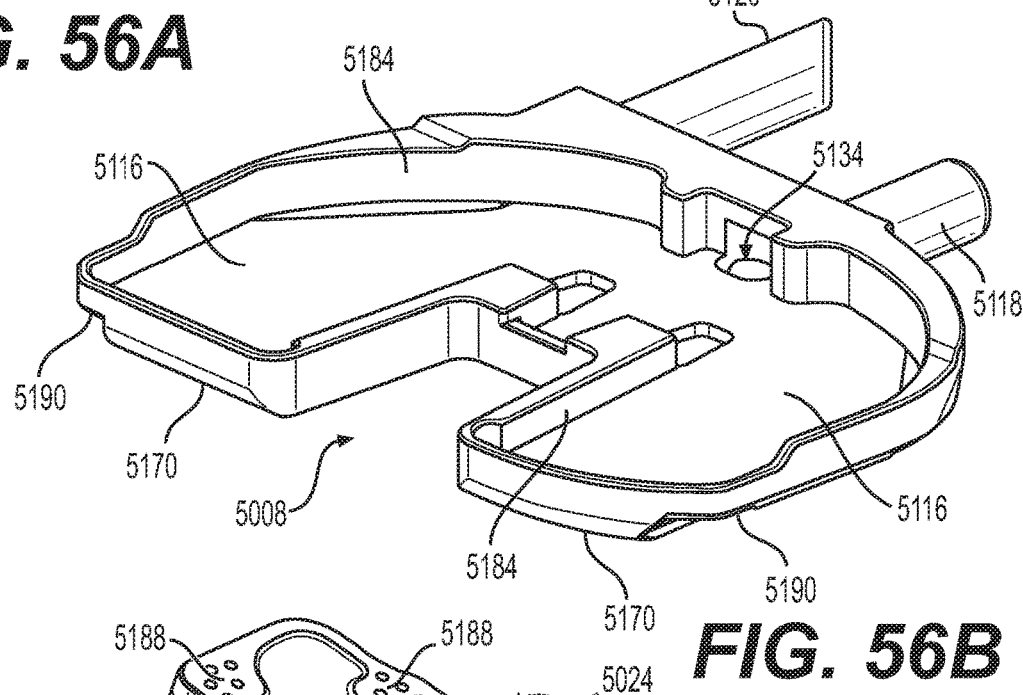
FIG. 56B illustrates femoral support 5008 in accordance with an example embodiment.

FIG. 56B illustrates femoral support 5008 in accordance with an example embodiment. In one embodiment, femoral support 5008 comprises major surface 5116, bottom surface 5170, sidewalls 5184, pin 5120, pin 5118, and opening 5134. In one embodiment, a peripheral surface 5190 of femoral support 5008 is configured to couple to the tibial support when surgical apparatus is at a minimum height. Pins 5118 and 5120 are configured to respectively couple to the medial support structure and the lateral support structure and allow femoral support 5008 to medially and laterally pivot. In one embodiment, pins 5118 and 5120 can be offset to support patellar loading for a kinetic assessment that generates quantitative measurement data. Loading applied to femoral support 5008 will be distributed through pins 5118 and 5120. Thus, a single pin or pivot is not supporting the entire load.

Figure 56C:
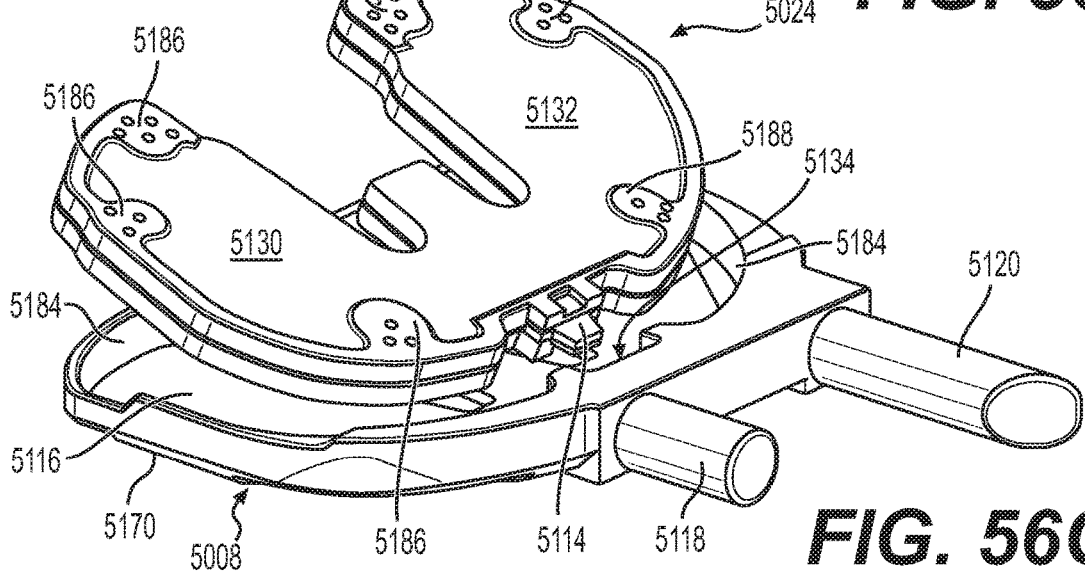
FIG. 56C illustrates the module being inserted into the femoral support in accordance with an example embodiment.

FIG. 56C illustrates module 5024 being inserted into femoral support 5008 in accordance with an example embodiment. In one embodiment, module 5024 is a disposable item. Module 5024 includes one or more sensors and is configured to measure one or more parameters related to the musculoskeletal system. Referring briefly to FIG. 15, module 5024 includes electronic circuitry 150 and couples to one or more sensors 152. In one embodiment, module 5024 is a hermetically sealed device including a power source configured to power the device for a single application. Module 5024 is configured similarly to module 150. For example, module 5024 is configured to measure such parameters as loading, balance, position, alignment, position of load, medial-lateral tilt, anterior-posterior tilt, and movement when placed in surgical apparatus 5000. In one embodiment, loading applied to a medial side and loading applied to a lateral side of measurement module 5024 is measured and transmitted to computer 5026 of FIG. 53. In one embodiment, the quantitative measurement data from surgical apparatus 5000 and module 5024 is used to support one or more bone cuts to install one or more prosthetic components.

Module 5024 can be used later in the installation prior to a final installation of the prosthetic components to confirm quantitative measurements of the installation after one or more final prosthetic components have been installed on the bone cuts made with surgical apparatus 5000. Module 5024 can be removed from surgical apparatus 5000 and then placed into a shim such that the shim and module 5024 forms a trial prosthetic component substantially equal to a final prosthetic component. The trial prosthetic component is then inserted into the prosthetic joint to take further measurements using the one or more sensors of module 5024 to verify installation parameters previously measured. Once confirmed that the measurements are within predetermined acceptable parameter ranges a final prosthetic component can be installed in the prosthetic joint. The final prosthetic component will have similar or equal measurements since it will have be substantially equal in shape and size as the trial prosthetic component. Module 5024 is disposed of after the surgical procedure has been completed.

Module 5024 couples to a major surface 5116 of femoral support 5008. In one embodiment, module 5024 is non-symmetrical about the medial-lateral axis. For example, module 5024 can only be inserted one way into a right knee joint femoral support 5008. An opposing side of module 5024 is visible when inserted into a left knee joint femoral support 5008. In one embodiment, module 5024 fits into all left and right knee joint femoral supports such that a single module is used during an operation on the musculoskeletal system independent of the type or size of the femoral support. Module 5024 has at least one retaining feature to retain module 5024 within femoral support 5008. In one embodiment, retaining feature 5114 is a tab that extends from a posterior side of module 5024. An opening 5134 in femoral support 5008 is configured to receive retaining feature 5114. Module 5024 is angled to clear the sidewalls 5184 of femoral support 5008 such that retaining feature 5114 can be inserted into opening 5134 of femoral support 5008. Module 5024 can be dropped or placed into femoral support 5008 once retaining feature 5114 is in opening 5134 of femoral support 5008. Retaining feature 5114 and sidewalls 5184 of femoral support 5008 prevent movement of module 5024 during a measurement process.

Module 5024 has a medial side 5130 and a lateral side 5132. In one embodiment, medial side 5130 of module 5024 has raised regions 5186 that have a surface above the major medial side surface. Similarly, lateral side 5132 of module 5024 has raised regions 5188 that a surface above the major medial side surface. In one embodiment, load sensors underlie raised regions 5186 and 5188. The position of the load sensors are known within module 5024. A load magnitude and a position of applied load can be calculated from the load values and position of the load sensors underlying raised region 5186 and 5188 respectively on medial side 5130 and lateral side 5132. The calculation of the load magnitude and the position of applied load on medial side 5130 and lateral side 5132 is calculated by the computer as shown in FIG. 53 after receiving measurement data from each load sensor from module 5024. Note that the medial side and the lateral sides are the same side when module 5024 is flipped over to use on an opposite type (e.g. right knee to left knee).

Figure 57:
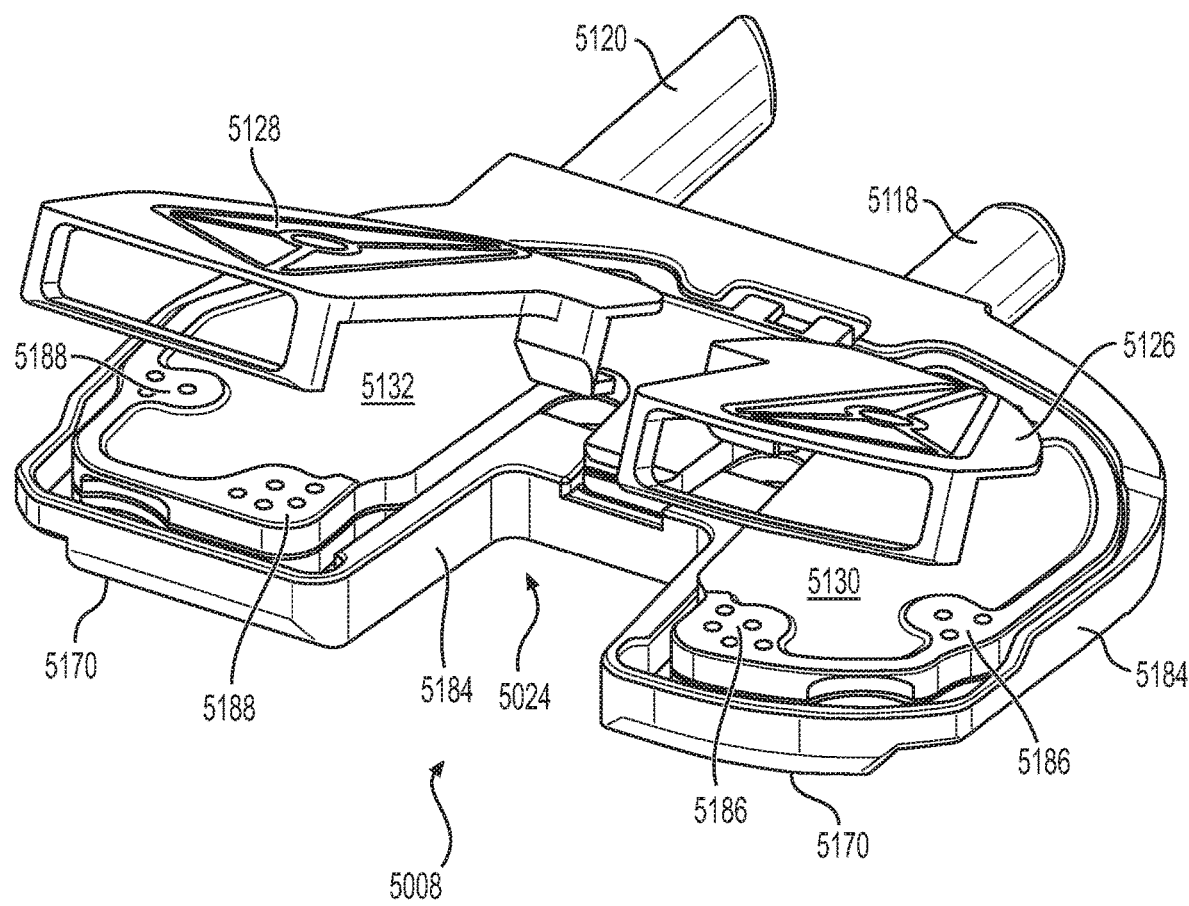
FIG. 57 is an illustration of a first cover and a second cover prior to coupling to the module in accordance with an example embodiment.

FIG. 57 is an illustration of cover 5126 and cover 5128 prior to coupling to module 5024 in accordance with an example embodiment. Cover 5126 and cover 5128 are configured to respectively couple to medial side 5130 and lateral side 5132 of module 5024. In the example, femoral support 5008 is configured for a left knee insertion. As mentioned previously, module 5024 is non-symmetrical having medial side 5130 of module 5024 having a different shape, area, or contour than lateral side 5132 of module 5024. In one embodiment, cover 5126 has a different shape or area than cover 5128. In one embodiment, covers 5126 and 5128 comprise a rigid material such as metal, metal alloy, a composite material, of a polymer material. In one embodiment, covers 5126 and 5128 do not flex or bend when loaded. Covers 5126 and 5128 respectively are configured to distribute loading to raised regions 5186 on medial side 5130 and raised regions 5188 on lateral side 5132 of module 5024. In one embodiment, raised regions 5186 and 5188 extend above sidewalls 5184 of femoral support 5008 such that covers 5126 and 5128 couple to raised region 5186 and 5188 and not sidewalls 5184. In one embodiment, covers 5126 and 5128 overlie the major surfaces of medial side 5130 and lateral side 5132 of module 5024. In the example, a medial condyle and a lateral condyle of a femur respectively couple to cover 5126 on medial side 5130 of module 5024 and cover 5128 on lateral side 5132 of module 5024. The medial and lateral condyles of the femur respectively apply a force, pressure, or load to sensors underlying raised regions 5186 and 5188. Electronic circuitry within module 5024 couples to one or more sensors and transmits quantitative measurement data to a computer for viewing by the surgical team. Covers 5126 and 5128 can be retained to module 5024 or femoral support 5008 to prevent movement of covers 5126 and 5128.

Figure 58:
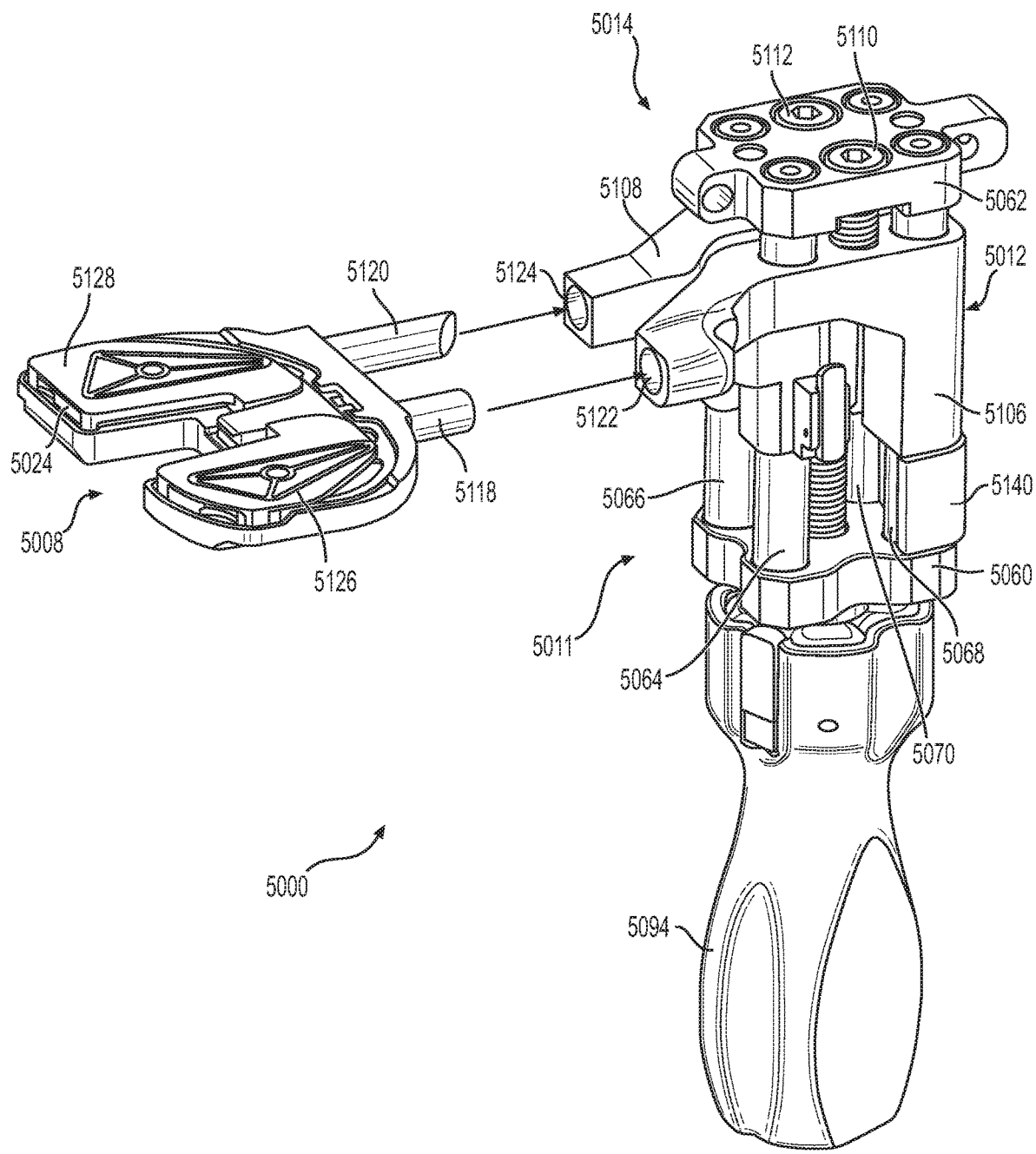
FIG. 58 is an illustration of the femoral support being coupled to the medial support structure and the lateral support structure in accordance with an example embodiment.

FIG. 58 is an illustration of femoral support 5008 being coupled to medial support structure 5106 and lateral support structure 5108 in accordance with an example embodiment. The tibial support and the tibial support holder are not shown in the illustration to allow detail of the operation of distraction mechanisms 5012 and 5014 to be shown. Module 5024 is coupled to femoral support 5008. Covers 5126 and 5128 couple to module 5024 to distribute loading to underlying load sensors in module 5024. Pin 5118 and pin 5120 respectively extend from the medial side and the lateral side of femoral support 5008. In one embodiment, pins 5118 and 5120 are cylindrical to support movement or rotation of femoral support 5008.

Distraction mechanism 5012 comprises medial support structure 5106, anterior medial guide shaft 5064, posterior medial guide shaft 5068, base 5060, cap 5062, spacer 5140, and screw 5110. Distraction mechanism 5012 of surgical apparatus 5000 raises or lowers the height of the medial compartment of a knee joint. Medial support structure 5106 couples to and moves on a trajectory determined by anterior medial guide shaft 5064 and posterior medial guide shaft 5068. Rotating screw 5110 raises or lowers medial support structure 5106. In one embodiment, rotating screw 5110 clockwise raises medial support structure 5106. Conversely, rotating screw 5110 counterclockwise lowers medial support structure 5106 unless spacer 5140 and base 5060 prevent movement.

Distraction mechanism 5014 comprises lateral support structure 5108, anterior lateral guide shaft 5066, posterior lateral guide shaft 5070, base 5060, cap 5062, spacer 5140, and screw 5112. Distraction mechanism 5014 of surgical apparatus 5000 raises or lowers the height of the lateral compartment of a knee joint. Lateral support structure 5108 couples to and moves on a trajectory determined by anterior lateral guide shaft 5066 and posterior lateral guide shaft 5070. Rotating screw 5112 raises or lowers lateral support structure 5108. In one embodiment, rotating screw 5112 clockwise raises lateral support structure 5108. Conversely, rotating screw 5112 counterclockwise lowers lateral support structure 5108 unless spacer 5140 and base 5060 prevent movement.

Cage system 5011 comprises medial guide shaft 5064, posterior medial guide shaft 5068, anterior lateral guide shaft 5066, posterior lateral guide shaft 5070, cap 5062, and base 5060. In one embodiment, medial guide shaft 5064, posterior medial guide shaft 5068, anterior lateral guide shaft 5066, posterior lateral guide shaft 5070 are parallel to one another. Base 5060 couples to the distal ends of anterior medial guide shaft 5064, anterior lateral guide shaft 5066, posterior medial guide shaft 5068, and posterior lateral guide shaft 5070. Cap 5062 couples to the proximal ends of anterior medial guide shaft 5064, anterior lateral guide shaft 5066, posterior medial guide shaft 5068, and posterior lateral guide shaft 5070. Medial guide shaft 5064 and posterior medial guide shaft 5068 couples through openings in medial support structure 5012. Screw 5110 couples through cap 5062 to a threaded opening in medial support structure 5106. Anterior lateral guide shaft 5066 and posterior lateral guide shaft 5070 couples through opening in lateral support structure 5014. Screw 5112 couples through cap 5062 to a threaded opening in lateral support structure 5108. As shown, spacer 5140 couples between base 5060 and medial support structure 5106 or lateral support structure 5108. In one embodiment, a minimum height medial compartment or a minimum height lateral compartment corresponds to medial support structure 5012 or lateral support structure 5104 coupled to spacer 5140 and base 5060 such that screws 5110 or 5112 respectively cannot be rotated to move medial support structure 5012 or lateral support structure away from cap 5062. Screws 5110 or 5112 can be rotated to respectively move medial support structure 5106 or lateral support structure 5108 towards cap 5062 as a gap exists between cap 5062 and medial support structure 5106 or lateral support structure 5108 to support movement to adjust a medial or lateral compartment height.

Pins 5118 and 5120 can have a bearing surface that supports rotational movement. Pin 5118 and pin 5120 respectively couple within opening 5122 in medial support structure 5106 and opening 5124 in lateral support structure 5124. Surfaces within openings 5122 and 5124 can also be bearing surfaces to support rotational movement. Pin 5118 within opening 5122 is a first pivot point that allows femoral support structure 5008 to rotate medially or laterally. Pin 5120 within opening 5124 is a second pivot point that allows femoral support structure 5008 to also rotate medially or laterally. Loading applied to femoral support 5008 is distributed between the first and second pivot points thereby reducing the load distribution on each pivot point. Reducing load pivot point loading increases mechanical reliability of operation of surgical apparatus 5000 and improves measurement performance as flexing and torsional forces are reduced as the load is distributed.

Figure 59A:
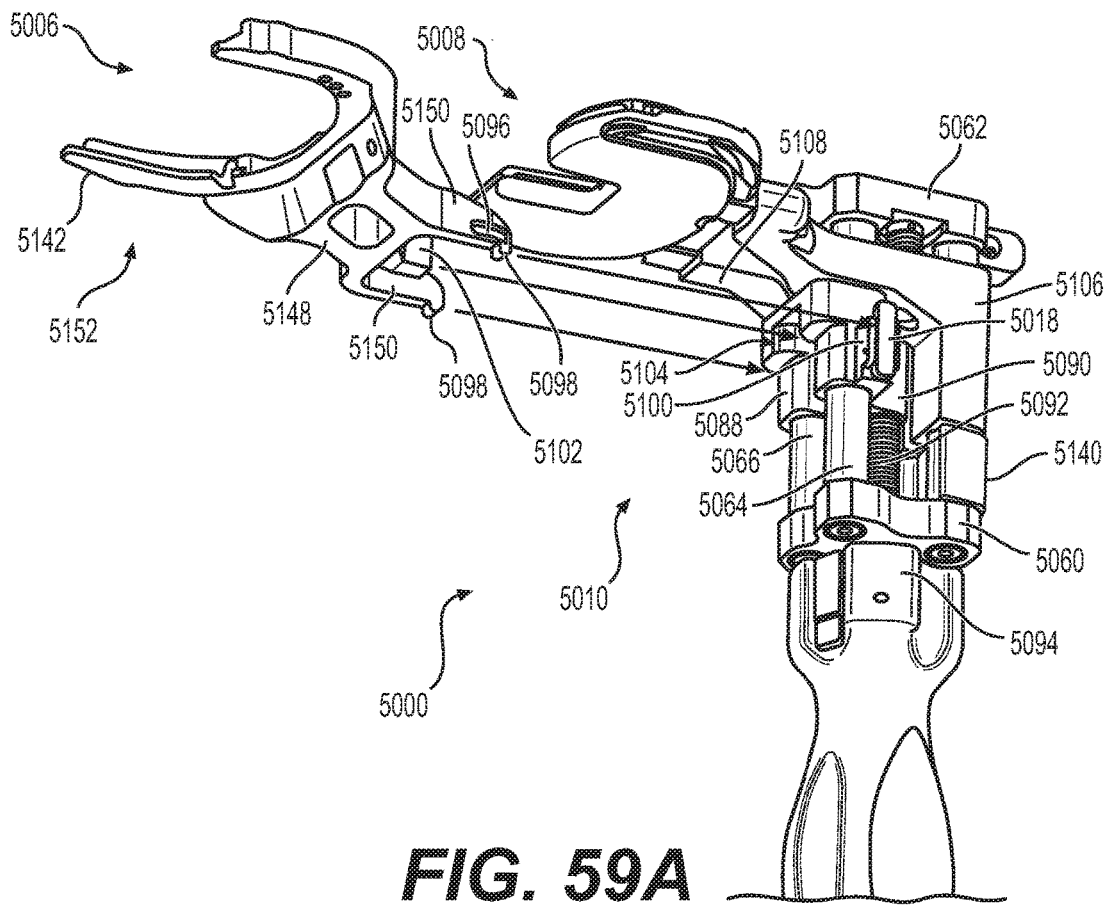
FIG. 59A is an illustration of the surgical apparatus showing the tibial support being coupled to the tibial support holder in accordance with an example embodiment.

FIG. 59A is an illustration of surgical apparatus 5000 showing tibial support 5006 being coupled to tibial support holder 5088 in accordance with an example embodiment. In one embodiment, distraction mechanism 5010 comprises tibial support 5006, tibial support holder 5088, anterior medial guide shaft 5064, anterior posterior guide shaft 5066, distraction lead screw 5092, base 5060, cap 5062, and handle 5094. In one embodiment, distraction mechanism 5010 raises or lowers the medial and lateral compartments simultaneously and by the same amount. Tibial support structure 5008 moves on and along a trajectory determined by anterior medial guide shaft 5064 and anterior lateral guide shaft 5066. In one embodiment, anterior medial guide shaft 5064 and anterior lateral guide shaft 5066 are parallel to one another. Base 5060 couples to the distal ends of anterior medial guide shaft 5064 and anterior lateral guide shaft 5066. Cap 5062 couples to the proximal ends of anterior medial guide shaft 5064 and anterior lateral guide shaft 5066. Threaded structure 5090 couples to or is part of tibial support structure 5088. A proximal end of distraction lead screw 5092 couples through an opening in base 5060 to threaded structure 5090. Handle 5094 couples to a distal end of distraction lead screw 5092 to allow a user to hold surgical apparatus 5000 and distract the medial and lateral compartments of a knee joint simultaneously. Rotating handle 5094 turns distraction lead screw 5092 to raise or lower tibial support holder 5088 and thereby raise or lower tibial support 5006 which couples to tibial support holder 5088.

Similar to femoral support 5008, tibial support 5006 is a removable structure for coupling different size tibial supports to distraction mechanism 5010. In one embodiment, tibial support comes in a large, medium, and small size that can accommodate the variation of bone sizes over a large portion of the population. Tibial support 5008 includes support structure 5100 having retaining clip 5018 on the medial side. Support structure 5100 couples to and extends from the medial and the lateral side of tibial support structure 5088. In one embodiment, support structure 5100 is formed as part of tibial support structure 5088. Although not visible, tibial support structure 5088 has a second support structure 5100 having retaining clip 5018 on the lateral side. Support structures 5100 are designed to support and retain arms 5150 of tibial support 5006 to tibial support structure 5000. In one embodiment, tibial support 5006 has a medial arm and a lateral arm. In one embodiment, tibial support 5006 couples to tibial support holder 5088 in an over and under configuration. Arms 5150 each couple over support structure 5100 while structure 5102 of tibial support 5006 couples under tibial support holder 5088 into opening 5104. The over and under configuration holds tibial support 5006 to tibial support holder 5088 at the predetermined medial and lateral compartment heights under loading by the knee joint during distraction.

Figure 59B:
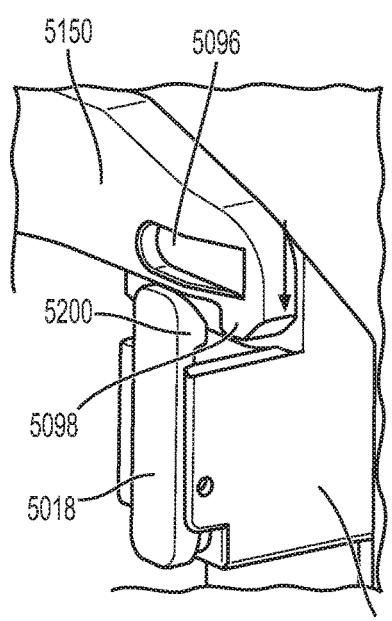
FIG. 59B is an illustration of the arm of the tibial support positioned in relation to the retaining clip prior to coupling in accordance with an example embodiment.

In FIG. 59B, arm 5150 is shown positioned in relation to retaining clip 5018 prior to coupling. As disclosed, coupling of arm 5150 of tibial support 5006 to support structure 5100 of tibial support holder 5088 is the same on the medial or lateral sides. Arm 5150 extends past support structure 5100. Retaining structure 5098 of arm 5150 is placed past support structure 5100. Arm 5150 is configured to couple to support structure 5100 once retaining structure 5098 is past support structure 5100 as indicated by arrow 5201. Arm 5150 is supported by support structure 5100 and retaining structure 5098 is configured to prevent removing tibial support 5006 from surgical apparatus 5000. Arm 5150 includes a cavity 5096 configured to couple to retaining clip 5018. Retaining clip 5018 has a raised region 5200 that faces cavity 5096 that is configured to fit within cavity 5096 of arm 5150 to retain and prevent movement once engaged. In one embodiment, raised region 5200 is shaped identical to at least a portion of cavity 5096 and is configured to fit within cavity 5096.

Figure 59C:
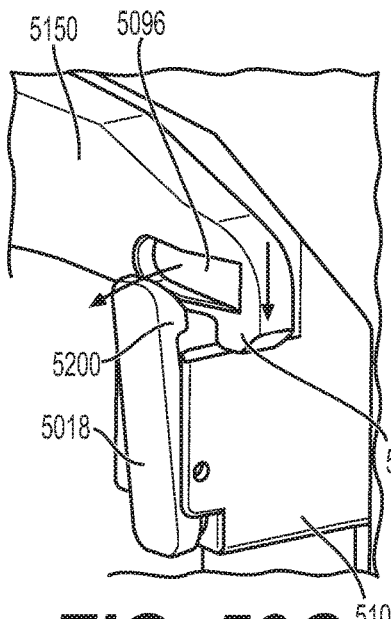
FIG. 59C is an illustration showing the clip being pressed to allow clearance for the arm of the tibial support to allow movement past the support structure of the tibial support holder in accordance with an example embodiment.

Clip 5018 pivots as shown in FIG. 59C to allow clearance for arm 5150 to move past support structure 5100. In one embodiment, a user presses a distal portion of clips 5018 on both sides of support structure 5100 to provide clearance to move arms 5150 between tibial support holder 5088 and clips 5018. Clip 5018 and raised region 5200 is shown providing clearance for arm 5150 as indicated by arrow 5203 when a distal portion of clip 5018 is pressed. Arm 5150 can couple to support structure 5100 once retaining structure 5098 is past support structure 5100 as indicated by arrow 5201. In one embodiment, clips 5018 can be spring loaded such that a force is applied to a distal end of clip 5018 to create the clearance. Arm 5150 can then couple to support structure 5100 in the over and under configuration disclosed herein above.

Figure 59D:
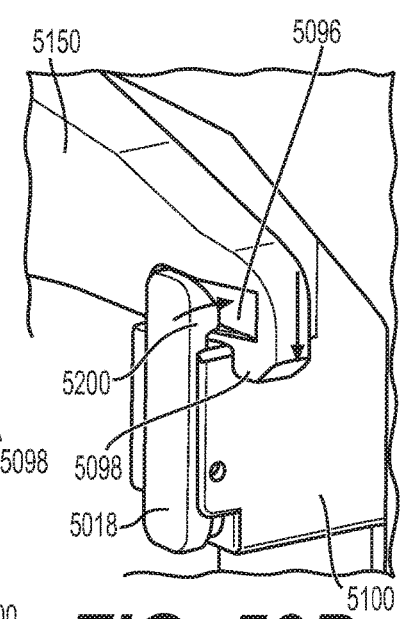
FIG. 59D is an illustration showing the arm of the tibial support being supported by a support ledge of the support structure of the tibial support structure in accordance with an example embodiment.

Clip 5018 can be released as shown in FIG. 59D when arm 5150 couples to a support ledge of support structure 5100. Raised region 5200 of clip 5018 will move towards cavity 5096 when released as indicated by arrow 5205. In one embodiment, arm 5150 also couples to a side wall of tibial support holder 5088. In one embodiment, releasing clip 5018 places raised regions 5200 into cavity 5096 of arm 5150. In one embodiment, fitting raised regions 5200 into cavities 5096 moves arms 5150 in an optimal position for retention. In one embodiment, raised region 5200 has a three dimensional shape that that fits within an identically shaped cavity 5096 such that clip 5018 locks into place when released. The position of clip 5018 in relation to cavity 5096 in the locked position corresponds to an edge of retaining feature 5098 coupling to support structure 5100 as shown in FIG. 59D. As mentioned the spring force of clips 5018 can hold raised region 5200 into cavity 5096 of arm 5150. Alternatively, a magnetic force or magnetic materials can be used to retain clip 5200 within cavity 5096 where at least one of retaining clip 5200 or cavity walls within cavity 5096 are magnetic and the other is a ferrous material. As mentioned previously, clips 5018 couple to arms 5150 on the medial and lateral sides of tibial support 5006. Thus, what is disclosed above occurs simultaneously on the medial and lateral sides when arms 5150 of tibial support 5006 couple to tibial support holder 5088.

Figure 60:
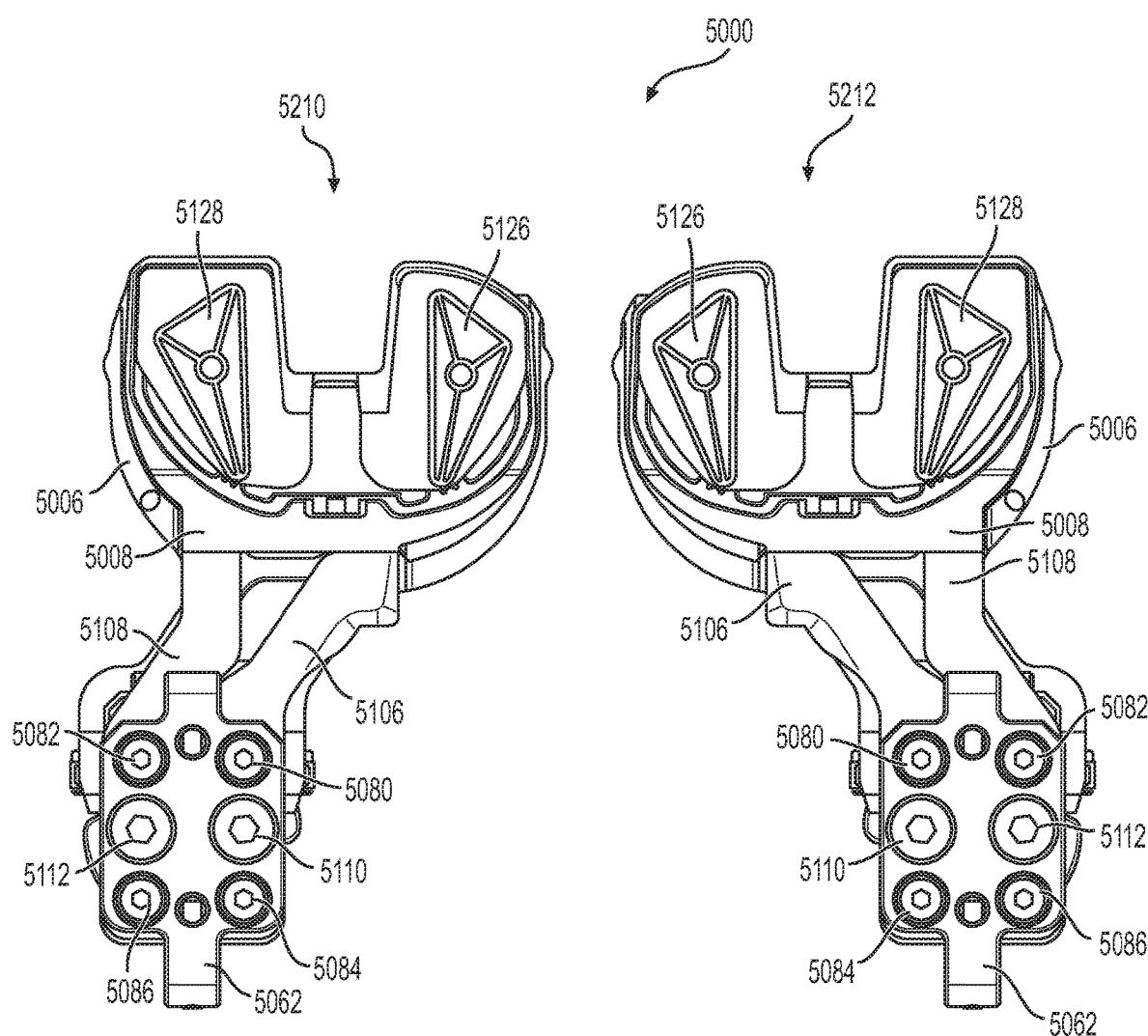
FIG. 60 is a top view of the surgical apparatus having an offset for a right knee joint and an offset for a left knee joint in accordance with an example embodiment.

FIG. 60 is a top view of surgical apparatus 5000 having an offset for a right knee joint and an offset for a left knee joint in accordance with an example embodiment. In the example, surgical apparatus 5000 is provided in a right knee surgical apparatus 5210 and a left knee surgical apparatus 5212. The right knee surgical apparatus 5210 has an offset towards the medial side of the right knee when inserted into the right knee joint. The left knee surgical apparatus 5212 has an offset towards the medial side of the left knee when inserted into the knee joint. Operation of surgical apparatus 5000 as disclosed herein above is identical for right knee surgical apparatus 5210 or left knee surgical apparatus 5212. Thus, surgical apparatus 5000 can be separate devices for a left knee joint or a right knee joint. The components comprising right knee apparatus 5210 and left knee apparatus 5212 are the same except for components introducing the offset. In one embodiment, the offset can be placed in one of or all of medial support structure 5106, lateral support structure 5108, femoral support 5008, and tibial support 5006 for the right knee or the left knee surgical apparatus. The offset of surgical apparatus 5000 allows the patella or extensor mechanism to be anatomical positioned while surgical apparatus 5000 is placed in the knee joint. Alternatively, a single surgical apparatus could be used whereby it is assembled prior to surgery with medial support structure 5106, lateral support structure 5108, femoral support 5008, or tibial support 5006 for the left or right knee joint. Typically, surgical apparatus 5210 and 5212 will be provided in a surgical environment. Once surgical apparatus 5000 is in the knee joint, the patella can be repositioned on the knee joint. Thus, patellar loading is incorporated into all measurements such as alignment, loading, or balance that affect prosthetic component installation for a true kinetic assessment and prosthetic component installation.

Figure 61:
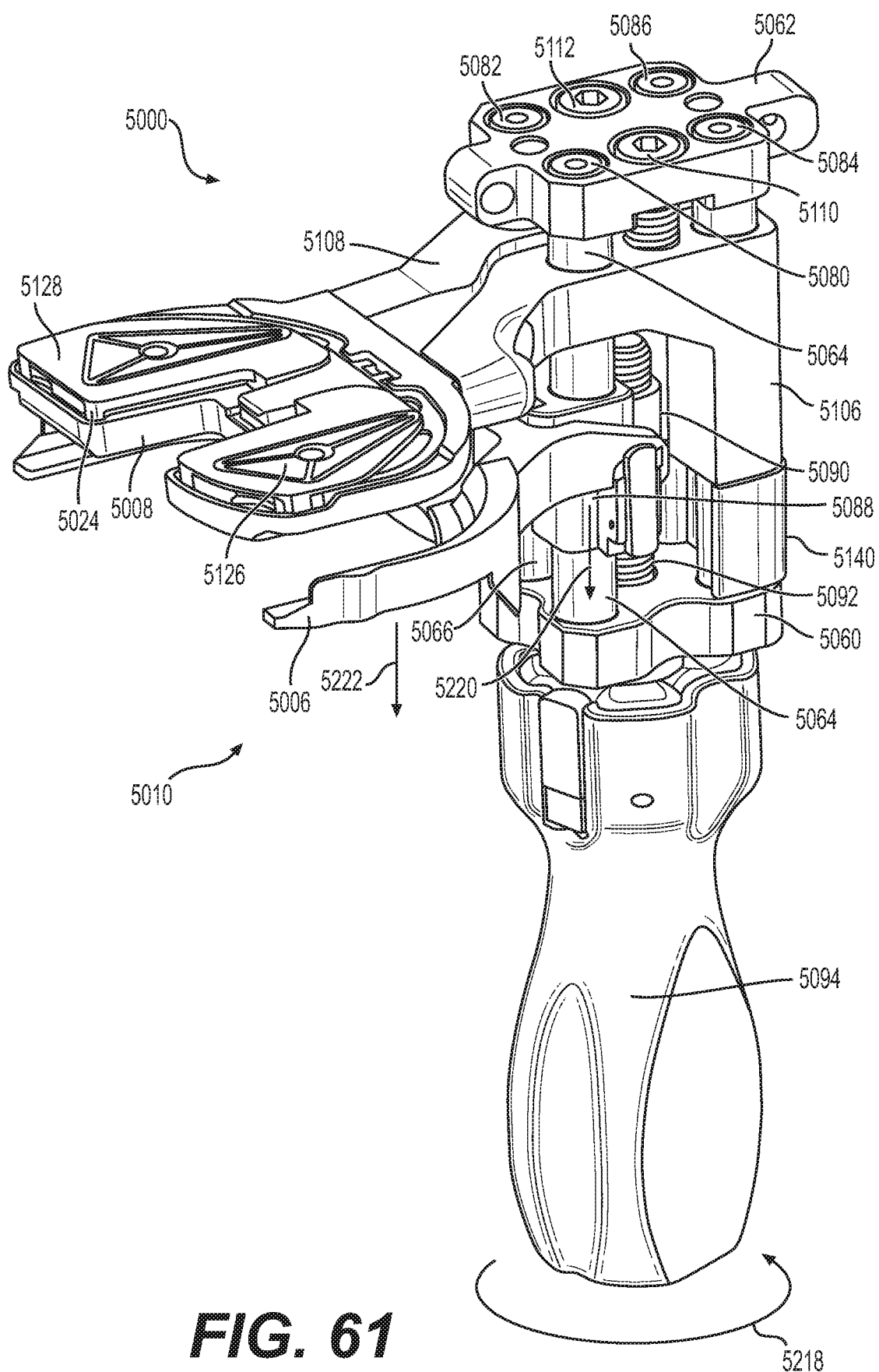
FIG. 61 is an illustration of a first distraction mechanism of the surgical apparatus in accordance with an example embodiment.

FIG. 61 is an illustration of distraction mechanism 5010 of surgical apparatus 5000 in accordance with an example embodiment. Distraction mechanism 5010 comprises tibial support 5006, tibial support holder 5088, anterior medial guide shaft 5064, anterior lateral guide shaft 5066, base 5060, cap 5062, distraction lead screw 5092, and handle 5094. Cap 5062 couples to a proximal end of anterior medial guide shaft 5064 and a proximal end of anterior lateral guide shaft 5066. Screw 5080 couples cap 5062 to anterior medial guide shaft 5064. Screw 5082 couples cap 5062 to anterior lateral guide shaft 5066. Base 5060 couples to a distal end of anterior medial guide shaft 5064 and a distal end of anterior lateral guide shaft 5066. Referring briefly to FIG. 55, screw 5072 couples base 5060 to anterior medial guide shaft 5064. Screw 5074 couples base 5060 to anterior lateral guide shaft 5066. Anterior medial guide shaft 5064 and anterior lateral guide shaft 5066 respectively couples through a medial opening and lateral opening of tibial support holder 5088. Tibial support holder 5088 is configured to move on and aligned to the trajectory of anterior medial guide shaft 5064 and anterior lateral guide shaft 5066. Anterior medial guide shaft 5064 and anterior lateral guide shaft 5066 are parallel to one another. Distraction lead screw 5092 couples through base 5060 to threaded structure 5090 of tibial support holder 5088. Handle 5094 couples to a distal end of distraction lead screw 5092.

Rotating handle 5094 is configured to move tibial support holder 5088 relative to base 5060. In one embodiment, rotating handle 5094 clockwise (as indicated by arrow 5218) is configured to move tibial support holder 5088 towards base 5060. Tibial support 5006 is coupled to tibial support holder 5088 and moves with tibial support holder 5088. Conversely, rotating handle 5094 counter-clockwise moves tibial support holder 5088 in an opposite direction away from base 5060. As shown in FIG. 61, handle 5094 is rotated in a clockwise direction thereby rotating distraction lead screw 5092 within threaded structure 5090 of tibial support holder 5088. Tibial support holder 5088 moves towards base 5060 as indicated by arrow 5220. Similarly, tibial support 5006 moves in a direction indicated by arrow 5222. Thus, the medial and lateral compartment heights with tibial support 5006 moving towards base 5060. Conversely, tibial support 5006 moving in the opposite direction as arrow 5222 will reduce the height of the medial and lateral compartments. In one embodiment, a plane of tibial support 5006 is perpendicular to a plane comprising anterior medial guide shaft 5064 and anterior lateral guide shaft 5066. In one embodiment, distraction mechanism 5010 raises or lowers the medial compartment and the lateral compartment of the knee joint by an equal distance.

Referring to FIGS. 58 and 61, the height or change of height of the medial and lateral compartments can be measured by a mechanical gauge that couples to distractor mechanisms 5010, 5012, or 5014. In general, a mechanical gauge couples to moving parts of surgical apparatus 5000 and includes an indicator that shows a measurement of a parameter based on the movement of the components. The indicator can be electrical or mechanical. The mechanical gauge can be configured to measure a distance between a bottom surface of tibial support 5006 and a surface of cover 5126 or a surface of plate 5128. A second mechanical gauge can be configured to measure the medial-lateral tilt of femoral support 5008. The medial-lateral tilt corresponds to a position difference of pin 5120 and 5118 or the tilt of femoral support 5008. In one embodiment, the mechanical gauges will have an indicator that allows the surgeon to read the compartment heights and medial-lateral tilt on surgical apparatus 5000.

Electronic circuitry 150 of FIG. 15 can be coupled on or in surgical apparatus 5000. Electronic circuitry 150 will couple to one or more sensors for measuring a parameter and transmitting quantitative measurement data to a computer as disclosed in FIG. 53 and further described in detail herein above for other variations of the surgical apparatus or distractor. A computer 5026 that is configured to receive and provide the quantitative measurement data to the surgeon. Computer 5026 includes a display 5028 for providing quantitative measurement data to the surgical team in the operating room in real-time. In one embodiment, a Hall Effect sensor 204 or linear Hall sensor 222 of FIGS. 16-20 can be configured to measure femoral support tilt or compartment height on surgical apparatus 5000. Hall Effect sensor 204 and linear hall sensor 222 couple to electronic circuitry 150. The components of FIGS. 15-20 will be adapted for use on surgical apparatus 5000 to illustrate how it can be measured. In one embodiment, magnet 200 can be coupled to pin 5118 or pin 5120 such that magnet 200 rotates from a reference position. In one embodiment, the reference position corresponds to the medial-lateral compartment heights being equal. Hall Effect sensor 204 is located within the magnetic field of magnet 200. As magnet 200 rotates Hall Effect sensor 204 measures the amount of rotation which is then transmitted by electronic circuitry 150 and displayed on display 5028 of computer 5026. Display 5028 can numerically display the amount of rotation or have an indicator bar to display the medial-lateral tilt as disclosed in FIG. 36.

Linear Hall sensor 222 can be used to measure compartment height. Linear Hall sensor 222 operates in the presence of a magnetic field like Hall Effect sensor 204. A first magnet 220 and a second magnet 220 can be respectively coupled to a medial side and a lateral side of femoral support 5008. Similarly, a first linear Hall sensor 222 and a second linear hall sensor 222 can be respectively coupled to the medial side and the lateral side of tibial support 5006 such that first linear Hall sensor 222 is within the magnetic field of the first magnet 220 and the second linear Hall sensor 222 is within the magnetic field of the second magnet 220. The strength of the magnetic field measured by the first and second linear Hall sensors 222 corresponds to the distance. The medial compartment height and the lateral compartment height can be displayed as a numerical number on display 5028 of computer 5026 or displayed visually such as a bar graph as shown in FIG. 20. Alternatively, a single linear Hall sensor 222 can be used. Magnet 220 can be placed between the medial and lateral sides of femoral support 5008. Thus, linear Hall sensor 222 measures the average of the medial and lateral compartment heights. Measurement data from Hall effect sensor 204 corresponding to the medial-lateral tilt can be used with the measurement data from the single linear Hall sensor 222 to calculate the height of the medial compartment and the lateral compartment using computer 5026.

Figure 62:
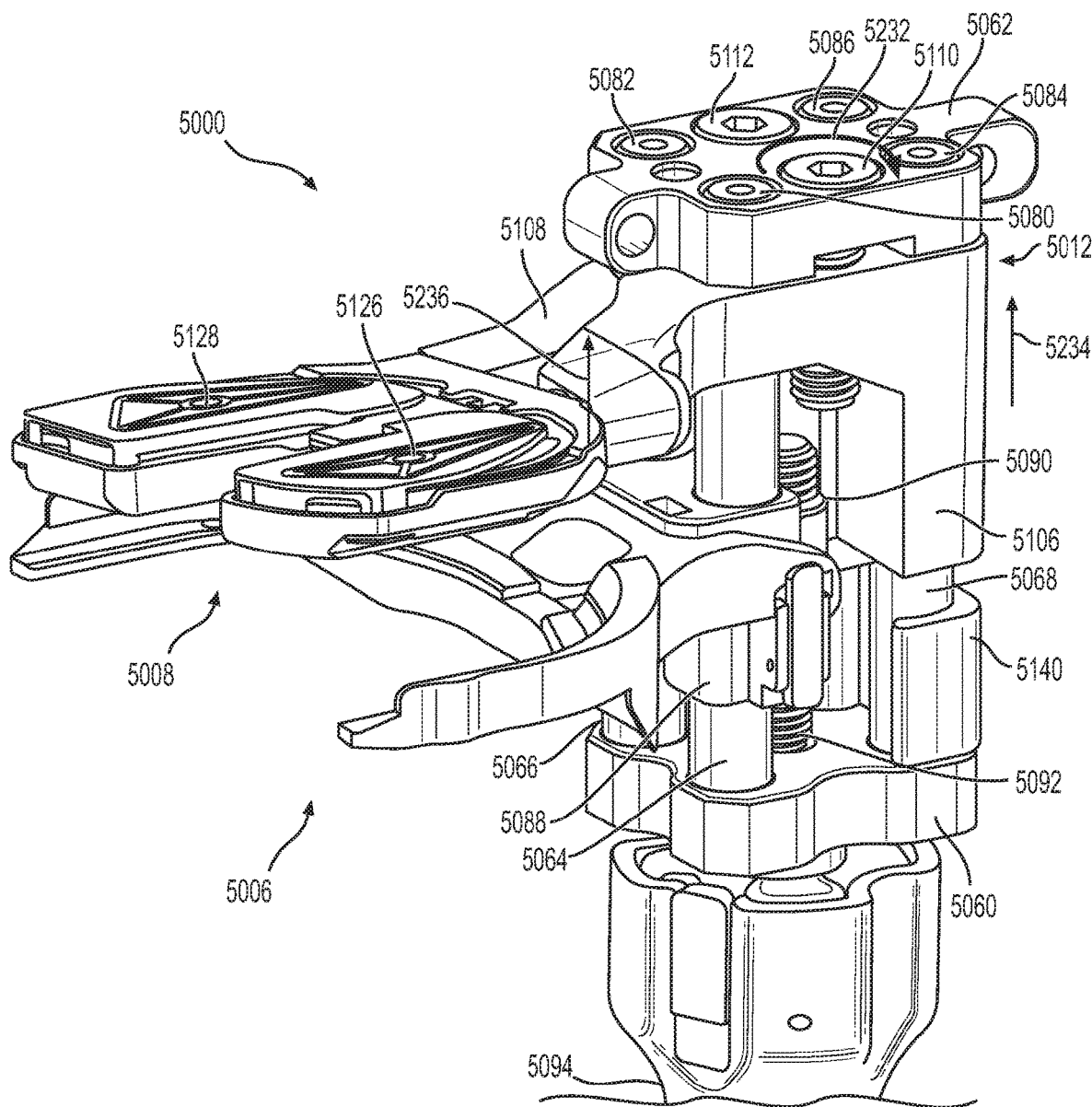
FIG. 62 is an illustration of a second distraction mechanism of the surgical apparatus in accordance with an example embodiment.

FIG. 62 is an illustration of distraction mechanism 5012 of surgical apparatus 5000 in accordance with an example embodiment. Distraction mechanism 5012 comprises femoral support 5008, medial support structure 5106, anterior medial guide shaft 5064, posterior medial guide shaft 5068, base 5060, cap 5062, and medial tilting screw 5110. Cap 5062 couples to a proximal end of anterior medial guide shaft 5064 and posterior medial guide shaft 5068. Screw 5080 couples cap 5062 to anterior medial guide shaft 5064. Screw 5084 couples cap 5062 to posterior medial guide shaft 5068. Base 5060 couples to a distal end of anterior medial guide shaft 5064 and a distal end of posterior medial guide shaft 5068. Referring briefly to FIG. 55, screw 5072 couples base 5060 to anterior medial guide shaft 5064. Screw 5076 couples base 5060 to posterior medial guide shaft 5068. Anterior medial guide shaft 5064 and posterior medial guide shaft 5068 respectively couples through an anterior opening and posterior opening of medial support structure 5106. Medial support structure 5106 is configured to move on and aligned to the trajectory of anterior medial guide shaft 5064 and posterior medial guide shaft 5068. Anterior medial guide shaft 5064 and posterior medial guide shaft 5068 are parallel to one another. Medial tilting screw 5110 couples through cap 5062 to a threaded opening in medial support structure 5106. Femoral support 5008 couples to medial support structure 5106 through a first pivot point that supports medial side tilting of femoral support 5008. Referring briefly to FIG. 54, the first pivot point comprises pin 5118 of femoral support 5008 rotatably coupling to an opening 5122 of lateral support structure 5108.

In one embodiment, medial tilting screw 5110 is configured to move medial support structure 5106 relative to cap 5062. Medial tilting screw 5110 couples to the threaded opening in medial support structure 5106. In one embodiment, rotating medial tilting screw 5110 clockwise (as indicated by arrow 5232) is configured to move medial support structure 5106 towards cap 5062. Femoral support 5008 couples to medial support structure 5106 through the first pivot point. In the example of clockwise rotation of medial tilting screw 5110, the medial side of femoral support 5008 is raised towards cap 5062 thereby changing the medial-lateral tilt. Medial support structure 5106 moves towards cap 5062 as indicated by arrow 5234. As shown, the height of the medial compartment is greater than the height of the lateral compartment. Similarly, femoral support 5008 on the medial side moves in a direction indicated by arrow 5236. Conversely, rotating medial tilting screw 5110 counter-clockwise moves medial support structure 5106 in an opposite direction away from cap 5062 thereby changing the medial-lateral tilt. In one embodiment, distraction mechanism 5012 is configured to increase or decrease the height of the medial compartment of the knee joint. The height or change of height of the medial compartment can be measured by electronic circuitry and sensors as disclosed herein above. Alternatively, the height or change of height of the medial and lateral compartment can measured by mechanical gauges coupled to surgical apparatus 5000.

Figure 63:
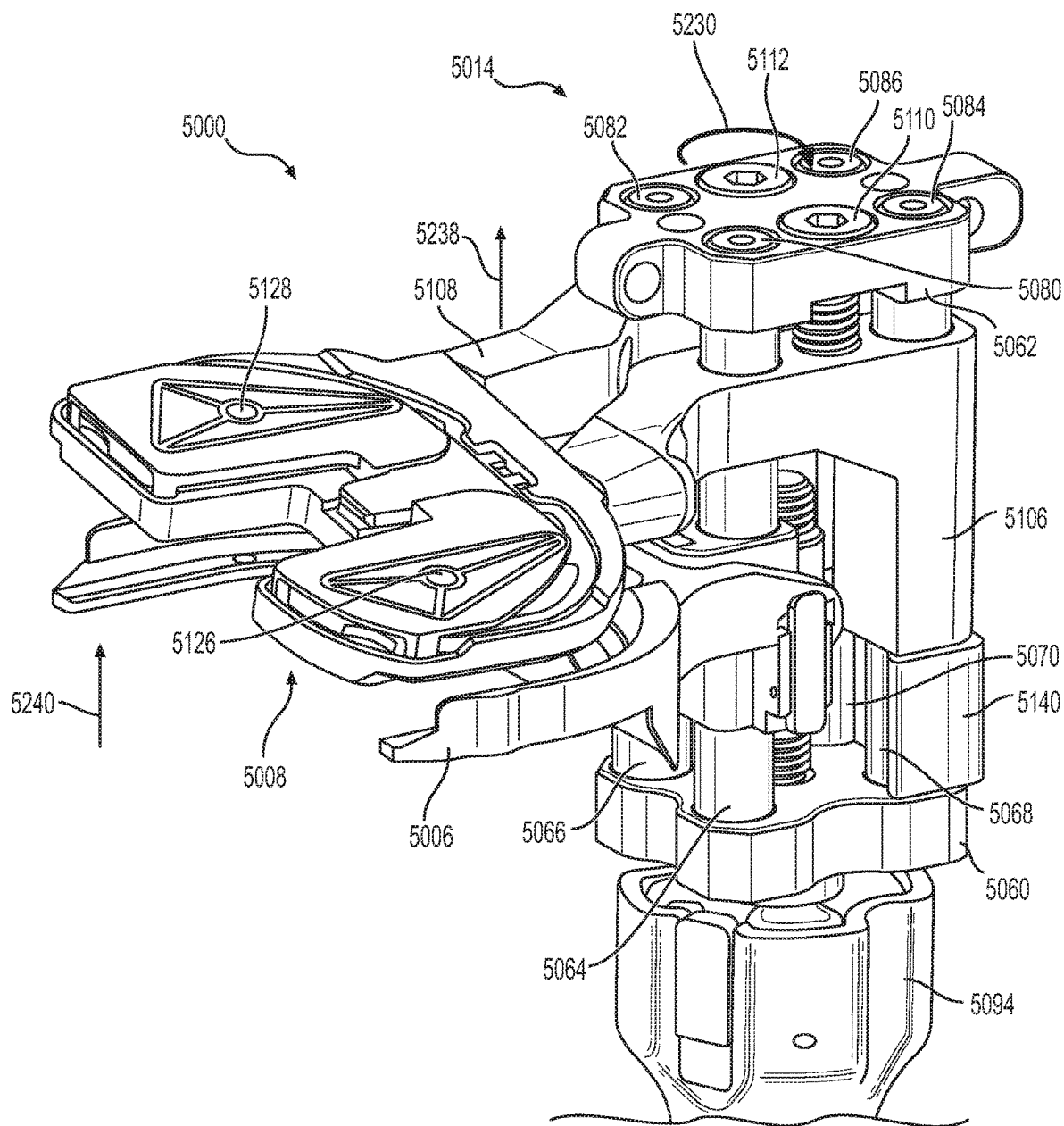
FIG. 63 is an illustration of a third distraction mechanism of the surgical apparatus in accordance with an example embodiment.

FIG. 63 is an illustration of distraction mechanism 5014 of surgical apparatus 5000 in accordance with an example embodiment. Distraction mechanism 5014 comprises femoral support 5008, lateral support structure 5108, anterior lateral guide shaft 5066, posterior lateral guide shaft 5070, base 5060, cap 5062, and lateral tilting screw 5112. Cap 5062 couples to a proximal end of anterior lateral guide shaft 5066 and posterior lateral guide shaft 5070. Screw 5082 couples cap 5062 to the proximal end of anterior lateral guide shaft 5066. Screw 5086 couples cap 5062 to the proximal end of posterior lateral guide shaft 5070. Base 5060 couples to a distal end of anterior lateral guide shaft 5066 and a distal end of posterior lateral guide shaft 5070. Referring briefly to FIG. 54, screw 5074 couples base 5060 to a distal end anterior lateral guide shaft 5066. Screw 5078 couples base 5060 to a distal end of posterior lateral guide shaft 5070. Anterior lateral guide shaft 5066 and posterior lateral guide shaft 5070 respectively couples through an anterior opening and posterior opening of lateral support structure 5108. Lateral support structure 5108 is configured to move on and aligned to the trajectory of anterior lateral guide shaft 5066 and posterior lateral guide shaft 5070. In one embodiment, anterior lateral guide shaft 5066 and posterior lateral guide shaft 5070 are parallel to one another. Lateral tilting screw 5112 couples through cap 5062 to a threaded opening within lateral support structure 5108.

Femoral support 5008 couples to lateral support structure 5108 through a second pivot point that supports lateral side tilting of femoral support 5008. Referring briefly to FIG. 54, the second pivot point comprises pin 5120 of femoral support 5008 rotatably coupling to an opening 5124 of lateral support structure 5108.

In one embodiment, medial tilting screw 5112 is configured to move lateral support structure 5108 relative to cap 5062. Lateral tilting screw 5112 couples to the threaded opening in lateral support structure 5108. In one embodiment, rotating lateral tilting screw 5112 clockwise (as indicated by arrow 5230) is configured to move lateral support structure 5108 towards cap 5062. Femoral support 5008 couples to lateral support structure 5108 through the second pivot point. The lateral side of femoral support 5008 is raised towards cap 5062 thereby changing the medial-lateral tilt. Lateral support structure 5108 moves towards cap 5062 as indicated by arrow 5238. As shown, the height of the lateral compartment is greater than the height of the medial compartment. Similarly, femoral support 5008 on the lateral side moves in a direction indicated by arrow 5240. Thus, rotating lateral tilting screw 5112 clockwise increases the lateral compartment height. Conversely, rotating medial tilting screw 5112 counter-clockwise moves lateral support structure 5108 in an opposite direction away from cap 5062 thereby changing the medial-lateral tilt. In one embodiment, distraction mechanism 5014 raises or lowers the lateral compartment of the knee joint. The height or change of height of the lateral compartment can be measured by electronic circuitry and sensors as disclosed herein above. Alternatively, the height or change of height of the medial and lateral compartment can measured by mechanical gauges coupled to surgical apparatus 5000.

FIG. 64 is an illustration of a surgical apparatus 6000 in accordance with an example embodiment. Surgical apparatus 6000 is similar to surgical apparatus 5000 disclosed herein above and comprises many of the same components. Surgical apparatus 6000 is configured for use in the musculoskeletal system. In one embodiment, surgical apparatus comprises at least one sensor for measuring a parameter. Surgical apparatus 6000 can be adapted for use in a kinetic assessment for providing quantitative measurement data from the musculoskeletal system, knee, hip, shoulder, spine, ankle, wrist, hand, foot, or bone. In one embodiment, surgical apparatus 6000 is configured to support installation of a knee joint that includes quantitative measurement of applied load, position, component rotation, height, medial-lateral tilt, position of load, or alignment over a range of motion and in real-time. In one embodiment, the quantitative measurement data is used to cut bone for installing a prosthetic component, reduce leg alignment error, optimize knee loading, optimize knee balance, optimize contact point location, improve range of motion, or support ligament tensioning. The quantitative measurement data is received by computer 5026 and displayed on display 5028 in real-time such that adjustments that change measured parameters can be incorporated into the installation in real-time. In one embodiment, at least one adjustment is made using surgical apparatus 6000 that adjusts a parameter such that the change in the parameter is measured and improves the prosthetic joint installation. In general, surgical apparatus 6000 differs from surgical apparatus 5000 of FIG. 53 in that measurements are made by separate measurement modules on a medial and lateral side of surgical apparatus 6000. Surgical apparatus 5000 uses a single measurement module. Loading on the medial or the lateral side of surgical apparatus 6000 is supported by independent pins that do not rotate. Conversely, medial-lateral loading on surgical apparatus 5000 is configured to pivot through two pivot points and loading is distributed between the two pivot points as disclosed herein above. In one embodiment, surgical apparatus 6000 has an offset that supports patella loading of the knee joint. The offset supports placement of the patella on a lateral side of the knee joint and allows the patella to be placed back on the knee joint after distractor 6000 is inserted. The patella loads the knee joint and is taken into account in all the quantitative measurement data and subsequent steps taken prior to the knee joint installation to provide a true kinetic assessment. In one embodiment, the offset is specific for the left knee and the right knee. In one embodiment, surgical apparatus 6000 comprises two separate devices, one for the left knee and one for the right knee. In the example, the offset of surgical apparatus 6000 is configured for a left knee joint. As described herein, description of the operation and components will apply to both the left knee and right surgical apparatus 6000.

Surgical apparatus 6000 has three distracting mechanisms configured to increase a medial compartment height, a lateral compartment height, or both simultaneously in accordance with an example embodiment. In general, surgical apparatus 6000 is configured to support installation of a prosthetic joint of the musculoskeletal system. Surgical apparatus 6000 can include, but is not limited to measurement of parameters such as height, length, width, tilt/slope, position, orientation, alignment, offset, rotation, tension, load magnitude, force, pressure, contact point location, displacement, density, viscosity, pH, light, color, sound, optical, vascular flow, visual recognition, humidity, alignment, rotation, inertial sensing, turbidity, bone density, fluid viscosity, strain, angular deformity, vibration, torque, elasticity, motion, and temperature. Electronic circuitry 150 as disclosed herein in FIG. 15 can be coupled to the sensors listed above to control a measurement process, generate quantitative measurement data, and transmit the quantitative measurement data of surgical apparatus 6000 to the computer 5026. Electronic circuitry 150 of FIG. 15 can be housed on or in surgical apparatus 6000 that couples to one or more sensors on or in surgical apparatus 6000. Similarly, electronic circuitry 150 of FIG. 15 can be within two or more measurement module having one or more sensors. Computer 5026 with display 5028 can be configured to receive and provide quantitative measurement data from multiple measurement systems or modules each comprising electronic circuitry 150 and one or more sensors. In one embodiment, transmissions can be at different frequencies or provided at different times on the same frequency managed by computer 5026.

The three distracting mechanisms of surgical apparatus 6000 are distraction mechanism 5010, distraction mechanism 5012, and distraction mechanism 5014. The three distractor mechanisms are the same and operate identically to the distractor mechanisms disclosed for distractor 5000 herein above. The three distractor mechanisms are supported and aligned by a cage system 5011. Cage system 5011 comprises a cap 5062, an anterior medial guide shaft 5064, an anterior lateral guide shaft 5066, a posterior medial guide shaft 5068, a posterior lateral guide shaft 5070, and a base 5060. In one embodiment, anterior medial guide shaft 5064, anterior lateral guide shaft 5066, posterior medial guide shaft 5068, and posterior lateral guide shaft 5070 are parallel to one another and couple between base 5060 and cap 5062 in a square or rectangular pattern to support movement of distraction mechanism 5010, distraction mechanism 5012, and distraction mechanism 5014. Movement of tibial support holder 5088, medial support structure 5106, and lateral support structure 5108 are aligned to and guided by cage system 5011 under user control. How tibial support holder 5088, medial support structure 5106, and lateral support structure 5108 couple to cage system 5011 is disclosed in FIG. 54 herein above. Similarly, screws that couple cage system 5011 together are shown in FIG. 54. Details of components of surgical apparatus 6000 that are identical to surgical apparatus 5000 are disclosed herein above and will not be repeated for brevity. The components that are identical in surgical apparatus 5000 and 6000 will also have the same numbering and perform identically. Also, detail provided about surgical apparatus 6000 and more specifically the identical components in surgical apparatus 5000 and 6000 also applies to surgical apparatus 5000.

A spacer 5140 can be used to place medial support structure 5106 and lateral support structure 5108 in a reference position in surgical apparatus 6000. Spacer 5140 has a predetermined height that determines the reference position. Spacer 5140 has a first opening and a second opening that respectively couples through posterior medial guide shaft 5068 and posterior lateral guide shaft 5070 of cage system 5011. Spacer 5140 couples between base 5060 and medial support structure 5106. Similarly, spacer 5140 couples between base 5060 and lateral support structure 5108. In one embodiment, the reference position is established when surgical apparatus 6000 is in a minimum height position. In one embodiment, the minimum height position corresponds to a minimum height of surgical device 6000 measured from a bottom surface 5142 of tibial support 5006 to exposed surfaces of measurement module 6002 or measurement module 6004. A first side of spacer 5140 will couple to base 5060 and second side of spacer 5140 will couple to medial support structure 5106 and lateral support structure 5108. In one embodiment, the minimum height of surgical apparatus 6000 corresponds to a bottom surface of medial femoral support 6006 or lateral femoral support 6008 being coplanar with bottom surface 5142 of tibial support 5006. In one embodiment, the position of spacer 5140 can be fixed such that spacer 5140 remains coupled to base 5060 when medial or lateral compartment heights are changed.

Distraction mechanism 5010 of surgical apparatus 6000 comprises tibial support holder 5088, cage system 5011, distraction lead screw 5092, and handle 5094. Distraction mechanism 5010 is configured to move tibial support 5006 relative to femoral support 5008. In one embodiment, tibial support 5006 couples to a prepared bone surface of a proximal end of a tibia. In one embodiment, distraction mechanism 5010 simultaneously distracts a medial compartment and a lateral compartment of a knee joint by equal amounts. Tibial support holder 5088 comprises a structure having a medial opening and a lateral opening. Anterior medial guide shaft 5064 and anterior lateral guide shaft 5066 respectively couple through the medial opening and the lateral opening of tibial support holder 5088. Distraction lead screw 5092 is configured to move tibial support holder 5088 under user control. Distraction lead screw 5092 couples through an opening in base 5060 to couple to threaded structure 5090 of tibial support structure 5088. Threaded structure 5090 has a threaded opening configured to receive distraction lead screw 5092. Distraction lead screw 5092 couples thru the threaded opening of threaded structure 5090 to motivate tibial support holder 5088 when rotated. Rotating handle 5094 engages distraction lead screw 5092 to threads within threaded structure 5090 of tibial support holder 5088 to move tibial support holder 5088 along a trajectory defined by anterior medial guide shaft 5064 and anterior lateral guide shaft 5066. Tibial support holder 5088 can move towards or away from base 5060 depending on the direction of rotation of distraction lead screw 5092. This is shown and described in detail in FIG. 61 disclosed herein above.

Tibial support 5006 couples to tibial support holder 5088. In one embodiment, tibial support 5006 is supported under load by tibial support holder 5088. Retaining clips 5018 on the medial and lateral sides of tibial support holder 5008 are pressed to allow arms 5150 and structure 5102 of tibial support 5006 to couple to tibial support holder 5088. Releasing clips 5018 locks tibial support 5006 to tibial support holder 5088 into a predetermined position. In one embodiment, tibial support 5006 has more than one size and is removable from tibial support holder 5088. In one embodiment, tibial support 5006 comprises a U-shaped structure 5152 that has a bottom surface 5142 configured to couple to a prepared bone surface at the proximal end of a tibia. Alternatively, tibial support structure can couple to a proximal end of a natural tibia or a tibial prosthetic component. In one embodiment, the bottom surface 5142 of U-shaped structure 5152 is planar. Removing tibial support 5006 from tibial support holder 5088 is an opposite process comprising pressing retaining clips 5018 to release tibial support 5006 and pulling tibial support 5006 away from tibial support holder 5088.

Distraction mechanism 5012 comprises a medial support structure 5106, cage system 5011, and a medial tilting screw 5110. Distraction mechanism 5012 is configured to move medial support structure 5106 relative to tibial support 5006. A medial femoral support 6006 is configured to couple to medial support structure 5106. A pin 6010 extends from medial femoral support 6006. Pin 6010 is configured to couple to opening 5122 of medial support structure 5106. In one embodiment, pin 6010 does not rotate in opening 5122. Pin 6010 is configured to place medial femoral support 6006 in a predetermined position. In one embodiment, pin 6010 is square or rectangular in shape with rounded edges. Pin 6010 can be formed in a shape that allows insertion into opening 5122 in only a single orientation. Pin 6010 can lock into place when inserted into opening 5122 but is removable. Similar to tibial support 5006, medial femoral support 6006 can come in several sizes (example large, medium, and small) that can be used in surgical apparatus 6000 to accommodate different bone sizes. Medial femoral support 6006 has a surface 6014. Measurement module 6002 couples to medial femoral support 6006 and is supported by surface 6014. An exterior surface of measurement module 6002 extends above medial femoral support 6006. In one embodiment, the external surface of measurement module 6002 is configured to couple to a medial condyle of a knee to support movement of the knee joint. Although not shown, a cover can be placed on measurement module 6002 as shown in FIG. 54.

Measurement module 6002 includes electronic circuitry 150 as disclosed in FIG. 15 herein above. Measurement module 6002 couples to one or more sensors. In one embodiment, measurement module 6002 controls a measurement process and transmits measurement data to computer 5026. In one embodiment, measurement module 6002 includes a plurality of load sensors configured to measure loading applied at predetermined locations of the external surface of measurement module 6002 by the medial condyle of the knee joint. Computer 5026 is configured to receive the measurement data from the load sensors and calculate a magnitude of applied load by the medial condyle and the position of applied load on the external surface of measurement module 6002. The placement of the load sensors in measurement module 6002 is similar to that shown for the medial side of module 32 of FIG. 22. As shown in FIG. 22, three load sensors are used. One difference between module 32 and measurement module 6002 is that electronic circuitry 150 of FIG. 15 is placed within measurement module 6002 and is not shared between the medial and lateral sides as shown in FIG. 22. Measurement module 6002 can have raised regions similar to that shown in FIG. 56C that are aligned with and overlie each load sensor. The raised regions are reinforced areas that direct loading to the load sensors. A raised region of measurement module 6002 is configured to distribute loading evenly across a surface of a corresponding load sensor for more accurate load measurement.

Raising or lowering medial support structure 5106 changes a height of the medial compartment of the knee joint by raising or lowering medial femoral support 6006 relative to tibial support 5006. Medial support structure 5106 includes a first opening, a second opening, and a threaded opening. In one embodiment, a direction of movement of medial support structure 5106 is determined by cage system 5011. Anterior medial guide shaft 5064 couples through the first opening in medial support structure 5106. Similarly, posterior medial guide shaft 5068 couples through the second opening in medial support structure 5106. Movement and trajectory of medial support structure 5106 are aligned to anterior medial guide shaft 5064 and posterior medial guide shaft 5068. Medial tilting screw 5110 couples through an opening in cap 5062. Medial tilting screw 5110 couples through the opening into the threaded opening of medial support structure 5106. In one embodiment, the threads of medial tilting screw 5110 engage with the threads in the threaded opening of medial support structure 5106 to hold medial support structure 5106 in a fixed position. The engaged threads between medial tilting screw 5110 and the threaded opening in medial support structure 5106 can support loading applied to femoral support 5008 and will not change the medial compartment height unless medial tilting screw 5110 is rotated. In one embodiment, an Allen wrench can be used to rotate medial tilting screw 5110. Rotating medial tilting screw 5110 can pull medial support structure 5106 towards cap 5062 or away from cap 5062 depending on the direction of rotation. In one embodiment, turning medial tilting screw 5110 clockwise raises medial support structure 5106 and medial femoral support 6006 towards cap 5062. Conversely, turning medial tilting screw 5110 counter clockwise lowers medial support structure and medial femoral support 6006 away from cap 5062. Thus, rotation of medial tilting screw 5110 is configured to adjust the medial compartment height and the medial-lateral tilt of surgical apparatus 6000. In one embodiment, measurement module 6002 can be used after removing surgical apparatus 6000 from the knee joint in a trialing process with installed prosthetic components of the knee joint to take further measurements.

Distraction mechanism 5014 comprises a lateral support structure 5108, cage system 5011, and a medial tilting screw 5112. Distraction mechanism 5014 is configured to move lateral support structure 5108 relative to tibial support 5006. A lateral femoral support 6008 is configured to couple to lateral support structure 5108. A pin 6012 extends from medial femoral support 6006. Pin 6012 is configured to couple to opening 5124 of lateral support structure 5108. In one embodiment, pin 6012 does not rotate in opening 5124. Pin 6012 is configured to place lateral femoral support 6008 in a predetermined position. In one embodiment, pin 6012 is square or rectangular in shape with rounded edges. Pin 6012 can be formed in a shape that allows insertion into opening 5124 in only a single orientation. Pin 6012 can lock into place when inserted into opening 5124 but is removable. Similar to tibial support 5006, lateral femoral support 6008 can come in several sizes (example large, medium, and small) that can be used in surgical apparatus 6000 to accommodate different bone sizes. Lateral femoral support 6008 has a surface 6018. Measurement module 6004 couples to medial femoral support 6008 and is supported by surface 6018. An exterior surface of measurement module 6004 extends above lateral femoral support 6008. In one embodiment, the external surface of measurement module 6004 is configured to couple to a lateral condyle of a knee to support movement of the knee joint. Although not shown, a cover can be placed on measurement module 6004 similar to that shown in FIG. 54.

Measurement module 6004 includes electronic circuitry 150 as disclosed in FIG. 15 herein above. Measurement module 6004 couples to one or more sensors. In one embodiment, measurement module 6004 controls a measurement process and transmits measurement data to computer 5026. In one embodiment, measurement module 6004 includes a plurality of load sensors configured to measure loading applied at predetermined locations of the external surface of measurement module 6004 by the lateral condyle of the knee joint. Computer 5026 is configured to receive the measurement data from the load sensors and calculate a magnitude of applied load by the lateral condyle and the position of applied load on the external surface of measurement module 6004. The placement of the load sensors in measurement module 6004 is similar to that shown for the lateral side of module 32 of FIG. 22. As shown in FIG. 22, three load sensors are used. One difference between module 32 and measurement module 6004 is that electronic circuitry 150 of FIG. 15 is placed within measurement module 6004 and is not shared between the medial and lateral sides as shown in FIG. 22. Measurement module 6004 can have raised regions similar to that shown in FIG. 56C that are aligned with and overlie each load sensor. The raised regions are reinforced areas that direct loading to the load sensors. A raised region of measurement module 6004 is configured to distribute loading evenly across a surface of a corresponding load sensor for more accurate load measurement. Measurement modules 6002 and 6004 include a position tracking system that measures position and alignment of the leg. In one embodiment, the position tracking system comprises one or more sensors such as accelerometers, gyroscopes, magnetometers, GPS system, or IMU's (inertial measurement units). In one embodiment, the load sensors used in surgical apparatus 5000 and 6000 are elastically compressible capacitors that can be integrated within flexible interconnect to lower cost, increase reliability, increase uniformity, and sensitivity. Alternatively, load sensors can comprise strain gauges, MEMs device, piezo-resistive sensors, mechanical sensors, polymer sensors, optical sensors, or ultrasonic sensors. In one embodiment, quantitative measurement data from measurement modules 6002 and 6004 is used by computer 5026 to calculate leg position, alignment of a bone of the leg, or alignment of the leg relative to a mechanical axis.

Raising or lowering medial support structure 5108 changes a height of the lateral compartment of the knee joint by raising or lowering lateral femoral support 6008 relative to tibial support 5006. Lateral support structure 5108 includes a first opening, a second opening, and a threaded opening. In one embodiment, a direction of movement of lateral support structure 5108 is determined by cage system 5011. Anterior lateral guide shaft 5066 couples through the first opening in lateral support structure 5108. Similarly, posterior lateral guide shaft 5070 couples through the second opening in lateral support structure 5108. Movement and trajectory of lateral support structure 5108 are aligned to anterior lateral guide shaft 5066 and posterior lateral guide shaft 5070. Lateral tilting screw 5112 couples through an opening in cap 5062. Lateral tilting screw 5112 couples through the opening into the threaded opening of medial support structure 5108. In one embodiment, the threads of lateral tilting screw 5112 engage with the threads in the threaded opening of lateral support structure 5108 to hold lateral support structure 5108 in a fixed position. The engaged threads between lateral tilting screw 5112 and the threaded opening in lateral support structure 5108 can support loading applied to femoral support 5008 and will not change the lateral compartment height unless lateral tilting screw 5112 is rotated. In one embodiment, an Allen wrench can be used to rotate lateral tilting screw 5112. Rotating lateral tilting screw 5112 can pull lateral support structure 5108 towards cap 5062 or away from cap 5062 depending on the direction of rotation. In one embodiment, turning lateral tilting screw 5112 clockwise raises lateral support structure and lateral femoral support 6008 towards cap 5062. Conversely, turning lateral tilting screw 5112 counter clockwise lowers lateral support structure 5108 and lateral femoral support 6008 away from cap 5062. Thus, rotation of lateral tilting screw 5112 is configured to adjust the lateral compartment height and the medial-lateral tilt of surgical apparatus 6000. In one embodiment, measurement module 6004 can be used after removing surgical apparatus 6000 from the knee joint in a trialing process with installed prosthetic components of the knee joint to take further measurements.

As mentioned previously, surgical apparatus 6000 has separate independent paddles for increasing or decreasing the medial compartment height or the lateral compartment height relative to tibial support 5006. Medial femoral support 6006 and lateral femoral support 6008 respectively supports loading on the medial compartment and the lateral compartment by the medial condyle and the lateral condyle of the knee joint. The medial and lateral condyles can be natural condyles of the femur or condyles of a femoral prosthetic component. In one embodiment, loading applied to medial femoral support 6006 and measurement module 6002 is coupled through pin 6010 to medial support structure 5106. Similarly, loading applied to lateral femoral support 6008 and measurement module 6004 is coupled through pin 6012 to lateral support structure 5108. Surgical apparatus 6000 and measurement modules 6002 and 6004 support rotation of the leg through a range of motion. Measurement modules 6002 and 6004 each transmit measurement data to computer 5026 where the measurement data is displayed.

The height and medial lateral tilt can be measured by mechanical gauges coupled to the moving components of surgical apparatus 6000 that affect compartment height. The benefit of the mechanical gauges are that they are implemented on apparatus 6000 and do not require electronic circuitry 150, sensors, or a power source. Similarly, Hall effect sensor 204 and linear Hall effect sensor 222 of FIGS. 16-20 can be adapted to measure medial or lateral compartment height and medial-lateral tilt of surgical apparatus 6000. In one embodiment, the medial-lateral tilt can be calculated by measuring the height of the medial compartment and the height of the lateral compartment. The measurement data is sent to the computer 5026 and can be displayed as indicated in FIGS. 36-38 in a manner that allows the surgeon to determine height and medial-lateral tilt at a glance. The difference in compartment height corresponds to the medial-lateral tilt. The angle can be determined from a predetermined point on medial femoral support 6006 (such as the center of surface 6014 and a predetermined point on lateral femoral support 6008 (such as the center of surface 6016). The angle corresponds to a line drawn through the two center points of surface 6014 and 6016. Alternatively, other sensors can be used for measuring compartment height or medial-lateral tilt of surgical apparatus 5000 and 6000. These sensors could also be adapted to couple to the moving components that change the medial and lateral compartment heights. Examples of systems or sensors measuring distance or height are imaging, optical, laser, altimeter, GPS, MEMs devices, ultrasonic sensors, inertial sensors, magnetic sensors, Eddy current sensors, and light emitting diodes to name but a few. Similarly, an inclinometer, inertial sensors, rotary encoder, MEMs sensors, magnetic sensors, imaging, optical, laser, altimeter, GPS, ultrasonic sensors, light emitting diodes can be adapted for measuring an angle or tilt.

Figure 65:
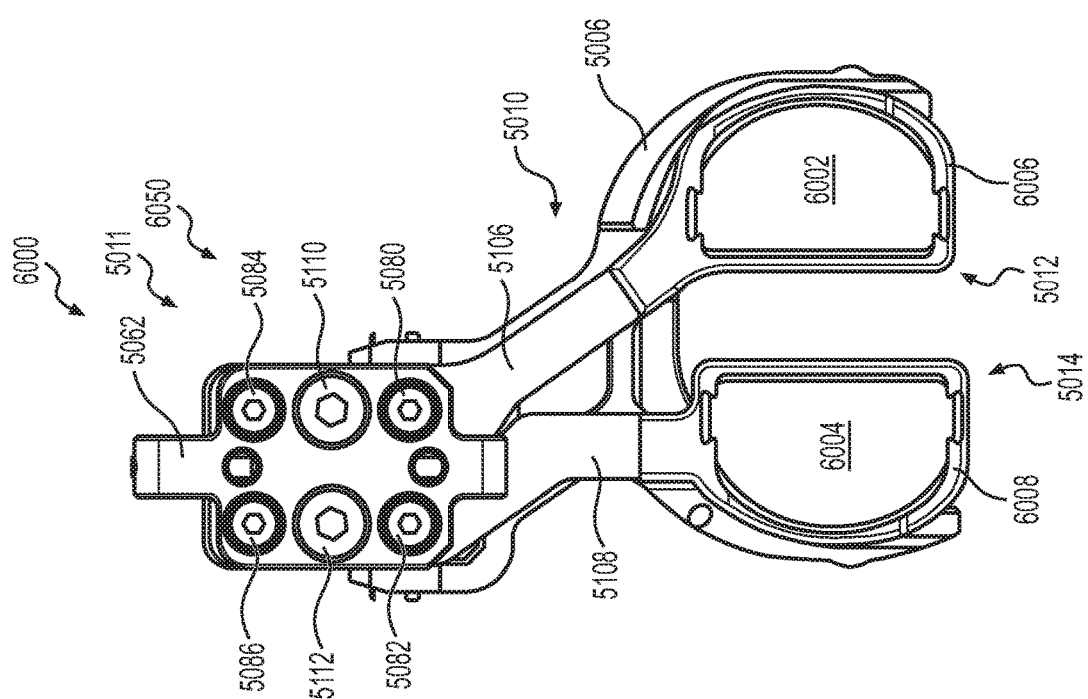
FIG. 65 is a top view of an offset of the surgical apparatus for use in a left knee in accordance with an example embodiment.

FIG. 65 is a top view of an offset of surgical apparatus 6000 for use in a left knee in accordance with an example embodiment. In the example, surgical apparatus 6000 comprises a left leg surgical apparatus 6050 configured for supporting a left leg prosthetic knee joint installation. Left leg surgical apparatus 6050 has an offset that supports placing the patella to the one side of the knee joint while left leg surgical apparatus 6050 is inserted. The patella can then be placed back on the left knee joint with left leg surgical apparatus 6050 in place due to the offset. Placing the patella on the knee joint while left leg surgical apparatus 6050 is being used loads the knee joint as it would once the prosthetic knee joint has been installed. Thus, loading of the patella is taken into account in regards to leg alignment, loading, and balance as left leg surgical apparatus 6050 is used to support a left leg prosthetic knee joint installation.

Tibial support 5006 of distraction mechanism 5010 couples to cage system 5011 in a manner that allows movement of tibial support 5006 under loading of the left knee joint. In one embodiment, a user controls movement of tibial support 5006 using distraction mechanism 5010 such that a medial and a lateral compartment height of the left knee joint can be changed. Alternatively, movement of distraction mechanism 5010 can be automated such that the medial and lateral compartment height is changed by motor, pneumatic, electrical, or other mechanical system. In either case, measurement data is provided to computer 5026 of FIG. 64 for display and analysis.

Medial femoral support 6006 couples to medial support structure 5106. Medial support structure 5106 of distraction mechanism 5012 couples to cage system 5011 in a manner that allows movement of medial femoral support 6006 under loading of the left knee joint. Measurement module 6002 couples to medial femoral support 6006. In one embodiment, the medial compartment height can be raised or lowered under loading on the medial side of the left knee joint by distraction mechanism 5012. A user controls movement of the medial support structure 5106 and thereby medial femoral support 6006. In the example, medial tilting screw 5110 couples to medial support structure 5106 through cap 5062 of cage system 5011. The user can rotate medial tilting screw 5110 with a wrench where the rotation moves medial support structure 5106 towards cap 5062 or away from cap 5062 depending on the direction of rotation. Alternatively, movement of distraction mechanism 5012 can be automated such that the medial compartment height is changed by motor, pneumatic, electrical, or other mechanical system without the need of a user in contact with surgical apparatus 6000. A measurement module 6002 couples to medial femoral support 6006. Medial side loading of the left knee joint is applied to measurement module 6002 and thereby medial femoral support 6006. Measurement module 6002 is configured with at least one sensor to generate quantitative measurement data related to the left knee joint. In one embodiment, measurement module 6002 measures loading, position of load, alignment, and balance. Screws 5080, 5082, 5084, and 5086 hold cap 5062 to cage system 5011.

Lateral femoral support 6008 couples to lateral support structure 5108. Lateral support structure 5108 of distraction mechanism 5014 couples to cage system 5011 in a manner that allows movement of lateral femoral support 6006 under loading of the left knee joint. Measurement module 6004 couples to lateral femoral support 6008. In one embodiment, the lateral compartment height can be raised or lowered under loading on the lateral side of the left knee joint by distraction mechanism 5014. A user controls movement of the lateral support structure 5108 and thereby lateral femoral support 6008. In the example, lateral tilting screw 5112 couples to lateral support structure 5108 through cap 5062 of cage system 5011. The user can rotate lateral tilting screw 5112 with a wrench where the rotation moves lateral support structure 5108 towards cap 5062 or away from cap 5062 depending on the direction of rotation. Alternatively, movement of distraction mechanism 5014 can be automated such that the lateral compartment height is changed by motor, pneumatic, electrical, or other mechanical system without the need of a user in contact with surgical apparatus 6000. A measurement module 6004 couples to lateral femoral support 6008. Lateral side loading of the left knee joint is applied to measurement module 6008 and thereby lateral femoral support 6008. Measurement module 6004 is configured with at least one sensor to generate quantitative measurement data related to the left knee joint. In one embodiment, measurement module 6004 measures loading, position of load, alignment, and balance. In one embodiment, measurement modules 6002 and 6004 respectively measure and transmit measurement data to computer 5026 of FIG. 64. Thus, the medial compartment height and the lateral compartment of the left knee joint can be raised and lowered independently through medial tilting screw 5110 and lateral tilting screw 5112 by the user whereas both the medial and lateral compartment heights can be adjusted by raising or lowering tibial support 5006.

Figure 66:
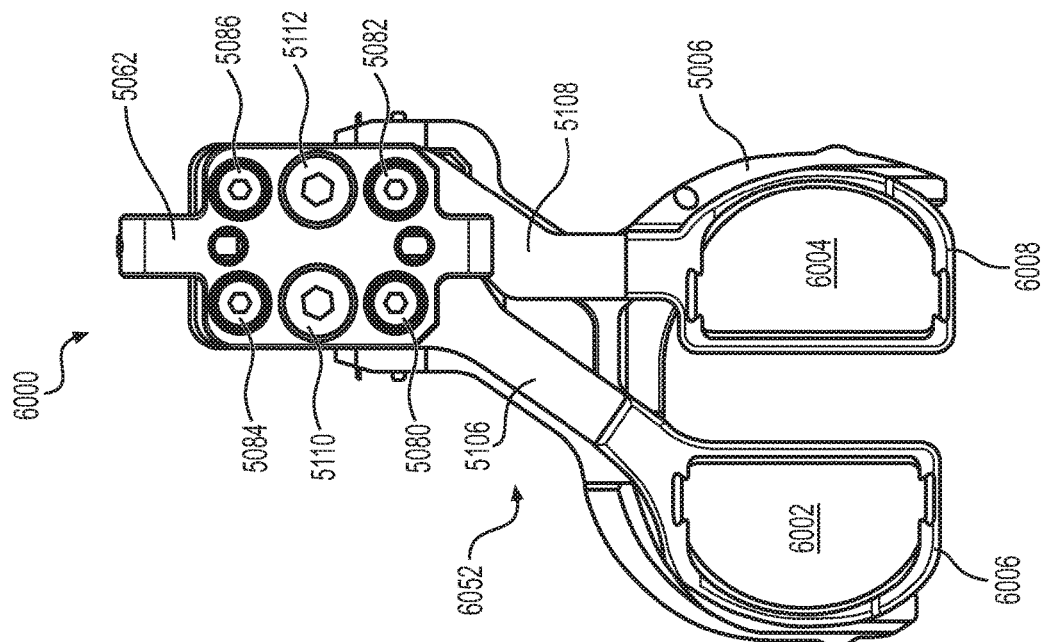
FIG. 66 is a top view of an offset of the surgical apparatus for use in a right knee in accordance with an example embodiment.

FIG. 66 is a top view of an offset of surgical apparatus 6000 for use in a right knee in accordance with an example embodiment. In the example, surgical apparatus 6000 comprises a right leg surgical apparatus 6052 configured for supporting a right leg prosthetic knee joint installation. Right leg surgical apparatus 6052 has an offset that supports placing the patella to the one side of the knee joint while right leg surgical apparatus 6052 is inserted. The patella can then be placed back on the right knee joint with right leg surgical apparatus 6052 in place due to the offset. Placing the patella on the knee joint while right leg surgical apparatus 6052 is being used loads the knee joint as it would once the prosthetic knee joint has been installed. Thus, loading of the patella is taken into account in regards to leg alignment, loading, and balance as right leg surgical apparatus 6052 is used to support a right leg prosthetic knee joint installation.

Tibial support 5006 of distraction mechanism 5010 couples to cage system 5011 in a manner that allows movement of tibial support 5006 under loading of the right knee joint. In one embodiment, a user controls movement of tibial support 5006 using distraction mechanism 5010 such that a medial and a lateral compartment height of the left knee joint can be changed. Alternatively, movement of distraction mechanism 5010 can be automated such that the medial and lateral compartment height is changed by motor, pneumatic, electrical, or other mechanical system. In either case, measurement data is provided to computer 5026 of FIG. 64 for display and analysis.

Medial femoral support 6006 couples to medial support structure 5106. Medial support structure 5106 of distraction mechanism 5012 couples to cage system 5011 in a manner that allows movement of medial femoral support 6006 under loading of the left knee joint. Measurement module 6002 couples to medial femoral support 6006. In one embodiment, the medial compartment height can be raised or lowered under loading on the medial side of the right knee joint by distraction mechanism 5012. A user controls movement of the medial support structure 5106 and thereby medial femoral support 6006. In the example, medial tilting screw 5110 couples to medial support structure 5106 through cap 5062 of cage system 5011. The user can rotate medial tilting screw 5110 with a wrench where the rotation moves medial support structure 5106 towards cap 5062 or away from cap 5062 depending on the direction of rotation. Alternatively, movement of distraction mechanism 5012 can be automated such that the medial compartment height is changed by motor, pneumatic, electrical, or other mechanical system without the need of a user in contact with surgical apparatus 6000. A measurement module 6002 couples to medial femoral support 6006. Medial side loading of the left knee joint is applied to measurement module 6002 and thereby medial femoral support 6006. Measurement module 6002 is configured with at least one sensor to generate quantitative measurement data related to the left knee joint. In one embodiment, measurement module 6002 measures loading, position of load, alignment, and balance. Screws 5080, 5082, 5084, and 5086 hold cap 5062 to cage system 5011.

Lateral femoral support 6008 couples to lateral support structure 5108. Lateral support structure 5108 of distraction mechanism 5014 couples to cage system 5011 in a manner that allows movement of lateral femoral support 6006 under loading of the right knee joint. Measurement module 6004 couples to lateral femoral support 6008. In one embodiment, the lateral compartment height can be raised or lowered under loading on the lateral side of the right knee joint by distraction mechanism 5014. A user controls movement of the lateral support structure 5108 and thereby lateral femoral support 6008. In the example, lateral tilting screw 5112 couples to lateral support structure 5108 through cap 5062 of cage system 5011. The user can rotate lateral tilting screw 5112 with a wrench where the rotation moves lateral support structure 5108 towards cap 5062 or away from cap 5062 depending on the direction of rotation. Alternatively, movement of distraction mechanism 5014 can be automated such that the lateral compartment height is changed by motor, pneumatic, electrical, or other mechanical system without the need of a user in contact with surgical apparatus 6000. A measurement module 6004 couples to lateral femoral support 6008. Lateral side loading of the right knee joint is applied to measurement module 6008 and thereby lateral femoral support 6008. Measurement module 6004 is configured with at least one sensor to generate quantitative measurement data related to the right knee joint. In one embodiment, measurement module 6004 measures loading, position of load, alignment, and balance. In one embodiment, measurement modules 6002 and 6004 respectively measure and transmit measurement data to computer 5026 of FIG. 64. Thus, the medial compartment height and the lateral compartment of the right knee joint can be raised and lowered independently through medial tilting screw 5110 and lateral tilting screw 5112 by the user whereas both the medial and lateral compartment heights can be adjusted equally by raising or lowering tibial support 5006. Note that the operation of left leg surgical apparatus 6050 and right leg surgical apparatus 6052 are identical. Thus, when discussing surgical apparatus 6000 the description applies to both the left leg surgical apparatus 6050 and a right leg surgical apparatus 6052. In one embodiment, left leg surgical apparatus 6050 and right leg surgical apparatus 6052 are symmetrical about an anterior-posterior access.

Figure 67:
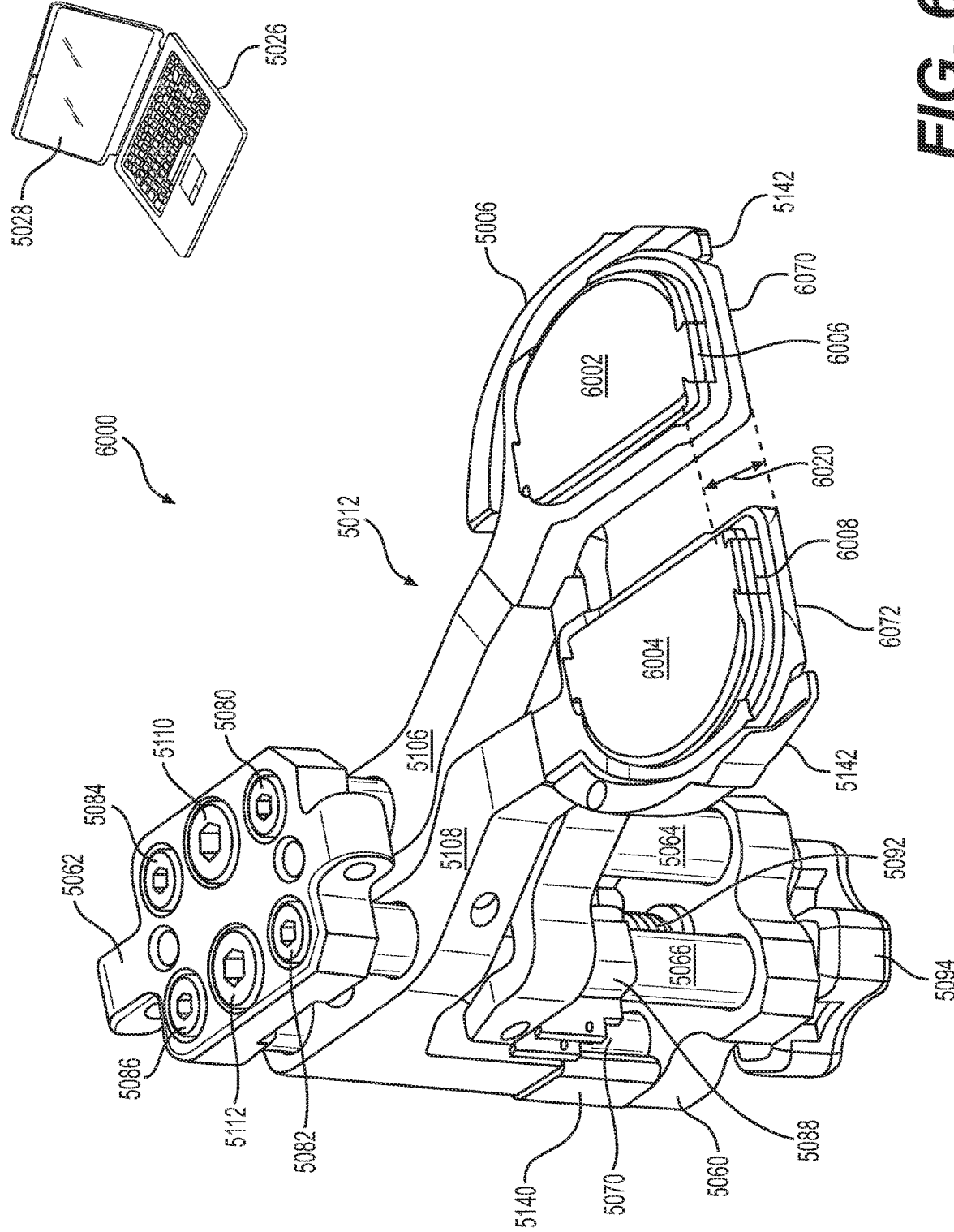
FIG. 67 is an illustration of the surgical apparatus with a medial and a lateral compartment height in a minimum height position in accordance with an example embodiment.

FIG. 67 is an illustration of a surgical apparatus 6000 with a medial and a lateral compartment height in a minimum height position in accordance with an example embodiment. In the example, medial femoral support 6006 and lateral femoral support 6008 are lowered to couple to tibial support 5006. In one embodiment, the minimum height occurs when the bottom surface 5142 of tibial support 5006 is co-planar to bottom surfaces 6070 and 6072 respectively of medial femoral support 6006 and lateral femoral support 6008. In one embodiment, the minimum height corresponds to a distance between bottom surface 5142 of tibial support 5006 and a surface of measurement module 6002 and 6004 as indicated by double headed arrow 6020.

A process of placing surgical apparatus 6000 in the minimum height position comprises rotating medial tilting screw 5110 to move medial femoral support 6006 towards base 5060 until medial support structure 5106 couples to spacer block 5104. Lateral tilting screw 5112 is rotated to move lateral femoral support 6008 towards base 5060 until lateral support structure 5108 couples to spacer block 5104. Handle 5094 is rotated to move tibial support 5006 towards cap 5062 until tibial support 5006 couples to medial femoral support 6006 and lateral femoral support 6008. No order is implied by these steps. Surgical apparatus 6000 in the minimum height position is now configured to be inserted into a knee joint. The minimum medial and lateral compartment heights of surgical apparatus 6000 is less than the height of the one or more inserts that can be used in a final prosthetic knee joint. Once inserted, surgical apparatus 6000 can be used to change the medial or lateral compartment heights to support installation of the prosthetic knee joint by adjusting the distractor mechanisms. In one embodiment, surgical apparatus 6000 can distract the knee joint to compartment heights corresponding to final inserts used in the prosthetic knee joint.

A first cap and a second cap may respectively overlie measurement module 6002 and measurement module 6004. The first cap and the second cap provides a surface to interface with the medial condyle and the lateral condyles of the femur or condyles of the femoral prosthetic component. The first cap and the second cap distribute loading respectively to the surface of measurement module 6002 and measurement module 6004. In one embodiment, the first cap and the second cap can comprise a metal, a metal alloy, a polymer, or organic material. In one embodiment, the first cap and the second cap are rigid and does not flex. Alternatively, the first cap and the second cap can be designed to flex.

FIG. 68 is an illustration of surgical apparatus 6000 changing a height of the medial and lateral compartments simultaneously in accordance with an example embodiment. The offset of surgical apparatus 6000 is for use in a left leg. All steps or actions disclosed herein can be performed for surgical apparatus in a right leg or left leg configuration. In the example, a surface of measurement module 6002 and a surface of measurement module 6004 are co-planar. Although not shown, measurement module 6002 and measurement module 6004 would respectively couple to a medial condyle and a lateral condyle of a femur when inserted in the knee joint similar to that shown in FIG. 53. The medial or lateral condyles can be natural condyles or condyles of a femoral prosthetic component. In the example, surgical apparatus 6000 is inserted into the knee joint with the medial and lateral compartments of surgical apparatus 6000 at a minimum height. Tibial support 5006 couples to a proximal end of the tibia. The proximal end of the tibia can be either the natural surface or a prepared surface of the tibia. In one embodiment, surgical apparatus 6000 is inserted into the knee joint with the leg in extension. Once inserted, the medial compartment height corresponds to the distance from the surface of measurement module 6002 to bottom surface 5142 of tibial support 5006. Likewise, the lateral compartment height corresponds to the distance from the surface of measurement module 6004 to bottom surface 5142 of tibial support 5006. In the example, the medial and lateral compartments of surgical apparatus 6000 have been set to the minimum height prior to insertion. Once inserted, surgical apparatus the medial and lateral compartments will be at least be distracted to the minimum height. Surgical apparatus 6000 may be under load when inserted into the knee joint or alternatively the medial and lateral compartment heights may have to be increased from the minimum height to be loaded by the knee joint.

Distraction mechanism 5010 moves tibial support 5006 towards base 5060 or away from base 5060. Knob 5094 is coupled to distraction lead screw 5092 which threads into a threaded opening of tibial support holder 5088. Rotating knob 5094 engages threads of distraction lead screw 5092 with the threads of tibial support holder 5088. In the example, knob 5094 is rotated as indicated by arrow 6094 in a clockwise direction. Rotating knob 5094 clockwise moves tibial support holder 5088 towards base 5060 on a trajectory determined by cage system 5011 and thereby also moving tibial support 5006 by the same distance. Note that moving tibial support 5006 changes the distance of both the medial and lateral compartment heights simultaneously. In the example, the medial compartment height is indicated by arrow 6090 which is the distance from the surface of measurement module 6002 to bottom surface 5142 of tibial support 5006. Similarly, the lateral compartment height is indicated by arrow 6092 which is the distance from the surface of measurement module 6004 to bottom surface 5142 of tibial support 5006. The medial and lateral compartments have the same height after rotation of knob 5094 because the surfaces of measurement modules 6002 and 6004 were co-planar to one another prior to rotation of knob 5094.

Conversely, the medial and lateral compartment heights can be decreased by rotating knob 5094 counterclockwise which moves tibial support 5006 away from base 5060. In one embodiment, knob 5094 cannot be rotated when the medial and lateral compartments are at the minimum height because tibial support 5006 will be in contact with medial femoral support 6006 and lateral femoral support 6008 thereby preventing further movement of tibial support 5006. In another example, assume that the medial and lateral compartments heights were different. Rotating knob 5094 will produce an equal change in height for both the medial and lateral compartments. For example, assume a medial compartment height of 11 cm and a lateral compartment height of 10 cm prior to rotation of knob 5094. Knob 5094 is then rotated to move tibial support 5006 1.0 centimeters away from base 5060. The medial compartment height would be 10 cm and the lateral compartment height would be at 9 cm after rotation of knob 5094. Thus, the change in height affects both the medial and lateral compartments equally whether increasing or decreasing the compartment heights with distraction mechanism 5010.

FIG. 69 is an illustration of surgical apparatus 6000 changing a height of the medial compartment in accordance with an example embodiment. The offset of surgical apparatus 6000 is for use in a left leg. All steps or actions disclosed herein can be performed using surgical apparatus 6000 for a right leg or left leg configuration. In the example, a surface of measurement module 6002 and a surface of measurement module 6004 are non-planar to one another. Although not shown, measurement module 6002 and measurement module 6004 would respectively couple to a medial condyle and a lateral condyle of a distal end of a femur similar to that shown in FIG. 53. Tibial support 5006 is configured to couple to a proximal end of a tibia similar to that shown in FIG. 53. In one embodiment, surgical apparatus 6000 is inserted into a left knee joint with the leg in extension and adjusted to change the medial and lateral compartment heights. The medial compartment height corresponds to the distance from the surface of measurement module 6002 to bottom surface 5142 of tibial support 5006 as indicated by arrow 6090. Likewise, the lateral compartment height corresponds to the distance from the surface of measurement module 6004 to bottom surface 5142 of tibial support 5006 as indicated by arrow 6092. Surgical apparatus 6000 is configured to have the medial and lateral compartments a minimum height of the device. Upon insertion, surgical apparatus 6000 distracts the knee joint to the minimum height. Surgical apparatus 6000 may be under load when inserted into the knee joint or alternatively the medial and lateral compartment heights may have to be increased from the minimum height to be loaded by the knee joint.

Distraction mechanism 5010 is configured to move tibial support 5006 such that the height of the medial and lateral compartments changes by the same amount. Knob 5094 is coupled to distraction lead screw 5092 which threads into tibial support holder 5088. Rotating knob 5094 engages threads of distraction lead screw 5092 with the threads of tibial support holder 5088. In the example, knob 5094 is rotated in a clockwise direction to change the height of the medial and lateral compartment from the minimum height to a first predetermined height. Rotating knob 5094 clockwise moves tibial support holder 5088 towards base 5060 on a trajectory determined by cage system 5011 and thereby also moving tibial support 5006 by the same distance. Note that moving tibial support 5006 changes the medial and lateral compartment heights simultaneously. Conversely, rotating knob 5094 counter-clockwise would move tibial support 5006 away from base 5060 thereby reducing the medial and lateral compartment heights by the same amount. Although not shown, both the medial and lateral compartment heights would be at the first predetermined height as indicated by arrow 6092 corresponding to the lateral compartment height in this intermediate step.

Distraction mechanism 5012 is then used to change the medial compartment height. In the example, the medial compartment height is further adjusted by rotating medial tilt screw 5110 in a clockwise direction as indicated by arrow 6094. Rotating medial tilt screw 5110 clockwise moves medial femoral support 6006 towards cap 5062 to increase the medial compartment height to a second predetermined height. In the example, the second predetermined height of the medial compartment is indicated by arrow 6090. Conversely, rotating medial tilt screw 5110 counterclockwise moves femoral support 6006 away from cap 5062 to reduce the medial compartment height. Note that the height of the lateral compartment does not change as medial tilt screw 5110 is rotated only the medial compartment height is changed. There is no order implied by the steps disclosed. For example, distraction mechanism 5012 could be adjusted followed by adjusting distraction mechanism 5010.

Distraction mechanism 5014 is not adjusted in the example. Thus, the lateral compartment height remains at the first predetermined height. The lateral compartment height is indicated by arrow 6092. As mentioned previously, surgical apparatus 6000 is inserted with the medial and lateral compartments at the minimum height. Increasing the medial and lateral compartment heights using distraction mechanism 5010 will load measurement modules 6002 and 6004 in the knee joint. Increasing the height of the medial compartment with distraction mechanism 5012 will further increase the loading on the medial compartment. In one embodiment, sensors in measurement module 6002 and 6004 provide load measurement data to computer 5026 of FIG. 67. Sensors or mechanical gauges in or on surgical apparatus 6000 provide measurement data related to tilt and height of the medial and lateral compartment. Computer 5026 can provide the measurement data in a visual, audible, or haptic manner that allows the user to rapidly assimilate the information during surgery. Computer 5026 can include one or more software programs that support the knee installation and utilize the measurement data in real-time to provide a surgical workflow and one or more options to optimize the procedure. In one embodiment, the measurement data and computer 5026 can provide information relating to the balance between medial and lateral compartments, the height of the medial or lateral compartments, the medial-lateral tilt, alignment of the femur, alignment of the tibia, alignment relative to the contact points on modules 6002 and 6004 where the medial and lateral condyles touch measurement modules 6002 and 6004, a load magnitude applied by the medial or lateral condyles to modules 6002 and 6004.

Figure 70:
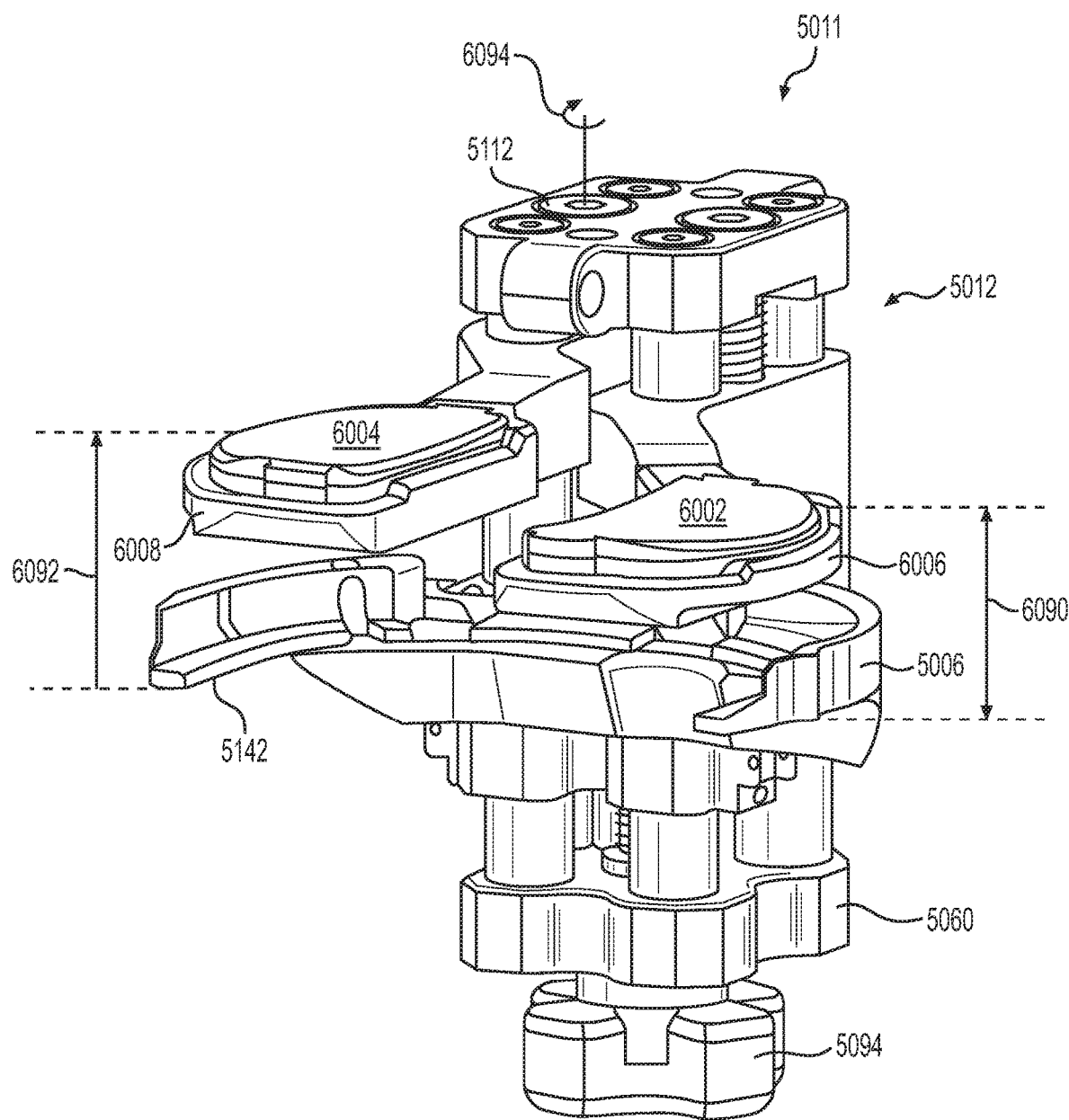
FIG. 70 is an illustration of the surgical apparatus changing a height of the lateral compartment in accordance with an example embodiment.

FIG. 70 is an illustration of surgical apparatus 6000 changing a height of the lateral compartment in accordance with an example embodiment. The offset of surgical apparatus 6000 is for use in a left leg in the example. All steps or actions disclosed herein can be performed using surgical apparatus 6000 for a right leg or left leg configuration. In the example, a surface of measurement module 6002 and a surface of measurement module 6004 are non-planar to one another. Although not shown, measurement module 6002 and measurement module 6004 would respectively couple to a medial condyle and a lateral condyle of a distal end of a femur similar to that shown in FIG. 53. Surgical apparatus 6000 can couple to a natural, prepared, or prosthetic component at the distal end of the femur. Tibial support 5006 is configured to couple to a proximal end of a tibia similar to that shown in FIG. 53. Similarly, surgical apparatus 6000 can couple to a natural, prepared, or prosthetic component at the proximal end of the tibia. In one embodiment, surgical apparatus 6000 is inserted into a left knee joint with the leg in extension and adjusted to change the medial and lateral compartment heights. The medial compartment height corresponds to the distance from the surface of measurement module 6002 to bottom surface 5142 of tibial support 5006 as indicated by arrow 6090. Likewise, the lateral compartment height corresponds to the distance from the surface of measurement module 6004 to bottom surface 5142 of tibial support 5006 as indicated by arrow 6092. In one embodiment, surgical apparatus 6000 is configured to have the medial and lateral compartments at the minimum height of the device prior to insertion. Upon insertion, surgical apparatus 6000 distracts the knee joint to the minimum height. Surgical apparatus 6000 may be under load when inserted into the knee joint or alternatively the medial and lateral compartment heights may have to be increased from the minimum height to be loaded by the knee joint.

Distraction mechanism 5010 is configured to move tibial support 5006 such that the height of the medial and lateral compartments changes by the same amount. Knob 5094 is coupled to distraction lead screw 5092 which threads into tibial support holder 5088. Rotating knob 5094 engages threads of distraction lead screw 5092 with the threads of tibial support holder 5088. In the example, knob 5094 is rotated in a clockwise direction to change the height of the medial and lateral compartment from the minimum height to a first predetermined height. Rotating knob 5094 clockwise moves tibial support holder 5088 towards base 5060 on a trajectory determined by cage system 5011 and thereby also moving tibial support 5006 by the same distance. Note that moving tibial support 5006 changes the medial and lateral compartment heights simultaneously. Conversely, rotating knob 5094 counter-clockwise would move tibial support 5006 away from base 5060 thereby reducing the medial and lateral compartment heights by the same amount. Although not shown, both the medial and lateral compartment heights would be at the first predetermined height as indicated by arrow 6090 corresponding to the medial compartment height in this intermediate step.

Distraction mechanism 5014 is then used to change the lateral compartment height. In the example, the lateral compartment height is further adjusted by rotating lateral tilt screw 5112 in a clockwise direction as indicated by arrow 6094. Rotating lateral tilt screw 5112 clockwise moves lateral femoral support 6008 towards cap 5062 to increase the lateral compartment height to a second predetermined height. In the example, the second predetermined height of the lateral compartment is indicated by arrow 6092. Conversely, rotating lateral tilt screw 5112 counterclockwise moves femoral support 6008 away from cap 5062 to reduce the lateral compartment height. Note that the height of the medial compartment does not change as lateral tilt screw 5112 is rotated; only the lateral compartment height is changed. There is no order implied by the steps disclosed. For example, distraction mechanism 5014 could be adjusted followed by adjusting distraction mechanism 5010.

Distraction mechanism 5012 is not adjusted in the example. Thus, the medial compartment height remains at the first predetermined height. The medial compartment height is indicated by arrow 6090. As mentioned previously, surgical apparatus 6000 is inserted with the medial and lateral compartments at the minimum height. Increasing the medial and lateral compartment heights using distraction mechanism 5010 will load measurement modules 6002 and 6004 in the knee joint. Increasing the height of the lateral compartment with distraction mechanism 5014 will further increase the loading on the lateral compartment. In one embodiment, sensors in measurement module 6002 and 6004 provide load measurement data to computer 5026 of FIG. 67. Sensors or mechanical gauges in or on surgical apparatus 6000 provide measurement data related to tilt and height of the medial and lateral compartment. Computer 5026 can provide the measurement data in a visual, audible, or haptic manner that allows the user to rapidly assimilate the information during surgery. Computer 5026 can include one or more software programs that support the knee installation and utilize the measurement data in real-time to provide a surgical workflow and one or more options to optimize the procedure. In one embodiment, the measurement data and computer 5026 can provide information relating to the balance between medial and lateral compartments, the height of the medial or lateral compartments, the medial-lateral tilt, alignment of the femur, alignment of the tibia, alignment relative to the contact points on modules 6002 and 6004 where the medial and lateral condyles touch measurement modules 6002 and 6004, a load magnitude applied by the medial or lateral condyles to modules 6002 and 6004.

It should be noted that very little data exists on implanted orthopedic devices. Most of the data is empirically obtained by analyzing orthopedic devices that have been used in a human subject or simulated use. Wear patterns, material issues, and failure mechanisms are studied. Although, information can be garnered through this type of study it does yield substantive data about the initial installation, post-operative use, and long term use from a measurement perspective. Just as each person is different, each device installation is different having variations in initial loading, balance, and alignment. Having measured data and using the data to install an orthopedic device will greatly increase the consistency of the implant procedure thereby reducing rework and maximizing the life of the device. In at least one exemplary embodiment, the measured data can be collected to a database where it can be stored and analyzed. For example, once a relevant sample of the measured data is collected, it can be used to define optimal initial measured settings, geometries, and alignments for maximizing the life and usability of an implanted orthopedic device.

The present invention is applicable to a wide range of medical and nonmedical applications including, but not limited to, frequency compensation; control of, or alarms for, physical systems; or monitoring or measuring physical parameters of interest. The level of accuracy and repeatability attainable in a highly compact sensing module or surgical apparatus may be applicable to many medical applications monitoring or measuring physiological parameters throughout the human body including, not limited to, bone density, movement, viscosity, and pressure of various fluids, localized temperature, etc. with applications in the vascular, lymph, respiratory, digestive system, muscles, bones, and joints, other soft tissue areas, and interstitial fluids.

While the present invention has been described with reference to particular embodiments, those skilled in the art will recognize that many changes may be made thereto without departing from the spirit and scope of the present invention. Each of these embodiments and obvious variations thereof is contemplated as falling within the spirit and scope of the invention.

What is claimed is:
1. A surgical apparatus comprising:
 a first distraction mechanism configured to simultaneously distract a first side and a second side of a joint of a musculoskeletal system by an equal amount;
 a second distraction mechanism configured to change a height of the first side of the joint; and
 a third distraction mechanism configured to change a height of the second side of the joint,
 wherein the first distraction mechanism comprises:

a base having a medial anterior opening, a lateral anterior opening, a medial posterior opening, a lateral posterior opening, and a distraction lead screw opening;

an anterior medial guide shaft coupled to the base through the medial anterior opening of the base;

an anterior lateral guide shaft coupled to the base through the lateral anterior opening of the base;

a first support holder having a threaded opening, a medial opening, and a lateral opening wherein the anterior medial guide shaft couples through the medial opening of the first support holder and wherein the lateral guide shaft couples through the lateral opening of the first support holder; and a distraction lead screw coupled through the distraction lead screw opening of the base and coupled to the threaded opening of the first support holder wherein rotating the distraction lead screw moves the first support holder relative to the base along a trajectory determined by the anterior medial guide shaft and the anterior lateral guide shaft.

2. The surgical apparatus of claim 1 further including a first support coupled to the first support holder wherein the first support is configured to couple to a surface of a first bone.

3. The surgical apparatus of claim 1 wherein the second distraction mechanism comprises:
a posterior medial guide shaft coupled to the medial posterior opening of the base; and
a medial support structure having a first opening and a second opening wherein the anterior medial guide shaft and the posterior medial guide shaft respectively couples through the first opening and the second opening of the medial support structure and wherein the medial support structure is configured to support movement along a trajectory determined by the anterior medial guide shaft and the posterior medial guide shaft.

4. The surgical apparatus of claim 3 wherein the third distraction mechanism comprises:
a posterior lateral guide shaft coupled to the lateral posterior opening of the base; and
a lateral support structure having a first opening and a second opening wherein the anterior lateral guide shaft and the posterior lateral guide shaft respectively couples through the first opening and the second opening of the lateral support structure and wherein the lateral support structure is configured to support movement along a trajectory determined by the anterior lateral guide shaft and the posterior lateral guide shaft.

5. The surgical apparatus of claim 4 further including a spacer of a predetermined height between the base and the medial and lateral support structures.

6. The surgical apparatus of claim 5 further including:
a cap having a medial anterior opening, a lateral anterior opening, a medial posterior opening, a lateral posterior opening, a first opening, and a second opening wherein the anterior medial guide shaft, the anterior lateral guide shaft, the posterior medial guide shaft, and the posterior lateral guide shaft respectively couples to the medial anterior opening, the lateral anterior opening, the medial posterior opening, and the lateral posterior opening of the cap;
a medial tilting screw coupling through the first opening of the cap wherein the medial tilting screw couples to a threaded opening of the medial support structure; and
a lateral tilting screw coupling through the second opening of the cap wherein the lateral tilting screw couples to a threaded opening of the lateral support structure.

7. The surgical apparatus of claim 6 wherein the medial support structure or the lateral support structure is offset to support placement of a patella to load a knee joint over a range of motion during distraction.

8. The surgical apparatus of claim 6 further including:
a second support respectively coupled to the medial support structure and the lateral support structure at a first pivot point and a second pivot point wherein rotating the medial tilting screw or the lateral tilting screw is configured to change the medial-lateral tilt of the second support and wherein loading applied to the second support is distributed between the first pivot point and the second pivot point;
a module configured to couple to the second support wherein the module includes electronic circuitry and at least one sensor; and
a computer configured to receive measurement data from the module.

9. The knee distractor of claim 6 further including:
a medial plate coupled to the medial support structure at a first pivot point;
a lateral plate coupled to the lateral support structure at a second pivot point;
a first module configured to couple to the medial plate wherein the first module includes electronic circuitry and at least one sensor;
a second module configured to couple to the lateral plate wherein the second module includes electronic circuitry and at least one sensor;
a computer configured to receive measurement data from the first module and the second module.

10. A surgical apparatus comprising:
a medial surface to contact a medial side of a joint and a lateral surface to contact a lateral side of the joint;
a first distraction mechanism configured to simultaneously change a height of the medial side and the lateral side of a joint of the musculoskeletal system by an equal amount wherein a first support couples to the first distraction mechanism;
a second distraction mechanism configured to change a height of the medial side of the joint;
a third distraction mechanism configured to change a height of the lateral side wherein a second support couples to the second and third distraction mechanisms; and
a module having electronic circuitry and at least one sensor wherein the module is configured to couple to the second support,
wherein the medial surface and the lateral surface lie on the same plane when the height of the medial side is varied by the second distraction mechanism.

11. The surgical apparatus of claim 10 wherein the second distraction mechanism couples to the second support at a first pivot point and wherein the third distraction mechanism couples to the second support at a second pivot point.

12. The surgical apparatus of claim 10 wherein the surgical apparatus is configured to be inserted into a joint of the musculoskeletal system such that the first support, second support, and module are placed in the joint and wherein the first distraction mechanism is configured to increase the height of the medial and lateral sides of the joint.

13. The surgical apparatus of claim 12 wherein the second distraction mechanism or the third distraction mechanism is configured to change a medial-lateral tilt of the joint.

14. The surgical apparatus of claim 10 wherein the module transmits measurement data to a computer and wherein the computer displays the measurement data in real-time.

15. A surgical apparatus comprising:
- a first distraction mechanism including a distraction screw configured to simultaneously change a height of a first side and a second side of a joint of the musculoskeletal system by an equal amount wherein a first support couples to the first distraction mechanism and is configured to couple to a first bone of the joint;
- a second distraction mechanism configured to change a height of the first side; and
- a third distraction mechanism configured to change a height of the second side;
- at least one module having at least one sensor configured to transmit measurement data wherein the surgical apparatus is configured to support at least one bone cut of the joint,
- wherein the distraction screw is located away from the first support and extends along an axis perpendicular to the first support, wherein the second distraction mechanism couples to a first plate at a first pivot point, wherein the third distraction mechanism couples to a second plate at a second pivot point, wherein a first module having at least one sensor couples to the first plate, wherein a second module having at least one sensor couples to the second plate, and wherein the first support, the first plate, the second plate, first module, and second module are configured to be inserted in the joint.

16. The surgical apparatus of claim 15 wherein the second distraction mechanism couples to a second support at a first pivot point, wherein the third distraction mechanism couples to the second support at a second pivot point, wherein the at least one module couples to the second support, and wherein the first support, the second support, and the at least one module is configured to be inserted in the joint.

17. The surgical apparatus of claim 15 wherein adjusting the second distraction mechanism or the third distraction mechanism changes a tilt of the surgical apparatus.

* * * * *